(12) United States Patent
Shakeel et al.

(10) Patent No.: US 12,324,431 B2
(45) Date of Patent: *Jun. 10, 2025

(54) COMPOSITIONS AND METHODS FOR SCALABLE PRODUCTION AND DELIVERY OF BIOLOGICALS

(71) Applicant: AgroSpheres, Inc., Charlottesville, VA (US)

(72) Inventors: Ameer Hamza Shakeel, Leesburg, VA (US); Zachery George Davis, Charlottesville, VA (US); Joseph Thomas Frank, Charlottesville, VA (US); Sepehr Zomorodi, Charlottesville, VA (US); Payam Pourtaheri, Charlottesville, VA (US)

(73) Assignee: AgroSpheres, Inc., Charlottesville, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/452,223

(22) Filed: Aug. 18, 2023

(65) Prior Publication Data

US 2024/0081325 A1 Mar. 14, 2024

Related U.S. Application Data

(63) Continuation of application No. 16/649,857, filed as application No. PCT/US2018/052690 on Sep. 25, 2018, now Pat. No. 11,812,743.

(60) Provisional application No. 62/562,723, filed on Sep. 25, 2017, provisional application No. 62/666,981, filed on May 4, 2018.

(51) Int. Cl.
  *A01N 25/28* (2006.01)
  *A01N 63/20* (2020.01)
  *A01N 63/50* (2020.01)
  *C12N 15/74* (2006.01)

(52) U.S. Cl.
  CPC ............ *A01N 25/28* (2013.01); *A01N 63/20* (2020.01); *A01N 63/50* (2020.01); *C12N 15/74* (2013.01)

(58) Field of Classification Search
  None
  See application file for complete search history.

(56) References Cited

U.S. PATENT DOCUMENTS

| | | |
|---|---|---|
| 4,311,797 A | 1/1982 | Khachatourians |
| 4,518,593 A | 5/1985 | Juvin et al. |
| 4,613,355 A | 9/1986 | Omura et al. |
| 4,861,762 A | 8/1989 | Puritch et al. |
| 4,904,645 A | 2/1990 | Puritch et al. |
| 4,983,591 A | 1/1991 | Puritch et al. |
| 5,047,424 A | 9/1991 | Puritch et al. |
| 5,346,704 A | 9/1994 | Lajoie |
| 5,451,513 A | 9/1995 | Maliga et al. |
| 5,501,967 A | 3/1996 | Offringa et al. |
| 5,527,695 A | 6/1996 | Hodges et al. |
| 5,738,984 A | 4/1998 | Shoseyov |
| 5,998,484 A | 12/1999 | Zobitne et al. |
| 6,071,725 A | 6/2000 | Pan et al. |
| 6,124,117 A | 9/2000 | Kilburn et al. |
| 6,231,865 B1 | 5/2001 | Hsu et al. |
| 6,548,085 B1 | 4/2003 | Zobitne et al. |
| 6,670,168 B1 | 12/2003 | Katz et al. |
| 7,071,188 B2 | 7/2006 | Watrin |
| 7,183,105 B2 | 2/2007 | Sabbadini et al. |
| 7,338,920 B2 | 3/2008 | Kotzian |
| 7,396,822 B2 | 7/2008 | Sabbadini et al. |
| 7,485,451 B2 | 2/2009 | Vandergheynst et al. |
| 7,534,447 B2 | 5/2009 | Bessette et al. |
| 7,871,815 B2 | 1/2011 | Sabbadini et al. |
| 8,101,396 B2 | 1/2012 | Sabbadini et al. |
| 8,124,565 B2 | 2/2012 | Zeun et al. |
| 8,129,166 B2 | 3/2012 | Sabbadini et al. |
| 8,349,345 B2 | 1/2013 | Forster et al. |
| 8,524,484 B2 | 9/2013 | Sabbadini et al. |
| 8,822,381 B2 | 9/2014 | Koivunen et al. |
| 9,017,986 B2 | 4/2015 | Sabbadini et al. |
| 9,045,761 B2 | 6/2015 | Giacalone et al. |
| 9,210,926 B2 | 12/2015 | Markus et al. |
| 9,267,108 B2 | 2/2016 | Giacalone |
| 9,566,321 B2 | 2/2017 | Giacalone |
| 9,655,360 B2 | 5/2017 | Franklin et al. |

(Continued)

FOREIGN PATENT DOCUMENTS

| | | |
|---|---|---|
| CA | 3056801 A1 | 11/2018 |
| CN | 1185809 A | 6/1998 |

(Continued)

OTHER PUBLICATIONS

Extended European Search Report for European Application No. EP20904351.2 dated Jan. 3, 2024, 7 pages.

(Continued)

*Primary Examiner* — Alton N Pryor

(74) *Attorney, Agent, or Firm* — Cooley LLP

(57) ABSTRACT

The present disclosure is generally directed to an agricultural formulation comprising an anucleated minicells and an anucleated cell-based platforms for encapsulation and scalable delivery of biologically active compounds. Disclosed herein are compositions for the stable and targeted delivery of biologically active compounds within achromosomal and/or anucleated cells onto and/or into a target cell. The present disclosure also provides methods of improving encapsulation and retention of biologically active compounds in achromosomal and/or anucleated cells and delivering biologically active compounds into a target cell.

24 Claims, 37 Drawing Sheets

Specification includes a Sequence Listing.

(56) References Cited

U.S. PATENT DOCUMENTS

| | | | |
|---|---|---|---|
| 9,670,270 B2 | 6/2017 | Sabbadini et al. |
| 9,743,676 B2 | 8/2017 | O'Connor |
| 10,005,820 B2 | 6/2018 | Giacalone et al. |
| 10,039,817 B2 | 8/2018 | Giacalone |
| 10,124,024 B2 | 11/2018 | Giacalone et al. |
| 10,258,033 B2 | 4/2019 | Ostroff |
| 10,342,839 B2 | 7/2019 | Lamb |
| 10,383,329 B2 | 8/2019 | Abrey et al. |
| 10,609,930 B2 | 4/2020 | Tao |
| 10,638,750 B2 | 5/2020 | Franklin et al. |
| 10,729,130 B2 | 8/2020 | Ostroff |
| 10,913,940 B2 | 2/2021 | Pourtaheri et al. |
| 11,219,679 B2 | 1/2022 | Giacalone |
| 11,312,954 B2 | 4/2022 | Linke et al. |
| 11,446,344 B1 | 9/2022 | Delagrave et al. |
| 11,485,976 B2 | 11/2022 | Brahmbhatt et al. |
| 11,504,402 B2 | 11/2022 | Brahmbhatt et al. |
| 11,564,953 B2 | 1/2023 | Giacalone et al. |
| 11,576,872 B2 | 2/2023 | Von Maltzahn et al. |
| 11,624,061 B2 | 4/2023 | Shakeel et al. |
| 11,649,265 B2 | 5/2023 | Shakeel et al. |
| 11,674,121 B2 | 6/2023 | Klemke et al. |
| 11,690,880 B2 | 7/2023 | Duportet et al. |
| 11,746,352 B2 | 9/2023 | Fernandez Rodriguez et al. |
| 11,812,743 B2 | 11/2023 | Shakeel et al. |
| 11,970,518 B2 | 4/2024 | Shakeel |
| 2003/0091657 A1 | 5/2003 | Chiasson |
| 2003/0166099 A1 | 9/2003 | Sabbadini et al. |
| 2003/0166279 A1 | 9/2003 | Sabbadini et al. |
| 2003/0194798 A1 | 10/2003 | Surber et al. |
| 2003/0203481 A1 | 10/2003 | Surber et al. |
| 2004/0109853 A1 | 6/2004 | McDaniel |
| 2005/0176117 A1 | 8/2005 | Russell et al. |
| 2005/0222057 A1 | 10/2005 | Brahmbhatt et al. |
| 2006/0014291 A1 | 1/2006 | Kebeler et al. |
| 2006/0039870 A1 | 2/2006 | Turner |
| 2006/0084136 A1 | 4/2006 | Kudlicki et al. |
| 2006/0225154 A1 | 10/2006 | Kasukabe et al. |
| 2006/0270040 A1 | 11/2006 | Filutowicz et al. |
| 2007/0048852 A1 | 3/2007 | Holker et al. |
| 2007/0191228 A1 | 8/2007 | Li et al. |
| 2008/0220038 A1 | 9/2008 | Franklin et al. |
| 2009/0030087 A1 | 1/2009 | Chiasson |
| 2010/0316738 A1 | 12/2010 | Jimenez et al. |
| 2011/0045975 A1 | 2/2011 | Ehr et al. |
| 2011/0104786 A1 | 5/2011 | Van Kimmenade et al. |
| 2011/0281330 A1 | 11/2011 | Sabbadini et al. |
| 2012/0016022 A1 | 1/2012 | Hirano et al. |
| 2012/0107875 A1 | 5/2012 | Liu et al. |
| 2012/0207754 A1 | 8/2012 | Giacalone et al. |
| 2013/0084559 A1 | 4/2013 | Simpson et al. |
| 2013/0142893 A1 | 6/2013 | Bessette et al. |
| 2013/0316007 A1 | 11/2013 | Ma et al. |
| 2013/0337545 A1 | 12/2013 | Sabbadini et al. |
| 2014/0045692 A1 | 2/2014 | Rossines et al. |
| 2014/0051571 A1 | 2/2014 | Asolkar et al. |
| 2014/0068797 A1 | 3/2014 | Doudna et al. |
| 2014/0147873 A1 | 5/2014 | Clubb et al. |
| 2014/0170198 A1 | 6/2014 | Franklin et al. |
| 2015/0087029 A1 | 3/2015 | Tan et al. |
| 2015/0140037 A1 | 5/2015 | Galan et al. |
| 2015/0218254 A1 | 8/2015 | Sabbadini et al. |
| 2015/0264938 A1 | 9/2015 | Gage et al. |
| 2015/0289503 A1 | 10/2015 | Abrey et al. |
| 2016/0100607 A1 | 4/2016 | Schmidt et al. |
| 2016/0174571 A1 | 6/2016 | Mensah |
| 2017/0268002 A1 | 9/2017 | Esau et al. |
| 2018/0000071 A1 | 1/2018 | Abrey et al. |
| 2018/0235257 A1 | 8/2018 | Wozniak |
| 2018/0325108 A1 | 11/2018 | Franklin et al. |
| 2019/0169582 A1 | 6/2019 | Pourtaheri et al. |
| 2019/0350206 A1 | 11/2019 | Lajeunesse |
| 2020/0113177 A1 | 4/2020 | Shakeel et al. |
| 2020/0123527 A1 | 4/2020 | Shakeel et al. |
| 2020/0236927 A1 | 7/2020 | Franklin et al. |
| 2020/0267971 A1 | 8/2020 | Shakeel et al. |
| 2020/0399618 A1 | 12/2020 | Pourtaheri et al. |
| 2022/0008557 A1 | 1/2022 | Von Maltzahn et al. |
| 2022/0031862 A1 | 2/2022 | Fisher et al. |
| 2022/0042042 A1 | 2/2022 | Weinstein et al. |
| 2022/0064661 A1 | 3/2022 | Van Rooijen et al. |
| 2022/0073950 A1 | 3/2022 | Weinstein et al. |
| 2022/0105166 A1 | 4/2022 | Sharei et al. |
| 2022/0152139 A1 | 5/2022 | Van Rooijen et al. |
| 2022/0192201 A1 | 6/2022 | Van Rooijen et al. |
| 2022/0195364 A1 | 6/2022 | Sharei et al. |
| 2022/0202950 A1 | 6/2022 | Brahmbhatt et al. |
| 2022/0273565 A1 | 9/2022 | Van Rooijen et al. |
| 2022/0288150 A1 | 9/2022 | Van Rooijen et al. |
| 2022/0304930 A1 | 9/2022 | Van Rooijen et al. |
| 2022/0389062 A1 | 12/2022 | Zhang et al. |
| 2023/0041309 A1 | 2/2023 | Brahmbhatt et al. |
| 2023/0043255 A1 | 2/2023 | Von Maltzahn et al. |
| 2023/0044257 A1 | 2/2023 | Shakeel et al. |
| 2023/0048166 A1 | 2/2023 | Von Maltzahn et al. |
| 2023/0048858 A1 | 2/2023 | Weinstein et al. |
| 2023/0079745 A1 | 3/2023 | Brahmbhatt et al. |
| 2023/0104113 A1 | 4/2023 | Kahvejian et al. |
| 2023/0113800 A1 | 4/2023 | Duportet et al. |
| 2023/0114520 A1 | 4/2023 | Duportet |
| 2023/0174939 A1 | 6/2023 | Falb |
| 2023/0189819 A1 | 6/2023 | Pourtaheri et al. |
| 2023/0242595 A1 | 8/2023 | Tam et al. |
| 2023/0242867 A1 | 8/2023 | Fisher et al. |
| 2023/0265413 A1 | 8/2023 | Shakeel |
| 2023/0313094 A1 | 10/2023 | Shakeel |
| 2023/0357330 A1 | 11/2023 | Shakeel |
| 2023/0413828 A1 | 12/2023 | Frank |
| 2024/0016147 A1 | 1/2024 | Frank et al. |
| 2024/0049706 A1 | 2/2024 | Shakeel et al. |
| 2024/0049721 A1 | 2/2024 | Shakeel et al. |
| 2024/0130363 A1 | 4/2024 | Shakeel et al. |
| 2024/0254170 A1 | 8/2024 | Shakeel et al. |

FOREIGN PATENT DOCUMENTS

| | | |
|---|---|---|
| CN | 1253591 A | 5/2000 |
| CN | 101072876 A | 11/2007 |
| CN | 101935669 A | 1/2011 |
| CN | 102021185 A | 4/2011 |
| CN | 102573460 A | 7/2012 |
| CN | 105854029 A | 8/2016 |
| CN | 111328803 A | 6/2020 |
| DK | 2865755 T3 | 5/2017 |
| EP | 0173327 B1 | 11/1991 |
| EP | 2299804 A2 | 3/2011 |
| WO | WO-9849328 A1 | 11/1998 |
| WO | WO-9852547 A1 | 11/1998 |
| WO | WO-9952367 A1 | 10/1999 |
| WO | WO-0167868 A2 | 9/2001 |
| WO | WO-0209722 A1 | 2/2002 |
| WO | WO-03031477 A1 | 4/2003 |
| WO | WO-03072014 A2 | 9/2003 |
| WO | WO-03106490 A1 | 12/2003 |
| WO | WO-2004006679 A2 | 1/2004 |
| WO | WO-2009027830 A2 | 3/2009 |
| WO | WO-2010144919 A1 | 12/2010 |
| WO | WO-2011017480 A2 | 2/2011 |
| WO | WO-2014088697 A2 | 6/2014 |
| WO | WO-2014093701 A1 | 6/2014 |
| WO | WO-2014165825 A2 | 10/2014 |
| WO | WO-2016124927 A1 | 8/2016 |
| WO | WO-2016198852 A1 | 12/2016 |
| WO | WO-2017180650 A1 | 10/2017 |
| WO | WO-2018201160 A1 | 11/2018 |
| WO | WO-2018201161 A1 | 11/2018 |
| WO | WO-2019060903 A1 | 3/2019 |
| WO | WO-2019222379 A1 | 11/2019 |
| WO | WO-2021133846 A2 | 7/2021 |
| WO | WO-2021236799 A2 | 11/2021 |
| WO | WO-2021257788 A1 | 12/2021 |
| WO | WO-2021257803 A1 | 12/2021 |
| WO | WO-2022010889 A1 | 1/2022 |
| WO | WO-2022076877 A1 | 4/2022 |

(56) References Cited

FOREIGN PATENT DOCUMENTS

| WO | WO-2022108944 A1 | 5/2022 |
|---|---|---|
| WO | WO-2022125996 A1 | 6/2022 |
| WO | WO-2022140638 A1 | 6/2022 |
| WO | WO-2022140639 A1 | 6/2022 |
| WO | WO-2022221535 A1 | 10/2022 |
| WO | WO-2022256427 A1 | 12/2022 |
| WO | WO-2022256519 A1 | 12/2022 |
| WO | WO-2022263824 A1 | 12/2022 |
| WO | WO-2023002433 A1 | 1/2023 |
| WO | WO-2023049155 A1 | 3/2023 |
| WO | WO-2023137383 A1 | 7/2023 |

OTHER PUBLICATIONS

Abbey, J.A., et al., "Biofungicides as alternative to synthetic fungicide control of grey mould (Botrytis cinerea)—prospects and challenges," Biocontrol Science and Technology, Nov. 2018, 29(3), p. 207-228., DOI: 10.1080/09583157.2018.1548574.

Adler et al., "Genetic control of cell division in bacteria", Science Jan. 1, 1966; 154 (3747): 417, 1 page.

Adler et al., "Miniature Escherichia coli cells deficient in DNA", Proceedings of the National Academy of Sciences, Feb. 1967; 57(2), pp. 321-326.

Aislabie et al., "A review of bacterial degradation of pesticides", Aust. J. Soil. Res., 1995; 33: 925-942.

Alshaal et al., "Foliar application: from plant nutrition to biofortification," Env. Biodiv. Soil Security (2017) 1:71-83.

Andrews, G.P., et al., "Protective efficacy of recombinant Yersinia outer proteins against bubonic plague caused by encapsulated and nonencapsulated Yersinia pestis," Infection and Immunity, Mar. 1, 1999 (Mar. 1, 1999), vol. 67, No. 3, pp. 1533-1537.

Barker et al., "Isolation by differential and zonal centrifugation of minicells segregated by Escherichia coli," Journal of General Microbiology, Apr. 1979, 111(2):387-397.

Baulcombe, D.C., "VIGS, HIGS and FIGS: small RNA silencing in the interactions of viruses or filamentous organisms with their plant hosts," Current Opinion in Plant Biology, Aug. 2015, 26, pp. 141-146.

Bergmann-Leitner et al., "Adjuvants in the driver's seat: How magnitude, ype, fine specificity and longevity on immune responses are driven by distinct classes of immune potentiators," Vaccines, Apr. 2014, 2(2), pp. 252-296.

Beys Da Silva et al., "Metarhizium anisopliae lipolytic activity plays a pivotal role in Rhipicephalus (Boophilus) microplus infection," Fungal Biology, Jan. 2010, 114(1), pp. 10-15.

Bhosale et al., "Molecular and Industrial Aspects of Glucose Isomerase," Microbiological Reviews, Jun. 1996, vol. 60, No. 2, pp. 280-300.

Bo et al., "Isolation, identification and characterization of Streptomyces metabolites as a potential bioherbicide," PLoS One, Sep. 23, 2019, 14(9): e0222933, 18 pages.

Borkow et al., "Copper as a biocidal tool," Current Medical Chemistry, Aug. 2005; 12(18), pp. 2163-2175.

Bouche et al., "On the birth and fate of bacterial division sites," Mol Microbiol. Jul. 1998; 29(1): 19-26.

Britton et al., "Characterization of a prokaryotic SMC protein involved in chromosome partitioning," Genes & Development, May 1998, 12(9): 1254-1259.

Brun et al., "Current strategies for subunit and genetic viral veterinary vaccine Development.," Virus Research, Apr. 2011, 157(1), pp. 1-12. https://doi.org/10.1016/j.virusres.2011.02.006.

Burwood-Taylor, "Brief: AgroSpheres raises $4m Series A with Ospraie, Wilbur Ellis, for 'Minicell' pesticide tech," AgFunder Network Partners (Aug. 28, 2019) https://agfundernews.com/agrospheres-raises-4m-series-a-with-ospraie-wilbur-ellis-forminicell-pesticide-tech: pp. 1-2.

Carleton et al., "Engineering the type III secretion system in non-replicating bacterial minicells for antigen delivery," Nature Communications, Mar. 2013, pp. 1-8.

Castano et al., "A novel family of TRF (DNA topoisomerase I-related function) genes required for proper nuclear segregation," Nucleic Acids Res. Jun. 15, 1996; 24(12): 2404-2410.

Choe et al., "Mechanisms and factors for edible oil oxidation," Comprehensive Reviews in Food Science and Food Safety, Sep. 2006, vol. 5, Issue 4, pp. 169-186, https://doi.org/10.1111/j.1541-4337.2006.00009.x.

Choquer et al., "A semi-quantitative RT-PCR method to readily compare expression levels into Botrytis cinerea multigenic families in vitro and in planta," Current Genetics, Jul. 2003, 43(4), pp. 303-309, 10.1007/s00294-003-0397-0.

Choquer et al., "Survey of the Botrytis cinerea chitin synthase multigenic family through the analysis of six euascomycetes genomes," European Journal of Biochemistry, Jun. 2004, 271(1), pp. 2153-2164.

Christen et al., "Rapid isolation of Escherichia coli minicells by glass-fiber filtration: study of plasmid-coded polypeptides," Gene, Aug. 1983, 23(2):195-198.

Cid et al., "Recognition of the helical structure of beta-1,4-galactan by a new family of carbohydrate-binding modules," The Journal of Biological Chemistry, Nov. 12, 2010, vol. 285, No. 46, pp. 35999-36009.

Colla et al., "Biostimulant Action of Protein Hydrolysates: Unraveling Their Effects on Plant Physiology and Microbiome," Frontiers in Plant Science, Dec. 2017, vol. 8, Article 2202, pp. 1-14.

Cooper, S., "The Escherichia coli cell cycle," Res Microbiol., Jan. 1990; 141(1):17-29.

Cork et al., "Control of yellow stem borer, Scirpophaga incertulas (Lepidoptera: Pyralidae) by mating disruption on rice in India: effect of unnatural pheromone blends and application time on efficacy," Bulletin of Entomological Research, (2009) 86(5):515-524.

Crowet et al., "Modeling of non-covalent complexes of the cell-penetrating peptide CADY and its siRNA cargo," Biochemica et Biophysica Acta, Feb. 2013, vol. 1828, No. 2; pp. 499-509.

Datta et al., "Enzyme immobilization: an overview on techniques and support materials," 3 Biotech, Feb. 2013; 3(1), pp. 1-9.

Dayan et al., "Natural products in crop protection," Bioorganic & Medicinal Chemistry, Jun. 15, 2009, 17(12), pp. 4022-4034.

Ebensen et al., "Bacterial ghosts are an efficient delivery system for DNA vaccines," The Journal of Immunology, Jun. 2004, 172(11), pp. 6858-6865.

Edwards et al., "Promiscuous targeting of Bacillus subtilis cell division protein DivIVA to division sites in Escherichia coli and fission yeast," EMBO Journal, Jun. 2000, 19(11):2719-2727.

Elish et al., "Biochemical analysis of spontaneous fepA mutants in escherichia coli," Journal of General Microbiology, May 1988, 134(5), pp. 1355-1364.

Extended European Search Report for Application No. 18791775.2, mailed Apr. 28, 2021, 10 pages.

Extended European Search Report for Application No. 18791868.5, mailed Dec. 7, 2020, 7 pages.

Extended European Search Report mailed on Jun. 14, 2021, in European Application No. 18859413.9, 10 pages.

Fan, F., et al., "Multiple Fungicide Resistance in Botrytis cinerea from Greenhouse Strawberries in Hubei Province, China," Plant Disease, Apr. 2017, 101(4), pp. 601-606.

Farley et al., "Minicells, Back in Fashion," Journal of Bacteriology, Mar. 3, 20161, vol. 198, No. 8, pp. 1186-1195.

Fernández-Ortuño, D., et al., "Independent Emergence of Resistance to Seven Chemical Classes of Fungicides in Botrytiz cinerea," Pathology, Apr. 2015, vol. 105, No. 4, pp. 424-432.

Filipovic-Grcic et al., "Mucoadhesive chitosan-coated liposomes: Characteristics and stability," Journal of Microencapsulation, Jan. 2001, 18(1), pp. 3-12, https://doi.org/10.1080/026520401750038557.

Fire, A., et al., "Potent and specific genetic interference by double-stranded RNA in Caenorhabditis elegans," Nature, vol. 391, Feb. 19, 1998, pp. 806-811.

Frazer et al., "Production, properties and utility of bacterial minicells," Curr. Topics Microbial. Immunol. (1975) 69: 1-84.

Gan, D., et al., "Bacterially expressed dsRNA protects maize against SCMV infection," Plant Cell Reports, Nov. 2010, 29, pp. 1261-1268.

(56) References Cited

OTHER PUBLICATIONS

Garcia-Sosa et al., "Peptide-Ligand Binding Modeling of siRNA with Cell-Penetrating Peptides," BioMed Research International, Jul. 24, 2014, vol. 2014, Article ID 257040, pp. 1-7.
Giacalone et al., "Immune responses elicited by bacterial minicells capable of simultaneous DNA and protein antigen delivery," Vaccine, Aug. 2006, 24(33-34), pp. 6009-6017.
Giacalone et al., "Immunization with non-replicating *E. coli* minicells delivering both protein antigen and DNA protects mice from lethal challenge with lymphocytic choriomeningitis virus," Vaccine, Mar. 2007, 25(12), pp. 2279-2287.
Giacalone et al., "The use of bacterial minicells to transfer plasmid DNA to eukaryotic cells," Cellular Microbiology, Oct. 2006, 8(10), pp. 1624-1633.
Giacalone et al., "Toxic protein expression in *Escherichia coli* using a rhamnose-based tightly regulated and tunable promoter system," Biotechniques, Mar. 2006, vol. 40, No. 3, pp. 355-364.
Gould et al., "The control of septum formation in fission yeast," Genes & Development, Nov. 15, 1997;11(22):2939-2951.
Ha et al., "The minicell generation in *Escherichia coli* harboring minD of Lactobacillus", J. Chemical and Pharmaceutical Research, 2016, 8(7):328-331.
Hajam et al., "Bacterial ghosts as adjuvants: mechanisms and potential," Veterinary Research, Dec. 2017, 48(1), pp. 1-13.
Hale et al., "Characterization of virulence plasmids and plasmid-associated outer membrane proteins in shigella flexneri, shigella sonnei, and *Escherichia coli*," Infection and Immunity, Apr. 1983, pp. 340-350.
Hallmann et al., "Bacterial endophytes in agricultural crops," Canadian Journal of Microbiology, Oct. 1997, vol. 43, No. 10, pp. 895-914.
Hayashi et al., "Structural and functional studies of MinD ATPase: implications for the molecular recognition of the bacterial cell division apparatus," EMBO Journal, Apr. 17, 2001;20(8):1819-1828.
Hou et al., "Effects of Origanum vulgare essential oil and its two main components, carvacrol and thymol, on the plant pathogen *Botrytis cinerea*," PeerJ., Aug. 14, 2020, 14:8:e9626, 25 pages.
Huang G., et al., "A Super Long-Acting and Anti-Photolysis Pesticide Release Platform Through Self-Assembled Natural Polymer-Based Polyelectrolyte," Reactive and Functional Polymers, Jan. 2020, vol. 146, No. 104429, pp. 1-8.
Huang J., et al., "Structural Investigation of a Self-Cross-Linked Chitosan/Alginate Dialdehyde Multilayered Film within Situ QCM-D and Spectroscopic Ellipsometry," ACS Omega, 2019, vol. 4(1), pp. 2019-2029.
International Preliminary Report on Patentability for Application No. PCT/US2020/066706, mailed Jul. 7, 2022, 10 pages.
International Search Report and Written Opinion for International Application No. PCT/US2021/054259 dated Feb. 18, 2022, 25 pages.
International Search Report and Written Opinion, mailed Apr. 15, 2022, for International Application No. PCT/US2021/062964, 16 pages.
International Search Report and Written Opinion mailed on Jan. 16, 2019, for International Application No. PCT/US2018/052690, 16 pages.
International Search Report and Written Opinion mailed on Jul. 10, 2018, for International Application No. PCT/US2018/030329, 18 pages.
International Search Report and Written Opinion mailed on Jul. 19, 2018, for International Application No. PCT/US2018/030328, 20 pages.
International Search Report and Written Opinion mailed on Mar. 28, 2022, for International Application No. PCT/US2021/065010, 9 pages.
International Search Report and Written Opinion mailed on Mar. 31, 2022, for International Application No. PCT/US2021/065009, 14 pages.
International Search Report dated Jul. 10, 2017, issued in PCT Application No. PCT/US2017/027048, 3 pages.
International Search Report, mailed Aug. 31, 2021, for International Application No. PCT/US2020/066706, 4 pages.
International Search Report, mailed Mar. 15, 2022, for International Application No. PCT/US2021/059571, 5 pages.
International Search Report, mailed Nov. 10, 2021, for International Application No. PCT/US2021/033208, 6 pages.
Islam et al., "Minicell-based fungal RNAi delivery for sustainable crop protection," Microbial Technology, vol. 14, Issue 4, Feb. 24, 2021, pp. 1847-1856.
Islam, M.T., et al., "RNAi-Based Biofungicides as a Promising Next-Generation Strategy for Controlling Devastating Gray Mold Diseases," International Journal of Molecular Sciences, vol. 21, Issue 6, Mar. 18, 2020, pp. 1-10.
Jacobs et al., "Bacterial cell division: a moveable feast," Proceedings of the National Academy of Sciences, May 25, 1999, 96(11), pp. 5891-5893.
Jarmander et al., "A dual tag system for facilitated detection of surface expressed proteins in *Escherichia coli*," Microbial Cell Factories, Sep. 3, 2012, 11:118, 10 pages.
Jeong et al., "Complete Genome Sequence of *Escherichia coli* Strain BL21", Genome Announcement, Mar. 2015, 3(2):e00134-15.
Jog et al., "Plant growth promoting potential and soil enzyme production of the most abundant *Streptomyces* spp. from wheat rhizosphere," Journal of Applied Microbiology, Nov. 2012, 113(5), 1154-1164.
Jose et al., "Autodisplay of enzymes—molecular basis and perspectives," Journal of Biotechnology, Oct. 15, 2012, 15;161(2), pp. 92-103.
Kanchiswamy et al., "Bioprospecting bacterial and fungal volatiles for sustainable agriculture," Trends in Plant Science, Apr. 1, 2015, 20(4), pp. 206-211.
Khachatourians et al., "Cell growth and division in *Escherichia coli*: a common genetic control involved in cell division and minicell formation," Journal of Bacteriology, Oct. 1973; 116(1):226-229.
Kiernan, "Ospraie Ag Science Leads Rounds Totaling $49M for Two Separate Crop Protection Startups," Global AgInvesting (Sep. 10, 2019) https://www.globalaginvesting.com/ospraie-ag-science-leads-rounds-totaling-49m-two-separate-crop-protection-startups/ : pp. 1-3. (A, used:2, 10,20).
Kirk et al., "Industrial enzyme applications," Current Opinion in Biotechnology, Aug. 1, 2002, 13(4), pp. 345-351.
Koch, "The bacterium's way for safe enlargement and division," Applied and Environmental Microbiology, Sep. 2000;66(9):3657-3663.
Konstantinou, S., et al. "Population Structure, Fungicide Resistance Profile, and sdhB Mutation Frequency of Botrytis cinerea from Strawberry and Greenhouse-Grown Tomato in Greece," Plant Disease, vol. 99, No. 2, Feb. 2015, pp. 240-248.
Kopecka et al., "A method of isolating anucleate yeast protoplasts unable to synthesize the glucan fibrillar component of the wall," Journal of General Microbiology, Mar. 1974, 8(1):111-120.
Kourti et al., "In Search of New Methodologies for Efficient Insect Pest Control: "The RNAi Movement"," Biological Control of Pest and Vector Insects, Apr. 5, 2017, InTech, ISBN: 978-953-51-3036-9 pp. 71-96, DOI: 10.5772/66633.
Labie et al., "Minicell-forming mutants of *Escherichia coli*: suppression of both DicB- and MinD-dependent division inhibition by inactivation of the minC gene product," Journal of Bacteriology, Oct. 1990;172(10):5852-5855.
Lasko et al., "On-Line Monitoring of Intracellular ATP Concentration in *Escherichia coli* Fermentations," Biotechnology and Bioengineering, Nov. 1996, vol. 52, pp. 364-372.
Lee at al., "Cell surface display of lipase in Pseudomonas putida KT2442 using OprF as an anchoring motif and its biocatalytic applications," Applied and Environmental Microbiology, Dec. 2005, 71(12):8581-8586.
Lee et al., "Ibd1p, a possible spindle pole body associated protein, regulates nuclear division and bud separation in *Saccharomyces cerevisiae*," Biochimica et Biophysics Acta (BBA)-Molecular Cell Research, Apr. 1, 1999, 1449(3), pp. 239-253.

(56) References Cited

OTHER PUBLICATIONS

Linder et al., "The roles and function of cellulose-binding domains," Journal of Biotechnology, Sep. 16, 1997, 57(1), pp. 15-28.
Macdiarmid et al., "Bacterially derived 400 nm particles for encapsulation and cancer cell targeting of chemotherapeutics," Cancer Cell, May 8, 2007, 11(5), pp. 431-445.
Macdiarmid et al., "Sequential treatment of drug-resistant tumors with targeted minicells containing siRNA or a cytotoxic drug," Nature Biotech, 2009, 27, pp. 643-651, 10.1038/nbt.1547.
Madhavi, V., et al., "A Scrupulous Overview on Controlled Release Fertilizers," Research Reviews: Journal of Agriculture and Alfred Sciences, Mar. 17, 2016, vol. 5, Issue 1, pp. 1-8.
Madrigal-Carballo et al., "Chitosomes loaded with cranberry proanthocyanidins attenuate the bacterial lipopolysaccharide induced expression of iNOS and COX-2 in Raw 264.7 macrophages," Journal of Liposome Research, Sep. 2009, 19(3), pp. 189-196, https://doi.org/10.1080/08982100902729436.
Madrigal-Carballo et al., "In vitro uptake of lysozyme-loaded liposomes coated with chitosan biopolymer as model immunoadjuvants," Journal of Liposome Research, Mar. 2010, 20(1), pp. 1-8, https://doi.org/10.3109/08982100903015009.
Malandrin et al., "Nucleoid structure and partition in Methanococcus jannaschii: an archaeon with multiple copies of the chromosome," Genetics, Aug. 1999, 152(4):1315-1323.
Manwaring et al., "Nucleoside Triphosphate Pools in Minicells of *Escherichia coli*," Journal of Bacteriology, May 1977, pp. 960-962.
Markiewicz et al., "Failure to trigger the autolytic enzymes in minicells of *Escherichia coli*," FEMS Microbiology Letters, Mar. 1992; 70(2):119-123.
Martin et al., "Clen, green, ethical (CGE) management: What research do we really need?," The International Journal of Tropical Veterinary and Biomedical Research, vol. 1, No. 1, May 2016, pp. 1-8.
Mathis et al., "ATP concentration in escherichia coli during oxygen toxicity," Biochimica et Biophysica Act, Sep. 1976, 440(3), pp. 723-732.
Maurer et al., "Autodisplay: One-Component System for Efficient Surface Display and Release of Soluble Recombinant Proteins from *Escherichia coli*," Journal of Bacteriology, Feb. 1997, vol. 179, No. 3, pp. 794-804.
Mayne, C.G., et al., "The cellular membrane as a mediator for small molecule interaction with membrane proteins," Biochimica et Biophysica Acta, May 6, 2016, vol. 1858, pp. 2290-2304.
McLoughlin, A.G., et al., "Developing new RNA interference technologies to control fungal pathogens," Canadian Journal of Plant Pathology, Jul. 2018, vol. 40, No. 3, pp. 325-335.
McLoughlin, A.G., et al., "Identification and application of exogenous dsRNA confers plant protection against Sclerotinia sclerotiorum and Botrytis cinerea," Scientific Reports, May 2018, 14 pages.
Mempin et al., "Release of extracellular ATP by bacteria during growth," BMC Microbiology, Dec. 2013, 13:301, 13 pages.
Mendelson et al., "Physiological Studies of Bacillus subtilis Minicells," Journal of Bacteriology, Mar. 1974, vol. 117, No. 3, pp. 1312-1319.
Mengoni et al., "A Chitosan-Based Liposome Formulation Enhances the In Vitro Wound Healing Efficacy of Substance p. Neuropeptide," Pharmaceutics, Dec. 2017, 9(4):56, pp. 1-17.
Mitra et al., "Right Place, Right Time: Focalization of Membrane Proteins in Gram-Positive Bacteria," Trends in Microbiology, Aug. 1, 2016, 24(8), pp. 611-621.
Mitter, N., et al., "Clay nanosheets for topical delivery of RNAi for sustained protection against plant viruses," Nature Plants 3, 16207, Jan. 2017, pp. 1-10.
Moriya et al., "A Bacillus subtilis gene-encoding protein homologous to eukaryotic SMC motor protein is necessary for chromosome partition," Molecular Microbiology, Jul. 1998; 29(1):179-187.
Mulder et al., "The *Escherichia coli* minB mutation resembles gyrB in defective nucleoid segregation and decreased negative supercoiling of plasmids," Molecular and General Genetics, Mar. 1990; 221(1):87-93.

Nakatani et al., "Cell surface protein engineering for high-performance whole-cell catalysts," Frontiers of Chemical Science and Engineering, Mar. 2017, 11(1), pp. 46-57.
Nerva, L., et al., "Doubled-Stranded RNAs (dsRNAs) as a Sustainable Tool against Gray Mold (*Botrytis cinerea*) in Grapevine: Effectiveness of Different Application Methods in an Open-Air Environment," Biomolecules, 10(2), Jan. 2020, pp. 1-14.
Nguyen et al., "Nanosized Minicells Generated by Lactic Acid Bacteria for Drug Delivery", Journal of Nanomaterials, vol. 2017, Article 6847297 (Sep. 7, 2017): pp. 1-11.
Nurussaman et al., "Nanoencapsulation, Nano-guard for Pesticides: A New Window for Safe Application," Journal of Agricultural and Food Chemistry, Feb. 24, 2016, 64(7), pp. 1447-1483.
Ota et al., "Display of Clostridium cellulovorans Xylose Isomerase on the Cell Surface of *Saccharomyces cerevisiae* and its Direct Application to Xylose Fermentation," Biotechnology Progress, vol. 29, No. 2, Mar. 1, 2013, pp. 346-351.
Parker et al., "High fructose corn syrup: Production, uses and public health concerns," Biotechnology and Molecular Biology Reviews, Sep. 30, 2010, vol. 5, No. 5, pp. 71-78.
Petrasch, S., et al., "Grey mould of strawberry, a devastating disease caused by the ubiquitous necrotrophic fungal pathogen Botrytis cinerea," Molecular Plant Pathology, Jun. 2019, 20(6), pp. 877-892.
Pichyangkura et al., "Biostimulant activity of chitosan in horticulture," Scientia Horticulturae, Nov. 30, 2015, 196, pp. 49-65.
Quarles, "Botanical pesticides from Chenopodium," IPM Practitioner, Birc special publications, Feb. 1992, 14(2):1-11.
Rahimzadeh et al., "Impact of heat shock step on bacterial transformation efficiency," Molecular Biology Research Communications, Dec. 2016, 5(4):257-261.
Rampley et al., "Development of SimCells as a novel chassis for functional biosensors," Scientific Reports, Aug. 2017, 7(1):7261, 10 pages.
Reeve et al., "Pronase digestion of amino-acid binding components on the surface of Bacillus subtilis cells and minicells," Biochemical and Biophysical Research Communications, Aug. 1973; 53(4):1325-1330.
Reeve, J.N., et al., "Minicells of Bacillus subtilis," Journal of Bacteriology, vol. 114, No. 2, May 1973, pp. 860-873.
Rothfield et al., "Bacterial cell division," Annual Review Genetics, Dec. 1999, 33(1):423-448.
Rupp, S., et al., "Spread of Botrytis cinerea Strains with Multiple Fungicide Resistance in German Horticulture," Frontiers in Microbiology, Jan. 2017, vol. 7, Article 2075, pp. 1-12.
Ryu et al., "Bacterial Volatiles Induce Systemic Resistance in *Arabidopsis*," Plant Physiology, 2004, 134(3), 1017-1026.
Ryu et al., "Bacterial volatiles promote growth in *Arabidopsis*," Proceedings of the National Academy of Sciences, Apr. 2003, 100(8), pp. 4927-4932.
Sagrero-Nieves et al., "Volatile Constituents from the Leaves of *Chenopodium ambrosioides* L.," Journal of Essential Oil Research, Nov. 28, 2011, 7, 221-223.
Sathya et al., "Plant growth-promoting actinobacteria: a new strategy for enhancing sustainable production and protection of grain legumes," 3 Biotech, May 30, 2017,7(2), pp. 1-10.
Sauerbrei et al., "Lon Protease Removes Excess Signal Recognition Particle Protein in *Escherichia coli*," Journal of Bacteriology, Jun. 25, 2020, 202(14), e00161-20, 15 pages.
Schneider et al., "Relationship between Growth Rate and ATP Concentration in *Escherichia coli*," The Journal of Biological Chemistry, Feb. 27, 2004, vol. 279, No. 9, pp. 8262-8268.
Schüürmann et al., "Bacterial whole-cell biocatalysts by surface display of enzymes: toward industrial application," Application Microbiology and Biotechnology, Oct. 2014, 98(19), pp. 8031-8046.
Shi et al., "Herbicidal Secondary Metabolites from Actinomycetes: Structure Diversity, Modes of Action, and Their Roles in the Development of Herbicides," Journal of Agricultural and Food Chemistry, (2020), 68: 17-32.
Shoseyov et al., "Carbohydrate binding modules: biochemical properties and novel applications," Microbiology and Molecular Biology Reviews, Jun. 2006, 70(2), pp. 283-295.

(56) References Cited

OTHER PUBLICATIONS

Singh et al., "Microbial degradation of organophosphorus compounds", FEMS Microbiology Reviews, Apr. 2006, pp. 428-471.

Soini et al., "Transient increase of ATP as a response to temperature up-shift in *Escherichia coli*," Microbial Cell Factories, Apr. 2005, 4:9 doi: 10.1186/1475-2859-4-9, 8 pages.

Soulie et al., "Botrytis cinerea virulence is drastically reduced after disruption of chitin synthase class III gene (Bcchs3a)," Cellular Microbiology, Aug. 2006, 8(8), pp. 1310-1321.

Souza et al., "Plant growth-promoting bacteria as inoculants in agricultural soils," Genetics and Molecular Biology, Nov. 2015, 38(4), pp. 401-419.

St. Leger et al., "New perspectives on insect pathogens," Fungal Biology Reviews, Apr. 2011, 25(2), pp. 84-88.

Stemmer, W.P., "Rapid evolution of a protein in vitro by DNA shuffling." Nature (Aug. 4, 1994); 370(6488): 389-391.

Stevanovic et al., "Essential oils as feed additives—future perspectives," Molecules, Jul. 2018, 23, 1717, pp. 1-20.

Sun et al., "BrkAutoDisplay: functional display of multiple exogenous proteins on the surface of *Escherichia coli* by using BrkA autotransporter," Microbial Cell Factories, Sep. 2015, 14:129, 13 pages.

Supplemental European Search Report mailed on Jan. 25, 2021, for European Application No. 18791775.2, 15 pages.

Takiff et al., "Genetic analysis of the rnc Operon of *Escherichia coli*," Journal of Bacteriology, May 1989, pp. 2581-2590.

Tankersley et al., "Induction and isolation of a minicell-producing strain of *Salmonella typhimurium*," Proceedings of the Society for Experimental Biology and Medicine, Mar. 1974; 145(3):802-805.

Thomassin, J.L. et al., "OmpT Outer Membrane Proteases of Enterohemorrhagic and Enteropathogenic *Escherichia coli* Contribute Differently to the Degradation of Human LL-37", Infection and Immunity, Feb. 2012, 80(2):483-492.

Tsuji et al., "An Efficient Thermoinducible Bacterial Suicide System—Elimination of Viable Parental Bacteria from Minicells," BioProcess International, Apr. 2010, vol. 8, No. 4, pp. 28-40.

Turek et al., "Stability of Essential Oils: A Review," Comprehensive Reviews in Food Science and Food Safety, Jan. 2013, 12(1), pp. 40-53, https://doi.org/10.1111/1541-4337.12006.

Ulmanen et al., "Transcription and Translation of Foreign Genes in Bacillus subtilis by the Aid of a Secretion Vector," Journal of Bacteriology, Apr. 30, 1985, vol. 162, No. 1, pp. 176-182.

Ultee et al., "The Phenolic Hydroxyl Group of Carvacrol Is Essential for Action against the Food-Borne Pathogen Bacillus cereus," Applied and Environmental Microbiology, Apirl 2002; 68(4):1561-1568.

Varley et al., "The divIVB region of the Bacillus subtilis chromosome encodes homologs of *Escherichia coli* septum placement (minCD) and cell shape (mreBCD) determinants," Journal of Bacteriology, Nov. 1, 1992, vol. 174, pp. 6729-6742.

Wang et al., "Cross-kingdom RNA trafficking and environmental RNAi for powerful innovative pre-and-post-harvest plant protection," Current Opinion in Plant Biology, Aug. 2017, 38, pp. 133-141.

Wang et al., "Foliar uptake of pesticides—Present status and future challenge," Pesticide Biochemistry and Physiology, Jan. 2007; 87(1):1-8.

Wang, M., et al., "Bidirectional cross-kingdom RNAi and fungal uptake of external RNAs confer plant protection," Nature Plants, Sep. 2016, 2(10), pp. 1-19.

Weiberg, A., et al., "Fungal Small RNAs Suppress Plant Immunity by Hijacking Host RNA Interference Pathways," Science, Oct. 2013, 342(6154):118-123, 11 pages.

Witzgall et al., "Sex Pheromones and Their Impact on Pest Management," Journal of Chemical Ecology, Jan. 2010, 36(1), pp. 80-100.

Written Opinion Aug. 31, 2021, issued in PCT Application No. PCT/US2020/066706, 8 pages.

Written Opinion Jul. 10, 2017, issued in PCT Application No. PCT/US2017/027048, 7 pages.

Written Opinion Nov. 10, 2021, issued in PCT Application No. PCT/US2021/033208, 9 pages.

Xiong,F., et al., "Host-induced gene silencing of BcTOR in Botrytis cinerea enhances plant resistance to grey mould," Molecular Plant Pathology, Dec. 2019, 20(2), pp. 1722-1739.

Yaginuma et al., "Diversity in ATP concentrations in a single bacterial cell population revealed by quantitative single-cell imaging," Scientific Reports, Oct. 6, 2014, 4:6522, 7 pages.

Yamamoto et al., "Localization of the Vegetative Cell Wall Hydrolases LytC, LytE, and LytF on the Bacillus subtilis Cell Surface and Stability of These Enzymes to Cell Wall-Bound or Extracellular Proteases," Journal of Bacteriology, Nov. 30, 2003, vol. 185, No. 22, pp. 6666-6677.

Yang et al., "Comparison of Autotransporter and Ice Nucleation Protein as Carrier Proteins for Antibody Display on The Cell Surface of *Escherichia coli*," Progress in Biochemistry and Biophysics, 2013, 40(12), pp. 1209-1219.

Yoo et al., "Fission yeast hrp1, a chromodomain ATPase, is required for proper chromosome segregation and its overexpression interferes with chromatin condensation," Nucleic Acids Research, May 1, 2000;28(9):2004-2011.

Yu et al., "Deletion of the min operon results in increased thermosensitivity of an ftsZ84 mutant and abnormal FtsZ ring assembly, placement, and disassembly," Journal of Bacteriology, Nov. 2000;182(21):6203-6213.

Zeigler D.R. "New! Protease-free Bacillus subtilis host," Bacillus Genetic Stock Center News, Jun. 30, 2016, pp. 1-3, Retrieved from the Internet:< http:www.bgsc.org/new.php?page=2 on Jul. 4, 2018.< / http:>.

Zeigler et al., "Bacillus Genetic Stock Center Catalog of Strains," Seventh Edition 1: Bacillus subtilis 168, Retrieved online from URL:https://bgsc.org/_catalogs/Catpart1.pdf (2000), 72 pages.

Zhang et al., "*E. coli* Nissle 1917-Derived Minicells for Targeted Delivery of Chemotherapeutic Drug to Hypoxic Regions for Cancer Therapy," Theranostics, Feb. 2018, vol. 8 Issue 6, pp. 1690-1705.

Zhang et al., "Surface Immobilization of Human Arginase-1 with an Engineered Ice Nucleation Protein Display System in *E. coli*," PLoS One, Aug. 1, 2016, 11(8), 13 pages.

Restriction Requirement for U.S. Appl. No. 18/396,296 mailed Mar. 21, 2024, 9 pages.

Non-Final Office Action for U.S. Appl. No. 18/396,296 mailed Jun. 20, 2024, 7 pages.

Office Action and Search Report for Chinese Application No. CN201880068836.1 dated Apr. 22, 2024, 19 pages.

Office Action for Australia Application No. AU2018335571 dated May 24, 2024, 4 pages.

Office Action for Brazil Application No. BR20201105803 mailed Jun. 4, 2024, 6 pages.

Tsiji, S., et al., "Preclinical evaluation of VAX-IP, a novel bacterial minicell-based biopharmaceutical for nonmuscle invasive bladder cancer," Molecular Therapy-Oncolytics, Jan. 2016, vol. 3, 16004, 39 pages.

SEQUENCE LISTING

```
Sequence total quantity: 45
SEQ ID NO: 1            moltype = DNA  length = 50
FEATURE                 Location/Qualifiers
source                  1..50
                        mol_type = genomic DNA
                        organism = Escherichia coli
SEQUENCE: 1
cgaagtaaca acaataatgc gtgccataga aattccttgt taaaaaggga            50

SEQ ID NO: 2            moltype = DNA  length = 50
FEATURE                 Location/Qualifiers
source                  1..50
                        mol_type = genomic DNA
                        organism = Escherichia coli
SEQUENCE: 2
cctggcctta ctcaattagc tattaatcat cgccagcgcg cgatgatgtt            50

SEQ ID NO: 3            moltype = DNA  length = 50
FEATURE                 Location/Qualifiers
source                  1..50
                        mol_type = genomic DNA
                        organism = Escherichia coli
SEQUENCE: 3
ttggctgtgt ttttcttccg cgagagaaag aaatcgagta atgccataac            50

SEQ ID NO: 4            moltype = DNA  length = 50
FEATURE                 Location/Qualifiers
source                  1..50
                        mol_type = genomic DNA
                        organism = Escherichia coli
SEQUENCE: 4
agaaattcct tgttaaaaag ggatcaattt aacggttgaa cggtcaaagc            50

SEQ ID NO: 5            moltype = DNA  length = 1773
FEATURE                 Location/Qualifiers
misc_feature            1..1773
                        note = AIDA-1 annotated
source                  1..1773
                        mol_type = other DNA
                        organism = synthetic construct
SEQUENCE: 5
```

```
atgaataagg cctacagtat catttggagc cactccagac aggcctggat tgtggcctca    60
gagttagcca gaggacatgg ttttgtcctt gcaaaaaata cactgctggt attggcggtt   120
gtttccacaa tcggaaatgc atttgcagtc gaccaccatc accatcacca tctggaagcg   180
ctgttccagg gtccgggtac ccagaaacag cgtaccgagc tcgaaaacct gtacttccag   240
ggtgaacaga aactgattag cgaagaagat ctgtctgaga tgaataacaa tggaagcatt   300
gtcattaata acagcattat aaacgggaat attacgaatg atgctgactt aagttttggt   360
acagcaaagc tgctctctgc tacagtgaat ggtagtcttg ttaataacaa aaatatcatt   420
cttaatccta caaaagaaag tgcggccgct ataggtaata ctcttaccgt gtcaaattat   480
actgggacac cggaagtgt tatttctctt ggtggtgtgc ttgaaggaga taattcactt   540
acggaccgtc tggtggtgaa aggtaatacc tctggtcaaa gtgacatcgt ttatgtcaat   600
gaagatggca gtggtggtca gacgagagat ggtattaata ttatttctgt agagggaaat   660
tctgatgcag aattctctct gaagaaccgc gtagttgccg gagcttatga ttacacactg   720
cagaaaggaa acgagagtgg gacagataat aagggatggt atttaaccag tcatcttccc   780
acatctgata cccggcaata cagaccggag aacggaagtt atgctaccaa tatggcactg   840
gctaactcac tgttcctcat ggatttgaat gagcgtaagc aattcagggc catgagtgat   900
aatacacagc ctgagtctgc atccgtgtgg atgaagatca ctggaggaat aagctctggt   960
aagctgaatg acgggcaaaa taaaacaaca accaatcagt ttatcaatca gctcgggggg  1020
gatatttata aattccatgc tgaacaactg ggtgatttta ccttagggat tatgggagga  1080
tacgcgaatg caaaaggtaa aacgataaat tacacgagca acaaagctgc cagaaacaca  1140
ctggatggtt attctgtcgg ggtatacggt acgtggtatc agaatgggga aaatgcaaca  1200
gggctctttg ctgaaacttg gatgcaatat aactggttta tgcatcagt gaaaggtgac  1260
ggactggaag aagaaaaata taatctgaat tgtttaaccg cttctgcagg tgggggatat  1320
aacctgaatg tgcacacatg gacatccacct gaaggaataa caggtgaatt ctggttacag  1380
cctcatttgc aggctgtctg gatggggtt acaccggata cacatcagga ggataacgga  1440
acggtggtgc agggagcagg gaaaaataat attcagacaa aagcaggtat tcgtgcatcc  1500
tggaaggtga aaagcaccct ggataaggat accgggcgga ggttccgtcc gtatatagag  1560
gcaaactgga tccataacac tcatgaattt ggtgttaaaa tgagtgatga cagccagttg  1620
ttgtcaggta gccgaaatca gggagagata aagacaggta ttgaaggggt gattactcaa  1680
aacttgtcag tgaatggcgg agtcgcatat caggcaggag gtcacgggag caatgccatc  1740
tccggagcac tggggataaa atacagcttc tga                               1773

SEQ ID NO: 6           moltype = DNA   length = 3033
FEATURE                Location/Qualifiers
misc_feature           1..3033
                       note = BrkAutoTransporter_Annotated
source                 1..3033
                       mol_type = other DNA
                       organism = synthetic construct
SEQUENCE: 6
atgtatctgg atcgctttcg ccagtgcccg agcagcctgc agattccgcg cagcgcgtgg    60
cgcctgcatg cgctggcggc ggcgctggcg ctggcgggca tggcgcgcct ggcgccggcg   120
gcggcgcagg cgccgcagcc gccggtggcg ggcgcgccgc atgcgcagga tgcgggccag   180
gaaggcgaat ttgatcatcg cgataacacc ctgattgcgg tgtttgatga tggcgtgggc   240
attaacctgg atgatgatcc ggatgaactg ggcgaaaccg cgccgccgac cctgaaagat   300
attcatatta gcgtggaaca taaaaacccg atgagcaaac cggcgattgg cgtgcgcgtg   360
agcggcgcg gccgcgcgct gaccctggcg ggcagccacca ttgatgcgac cgaaggcggc   420
attccggcgg tggtgcgccg cggcggcacc ctggaactgg atggcgtgac cgtggcgggc   480
ggcgaaggca tggaaccgat gaccgtgagc gatgcgggca gccgcctgag cgtgcgcggc   540
ggcgtgctgg cggcgaagc gccgggcgtg gcctggtgc gcggcgca gggcggccag   600
gcgagcatta ttgatgcgac cctgcagagc attctgggcc cggcgctgat tgcggatggc   660
ggcagcatta gcgtggcggg cggcagcatt gatatggata tgggcccggc cttttccgcg   720
ccgccgccgc cgctgccggg cgcgccgctg gcgcgcatc gccgctgga tcgcgtggcg   780
gcggtgcatg cgggccagga tgcaaagtg accctgcgcg aagtggccgct gcgcgcgcat   840
ggcccgcagg cgaccggcgt gtatgcgtat atgccgggca gcgaaattac cctgcagggc   900
ggcaccgtga gcgtgcaggg cgatgatggc gggcgggtg tggcgggcgc gggccttgctg   960
gatgcgctgc cgccgggcgg caccgtgcgc ctggatggca ccaccgtgag caccgatggc  1020
gcgaacaccg atgcggtgct ggtgcgcggc gatgcggcgc gcgggaagt ggtgaacacc  1080
gtgctgcgca ccgcgaaaag cctggcgcgc ggcgtgagcg cgcagcatgg cggccgcgtg  1140
accctgcgcc agacccgcat tgaaaccgcg ggcgcgggcg cggaaggcat tagcgtgctg  1200
ggctttgaac cgcagagcgg cagcggcccg gcgagcgtgg atatgcaggg cgcagcatt  1260
accaccaccg gcaaccgcgc ggcgggcatt gcgctgaccc atggcagcgc gcgcctggaa  1320
ggcgtggcgg tgcgcgcgga aggcagcggc agcagcgcgg cgcagctggc gaacggcacc  1380
ctggtggtga gcgcgggcag cctggcgagc gcgcagagcg gcgcgattag cgtgaccgat  1440
accccgctga aactgatgcc gggcgcgctg gcgagccgca ccgtgaccgc cgtgaccgcc  1500
gatggcgcga ccgcgcaggg cggcaacggc gtgtttctgc agcagcatag caccattccg  1560
gtggcggtgg cgctggaaag cggcgcgctg gcgcgcggca atattgtggc ggatgcgaac  1620
aaaccgctga tgcgggcat agcctgagc gtggcgagcg cgcggcgtg gcatggcgcg  1680
acccaggtgc tgcagagcgc gaccctgggc aaagcggca cctggtggt gaacgcggat  1740
agccgcgtga aggatatgag catgcgcggc ggccgcgtg aatttcaggc gccggcgcg  1800
gaagcgagct ataaaaccct gaccctgcag accctggatg caacggcgt gtttgtgctg  1860
aacaccaacg tggcggcggg ccagaacgat cagctgcgcg tgaccggccg cgcggatggc  1920
cagcatcgcg tgctggtgcg caacgcgggc ggcgaagcgg atagccgcgg cgcgcgcctg  1980
ggcctggtgc atacccaggg ccagggcaac gcgaccttc gcctgcgaa cgtgggcaaa  2040
gcggtgagtc tgggcacctg gcgctatagc ctggcggaag atccgaaaac ccatgtggtg  2100
agcctgcagc gcgcgggcca ggcgctgagc ggcgcggaa acgcgcggt gaacgcggcg  2160
gatctgagca gcattgcgct ggcggaaagc aacgcgctgg ataaacgcct gggcgaactg  2220
cgcctgcgcg cggatgcggg cggccgtg gcgcgcacct ttagcgaacg ccagcagatt  2280
agcaaccgcc atgcgcgcgc gtatgatcag accgtgagcg gcctggaaat tggcctggat  2340
cgcggctgga gcgcgagcgg cggccgctgg tatgcgggcg gcctgctggg ctataccttat  2400
```

```
gcggatcgca cctatccggg cgatggcggc ggcaaagtga aaggcctgca tgtgggcggc  2460
tatgcggcgt atgtgggcga tggcggctat tatctggata ccgtgctgcg cctgggccgc  2520
tatgatcagc agtataacat tgcgggcacc gatggcggcc gcgtgaccgc ggattatcgc  2580
accagcggcc cggcgtggag cctggaaggc ggccgccgct tgaactgcc gaacgattgg   2640
tttgcggaac cgcaggcgga agtgatgctg tggcgcacca gcggcaaacg ctatcgcgcg  2700
agcaacggcc tgcgcgtgaa agtggatgcg aacaccgcga ccctgggccg cctgggcctg  2760
cgctttggcc gccgcattgc gctggcgggc ggcaacattg tgcagccgta tgcgcgcctg  2820
ggctggaccc aggaatttaa aagcaccggc gatgtgcgca ccaacggcat tggccatgcg  2880
ggcgcgggcc gccatggccg cgtggaactg ggcgcgggcg tggatgcggc gctgggcaaa  2940
ggccataacc tgtatgcgag ctatgaatat gcggcgggcg atcgcattaa cattccgtgg  3000
agctttcatg cgggctatcg ctatagcttt tga                               3033

SEQ ID NO: 7              moltype = DNA  length = 2343
FEATURE                   Location/Qualifiers
misc_feature              1..2343
                          note = BrkAutoTransporter_CBM
source                    1..2343
                          mol_type = other DNA
                          organism = synthetic construct
SEQUENCE: 7
atgtatctgg atcgctttcg ccagtgcccg agcagcctgc agattccgcg cagcgcgtgg  60
cgcctgcatg cgctggcggc ggcgctggcg ctggcgcgcc tgtggcgcgc ctgggccgc   120
gcggcgcagg cgccgcagcc gccggtggcg ggcgcgccgc atgcgcagga tgcgggccac  180
catcaccatc accatgttca gctggttgaa agcggtggtg cactggttca gcctggtggt  240
agcctgcgtc tgagctgtgc agcaagcggt tttccggtta tcgttatag catgcgttgg   300
tatcgtcagg caccgggtaa agaacgtgaa tgggttgac gtatgagcag tgccggtgat   360
cgtagcagct acgaagatag cgttaaaggt cgttttacca tcagccgtga tgatgcacgt  420
aataccgttt atctgcaaat gaatagcctg aaaccggaag ataccgcagt gtattattgc  480
aacgttaacg tgggctttga atattggggt cagggcaccc aggttaccgt tagcagcaaa  540
ctcgagcggc cgcatcgtga cgcgtcgtct ggtcctgccg gctgccaagt cctttggggc  600
gtgaatcagt ggaacacagg tttcacggcg aatgttaccg tcaagaatac gtcctccgct  660
cctgttgacg gctggacctt gaccttcagt ttcccatcag gacaacaagt cactcaagcc  720
tggtcatcta ccgtgaccca gagtggatct cggtcacag tacgtaacgc tccgtggaac  780
ggtcgattc ccgcgggcgg gactgctcag ttcgggttta acggaagcca cactggcact   840
aatgctgcac caactgcctt ctcacttaac ggcacgccgt gcaccgtagg cgaacagaaa  900
ctgattagcg aagaagatct ggaaaacctg tacttccagg gtgcgggcat tagcctgagc  960
gtggcgagcg cgcggcgtg gcatggcgcg cccaggtgc tgcagagcgc gaccctgggc   1020
aaaggcggca cctgggtggt gaacgcggat agccgcgtgc aggatatgag catgcgcggc  1080
ggccgcgtgg aatttcaggc gccggcgccg gaagcgagct ataaaaccct gaccctgcag  1140
accctggatg gcaacggcgt gtttgtgctg aacaccaacg tggcggcggg ccagaacgat  1200
cagctgcgcg tgaccggccg cgcggatggc cagcatcgcg tgctggtgcg caacgcgggc  1260
ggcgaagcgg atagccgcgg cgcgcgcctg ggcctggtgc ataccagg ccagggcaac    1320
gcgacctttc gcctggcgaa cgtgggcaaa gcgttggatc tgggcacctg gcgctatagc  1380
ctggcgaaag atccgaaaac ccatgtgtgg agcctgcagc gcgcgggcca ggcgctgagc  1440
ggcgcggcga acgcggcgt gaacgcgcg gatctgagca gcattgcgct ggcggaaagc   1500
aacgcgctgc ataaacgcct gggcgaactg cgcctgcgcg cggatgcggg cggcccgtgg  1560
gcgcgcacct ttagcgaacg ccagcagatt agcaaccgcc atcgcgcgc gtatgatcag   1620
accgtgagcg gcctgaaat tggcctggat cgcggctgga gcgcgagcgg cggccgctgg  1680
tatgcgggcg gcctgctggg ctataccat gcggatcgca cctatccggg cgatggcggc   1740
ggcaaagtga aaggcctgca tgtgggcggc tatgcggcgt atgtgggcga tggcggctat  1800
tatctggata ccgtgctgcg cctgggccgc tatgatcagc agtataacat tgcgggcacc  1860
gatggcggcc gcgtgaccgc ggattatcgc accagcggcg cggcgtggag cctggaaggc  1920
ggccgccgct tgaactgcc gaacgattgg tttgcggaac cgcaggcgga agtgatgctg   1980
tggcgcacca gcggcaaacg ctatcgcgcg agcaacggcc tgcgcgtgaa agtggatgcg  2040
aacaccgcga ccctgggccg cctgggcctg cgctttggcc gccgcattgc gctggcgggc  2100
ggcaacattg tgcagccgta tgcgcgcctg ggctggaccc aggaatttaa aagcaccggc  2160
gatgtgcgca ccaacggcat tggccatgcg ggcgcgggcc gccatggccg cgtggaactg  2220
ggcgcgggcg tggatgcggc gctgggcaaa ggccataacc tgtatgcgag ctatgaatat  2280
gcggcgggcg atcgcattaa cattccgtgg agctttcatg cgggctatcg ctatagcttt  2340
tga                                                                2343

SEQ ID NO: 8              moltype = DNA  length = 330
FEATURE                   Location/Qualifiers
misc_feature              1..330
                          note = CBM
source                    1..330
                          mol_type = other DNA
                          organism = synthetic construct
SEQUENCE: 8
gcgtcgtctg gtcctgccgg ctgccaagtc ctttggggcg tgaatcagtg gaacacaggt  60
ttcacggcga atgttaccgt caagaatacg tcctccgctc tgttgacgg ctggaccttg   120
accttcagtt tcccatcagg acaacaagtc actcaagcct ggtcatctac cgtgacccag  180
agtggatctc ggtcacagt acgtaacgct ccgtggaacg gttcgattcc cgcgggcggg   240
actgctcagt tcgggtttaa cggaagccac actggcacta tgctgcacc aactgccttc   300
tcacttaacg gcacgccgtg caccgtaggc                                   330

SEQ ID NO: 9              moltype = DNA  length = 696
FEATURE                   Location/Qualifiers
misc_feature              1..696
```

```
                        note = GFP-Nanobody CBM
source                  1..696
                        mol_type = other DNA
                        organism = synthetic construct
SEQUENCE: 9
gttcagctgg ttgaaagcgg tggtgcactg gttcagcctg gtggtagcct gcgtctgagc    60
tgtgcagcaa gcggttttcc ggttaatcgt tatagcatgc gttggtatcg tcaggcaccg   120
ggtaaagaac gtgaatgggt tgcaggtatg agcagtgccg gtgatcgtag cagctacgaa   180
gatagcgtta aaggtcgttt taccatcagc cgtgatgatg cacgtaatac cgtttatctg   240
caaatgaata gcctgaaacc ggaagatacc gcagtgtatt attgcaacgt taacgtgggc   300
tttgaatatt ggggtcaggg cacccaggtt accgttagca gcaaactcga gcggccgcat   360
cgtgacgcgt cgtctggtcc tgccggctgc caagtccttt ggggcgtgaa tcagtggaac   420
acaggtttca cggcgaatgt taccgtcaag aatacgtcct ccgctcctgt tgacggctgg   480
accttgacct tcagtttccc atcaggacaa caagtcactc aagcctggtc atctaccgtg   540
acccagagtg gatctgcggt cacagtacgt aacgctccgt ggaacggttc gattcccgcg   600
ggcgggactg ctcagttcgg gtttaacgga agccacactg gcactaatgc tgcaccaact   660
gccttctcac ttaacggcac gccgtgcacc gtaggc                             696

SEQ ID NO: 10           moltype = DNA  length = 537
FEATURE                 Location/Qualifiers
misc_feature            1..537
                        note = InaK
source                  1..537
                        mol_type = other DNA
                        organism = synthetic construct
SEQUENCE: 10
atggtcttag acaaggcgct agttctacgt acctgcgcta ataatatggc cgatcactgc    60
ggcttgattt ggcctgcctc agggaccgtc gagtcaaggt attggcaatc tacacgtcgt   120
cacgagaacg gactggtagg tcttctttgg ggagcaggaa cttctgcttt cttgtcagtc   180
catgcagacg cccgctggat cgtgtgcgaa gtggctgttg ccgatattat ctccctagag   240
gagcccggaa tggttaaatt tcctcgggcc gaagtggtgc atgtgggcga tcgaatcagc   300
gcttctcatt ttatttcggc gcggcaggca gatcccgcga gtacgagtac ttcaacgtcg   360
acaagtactc ttactcccat gcccacggca atccccaccc ctatgccagc ggtggcgtca   420
gtgacgttac cggtggctga gcaagcgcgg catgaggtgt tgatgtagc tagtgtgagc    480
gccgcggctg ctcccgtgaa cactttacct gtcacgacac cccaaaacct ccagacg      537

SEQ ID NO: 11           moltype = DNA  length = 1305
FEATURE                 Location/Qualifiers
misc_feature            1..1305
                        note = InaK-TEV-CBM-His-Myc-GFPNB
source                  1..1305
                        mol_type = other DNA
                        organism = synthetic construct
SEQUENCE: 11
atggtcttag acaaggcgct agttctacgt acctgcgcta ataatatggc cgatcactgc    60
ggcttgattt ggcctgcctc agggaccgtc gagtcaaggt attggcaatc tacacgtcgt   120
cacgagaacg gactggtagg tcttctttgg ggagcaggaa cttctgcttt cttgtcagtc   180
catgcagacg cccgctggat cgtgtgcgaa gtggctgttg ccgatattat ctccctagag   240
gagcccggaa tggttaaatt tcctcgggcc gaagtggtgc atgtgggcga tcgaatcagc   300
gcttctcatt ttatttcggc gcggcaggca gatcccgcga gtacgagtac ttcaacgtcg   360
acaagtactc ttactcccat gcccacggca atccccaccc ctatgccagc ggtggcgtca   420
gtgacgttac cggtggctga gcaagcgcgg catgaggtgt tgatgtagc tagtgtgagc    480
gccgcggctg ctcccgtgaa cactttacct gtcacgacac cccaaaacct ccagacggaa   540
aacctgtact ccagggtgc gtcgtctggt cctgccggct gccaagtcct tggggcgtg    600
aatcagtgga acacaggttt cacggcgaat gttaccgtca agaatacgtc ctccgctcct   660
gttgacggct ggaccttgac cttcagtttc ccatcaggac aacaagtcac tcaagcctgg   720
tcatctaccg tgacccagag tggatctgcg gtcacagtac gtaacgctcc gtggaacggt   780
tcgattcccg cggcgggac tgctcagttc gggtttaacg gaagccacac tggcactaat    840
gctgcaccaa ctgccttctc acttaacggc acgccgtgca ccgtaggcca ccatcaccat   900
caccatgttc agctggtga aagcggtggt gcactgttc agcctggtgg tagcctgcgt   960
ctgagctgtg cagcaagcgg ttttccggtt aatcgttata gcatgcgttg gtatcgtcag  1020
gcaccgggta agaacgtga atgggttgca ggtatgagca gtgccggtga tcgtagcagc  1080
tacgaagata gcgttaaagg tcgttttacc atcagccgtg atgatgcacg taataccgtt  1140
tatctgcaaa tgaatagcct gaaaccggaa gataccgcag tgtattattg caacgttaac  1200
gtgggctttg aatattgggg tcagggcacc caggttaccg ttagcagcaa actcgagcgg  1260
ccgcatcgtg acgaacagaa actgattagc gaagaagatc tgtga                  1305

SEQ ID NO: 12           moltype = DNA  length = 5561
FEATURE                 Location/Qualifiers
misc_feature            1..5561
                        note = pAIDA-1
source                  1..5561
                        mol_type = other DNA
                        organism = synthetic construct
SEQUENCE: 12
tttacacttt atgcttccgg ctcgtataat gtgtggaatt gtgagcggat aacaatttca    60
cacaggaaag cttcatatga ataaggccta cagtatcatt tggagccact ccagacaggc   120
ctggattgtg gcctcagagt tagccagagg acatggtttt gtccttgcaa aaaatacact   180
gctggtattg gcggttgttt ccacaatcgg aaatgcattt gcagtcgacc accatcacca   240
```

```
tcaccatctg gaagcgctgt tccagggtcc gggtacccag aaacagcgta ccgagctcga   300
aaacctgtac ttccagggtg aacagaaact gattagcgaa gaagatctgt ctagagtgaa   360
taacaatgga agcattgtca ttaataacag cattataaac gggaatatta cgaatgatgc   420
tgacttaagt tttggtacag caaagctgct ctctgctaca gtgaatggta gtcttgttaa   480
taacaaaaat atcattctta atcctacaaa agaaagtgcg gccgctatag gtaatactct   540
taccgtgtca aatttatactg ggacaccggg aagtgttatt tctcttggtg gtgtgctga   600
aggagataat tcacttacgg accgtctggt ggtgaaaggt aatacctctg tcaaagtga   660
catcgtttat gtcaatgaag atggcagtgg tggtcagacg agagatggta ttaatattat   720
ttctgtagag ggaaattctg atgcagaatt ctctctgaag aaccgcgtag ttgccggagc   780
ttatgattac acactgcaga aaggaaacga gagtgggaca gataataagg gatggtattt   840
aaccagtcat cttcccacat ctgatacccg gcaatacaga ccggagaacg gaagttatgc   900
taccaatatg gcactggcta actcactgtt cctcatggat ttgaatgagc gtaagcaatt   960
cagggccatg agtgataata cacagcctga gtctgcatcc gtgtgatga agatcactgg  1020
aggaataagc tctggtaagc tgaatgacgg gcaaaataaa acaaccaaca atcagtttat  1080
caatcagctc ggggggggata tttataaatt ccatgctgca caactgggtg attttacctt  1140
agggattatg gaggatacg cgaatgcaaa aggtaaaacg ataaattaca cgagcaacaa  1200
agctgccaga aacacactgg atggttattc tgtcggggta tacggtacgt ggtatcagaa  1260
tggggaaaat gcaacagggc tcttttgctga aacttggatg caatataact ggtttaatgc  1320
atcagtgaaa ggtgacggac tggaagaaga aaaatataat ctgaatggtt taaccgcttc  1380
tgcaggtggg ggatataacc tgaatgtgca cacatggaca tcacctgaag gaataacagg  1440
tgaattctgt ttacagcctc atttgcaggc tgtctggatg ggggttacac cggatacaca  1500
tcaggaggat aacggaacgg tggtgcaggg agcagggaaa aataatattc agacaaaagc  1560
aggtattcgt gcatcctgga aggtgaaaag caccctggaa aaggataccg ggcggaggtt  1620
ccgtccgtat atagaggcaa actgatccaa taacactcat gaatttggtg ttaaaatgag  1680
tgatgacagc cagttgttgt caggtagccg aaatcaggga gagataaaga caggtattga  1740
aggggtgatt actcaaaact tgtcagtgaa tggcggagtc tgcatatcagg caggaggtca  1800
cgggagcaat gccatctccg gagcactggg gataaaatac agcttctgat aatgatcctg  1860
gcacgcggcg cgcccttgg tgcgcaaact attaactggc gaactactta ctctagcttc  1920
ccggcaacaa ttaatagact ggatggaggc ggataaagtt gcaggaccac ttctgcgctc  1980
ggcccttccg gctggctggt ttattgctga taatcgtgga gccggtagc tggggtctcg  2040
cggtatcatt gcagcactgg ggccagatgg taagccctcc cgtatcgtag ttatctacac  2100
gacgggagt caggcaacta tggatgaacg aaatagacag atcgctgaga taggtgcctc  2160
actgattaag cattggtaac tgtcagacca agtttactca tatatacttt agattgattt  2220
aaaacttcat tttaatttaa aaaggatcta ggtgaagatc cttttttgata atctcatgac  2280
caaaatccct taacgtgagt tttcgttcca ctgagcgtca gacccttaa taagatgatc  2340
ttcttgagat cgtttggtc tgcgcgtaat ctcttgctct gaaaacgaaa aaaccgcctt  2400
gcagggcggt ttttcgaagg ttctctgagc taccaactct ttgaaccgag gtaactggct  2460
tggaggagcg cagtcaccaa aacttgtcct ttcagttta ccttaaccgg cgcatgactt  2520
caagactaac tcctctaaat caattaccag tggctgctgc cagtggtgct tttgcatgtc  2580
tttccgggtt ggactcaaga cgatagttac cggataaggc gcagcggtcg gactgaacgg  2640
ggggttcgtg catacagtcc agcttggagc gaactgccta cccggaactg agtgtcaggc  2700
gtggaatgag acaaacgcgg ccataacagc ggaatgacac cggtaaaccg aaaggcagga  2760
acaggagagc gcacgaggga gccgccaggg ggaaacgcct ggtatcttta tagtcctgtc  2820
gggtttcgcc accactgatt tgagcgtcag atttcgtgat gcttgtcagg ggggcggagc  2880
ctatggaaaa acggctttgc cgcggccctc tcacttccct gttaagtatc ttcctggcat  2940
cttccaggaa atctccgccc cgttcgtaag ccatttccgc tcgccgcagt cgaacgaccg  3000
agcgtagcga gtcagtgagc gaggaagcgg aatatatcct gtatcacata ttctgctgac  3060
gcaccggtgc agccttttt ctcctgccac atgaagcact tcactgacac cctcatcagt  3120
gccaacatag taagcagta tacactccgc tagcgctgag gtctgcctcg tgaagaaggt  3180
gttgctgact cataccaggc ctgaatcgcc ccatcatcca gccagaaagt gagggagcca  3240
cggttgatga gagctttgtt gtaggtggac cagttggtga ttttgaactt ttgctttgaa  3300
acggaacggt ctgcgttgtc gggaagatgc gtgatctgat ccttcaactc agcaaaagtt  3360
cgatttattc aacaaagcca cgttgtgtct caaaatctct gatgttacat tgcacaagat  3420
aaaaatatat catcatgaac aataaaactg tctgcttaca taaacagtaa tacaaggggt  3480
gttatgagcc atattcaacg ggaaacgtct tgctcgagta tccgctcatg agattatcaa  3540
aaaggatctt cacctagatc cttttgtaag aggttccaac tttcaccata tgaaataag  3600
atcactaccg ggcgtatttt tgagttatc gagattttca ggagctaagg aagctaaaat  3660
ggagaaaaaa atcactggat ataccaccgt tgatatatcc caatggcatc gtaaagaaca  3720
ttttgaggca tttcagtcag ttgctcaatg tacctataac cagaccgttc agctggatat  3780
tacggccttt ttaaagaccg taaagaaaaa taagcacaag ttttatccgg cctttattca  3840
cattcttgcc cgcctgatga atgctcatcc ggagttcgt atggcaatga aagacggtga  3900
gctggtgata tgggatagtg ttcacccttg ttacaccgtt ttccatgagc aaactgaaac  3960
gttttcatcg ctctggagtg aataccacga cgatttccgg cagtttctac acatatattc  4020
gcaagatgtg gcgtgttacg gtgaaaacct ggcctatttc cctaaagggt ttattgagaa  4080
tatgtttttc gtctcagcca atccctgggt gagtttcacc agttttgatt taaacgtggc  4140
caatatggac aacttcttcg ccccgttttt caccatgggc aaatattata cgcaaggcga  4200
caaggtgctg atgccgctgg cgattcaggt tcatcatgcc gtttgtgatg cttccatgt  4260
cggcagaatg cttaatgaat tacaacagta ctgcgatgag tggcagggcg gggcgtaatt  4320
tttttaaggc agacaccatc aatggcgcaa aacctttcgc ggtatggcat gatagcgccc  4380
ggaagagagt caattcaggg tggtgaatgt gaaaccagta acgttatacg atgtcgcaga  4440
gtatgccggt gtctcttatc agaccgtttc ccgcgtggtg aaccaggcca gccacgtttc  4500
tgcgaaaacg cgggaaaaag tggaagcggc gatggcggag ctgaattaca ttcccaaccg  4560
cgtggcacaa caactggcgg gcaaacagtc gttgctgatt ggcgttgcca cctccagtct  4620
ggccctcacg cgccgtcgc aaattgtcgc ggcgattaaa tctcgcgccg atcaactggg  4680
tgccagcgtg gtggtgtcga tggtagaacg aagcggcgtc gaagcctgta aagcggcggt  4740
gcacaatctt ctcgcgcaac gcgtcagtgg gctgatcatt aactatccgc tggatgacca  4800
ggatgccatt gctgtggaag ctgcctgcac taatgttccg gcgttatttc ttgatgtctc  4860
tgaccagaca cccatcaaca gtattatttt ctcccatgaa gacggtacgc gactgggcgt  4920
ggagcatctg gtcgcattgg gtcaccagca aatcgcgctg ttagcgggcc cattaagttc  4980
```

```
tgtctcggcg cgtctgcgtc tggctggctg gcataaatat ctcactcgca atcaaattca 5040
gccgatagcg gaacgggaag gcgactggag tgccatgtcc ggttttcaac aaaccatgca 5100
aatgctgaat gagggcatcg ttcccactgc gatgctggtt gccaacgatc agatggcgct 5160
gggcgcaatg cgcgccatta ccgagtccgg gctgcgcgtt ggtgcggata tctcggtagt 5220
gggatacgac gataccgaag acagctcatg ttatatcccg ccgttaacca ccatcaaaca 5280
ggattttcgc ctgctgggcg aaaccagcgt ggaccgcttg ctgcaactct ctcagggcca 5340
ggcggtgaag ggcaatcagc tgttgcccgt ctcactggtg aaaagaaaaa ccaccctggc 5400
gcccaatacg caaaccgcct ctccccgcgc gttggccgat tcattaatgc agctggcacg 5460
acaggtttcc cgactggaaa gcgggcaagt gagtggataa ccgtattacc gcctttgagt 5520
gagctgatac cggaattct cactcattag gcaccccagg c         5561
```

SEQ ID NO: 13      moltype = DNA   length = 6242
FEATURE            Location/Qualifiers
misc_feature       1..6242
                   note = pAIDA-1_CBM-Nanobody
source             1..6242
                   mol_type = other DNA
                   organism = synthetic construct
SEQUENCE: 13

```
tttacactt atgcttccgg ctcgtataat gtgtggaatt gtgagcggat aacaatttca  60
cacaggaaag cttcatatga ataaggccta cagtatcatt tggagccact ccagacaggc 120
ctggattgtg gcctcagagt tagccagagg acatgtcttt gtccttgcaa aaaatacact 180
gctggtattg gcggttgttt ccacaatcgg aaatgcattt gcagtcgacc accatcacca 240
tcaccatctg gaagcgctgt tccagggtcc gggtaccgtt cagctggttg aaagcggtgg 300
tgcactggtt cagcctggtg gtagcctgcg tctgagctgt gcagcaagcg gttttccggt 360
taatcgttat agcatgcgtt ggtatcgtca ggcaccgggt aaagaacgtg aatgggttgc 420
aggtatgagc agtgccggtg atcgtagcag ctacgaagat agcgttaaag gtcgttttac 480
catcagccgt gatgatgcac gtaataccgt ttatctgcaa atgaatagcc tgaaaccgga 540
agataccgca gtgtattatt gcaacgttaa cgtgggcttt gaatattggg gtcagggcac 600
ccaggttacc gttagcagca aactcgagcg ccgcatcgt gacgcgtcgt ctggtcctgc 660
cggctgccaa gtcctttggg gcgtgaatca gtgaacacat ggtttcacgg cgaatgttac 720
cgtcaagaat acgtcctccg ctcctgttga cggctggacc ttgaccttca gtttcccatc 780
aggacaacaa gtcactcaag cctggtcatc taccgtgacc cagagtggat ctgcggtcac 840
agtacgtaac gctccgtgga acggttcgat tcccgcgggc gggactgctc agttcgggtt 900
taacggaagc cacactggca ctaatgctgc accaactgcc ttctcactta acggcacgcc 960
gtgcaccgta ggcgagctcg aaaacctgta cttccagggt gaacagaaac tgattagcga 1020
agaagatctg tctagagtga ataacaatgg aagcattgtc attaataaca gcattataaa 1080
cgggaatatt acgaatgatg ctgacttaag ttttggtaca gcaaagctgc tctctgctac 1140
agtgaatggt agtcttgtta ataacaaaaa tatcattctt aatcctacaa aagaaagtgc 1200
ggccgctata ggtaatactc ttaccgtgtc aaattatact gggacaccgg gaagtgttat 1260
ttctcttggt ggtgtgcttg aaggagataa ttcacttacg gaccgtctgg tggtgaaagg 1320
taatacctct ggtcaaagtg acatcgttta tgtcaatgaa gatggcagtg gtggtcagac 1380
gagagatggt attaatatta tttctgtaga gggaaattct gatgcagaat tctctctgaa 1440
gaaccgcgta gttgccggag cttatgatta cacactgcag aaaggaaacg agagtgggac 1500
agataataag ggatggtatt taaccagtca tcttcccaca tctgatatccc ggcaatacag 1560
accggagaac ggaagttatg ctaccaatat ggcactggct aactcactgt tcctcatgga 1620
tttgaatgag cgtaagcaat tcagggccat gagtgataat acacagcctg gatgtctgcatc 1680
cgtgtggatg aagatcactg gaggaataag ctctggtaag ctgaatgacg ggcaaaataa 1740
aacaacaacc aatcagttta tcaatcagct cgggggggat atttataaat tccatgctga 1800
acaactgggg gattttacct tagggattat gggaggatac gcgaatgcaa aaggtaaaac 1860
gataaattac acgagcaaca aagctgccag aaacacactg gatggttatt ctgtcgggggt 1920
atacggtacg tggtatcaga atggggaaaa tgcaacaggg ctctttgctg aaacttggat 1980
gcaatataac tggtttaatg catcagtgaa aggtgacgga ctggaagaag aaaaatataa 2040
tctgaatggt ttaaccgctt ctgcaggtgg gggatataac ctgaatgtgc acacatggac 2100
atcacctgaa ggaataacag gtgaattctg gttacagcct catttgcagg ctgtctggat 2160
ggggggttaca ccggatacac atcaggagga taacgaacg gtggtgcagg gagcagggaa 2220
aaataatatt cagacaaaag caggtattcg tgcatcctgg aaggtgaaaa gcaccctgga 2280
taaggatacc gggcggaggt tccgtccgta tatagaggca aactggatcc ataacactca 2340
tgaatttggt gttaaaatga gtgatgacag ccagttgttg tcaggtagcc gaaatcaggg 2400
agagataaag acaggtattg aagggggtgat tactcaaaac ttgtcagtga atgcggagt 2460
cgcatatcag gcaggaggtc acgggagcaa tgccatctcc ggagcactgg ggataaaata 2520
cagcttctga taatgatcct ggcacgcggc gcgcccttg gtgcgcaaac tattaactgg 2580
cgaactactt actctagctt cccggcaaca attaatagac tggatggagg cggataaagt 2640
tgcaggacca cttctgcgct cggccttcc ggctggctgg tttattgctg ataaatctgg 2700
agccggtgag cgtgggtctc gcggtatcat tgcagcactg ggccagatg gtaagccctc 2760
ccgtatcgta gttatctaca cgacggggag tcaggcaact atggatgaac gaaatagaca 2820
gatcgctgag ataggtgcct cactgattaa gcattggtaa ctgtcagacc aagtttactc 2880
atatatactt tagattgatt taaaacttca ttttttaattt aaaaggatct aggtgaagat 2940
cctttttgat aatctcatga ccaaaatccc ttaacgtgag ttttcgttcc actgagcgtc 3000
agaccccgta taagatgat cttcttgaga tcgtttggt ctgcgcgtaa tctcttgctc 3060
tgaaaacgaa aaaccgcct tgcagggcgg ttttttcgaag gttctctgag ctaccaactc 3120
tttgaaccga ggtaactggc ttggaggagc gcagtcacca aaacttgtcc tttcagttta 3180
gccttaaccg gcgcatgact tcaagactac ctcctctaaa tcaattacca gtggctgctg 3240
ccagtggtgc ttttgcatgt cttccgggt tggactcaag acgatagtta ccggataagg 3300
cgcagcggtc ggactgaacg ggggggttcgt gcatacagtc cagctggag cgaactgcct 3360
acccggaact gagtgtcagg cgtggaatga gacaaacgcg gccataacag cggaatgaca 3420
ccggtaaacc gaaaggcagg aacaggagag cgcacgaggg agccgccagg gggaaacgcc 3480
tggtatcttt atagtcctgt cgggtttcgc caccactgat ttgagcgtca gatttcgtga 3540
tgcttgtcag ggggcggag cctatggaaa aacggcttg ccgcggccct ctcacttccc 3600
```

-continued

```
tgttaagtat cttcctggca tcttccagga aatctccgcc ccgttcgtaa gccatttccg   3660
ctcgccgcag tcgaacgacc gagcgtagcg agtcagtgag cgaggaagcg aatatatcc    3720
tgtatcacat attctgctga cgcaccggtg cagccttttt tctcctgcca catgaagcac   3780
ttcactgaca ccctcatcag tgccaacata gtaagccagt atacactccg ctagcgctga   3840
ggtctgcctc gtgaagaagg tgttgctgac tcataccagg cctgaatcgc cccatcatcc   3900
agccagaaag tgagggagcc acggttgatg agagctttgt tgtaggtgga ccagttggtg   3960
attttgaact tttgctttgc cacggaacgg tctgcgttgt cgggaagatg cgtgatctga   4020
tccttcaact cagcaaaagt tcgatttatt caacaaagcc acgttgtgtc tcaaaatctc   4080
tgatgttaca ttgcacaaga taaaaatata tcatcatgaa caataaaact gtctgcttac   4140
ataaacagta atacaagggg tgttatgagc catattcaac gggaaacgtc ttgctcgagt   4200
atccgctcat gagattatca aaaaggatct tcacctagat cctttttgtaa gaggttccaa   4260
ctttttcaccat aatgaaataa gatcactacc gggcgtattt tttgagttat cgagattttc   4320
aggagctaag gaagctaaaa tggagaaaaa aatcactgga tataccaccg ttgatatatc   4380
ccaatggcat cgtaaagaac attttgaggc atttcagtca gttgctcaat gtacctataa   4440
ccagaccgtt cagctggata ttacggcctt tttaaagacc gtaaagaaaa ataagcacaa   4500
gttttatccg gcctttattc acattcttgc ccgcctgatg aatgctcatc cggagtttcg   4560
tatggcaatg aaagacggtg agctggtgat atgggatagt gttcacccct gttacaccgt   4620
tttccatgag caaactgaaa cgttttcatc gctctggagt gaataccacg acgatttccg   4680
gcagtttcta cacatatatt cgcaagatgt ggcgtgttac ggtgaaaacc tggcctattt   4740
ccctaaaggg tttattgaga atatgttttt cgtctcagcc aatccctggg tgagtttcac   4800
cagttttgat ttaaacgtgg ccaatatgga caacttcttc gcccccgttt tcaccatggg   4860
caaatattat acgcaaggcg acaaggtgct gatgccgctg gcgattcagg ttcatcatgc   4920
cgtttgtgat ggcttccatg tcggcagaat gcttaatgaa ttacaacagt actgcgatga   4980
gtggcagggc ggggcgtaat ttttttaagg cgacaccatc gaatggcgca aaacctttcg   5040
cggtatggca tgatagcgcc cggaagagag tcaattcagg gtggtgaatg tgaaaccagt   5100
aacgttatac gatgtcgcag agtatgccgg tgtctcttat cgaccgtttc cccgcgtggt   5160
gaaccaggcc agccacgttt ctgcgaaaac gcgggaaaaa gtggaagcgg cgatggcgga   5220
gctgaattac attcccaacc gcgtggcaca acaactggcg ggcaaacagt cgttgctgat   5280
tggcgttgcc acctccagtc tggccctgca cgcgccgtcg caaattgtcg cggcgattaa   5340
atctcgcgcc gatcaactgg gtgccagcgt ggtggtgtcg atggtagaac gaagcggcgt   5400
cgaagcctgt aaagcggcgg tgcacaatct tctcgcgcaa cgcgtcagtg ggctgatcat   5460
taactatccg ctgatgacc aggatgccat tgctgtggaa gctgcctgca ctaatgttcc   5520
ggcgttattt cttgatgtct ctgaccagac acccatcaac agtattattt ctcccatga    5580
agacggtacg cgactgggcg tggagcatct ggtctgcattg ggtcaccagc aaatcgcgct   5640
gttagcgggc ccattaagtt ctgtctcggc gcgtctgcgt ctggctggct ggcataaata   5700
tctcactcgc aatcaaattc agccgatagc ggaacgggaa ggcgactgga gtgccatgtc   5760
cggttttcaa caaaccatgc aaatgctgaa tgagggcatc gttcccactg cgatgctggt   5820
tgccaacgat cagatggcgc tgggcgcaat gcgcgccatt accgagtccg ggctgcgcgt   5880
tggtcggat atctcggtag tgggatacga cgataccgaa gacagctcat gttatatccg   5940
gccgttaacc accatcaaac aggattttcg cctgctgggg caaaccagcg tggaccgctt   6000
gctgcaactc tctcagggcc aggcggtgaa gggcaatcag ctgttgcccg tctcactggt   6060
gaaaagaaaa accaccctgg cgcccaatac gcaaaccgcc tctccccgcg cgttggccga   6120
ttcattaatg cagctggcac gacaggtttc ccgactggaa agcgggcaag tgagtggata   6180
accgtattac cgcctttgag tgagctgata ccgggaattc tcactcatta ggcaccccag   6240
gc                                                                  6242
```

```
SEQ ID NO: 14          moltype = DNA   length = 4341
FEATURE                Location/Qualifiers
misc_feature           1..4341
                       note = pET-9a
source                 1..4341
                       mol_type = other DNA
                       organism = synthetic construct
SEQUENCE: 14
ttctcatgtt tgacagctta tcatcgataa gctttaatgc ggtagtttat cacagttaaa    60
ttgctaacgc agtcaggcac cgtgtatgaa atctaacaat gcgctcatcg tcatcctcgg    120
caccgtcacc ctggatgctg taggcatagg cttggttatg ccggtactgc cgggcctctt   180
gcgggatatc gtccattccg acagcatcgc cagtcactat ggcgtgctgc tagcgctata   240
tgcgttgatg caatttctat gcgcacccgt tctcggagca ctgtccgacg ctttggccgc   300
cgcccagtc ctgctcgctt cgctacttgg agccactatc gactacgcg tcatggcgac    360
cacacccgtc ctgtggatat ccggatatag ttcctccttt cagcaaaaaa ccctcaaga    420
cccgtttaga ggccccaagg ggttatgcta gttattgctc agcggtggca gcagccaact   480
cagcttcctt tcgggctttg ttagcagccg gatccgcgac ccatttgctg tccaccagtc   540
atgctagcca tatgtatatc tccttcttaa agttaaacaa aatttattct agagggaaac   600
cgttgtggtc tccctatagt gagtcgtatt aatttcgcgg gatcgagatc tcgatcctct   660
acgccggacg catcgtggcc ggcatcaccg gcgccacagg tgcggttgct ggcgcctata   720
tcgccgacat caccgatggg gaagatcggg ctcgccactt cgggctcatg agcgcttgtt   780
tcggcgtggg tatggtggca ggccccgtgg ccggggggact gttgggcgcc atctccttgc   840
atgcaccatt ccttgcggcg gcggtgctca acggcctcaa cctactactg ggctgcttcc   900
taatgcagga gtcgcataag ggagagcgtc gaccgatgcc cttgagagcc ttcaacccag   960
tcagctcctt ccgtgggcg cggggcatga ctatcgtcgc cgcacttatg actgtcttct   1020
ttatcatgca actcgtagga caggtgccgg cagcgctctg gtcatttttc ggcgaggacc   1080
gctttcgctg gagcgcgacg atgatcggcc tgtcgcttgc ggtattcgga atcttgcacg   1140
ccctcgctca agccttcgtc actggtcccg ccaccaaacg tttcggcgag aagcaggcca   1200
ttatcgccgc catggcggcc gacgcgctgg gctacgtctt gctggcgttc gcgacgcgag   1260
gctggatggc cttccccatt atgattcttc tcgcttccgg cggcatcggg atgcccgcgt   1320
tgcaggccat gctgtccagg caggtagatg acgaccatca gggacagctt caaggatcgc   1380
tcgcggctct taccagccta acttcgatca ctggaccgct gatcgtcacg gcgatttatg   1440
ccgcctcggc gagcacatgg aacgggttgg catggattgt aggcgccgcc ctataccttg   1500
```

```
tctgcctccc cgcgttgcgt cgcggtgcat ggagccgggc cacctcgacc tgaatggaag    1560
ccggcggcac ctcgctaacg gattcaccac tccaagaatt ggagccaatc aattcttgcg    1620
gagaactgtg aatgcgcaaa ccaacccttg cagaacata tccatcgcgt ccgccatctc    1680
cagcagccgc acgcggcgca tctcgggcag cgttgggtcc tggccacggg tgcgcatgat    1740
cgtgctcctg tcgttgagga cccggctagg ctggcgggat tgccttactg gttagcagaa    1800
tgaatcaccg atacgcgagc gaacgtgaag cgactgctgc tgcaaaacgt ctgcgacctg    1860
agcaacaaca tgaatggtct tcggtttccg tgtttcgtaa agtctggaaa cgcggaagtc    1920
agcgccctgc accattatgt tccggatctg catcgcagga tgctgctggc taccctgtgg    1980
aacacctaca tctgtattaa cgaagcgctg gcattgaccc tgagtgattt ttctctggtc    2040
ccgccgcatc catccgcca gttgtttacc ctcacaacgt tccagtaacc gggcatgttc    2100
atcatcagta acccgtatcg tgagcatcct ctctcgtttc atcggtatca ttaccccat    2160
gaacagaaat ccccttaca cggaggcatc agtgaccaaa caggaaaaaa ccgcccttaa    2220
catggcccgc tttatcagaa gccagacatt aacgcttctg gagaaactca acgagctgga    2280
cgcggatgaa caggcagaca tctgtgaatc gcttcacgac cacgctgatg agctttaccg    2340
cagctgcctc gcgcgtttcg gtgatgacgg tgaaaacctc tgacacatgc agctcccgga    2400
gacggtcaca gcttgtctgt aagcggatgc cgggagcaga caagcccgtc agggcgcgtc    2460
agcgggtgtt ggcgggtgtc ggggcgcagc catgacccag tcacgtagcg atagcggagt    2520
gtatactggc ttaactatgc ggcatcagag cagattgtac tgagagtgca ccatatagg    2580
ggtgtgaaat accgcacaga tgcgtaagga gaaaataccg catcaggcgc tcttccgctt    2640
cctcgctcac tgactcgctg cgctcggtcg ttcggctgcg gcgagcggta tcagctcact    2700
caaaggcggt aatacggtta tccacagaat caggggataa cgcaggaaag aacatgtgag    2760
caaaaggcca gcaaaaggcc aggaaccgta aaaaggccgc gttgctggcg tttttccata    2820
ggctccgccc ccctgacgag catcacaaaa atcgacgctc aagtcagagg tggcgaaacc    2880
cgacaggact ataaagatac caggcgtttc cccctggaag ctccctcgtg cgctctcctg    2940
ttccgaccct gccgcttacc ggatacctgt ccgcctttct cccttcggga agcgtggcgc    3000
tttctcatag ctcacgctgt aggtatctca gttcggtgta ggtcgttcgc tccaagctgg    3060
gctgtgtgca cgaaccccc gttcagcccg accgctgcgc cttatccggt aactatcgtc    3120
ttgagtccaa cccggtaaga cacgacttat cgccactggc agcagccact ggtaacagga    3180
ttagcagagc gaggtatgta ggcggtgcta cagagttctt gaagtggtgg cctaactacg    3240
gctacactag aaggacagta tttggtatct gcgctctgct gaagccagtt accttcggaa    3300
aaagagttgg tagctcttga tccggcaaac aaaccaccgc tggtagcggt ggtttttttg    3360
tttgcaagca gcagattacg cgcagaaaaa aaggatctca agaagatcct ttgatctttt    3420
ctacggggtc tgacgctcag tggaacgaaa actcacgtta agggattttg gtcatgaaca    3480
ataaaactgt ctgcttacat aaacagtaat acaaggggtg ttatgagcca tattcaacgg    3540
gaaacgtctt gctcgaggcc gcgattaaat tccaacatgg atgctgattt atatgggtat    3600
aaatgggctc gcgataatgt cgggcaatca ggtgcgacaa tctatcgatt gtatgggaag    3660
cccgatgcgc cagagttgtt tctgaaacat ggcaaaggta gcgttgccaa tgatgttaca    3720
gatgagatgg tcagactaaa ctggctgacg gaatttatgc ctcttccgac catcaagcat    3780
tttatccgta ctcctgatga tgcatggtta ctcaccactg cgatccccgg gaaaacagca    3840
ttccaggtat tagaagaata tcctgattca ggtgaaaata ttgttgatgc gctggcagtg    3900
ttcctgcgcc ggttgcattc gattcctgtt tgtaattgtc cttttaacag cgatcgcgta    3960
tttcgtctcg ctcaggcgca atcacgaatg aataacggtt tggttgatgc gagtgatttt    4020
gatgacgagc gtaatggctg gcctgttgaa caagtctgga aagaaatgca taagcttttg    4080
ccattctcac cggattcagt cgtcactcat ggtgatttct cacttgataa ccttatttt    4140
gacgagggga attaatagg ttgtattgat gttggacgag tcggaatcgc agaccgatac    4200
caggatcttg ccatcctatg gaactgcctc ggtgagtttt ctccttcatt acagaaacgg    4260
cttttttcaaa aatatggtat tgataatcct gatatgaata aattgcagtt tcatttgatg    4320
ctcgatgagt ttttctaaga a                                              4341
```

SEQ ID NO: 15        moltype = DNA  length = 4981
FEATURE                Location/Qualifiers
misc_feature        1..4981
                        note = pGEX-6P-1_NoGST
source                1..4981
                        mol_type = other DNA
                        organism = synthetic construct
SEQUENCE: 15

```
acgttatcga ctgcacggtg caccaatgct tctggcgtca ggcagccatc ggaagctgtg      60
gtatggctgt gcaggtcgta aatcactgca taattcgtgt cgctcaaggc gcactcccgt     120
tctggataat gttttttgcg ccgacatcat aacggttctg gcaaatattc tgaaatgagc     180
tgttgacaat taatcatcgg ctcgtataat gtgtggaatt gtgagcggat aacaatttca     240
cacaggaaac agtattctcc cctatactag gttattggaa aattaagggc cttgtgcaac     300
ccactcgact tctttttggaa tatcttgaag aaaaatatga gagcatttg tatgagcgcg     360
atgaaggtga taattggcga aacaaaaagt ttgaattggt tttggagttt cccaatcttc     420
cttattatat tgatggtgat gttaaattaa cacagtctat ggccatcata cgttatatag     480
ctgacaagca acacatgttg ggtggttgtc aaaagagcg tgcagagatt caatgcttg     540
aaggagcggt tttggatatt agatacgtg tttgagaat tgcatatagt aaagactttg     600
aaactctcaa agttgatttt cttagcaagc tacctgcaag ctgaaaatg ttcgaagatc     660
gtttatgtca taaacatat ttaaatggtg atcatgtaac ccatcctgcc ttcatgttgt     720
atgacgctct tgatgttgtt ttatacatgg acccaatgtg cctggatgcg ttcccaaaat     780
tagtttgtt taaaaaacgt attgaagcta tcccacaaat tgataagtac ttgaaatcca     840
gcaagtatat agcatggcct tgcagggct ggcaagccac gttggtggt ggcgaccatc     900
ctccaaaatc ggatctggaa gttctgttcc aggggcccct gggatcccg gaattccgg     960
gtcatctcga gcggccgcat cgtgactgac tgacgatctg cctcgcgcgt ttcggtgatg    1020
acggtgaaaa cctctgacac atgcagctcc cggagacggt cacagcttgt ctgtaagcgg    1080
atgccgggag cagacaagcc cgtcagggcg cgtcagcggg tgttggcggg tgtcggggcg    1140
cagccatgac ccagtcacgt agcgatacg gagtgtataa ttcttgaaga cgaaagggcc    1200
tcgtgatacg cctatttta taggttaatg tcatgataat aatggtttct tagacgtcag    1260
gtggcacttt tcggggaaat gtgcgcggaa ccccctattg ttatttttc taaatacatt    1320
```

```
caaatatgta tccgctcatg agacaataac cctgataaat gcttcaataa tattgaaaaa  1380
ggaagagtat gagtattcaa catttccgtg tcgcccttat tccctttttt gcggcatttt  1440
gccttcctgt ttttgctcac ccagaaacgc tggtgaaagt aaaagatgct gaagatcagt  1500
tgggtgcacg agtgggttac atcgaactgg atctcaacag cggtaagatc cttgagagtt  1560
ttcgccccga agaacgtttt ccaatgatga gcacttttaa agttctgcta tgtggcgcgg  1620
tattatcccg tgttgacgcc gggcaagagc aactcggtcg ccgcatacac tattctcaga  1680
atgacttggt tgagtactca ccagtcacag aaaagcatct tacggatggc atgacagtaa  1740
gagaattatg cagtgctgcc ataaccatga gtgataacac tgcggccaac ttacttctga  1800
caacgatcgg aggaccgaag gagctaaccg cttttttgca caacatgggg gatcatgtaa  1860
ctcgccttga tcgttgggaa ccggagctga atgaagccat accaaacgac gagcgtgaca  1920
ccacgatgcc tgcagcaatg gcaacaacgt tgcgcaaact attaactggc gaactactta  1980
ctctagcttc ccggcaacaa ttaatagact ggatggaggc ggataaagtt gcaggaccac  2040
ttctgcgctc ggcccttccg gctggctggt ttattgctga taaatctgga gccggtgagc  2100
gtgggtctcg cggtatcatt gcagcactgg ggccagatgg taagccctcc cgtatcgtag  2160
ttatctacac gacggggagt caggcaacta tggatgaacg aaatagacag atcgctgaga  2220
taggtgcctc actgattaag cattggtaac tgtcagacca agtttactca tatatacttt  2280
agattgattt aaaacttcat ttttaattta aaaggatcta ggtgaagatc ctttttgata  2340
atctcatgac caaatccct taacgtgagt tttcgttcca ctgagcgtca gaccccgtag  2400
aaaagatcaa aggatcttct tgagatcctt ttttctgcg cgtaatctgc tgcttgcaaa  2460
caaaaaaacc accgctacca gcggtggttt gtttgccgga tcaagagcta ccaactcttt  2520
ttccgaaggt aactggcttc agcagagcgc agataccaaa tactgtcctt ctagtgtagc  2580
cgtagttagg ccaccacttc aagaactctg tagcaccgcc tacatacctc gctctgctaa  2640
tcctgttacc agtggctgct gccagtggcg ataagtcgtg tcttaccggg ttggactcaa  2700
gacgatagtt accggataag gcgcagcggt cgggctgaac ggggggttcg tgcacacagc  2760
ccagcttgga gcgaacgacc tacaccgaac tgagatacct acagcgtgag ctatgagaaa  2820
gcgccacgct tcccgaaggg agaaaggcgg acaggtatcc ggtaagcggc agggtcggaa  2880
caggagagcg cacgagggag cttccaggg gaaacgcctg gtatctttat agtcctgtcg  2940
ggtttcgcca cctctgactt gagcgtcgat ttttgtgatg ctcgtcaggg gggcggagcc  3000
tatgaaaaaa cgccagcaac gcggcctttt tacggttcct ggccttttgc tggccttttg  3060
ctcacatgtt ctttcctgcg ttatcccctg attctgtgat aaccgtatt accgcctttg  3120
agtgagctga taccgctcgc cgcagccgaa cgaccgagcg cagcgagtca gtgagcgagg  3180
aagcggaaga gcgcctgatg cggtattttc tccttacgca tctgtgcggt atttcacacc  3240
gcataaattc cgacaccatc gaatggtgca aaaccttcg cggtatggca tgatagcgcc  3300
cggaagagag tcaattcagg gtggtgaatg tgaaaccagt aacgttatac gatgtcgcag  3360
agtatgccgg tgtctcttat cagaccgttt ccgcgtggt gaaccaggcc agccacgttt  3420
ctgcgaaaac gcgggaaaaa gtggaagcgg cgatgcgga gctgaattac attcccaacc  3480
gcgtggcaca acaactggcg ggcaaacagt cgttgctgat tggcgttgcc acctccagtc  3540
tggccctgca cgcgccgtcg caaattgtcg cggcgattaa atctcgcgcc gatcaactgg  3600
gtgcccgcgt ggtggtgtcg atggtagaac gaagcggcgt cgaagcctgt aaagcggcgg  3660
tgcacaatct tctcgcgcaa cgcgtcagtg ggctgatcat taactatccg ctggatgacc  3720
aggatgccat tgctgtggaa gctgcctgca ctaatgttcc ggcgttattt cttgatgtct  3780
ctgaccagac acccatcaac agtattattt tctcccatga agacggtacg cgactgggcg  3840
tggagcatct ggtcgcattg ggtcaccagc aaatcgcgct gttagcgggc ccattaagtt  3900
ctgtctcggc gcgtctgcgt ctggctggct ggcataaata tctcactcgc aatcaaattc  3960
agccgatagc ggaacgggaa ggcgactgga gtgccatgtc cggttttcaa caaaccatgc  4020
aaatgctgaa tgagggcatc gttcccactg cgatgctggt tgccaacgat cagatggcgc  4080
tgggcgcaat gcgcgccatt accgagtccg ggctgcgcgt tggtgcggat atctcggtag  4140
tgggatacga cgataccgaa gacagctcat gttatatccc gccgtcaacc accatcaaac  4200
aggattttcg cctgctgggg caaaccagcg tggaccgctt gctgcaactc tctcagggcc  4260
aggcggtgaa gggcaatcag ctgttgcccg tctcactggt gaaaagaaaa accacccgg  4320
cgcccaatac gcaaaccgcc tctccccgcg cgttggccga ttcattaatg cagctggcac  4380
gacaggtttc ccgactggaa agcgggcagt gagcgcaacg caattaatgt gagttagctc  4440
actcattagg caccccaggc tttacacttt atgcttccgg ctcgtatgtt gtgtggaatt  4500
gtgagcggat aacaatttca cacaggaaac agctatgacc atgattacgg attcactggc  4560
cgtcgtttta caacgtcgtg actgggaaaa ccctggcgtt acccaactta atcgccttgc  4620
agcacatccc cctttcgcca gctggcgtaa tagcgaagag gcccgcaccg atcgcccttc  4680
ccaacagttg cgcagcctga atggcgaatg gcgctttgcc tggtttccgg caccagaagc  4740
ggtgccggaa agctggctgg agtgcgatct tcctgaggcc gatactgtcg tcgtcccctc  4800
aaactggcag atgcacggtt acgatgcgcc catctacacc aacgtaacct atcccattac  4860
ggtcaatccg ccgtttgttc ccacggagaa tccgacgggt tgttactcgc tcacatttaa  4920
tgttgatgaa agctggctac aggaaggcca gacgcgaatt atttttgatg gcgttggaat  4980
t                                                                 4981
```

SEQ ID NO: 16          moltype = DNA   length = 7321
FEATURE                Location/Qualifiers
misc_feature           1..7321
                       note = pGEX-6P-1_NoGST_Brk-CBM
source                 1..7321
                       mol_type = other DNA
                       organism = synthetic construct
SEQUENCE: 16

```
acgttatcga ctgcacggtg caccaatgct tctggcgtca ggcagccatc ggaagctgtg  60
gtatggctgt gcaggtcgta aatcactgca taattcgtgt cgctcaaggc gcactcccgt  120
tctgataat gttttttgcg ccgacatcat aacggttctg gcaaatattc tgaaatgagc  180
tgttgacaat taatcatcgg ctcgtataat gtgtggaatt gtgagcggat aacaatttca  240
cacaggaaac agtattctcc cctatactag gttattggaa aattaagggc cttgtgcaac  300
ccactcgact tcttttggaa tatcttgaag aaaaatatga gagcatttg tatgagcgcg  360
atgaaggtga taaatggcga aacaaaaagt ttgaattggg tttggagttt cccaatcttc  420
cttattatat tgatggtgat gttaaattaa cacagtctat ggccatcata cgttatatag  480
```

-continued

```
ctgacaagca caacatgttg ggtggttgtc caaaagagcg tgcagagatt tcaatgcttg   540
aaggagcggt tttggatatt agatacggtg tttcgagaat tgcatatagt aaagactttg   600
aaactctcaa agttgatttt cttagcaagc tacctgaaat gctgaaaatg ttcgaagatc   660
gtttatgtca taaaacatat ttaaatggtg atcatgtaac ccatcctgac ttcatgttgt   720
atgacgctct tgatgttgtt ttatacatgg acccaatgtg cctggatgcg ttcccaaaat   780
tagtttgttt taaaaaacgt attgaagcta tcccacaaat tgataagtac ttgaaatcca   840
gcaagtatat agcatggcct ttgcagggct ggcaagccac gtttggtggt ggcgaccatc   900
ctccaaaatc ggatctggaa gttctgttcc aggggcccct gggatccatg tatctggatc   960
gctttcgcca gtgcccgagc agcctgcaga ttccgcgcag cgcgtggcgc ctgcatgcgc  1020
tggcggcggc gctggcgctg gcgggcatgg cgcgcctggc gccggcggcg gcgcaggcgc  1080
cgcagccgcc ggtggcgggc gcgccgcatg cgcaggatgc gggccaccat caccatcacc  1140
atgttcagct ggttgaaagc ggtggtgcac tggttcagcc tggtggtagc ctgcgtctga  1200
gctgtgcagc aagcggtttt ccggttaatc gttatagcat gcgttggtat cgtcaggcac  1260
cgggtaaaga acgtgaatgg gttgcaggta tgagcagtga cggtgatcgt agcagctacg  1320
aagatagcgt taaaggtcgt tttaccatca gccgtgatga tgcacgtaat accgtttatc  1380
tgcaaatgaa tagcctgaaa ccggaagata ccgcagtgta ttattgcaac gttaacgtgg  1440
gctttgaata ttggggtcag ggcacccagg ttaccgttag cagcaaactc gagcggccgc  1500
atcgtgacgc gtcgtctggt cctgccggct gccaagtcct ttggggcgtg aatcagtgga  1560
acacaggttt cacggcgaat gttaccgtca agaatacgtc ctccgctcct gttgacggct  1620
ggaccttgac cttcagtttc ccatcaggac aacaagtcac tcaagcctgg tcatctaccg  1680
tgacccagag tggatctgcg gtcacagtac gtaacgctcc gtggaacggt tcgattcccg  1740
cgggcggaac tgctcagttc gggtttaacg gaagccacac tggcactaat gctgcaccaa  1800
ctgccttctc acttaacggc acgccgtgca ccgtaggcga acagaaactg attagcgaag  1860
aagatctgga aaacctgtac ttccagggtg cgggcattag cctgagcgtg gcgagcggcg  1920
cggcgtggca tggcgcgacc caggtgctgc agagcgcgac cctgggcaaa ggcggcacct  1980
gggtggtgaa cgcggatagc cgcgtgcagg atatgacgat gcgcggcggc gcgctggaat  2040
ttcaggcgcc ggcgccggaa gcgagctata aaacctgcac cctgcagacc ctggatggca  2100
acggcgtgtt tgtgctggaa ccaaccgtgg cggcgggcca gaacgatcag ctgcgcgtga  2160
ccggccgcgc ggatgccag catcgcgtgc tggtgcgcaa cgcgggcggc gaagcggata  2220
gccgcggccg cgcctgggc ctggtgcata cccagggcca gggcaacgcg acctttcgcc  2280
tggcgaacgt gggcaaagcg gtggatctgg gcacctggcg ctatagcctg gcggaagatc  2340
cgaaaaccca tgtgtggagc ctgcagcgcg cgggccaggc gctgagcggc gcggcgaacg  2400
cggcggtgaa cgcggcggat ctgagcagca ttgcgctggc ggaaagcaac gcgctggata  2460
aacgcctggg cgaactgcgc ctgcgcgcgg atgcgggcgg cccgtgggcg cgcaccttta  2520
gcgaaccgcca gcagattagc aaccgccatg cgcgcgcgta tgatcagacc gtgagcggcc  2580
tggaaattgg cctggatcgc ggctggagcg cgagccgcga ccgctggtat gcgggcggcc  2640
tgctgggcta tacctatgcg gatcgcacct atccgggcga tggcggcggc aaagtgaaag  2700
gcctgcatgt gggcggctat gcggcgtatg tgggcgatgg cggctattat ctggataccg  2760
tgctgccgcct gggccgctat gatcagcagt ataacattgc gggcaccgat ggcggccgcg  2820
tgaccgcgga ttatcgcacc agcgcgcgcg cgtggagcct ggaaggcggc cgccgctttg  2880
aactgccgaa cgattggttt gcggaaccgc aggcggaagt gatgctgtgg cgcaccagcg  2940
gcaaacgcta tcgcgcgagc aacggcctgc gcgtgaaagt ggatgcgaac accgcgaccc  3000
tgggccgcct gggcggcgcc gcattgcgct ggcggcgggc aacattgtgc  3060
agccgtatgc gcgcctgggc tggacccagg aatttaaaag caccggcgat gtgcgcacca  3120
acggcattgg ccatgcgggc gcgggccgcc atggccgcgt ggaactgggc gcgggcgtgg  3180
atgcggcgct gggcaaaggc cataacctgt atgcgagcta tgaatatgcg gcgggcgatc  3240
gcattaacat tccgtggagc tttcatgcgg gctatcgcta tagcttttga gaattcccgg  3300
gtcgactcga gcggccgcat cgtgactgac tgacgatctg cctcgcgcgt ttcggtgatg  3360
acggtgaaaa cctctgacac atgcagctcc cggagacggt cacagcttgt ctgtaagcgg  3420
atgccggag cagacaagcc cgtcagggcg cgtcagcggg tgttggcggg tgtcggggcg  3480
cagccatgac ccagtcacgt agcgatacgg gagtgtataa ttcttgaaga cgaaagggcc  3540
tcgtgatacg cctatttttta taggttaatg tcatgataat aatggtttct tagacgtcag  3600
gtggcacttt tcggggaaat gtgcgcggaa cccctatttg tttattttc taaatacatt  3660
caaatatgta tccgctcatg agacaataac cctgataaat gcttcaataa tattgaaaaa  3720
ggaagagtat gagtattcaa catttccgtg tcgcccttat tcccttttt gcggcatttt  3780
gccttcctgt ttttgctcac ccagaaacgc tggtgaaagt aaaagatgct gaagatcagt  3840
tgggtgcacg agtgggttac atcgaactgg atctcaacag cggtaagatc cttgagagtt  3900
ttcgccccga agaacgtttt ccaatgatga gcactttaa agttctgcta tgtggcgcgg  3960
tattatccg tgttgacgcc gggcaagagc aactcggtcg ccgcatacac tattctcaga  4020
atgacttggt tgagtactca ccagtcacag aaaagcatct tacggatggc atgacagtaa  4080
gagaattatg cagtgctgcc ataaccatga gtgataacac tgcggccaac ttacttctga  4140
caacgatcgg aggaccgaag gagctaaccg cttttttgca caacatgggg gatcatgtaa  4200
ctcgccttga tcgttgggaa ccggagctga atgaagccat accaaacgac gagcgtgaca  4260
ccacgatgcc tgcagcaatg gcaacaacgt tgcgcaaact attaactggc gaactactta  4320
ctctagcttc ccggcaacaa ttaatagact ggatggaggc ggataaagtt gcaggaccac  4380
ttctgcgctc ggcccttccg gctggctggt ttattgctga taaatctgga gccggtgagc  4440
gtgggtctcg cggtatcatt gcagcactgg ggccagatgg taagccctcc cgtatcgtag  4500
ttatctacac gacggggagt caggcaacta tggatgaacg aaatagacag atcgctgaga  4560
taggtgcctc actgattaag cattggtaac tgtcagacca agtttactca tatatacttt  4620
agattgattt aaaacttcat ttttaattta aaaggatcta ggtgaagatc ctttttgata  4680
atctcatgac caaaatccct taacgtgagt tttcgttcca ctgagcgtca gaccccgtag  4740
aaaagatcaa aggatcttct tgagatcctt ttttttctgcg cgtaatctgc tgcttgcaaa  4800
caaaaaaacc accgctacca gcggtggttt gtttgccgga tcaagagcta ccaactcttt  4860
ttccgaaggt aactggcttc agcagagcgc agataccaaa tactgttcctt ctagtgtagc  4920
cgtagttagg ccaccacttc aagaactctg tagcaccgcc tacatacctc gctctgctaa  4980
tcctgttacc agtggctgct gccagtggcg ataagtcgtg tcttaccggg ttggactcaa  5040
gacgatagtt accggataag gcgcagcggt cgggctgaac ggggggttcg tgcacacagc  5100
ccagcttgga gcgaacgacc tacaccgaac tgagatacct acagcgtgag ctatgagaaa  5160
gcgccacgct tcccgaaggg agaaaggcgg acaggtatcc ggtaagcggc agggtcggaa  5220
```

```
caggagagcg cacgagggag cttccagggg gaaacgcctg gtatctttat agtcctgtcg   5280
ggtttcgcca cctctgactt gagcgtcgat ttttgtgatg ctcgtcaggg gggcggagcc   5340
tatgaaaaaa cgccagcaac gcggccttt  tacggttcct ggcctttgc  tggccttttg   5400
ctcacatgtt ctttcctgcg ttatcccctg attctgtgga taaccgtatt accgcctttg   5460
agtgagctga taccgctcgc cgcagccgaa cgaccgagcg cagcgagtca gtgagcgagg   5520
aagcggaaga gcgcctgatg cggtattttc tccttacgca tctgtgcggt atttcacacc   5580
gcataaattc cgacaccatc gaatggtgca aaacctttcg cggtatggca tgatagcgcc   5640
cggaagagag tcaattcagg gtggtgaatg tgaaaccagt aacgttatac gatgtcgcag   5700
agtatgccgg tgtctcttat cagaccgttt cccgcgtggt gaaccaggcc agccacgttt   5760
ctgcgaaaac gcgggaaaaa gtggaagcgg cgatggcgga gctgaattac attcccaacc   5820
gcgtggcaca caactggcg  ggcaaacagt cgttgctgat tggcgttgcc acctccagtc   5880
tggccctgca cgcgccgtcg caaattgtcg cggcgattaa atctcgcgcc gatcaactgg   5940
gtgccagcgt ggtggtgtcg atggtagaac gaagcggcgt cgaagcctgt aaagcggcgg   6000
tgcacaatct tctcgcgcaa cgcgtcagtg ggctgatcat taactatccg ctggatgacc   6060
aggatgccat tgctgtggaa gctgcctgca ctaatgttcc ggcgttattt cttgatgtct   6120
ctgaccagac acccatcaac agtattattt ctcccatga  agacggtacg cgactgggcg   6180
tggagcatct ggtcgcattg gtcaccagc  aaatcgcgct gttagcgggc ccattaagtt   6240
ctgtctcggc gcgtctcgt  ctggctggct gcataaaata tctcactcgc aatcaaattc   6300
agccgatagc ggaacgggaa ggcgactgga gtgccatgtc cggttttcaa caaaccatgc   6360
aaatgctgaa tgagggcatc gttcccactg cgatgctggt tgccaacgat cagatggcgc   6420
tgggcgcaat gcgcgccatt accgagtccg ggctgcgcgt tggtgcggat atctcggtag   6480
tgggatacga cgataccgaa gacagctcat gttatatccg ccgtcaacc  accatcaaac   6540
aggattttcg cctgctgggg caaaccagcg tggaccgctt gctgcaactc tctcagggcc   6600
aggcggtgaa gggcaatcag ctgttgcccg tctcactggt gaaaagaaaa accaccctgg   6660
cgcccaatac gcaaaccgcc tctccccgcg cgttggccga ttcattaatg cagctggcac   6720
gacaggtttc ccgactggaa agcgggcagt gagcgcaacg caattaatgt gagttagctc   6780
actcattagg caccccaggc tttacacttt atgcttccgg ctcgtatgtt gtgtggaatt   6840
gtgagcggat aacaatttca cacaggaaac agctatgacc atgattacgg attcactggc   6900
cgtcgtttta caacgtcgtg actgggaaaa ccctggcgtt acccaactta atcgccttgc   6960
agcacatccc cctttcgcca gctggcgtaa tagcgaagag gcccgcaccg atcgcccttc   7020
ccaacagttg cgcagcctga atggcgaatg gcgctttgcc tggtttccgg caccagaagc   7080
ggtgccggaa agctggctgg agtgcgatct tcctgaggcc gatactgtcg tcgtccctc   7140
aaaactggcag atgcacggtt acgatgcgcc catctacacc aacgtaacct atcccattac   7200
ggtcaatccg ccgtttgttc ccacggagaa tccgacgggt tgttactcgc tcacatttaa   7260
tgttgatgaa agctggctac aggaaggcca gacgcgaatt ttttgatg  gcgttggaat   7320
t                                                                  7321

SEQ ID NO: 17           moltype = DNA  length = 6283
FEATURE                 Location/Qualifiers
misc_feature            1..6283
                        note = pGEX-6P-1_NoGST_InaK-CBM
source                  1..6283
                        mol_type = other DNA
                        organism = synthetic construct
SEQUENCE: 17
acgttatcga ctgcacggtg caccaatgct tctggcgtca ggcagccatc ggaagctgtg   60
gtatgctgt  gcaggtcgta aatcactgca taattcgtgt cgctcaaggc gcactcccgt   120
tctggataat gttttttgcg ccgacatcat aacggttctg gcaaatattc tgaaatgagc   180
tgttgacaat taatcatcgg ctcgtataat gtgtggaatt gtgagcggat aacaatttca   240
cacaggaaac agtattctcc cctatactag gttattggaa aattaagggc cttgtgcaac   300
ccactcgact tcttttggaa tatcttgaag aaaaatatga agagcatttg tatgagcgcg   360
atgaaggtga taaatggcga aacaaaaagt ttgaattggg tttggagttt cccaatcttc   420
cttattatat tgatggtgat gttaaattaa cacagtctat ggccatcata cgttatatag   480
ctgacaagca aacatgttg  gtggttgtc  caaaagagcg tgcagagatt tcaatgcttg   540
aaggagcggt tttggatatt agatacggtg tttcgagaat tgcatatagt aaagactttg   600
aaactctcaa agttgattt  cttagcaagc tacctgaaat gctgaaatgt tcgaagatc   660
gtttatgtca taaacatat  ttaaatggtg atcatgtaac catcctgac  ttcatgttgt   720
atgacgctct tgatgttgtt ttatacatgg acccaatgtg cctggatgcg ttcccaaaat   780
tagtttgttt taaaaaacgt attgaagcta tcccacaaat tgataagtac ttgaaatcca   840
gcaagtatat agcatggcct ttgcagggct ggcaagccac gtttggtggt ggcgaccatc   900
ctccaaaatc ggatctggaa gttctgttcc aggggcccct gggatccatg tcttagaca   960
aggcgctagt tctacgtacc tgcgctaata atatggccga tcactgcggc ttgatttggc  1020
ctgcctcagg gaccgtcgag tcaaggtatt ggcaatctac acgtcgtcac gagaacggac  1080
tggtaggtct tctttgggga gcaggaactt ctgctttctc gtcagtccat cgagacgccg  1140
gctggatcgt gtgcgaagtg gctgttgccg atattatctc cctagaggag cccggaatgg  1200
ttaaatttcc tcgggccgaa gtggtgcatg tgggcgatcg aatcagcgct tctcatttta  1260
tttcggcgcg gcaggcagat cccgcgagta cgagtacttc aacgtcgaca agtactctta  1320
ctcccatgcc cacggcaatc cccacccta  tgccagcggt ggcgtcagtg acgttaccgg  1380
tggctgagca agcgcggcat gaggtgttg  atgtagctac tgtgagcgcc gcggctgctc  1440
ccgtgaacac tttacctgtc acgacacccc aaaacctcca gacggaaaac ctgtacttcc  1500
agggtgcgtc gtctggtcct gccggctgcc aagtcctttg ggcgtgaat  cagtggaaca  1560
caggtttcac ggcgaatgtt accgtcaaga atacgtcctc cgctcctgtt gacggctgga  1620
ccttgacctt cagtttccca tcaggacaac aagtcactca agcctggtca tctaccgtga  1680
cccagagtgg atctgccgtg acagtacgta acgtcccgcg attcccgcgg  1740
gcgggactgc tcagttcggg tttaacgaa  gccacactgg cactaatgct gcaccaactg  1800
ccttctcact taacgcacg  ccgtgcaccg taggccacca tcaccatcac catgttcagc  1860
tggttgaaag cggtggtgca ctggttcagc tggtgtag  cctgcgtctg agctgtgcag  1920
caagcggttt tccggttaat cgttatagca tgcgttggta tcgtcaggca ccgggtaaag  1980
aacgtgaatg ggttgcaggt atgagcagtg ccggtgatcc tagcagctac gaagatagcg  2040
```

```
ttaaaggtcg ttttaccatc agccgtgatg atgcacgtaa taccgtttat ctgcaaatga   2100
atagcctgaa accggaagat accgcagtgt attattgcaa cgttaacgtg ggctttgaat   2160
attggggtca gggcacccag gttaccgtta gcagcaaact cgagcggccg catcgtgacg   2220
aacagaaact gattagcgaa gaagatctgt gagaattccc gggtcgactc gagcggccgc   2280
atcgtgactg actgacgatc tgcctcgcgc gtttcggtga tgacggtgaa aacctctgac   2340
acatgcagct cccggagacg gtcacagctt gtctgtaagc ggatgccggg agcagacaag   2400
cccgtcaggg cgcgtcagcg ggtgttggcg ggtgtcgggg cgcagccatg acccagtcac   2460
gtagcgatag cggagtgtat aattcttgaa gacgaaaggg cctcgtgata cgcctatttt   2520
tataggttaa tgtcatgata ataatggttt cttagacgtc aggtggcact tttcggggaa   2580
atgtgcgcgg aaccccctatt tgtttatttt tctaaataca ttcaaatatg tatccgctca   2640
tgagacaata accctgataa atgcttcaat aatattgaaa aaggaagagt atgagtattc   2700
aacatttccg tgtcgccctt attccctttt ttgcggcatt ttgccttcct gttttgctc    2760
acccagaaac gctggtgaaa gtaaaagatg ctgaagatca gttgggtgca cgagtgggtt   2820
acatcgaact ggatctcaac agcggtaaga tccttgagag ttttcgcccc gaagaacgtt   2880
ttccaatgat gagcactttt aaagttctgc tatgtggcgc ggtattatcc cgtgttgacg   2940
ccgggcaaga gcaactcggt cgccgcatac actattctca gaatgacttg gttgagtact   3000
caccagtcac agaaaagcat cttacggatg gcatgacagt aagagaatta tgcagtgctg   3060
ccataaccat gagtgataac actgcggcca acttacttct gacaacgatc ggaggaccga   3120
aggagctaac cgcttttttg cacaacatgg gggatcatgt aactcgcctt gatcgttggg   3180
aaccggagct gaatgaagcc ataccaaacg acgagcgtga ccacgatg cctgcagcaa     3240
tggcaacaac gttgcgcaaa ctattaactg gcgaactact tactctagct tcccggcaac   3300
aattaataga ctgatggag gcggataaag ttgcaggacc acttctgcgc tcggcccttc    3360
cggctggctg gtttattgct gataaatctg gagccggtga gcgtgggtct cgcggtatca   3420
ttgcagcact ggggccagat ggtaagccct cccgtatcgt agttatctac acgacgggga   3480
gtcaggcaac tatggatgaa cgaaatagac agatcgctga gataggtgcc tcactgatta   3540
agcattggta actgtcagac caagtttact catatatact ttagattgat ttaaaacttc   3600
atttttaatt taaaaggatc taggtgaaga tcctttttga taatctcatg accaaaatcc   3660
cttaacgtga gttttcgttc cactgagcgt cagaccccgt agaaaagatc aaaggatctt   3720
cttgagatcc ttttttctg cgcgtaatct gctgcttgca acaaaaaaa ccaccgctac     3780
cagcggtggt ttgtttgccg gatcaagagc taccaactct ttttccgaag gtaactggct   3840
tcagcagagc gcagatacca aatactgtcc ttctagtgta gccgtagtta ggccaccact   3900
tcaagaactc tgtagcaccg cctacatacc tcgctctgct aatcctgtta ccagtggctg   3960
ctgccagtgg cgataagtcg tgtcttaccg ggttggactc aagacgatag ttaccggata   4020
aggcgcagcg gtcgggctga acggggggtt cgtgcacaca gcccagcttg gagcgaacga   4080
cctacaccga actgagatac ctacagcgtg agctatgaga aagcgccacg cttcccgaag   4140
ggagaaaggc ggacaggtat ccggtaagcg gcagggtcgg aacaggagag cgcacgaggg   4200
agcttccagg gggaaacgcc tggtatcttt atagtcctgt cgggtttcgc cacctctgac   4260
ttgagcgtcg atttttgtga tgctcgtcag ggggcggag cctatggaaa aacgccagca    4320
acgcggcctt tttacggttc ctggccttt gctggccttt tgctcacatg ttctttcctg    4380
cgttatcccc tgattctgtg gataaccgta ttaccgcctt tgagtgagct gataccgctc   4440
gccgcagccg aacgaccgag cgcagcgagt cagtgagcga ggaagcggaa gagcgcctga   4500
tgcggtattt tctccttacg catctgtgcg gtatttcaca ccgcataaat tccgacacca   4560
tcgaatggtg caaaacctt cgcggtatgg catgatagcg cccggaagag agtcaattca    4620
gggtggtgaa tgtgaaacca gtaacgttat acgatgtcgc agagtatgcc ggtgtctctt   4680
atcagaccgt ttcccgcgtg gtgaaccagg ccagccacgt ttctgcgaaa acgcgggaaa   4740
aagtggaagc ggcgatggcg gagctgaatt acattcccaa ccgcgtggca caacaactgg   4800
cgggcaaaca gtcgttgctg attggcgttg ccacctccag tctggccctg cacgcgccgt   4860
cgcaaattgt cgcggcgatt aaatctcgcg ccgatcaact gggtgccagc gtggtggtgt   4920
cgatggtaga acgaagcggc gtcgaagcct gtaaagcggc ggtgcacaat cttctcgcgc   4980
aacgcgtcag tgggctgatc attaactatc cgctggatga ccaggatgcc attgctgtgg   5040
aagctgcctg cactaatgtt ccggcgttat tcttgatgt ctctgaccag acacccatca    5100
acagtattat tttctcccat gaagacggta cgcgactggg cgtggagcat ctggtcgcat   5160
tgggtcacca gcaaatcgcg ctgttagcgg gcccattaag ttctgtctcg gcgcgtctgc   5220
gtctggctgg ctggcataaa tatctcactc gcaatcaaat tcagccgata gcggaacggg   5280
aaggcgactg gagtgccatg tccggttttc aacaaaccat gcaaatgctg aatgagggca   5340
tcgttcccac tgcgatgctg gttgccaacg atcagatggc gctgggcgca atgcgcgcca   5400
ttaccgagtc cgggctgcgc gttggtgcgg atatctcggt agtgggatac gacgataccg   5460
aagacagctc atgttatatc ccgccgtcaa ccaccatcaa acaggatttt cgcctgctgg   5520
ggcaaaccag cgtggaccgc ttgctgcaac tctctcaggg ccaggcggtg aagggcaatc   5580
agctgttgcc cgtctcactg gtgaaaagaa aaaccacccct ggcgcccaat acgcaaaccg   5640
cctctccccg cgcgttggcc gattcattaa tgcagctggc acgacaggtt tcccgactgg   5700
aaagcgggca gtgagcgcaa cgcaattaat gtgagttagc tcactcatta ggcacccag    5760
gctttacact ttatgcttcc ggctcgtatg ttgtgtggaa ttgtgagcgg ataacaattt   5820
cacacaggaa acagctatga ccatgattac ggattcactg gccgtcgttt tacaacgtcg   5880
tgactgggaa aaccctggcg ttacccaact taatcgcctt gcagcacatc ccccttcgc    5940
cagctggcgt aatagcgaag aggcccgcac cgatcgccct tcccaacagt tgcgcagcct   6000
gaatggcgaa tggcgctttg cctggttcc ggcaccagaa gcggtgccgg aaagctggct    6060
ggagtgcgat cttcctgagg ccgatactgt cgtcgtcccc tcaaactggc agatgcacgg   6120
ttacgatgcg cccatctaca ccaacgtaac ctatcccatt acggtcaatc cgccgtttgt   6180
tcccacggag aatccgacgg gttgttactc gctcacattt aatgttgatg aaagctggct   6240
acaggaaggc cagacgcgaa ttatttttga tggcgttgga att                    6283
```

SEQ ID NO: 18      molytype = DNA   length = 21
FEATURE            Location/Qualifiers
misc_feature       1..21
                   note = synthetic primer F2 minCKO
source             1..21
                   mol_type = other DNA
                   organism = synthetic construct -continued

```
SEQUENCE: 18
aacaacaata atgcgtgcca t                                          21

SEQ ID NO: 19           moltype = DNA  length = 20
FEATURE                 Location/Qualifiers
misc_feature            1..20
                        note = synthetic primer R2 minCKO
source                  1..20
                        mol_type = other DNA
                        organism = synthetic construct
SEQUENCE: 19
gcgctggcga tgattaatag                                            20

SEQ ID NO: 20           moltype = DNA  length = 22
FEATURE                 Location/Qualifiers
misc_feature            1..22
                        note = synthetic primer F9 minCKO
source                  1..22
                        mol_type = other DNA
                        organism = synthetic construct
SEQUENCE: 20
agtaacaaca ataatgcgtg cc                                         22

SEQ ID NO: 21           moltype = DNA  length = 16
FEATURE                 Location/Qualifiers
misc_feature            1..16
                        note = synthetic primer R9 minCKO
source                  1..16
                        mol_type = other DNA
                        organism = synthetic construct
SEQUENCE: 21
cgcgctggcg atgatt                                                16

SEQ ID NO: 22           moltype = DNA  length = 21
FEATURE                 Location/Qualifiers
misc_feature            1..21
                        note = synthetic primer F7 minDKO
source                  1..21
                        mol_type = other DNA
                        organism = synthetic construct
SEQUENCE: 22
ttccgcgaga gaaagaaatc g                                          21

SEQ ID NO: 23           moltype = DNA  length = 23
FEATURE                 Location/Qualifiers
misc_feature            1..23
                        note = synthetic primer R7 minDKO
source                  1..23
                        mol_type = other DNA
                        organism = synthetic construct
SEQUENCE: 23
gaccgttcaa ccgttaaatt gat                                        23

SEQ ID NO: 24           moltype = DNA  length = 20
FEATURE                 Location/Qualifiers
misc_feature            1..20
                        note = synthetic primer F10 minDKO
source                  1..20
                        mol_type = other DNA
                        organism = synthetic construct
SEQUENCE: 24
ctgtgttttt cttccgcgag                                            20

SEQ ID NO: 25           moltype = DNA  length = 25
FEATURE                 Location/Qualifiers
misc_feature            1..25
                        note = synthetic primer R10 minDKO
source                  1..25
                        mol_type = other DNA
                        organism = synthetic construct
SEQUENCE: 25
tcaaccgtta aattgatccc ttttt                                      25

SEQ ID NO: 26           moltype = DNA  length = 20
FEATURE                 Location/Qualifiers
misc_feature            1..20
                        note = synthetic primer F6 minCDKO
source                  1..20
                        mol_type = other DNA
```

-continued

```
SEQUENCE: 26
tccgcgagag aaagaaatcg                                                20

SEQ ID NO: 27          moltype = DNA  length = 17
FEATURE                Location/Qualifiers
misc_feature           1..17
                       note = synthetic primer R6 minCDKO
source                 1..17
                       mol_type = other DNA
                       organism = synthetic construct
SEQUENCE: 27
cgcgctggcg atgatta                                                   17

SEQ ID NO: 28          moltype = DNA  length = 20
FEATURE                Location/Qualifiers
misc_feature           1..20
                       note = synthetic primer F9 minCDKO
source                 1..20
                       mol_type = other DNA
                       organism = synthetic construct
SEQUENCE: 28
ctgtgttttt cttccgcgag                                                20

SEQ ID NO: 29          moltype = DNA  length = 16
FEATURE                Location/Qualifiers
misc_feature           1..16
                       note = synthetic primer R9 minCDKO
source                 1..16
                       mol_type = other DNA
                       organism = synthetic construct
SEQUENCE: 29
cgcgctggcg atgatt                                                    16

SEQ ID NO: 30          moltype = DNA  length = 20
FEATURE                Location/Qualifiers
misc_feature           1..20
                       note = synthetic primer 3'minCKO_1
source                 1..20
                       mol_type = other DNA
                       organism = synthetic construct
SEQUENCE: 30
ggccggataa aacttgtgct                                                20

SEQ ID NO: 31          moltype = DNA  length = 20
FEATURE                Location/Qualifiers
misc_feature           1..20
                       note = synthetic primer 3'minCKO_2
source                 1..20
                       mol_type = other DNA
                       organism = synthetic construct
SEQUENCE: 31
agtcttcgga acatcatcgc                                                20

SEQ ID NO: 32          moltype = DNA  length = 20
FEATURE                Location/Qualifiers
misc_feature           1..20
                       note = synthetic primer 5'minCKO_1
source                 1..20
                       mol_type = other DNA
                       organism = synthetic construct
SEQUENCE: 32
ccctttgccc gaagtaacaa                                                20

SEQ ID NO: 33          moltype = DNA  length = 20
FEATURE                Location/Qualifiers
misc_feature           1..20
                       note = synthetic primer 5'minCKO_2
source                 1..20
                       mol_type = other DNA
                       organism = synthetic construct
SEQUENCE: 33
acggtgaaaa cctggcctat                                                20

SEQ ID NO: 34          moltype = DNA  length = 23
FEATURE                Location/Qualifiers
misc_feature           1..23
                       note = synthetic primer minC_check_4_1
source                 1..23
```

```
                         mol_type = other DNA
                         organism = synthetic construct
SEQUENCE: 34
tcaatttaac ggttgaacgg tca                                           23

SEQ ID NO: 35           moltype = DNA   length = 20
FEATURE                 Location/Qualifiers
misc_feature            1..20
                         note = synthetic primer minC_check_4_2
source                  1..20
                         mol_type = other DNA
                         organism = synthetic construct
SEQUENCE: 35
atgtcaaaca cgccaatcga                                               20

SEQ ID NO: 36           moltype = DNA   length = 23
FEATURE                 Location/Qualifiers
misc_feature            1..23
                         note = synthetic primer minD_check_2_1
source                  1..23
                         mol_type = other DNA
                         organism = synthetic construct
SEQUENCE: 36
ttatcctccg aacaagcgtt tga                                           23

SEQ ID NO: 37           moltype = DNA   length = 23
FEATURE                 Location/Qualifiers
misc_feature            1..23
                         note = synthetic primer minD_check_2_2
source                  1..23
                         mol_type = other DNA
                         organism = synthetic construct
SEQUENCE: 37
atggcacgca ttattgttgt tac                                           23

SEQ ID NO: 38           moltype = DNA   length = 20
FEATURE                 Location/Qualifiers
misc_feature            1..20
                         note = Amplication dsRNACassette 1
source                  1..20
                         mol_type = other DNA
                         organism = synthetic construct
SEQUENCE: 38
gttttcccag tcacgacgtt                                               20

SEQ ID NO: 39           moltype = DNA   length = 18
FEATURE                 Location/Qualifiers
misc_feature            1..18
                         note = Amplication dsRNACassette 2
source                  1..18
                         mol_type = other DNA
                         organism = synthetic construct
SEQUENCE: 39
agcgagtcag tgagcgag                                                 18

SEQ ID NO: 40           moltype = DNA   length = 601
FEATURE                 Location/Qualifiers
misc_feature            1..601
                         note = C. elegans UBC9 target
source                  1..601
                         mol_type = other DNA
                         organism = synthetic construct
SEQUENCE: 40
taatacgact cactataggg cgaattgggt accgggcccc ccctcgaggt cgacggtatc    60
gataagcttg atatctgtcg ggaattgctg caggacgcct cgcggaagaa aggaaacact   120
ggcgaaagga tcatccattc ggattcattg ccaaaccagt caagaacgcc gacgaacat    180
tgaacctctt caattgggaa tgtgcaatcc cagggagaaa ggatacgatt tgggaaggcg   240
gattatacag aattcggatg ctcttcaagg acgatttccc gtcaacgcca ccaaagtgca   300
agttcgagcc accactcttc catccaaatg tgtacccatc aggtaccgtg tgcttatctc   360
ttctggatga aaacaaggat tggaagccgt caatctcaat caagcaactt ctcattggaa   420
ttcaagattt gctgaaccat ccaaatattg aagatccagc tcaggctgaa gcctatcaga   480
tctactgtca aatagggct gaatatgaga agcgagtgaa aaggaagct gtgaagtatg     540
ctgccgaact cgtccagaag cgatatcaga tctgccggtc tccctatagt gagtcgtatt   600
a                                                                   601

SEQ ID NO: 41           moltype = DNA   length = 412
FEATURE                 Location/Qualifiers
misc_feature            1..412
                         note = Colorado Potato Beetle B-Actin target
```

```
source                  1..412
                        mol_type = other DNA
                        organism = synthetic construct
SEQUENCE: 41
taatacgact cactataggg cgaattgggt accgggcccc ccctcgaggt cgacggtatc   60
gataagcttg atatcgcacg aggtttttct gtctagtgag cagtgtccaa cctcaaaaga  120
caacatgtgt gacgacgatg tagcggctct tgtcgtagac aatggatccg gtatgtgcaa  180
agccggtttc gcaggagatg acgcaccccg tgccgtcttc ccctcgatcg tcggtcgccc  240
aaggcatcaa ggagtcatgg tcggtatggg acaaaaggac tcatacgtag gagatgaagc  300
ccaaagcaaa agaggtatcc tcaccctgaa atacccccatc gaacacggta tcatcaccaa  360
ctgggatgac atgatatcag atctgccggt ctccctatag tgagtcgtat ta          412

SEQ ID NO: 42           moltype = DNA  length = 3168
FEATURE                 Location/Qualifiers
misc_feature            1..3168
                        note = L4440 CElegans vector
source                  1..3168
                        mol_type = other DNA
                        organism = synthetic construct
SEQUENCE: 42
gtgctacaga gttcttgaag tggtggccta actacggcta cactagaaga acagtatttg   60
gtatctgcgc tctgctgaag ccagttacct tcggaaaaag agttggtagc tcttgatccg  120
gcaaacaaac caccgctggt agcggtggtt ttttttgtttg caagcagcag attacgcgca  180
gaaaaaaagg atctcaagaa gatcctttga tcttttctac ggggtctgac gctcagtgga  240
acgaaaaactc acgttaaggg attttggtca tgagattatc aaaaaggatc ttcacctaga  300
tccttttaaa ttaaaaatga gttttaaat caatctaaga tatatgag taaacttggt  360
ctgacagtta ccaatgctta atcagtgagg cacctatctc agcgatctgt ctatttcgtt  420
catccatagt tgcctgactc cccgtcgtgt agataactac gatacgggag gcttaccat  480
ctggccccag tgctgcaatg ataccgcgag acccacgctc accggctcca gatttatcag  540
caataaaacca gccagccgga agggccgagc cagaagtgg tcctgcaact ttatccgcct  600
ccatccagtc tattaattgt tgccgggaag ctagagtaag tagttcgcca gttaatagtt  660
tgcgcaacgt tgttgccatt gctacaggca tcgtggtgtc acgctcgtcg tttggtatgg  720
cttcattcag ctccggttcc caacgatcaa ggcgagttac atgatccccc atgttgtgca  780
aaaaagcggt tagctccttc ggtcctccga tcgttgtcaa aagtaagttg gccgcagtgt  840
tatcactcat ggttatggca gcactgcata attctcttac tgtcatgcca tccgtaagat  900
gcttttctgt gactggtgag tactcaacca agtcattctg agaatagtgt atgcggcgac  960
cgagttgctc ttgcccggcg tcaatacggg ataataccgc gccacatagc agaactttaa 1020
aagtgctcat cattggaaaa cgttcttcgg ggcgaaaact ctcaaggatc ttaccgctgt 1080
tgagatccag ttcgatgtaa cccactcgtg cacccaactg atcttcagca tcttttactt 1140
tcaccagcgt ttctgggtga gcaaaaacag gaaggcaaaa tgccgcaaaa aagggaataa 1200
gggcgacacg gaaatgttga atactcatac tcttcctttt tcaatattat tgaagcattt 1260
atcagggtta ttgtctcatg agcggataca tatttgaatg tatttagaaa aataaacaaa 1320
taggggttcc gcgcacattt ccccgaaaag tgccacctaa attgtaagcg ttaatatttt 1380
gttaaaattc gcgttaaatt tttgttaaat cagctcattt tttaaccaat aggccgaaat 1440
cggcaaaatc ccttataaat caaaagaata gaccgagata gggttgagtg ttgttccagt 1500
ttggaacaag agtccactat taagaacgt ggactccaac gtcaaaggc gaaaaaccgt 1560
ctatcagggc gatggcccac tacgtgaacc atcacccctaa tcaagtttttt tggggtcgag 1620
gtgccgtaaa gcactaaatc ggaacccctaa agggagcccc cgatttagag cttgacgggg 1680
aaagccggcg aacgtggcga aaggaagg gaagaaagcg aaaggagcgg cgctagggc 1740
gctggcaagt gtagcggtca cgctgcgcgt aaccaccaca cccgccgcgc ttaatgcgcc 1800
gctacaggcg cgtcccatt cgccattcag gctgcgcaac tgttgggaag ggcgatcgt 1860
gcgggcctct tcgctattac gccagctggc gaaaggggga tgtgctgcaa ggcgattaag 1920
ttgggtaacg ccagggtttt cccagtcacg acgttgtaaa acgacggcca gtgagcgcgc 1980
gtaatacgac tcactatagg gcgaattggg taccgggcccc ccctcgagg tcgacggtat 2040
cgataagctt gatatctgtc gggaattgct gcaggacgc ggtcggaaga aaggaaaac 2100
tggcgaaagg atcatccatt cggattcatt gccaaaccag tcaagaacgc gacggaaca 2160
ttgaacctct tcaattggga atgtgcaatc caaggagaa aggatacgat ttgggaaggc 2220
ggattataca gaattcggat gctcttcaag gacgatttcc cgtcaacgcc accaaagtgc 2280
aagttcgagc caccactctt ccatccaaat gtgtacccat gatgctaccgt gtgcttatct 2340
cttctggatg aaaacaagga ttggaagccg tcaatctcaa tcaagcaact tctcattgga 2400
attcaagatt tgctgaacca tccaaatatt gaagatccag ctcaggctga agcctatcag 2460
atctactgtc agaatagggc tgaatatgag aagcgagtga agaaggaagc tgtgaagtat 2520
gctgccgaac tcgtccagaa gcgatatcag atctgccggt ctccctatag tgagtcgtat 2580
taatttcgat aagccaggtt gcttcctcgc tcactgactc gctgcgctcg gtcgttcggc 2640
tgcggcgagc ggtatcagct cactcaaagg cggtaatacg gttatccaca gaatcagggg 2700
ataacgcagg aaagaacatg tgagcaaaag gccagcaaaa ggccaggaac cgtaaaaagg 2760
ccgcgttgct ggcgtttttc cataggctcc gccccctga cgagcatcac aaaaatcgac 2820
gctcaagtca gaggtggcga aacccgacag gactataaag ataccaggcg tttccccctg 2880
gaagctccct cgtgcgctct cctgttccga cctgccgat taccggatac ctgtccgcct 2940
ttctcccttc gggaagcgtg gcgctttctc atagctcacg ctgtaggtat ctcagttcgg 3000
tgtaggtcgt tcgctccaag ctgggctgtg tgcacgaacc ccccgttcag cccgaccgct 3060
gcgccttatc cggtaactat cgtcttgagt ccaacccggt aagacacgac ttatcgccac 3120
tggcagcagc cactggtaac aggattagca gagcgaggta tgtaggcg              3168

SEQ ID NO: 43           moltype = DNA  length = 2979
FEATURE                 Location/Qualifiers
misc_feature            1..2979
                        note = L4440 CPB B-Actin vector sequence
source                  1..2979
```

```
                    mol_type = other DNA
                    organism = synthetic construct
SEQUENCE: 43
gtgctacaga gttcttgaag tggtggccta actacggcta cactagaaga acagtatttg    60
gtatctgcgc tctgctgaag ccagttacct tcggaaaaag agttggtagc tcttgatccg   120
gcaaacaaac caccgctggt agcggtggtt tttttgtttg caagcagcag attacgcgca   180
gaaaaaaagg atctcaagaa gatcctttga tcttttctac ggggtctgac gctcagtgga   240
acgaaaactc acgttaaggg attttggtca tgagattatc aaaaaggatc ttcacctaga   300
tccttttaaa ttaaaaatga agttttaaat caatctaaag tatatatgag taaacttggt   360
ctgacagtta ccaatgctta atcagtgagg cacctatctc agcgatctgt ctatttcgtt   420
catccatagt tgcctgactc cccgtcgtgt agataactac gatacgggag ggcttaccat   480
ctggccccag tgctgcaatg ataccgcgag acccacgctc accggctcca gatttatcag   540
caataaacca gccagccgga agggccgagc gcagaagtgg tcctgcaact ttatccgcct   600
ccatccagtc tattaattgt tgccgggaag ctagagtaag tagttcgcca gttaatagtt   660
tgcgcaacgt tgttgccatt gctacaggca tcgtggtgtc acgctcgtcg tttggtatgg   720
cttcattcag ctccggttcc caacgatcaa ggcgagttac atgatccccc atgttgtgca   780
aaaaagcggt tagctccttc ggtcctccga tcgttgtcag aagtaagttg gccgcagtgt   840
tatcactcat ggttatggca gcactgcata attctcttac tgtcatgcca tccgtaagat   900
gcttttctgt gactggtgag tactcaacca agtcattctg agaatagtgt atgcggcgac   960
cgagttgctc ttgcccggcg tcaatacggg ataataccgc gccacatagc agaactttaa  1020
aagtgctcat cattggaaaa cgttcttcgg ggcgaaaact ctcaaggatc ttaccgctgt  1080
tgagatccag ttcgatgtaa cccactcgtg cacccaatctg atcttcagca tcttttactt  1140
tcaccagcgt ttctgggtga gcaaaaacag gaaggcaaaa tgccgcaaaa aagggaataa  1200
gggcgacacg gaaatgttga atactcatac tcttcctttt tcaatattat tgaagcattt  1260
atcagggtta ttgtctcatg agcggataca tatttgaatg tatttagaaa aataaacaaa  1320
taggggttcc gcgcacattt ccccgaaaag tgccacctaa attgtaagcg ttaatatttt  1380
gttaaaattc gcgttaaatt tttgttaaat cagctcattt tttaaccaat aggccgaaat  1440
cggcaaaatc ccttataaat caaaagaata gaccgagata gggttgagtg ttgttccagt  1500
ttggaacaag agtccactat taaagaacgt ggactccaac gtcaaagggc gaaaaaccgt  1560
ctatcagggc gatggcccac tacgtgaacc atcacccctaa tcaagttttt tggggtcgag  1620
gtgccgtaaa gcactaaatc ggaacccta agggagcccc cgatttagag cttgacgggg  1680
aaagccggcg aacgtggcga aaggaaggg aagaaagcg aaaggagcgg gcgctagggc   1740
gctggcaagt gtagcggtca cgctgcgcgt aaccaccaca cccgccgcgc ttaatgcgcc   1800
gctacagggc gcgtcccatt cgccattcag gctgcgcaac tgttgggaag ggcgatcggt   1860
gcgggcctct tcgctattac gccagctggc gaaaggggga tgtgctgcaa ggcgattaag   1920
ttgggtaacg ccagggtttt cccagtcacg acgttgtaaa acgacggcca gtgagcgcgc   1980
gtaatacgac tcactatagg gcgaattggg taccggcccc ccctcgagg tcgacggtat   2040
cgataagctt gatatcgcac gaggtttttc tgtctagtga gcagtgtcca acctcaaaag   2100
acaacatgtg tgacgacgat gtagcgggctc ttgtcgtaga caatggatcc ggtatgtgca   2160
aagccggttt cgcaggagat gacgcacccc gtgccgtctt cccctcgatc gtcggtcgcc   2220
caaggcatca aggagtcatg gtcggtatgg gacaaaagga ctcatacgta ggagatgaag   2280
cccaaagcaa aagaggtatc ctcaccctga aatacccat cgaacacggt atcatcacca   2340
actgggatga catgatatca gatctgccgg tctccctata gtgagtcgta ttaatttcga   2400
taagccaggt tgcttcctcg ctcactgact cgctgcgctc ggtcgttcgg ctgcggcgag   2460
cggtatcagc tcactcaaag gcggtaatac ggttatccac agaatcaggg gataacgcag   2520
gaaagaacat gtgagcaaaa ggccagcaaa aggccaggaa ccgtaaaaag gccgcgttgc   2580
tggcgttttt ccataggctc cgcccccctg acgagcatca caaaaatcga cgctcaagtc   2640
agaggtggcg aaacccgaca ggactataaa gataccaggc gtttcccct ggaagctccc   2700
tcgtgcgctc tcctgttccg accctgccgc ttaccggata cctgtccgcc tttctccctt   2760
cgggaagcgt ggcgctttct catagctcac gctgtaggta tctcagttcg gtgtaggtcg   2820
ttcgctccaa gctgggctgt gtgcacgaac cccccgttca gcccgaccgc tgcgccttat   2880
ccggtaacta tcgtcttgag tccaacccgg taagacacga cttatcgcca ctggcagcag   2940
ccactggtaa caggattagc agagcgaggt atgtaggcg                         2979

SEQ ID NO: 44         moltype = DNA  length = 3981
FEATURE               Location/Qualifiers
misc_feature          1..3981
                      note = BrK-ACC Deaminase expression cassette
source                1..3981
                      mol_type = other DNA
                      organism = synthetic construct
SEQUENCE: 44
ttgacaatta atcatcggct cgtataatgt gtggaattgt gagcggataa caatttcaca    60
caggaaacag tattctcccc tatactaggt tattggaaaa ttaagggcct tgtgcaaccc   120
actcgacttc ttttggaata tcttgaagaa aaatatgaag agcatttgta tgagcgcgat   180
gaaggtgata aatggcgaaa caaaaagttt gaattgggtt tggagtttcc caatcttcct   240
tattatattg atggtgatgt taaattaaca cagtctatgg ccatcatacg ttatatagct   300
gacaagcaca acatgttggg tggttgtcca aaagagcgtg cagagatttc aatgcttgaa   360
ggagcggttt tggatattag atacggtgtt tcgagaatga catatgtaa agactttgaa   420
actctcaaag ttgattttct tagcaagcta cctgaaatgc tgaaaatgtt cgaagatcgt   480
ttatgtcata aaacatattt aaatggtgat catgtaaccc atcctgactt catgttgtat   540
gacgctcttg atgttgtttt atacatggac caatgtgcc tggatgcgtt cccaaaatta   600
gttttgttta aaaacgtat tgaagctatc ccacaaattg ataagtactt gaaatccagc   660
aagtatatag catggccttt gcagggctgg caagccatgt tggtggtgg cgaccatcct   720
ccaaaatcgg atctgaagt tctgttccag gggcccctgg atccatgta tctgatcgc   780
tttcgccagt gcccgagcag cctgcagatt ccgcgcagcc cgtggcgcct gcatgcgctg   840
gcggcggcgc tggcgctggc gggcatggcg cgcctggcgc cggcggcggc gcaggcgccg   900
cagccgccgg tggcgggcgc gccgcatgcg caggatgcgg gccaccatca ccatcaccat   960
gttcagctgg ttgaaagcgg tggtgcactg gttcagcctg gtggtagcct gcgtctgagc  1020
```

```
tgtgcagcaa gcggttttcc ggttaatcgt tatagcatgc gttggtatcg tcaggcaccg 1080
ggtaaagaac gtgaatgggt tgcaggtatg agcagtgccg gtgatcgtag cagctacgaa 1140
gatagcgtta aaggtcgttt taccatcagc cgtgatgatg cacgtaatac cgtttatctg 1200
caaatgaata gcctgaaacc ggaagatacc gcagtgtatt attgcaacgt taacgtgggc 1260
tttgaatatt ggggtcaggg cacccaggtt accgttagca gcaaactgca gcggccgcat 1320
cgtgacatgc gcggacgctc actgacgctg agccgcgtaa agttggaact ggcccgccgc 1380
tccatgtcgg ctacttcagt gcctagcatg gcggacttct tgaccaagaa accctattcc 1440
cctccctcat gggcatcaca cttacgccct ttacctagcc ataccttctc gctggcccat 1500
cttccgaccc cgattcaccg ctggaatctt cccggtctgc cgaatgggac tgagttatgg 1560
attaagcgcg acgatttcac gggtatggaa ttgtcgggta acaaagttcg taaattggag 1620
tttcttatgg ccgaagcggt ggaccaacat gccgacacag ttatcaccat cggtggcatt 1680
cagagtaatc actgccgtgc taccgcgacg gcgtcgaatt atcttaacct gaattcgcac 1740
ttgattcttc gcacatccaa actgctggct gacgaagatc ctgggttggt tggcaacctt 1800
ctggtggaag gcctggtagg ggcaacgtt catcttattt cgaaggagga gtatagttca 1860
attgggtccg aagctttgac caacgcactg aaagagaagt tagagaaaga gggaaaaaag 1920
ccctatgtca tccccgtcgg tggctctaac tccctgggta catggggtta tatcgaagcc 1980
gctcgtgaga ttgaagaaca gttgaactat cgcccggatg acttaaaatt tgatgatatt 2040
gttgtggctt gtggtagcgg tggcactatc gcgggcattt ctctgggttc atggttaggg 2100
gcattgaagg ccaaagtcca cgcttttttct gtatgtgatg acccggacta cttttacgat 2160
ttcgtgcagg ggctgcttga cggtttgcat gcaggcgtga attctcgtga cattgttaat 2220
attcacaatg ctaagggtaa gggatacgcc atgaacacga gcgaagaatt ggagtttgtg 2280
aagaaggtgg cctcgtctac tggagtgatt ctggatccaa tttactccgg taaagccgct 2340
tatggcttga ttaacgaaat caccaaagat cccaagtgct gggagggcg taaaatcctt 2400
ttcattcata cgggcggttt gcttggctta tatgataaag ttgaccaaat ggcatccctt 2460
atgggaaact ggagtcgcat ggatgtcagc gaatccgtcc cacgcaagga cggtgttggc 2520
aagatgttcg aacagaaact gattagcgaa gaagatctgg aaaacctgta cttccagggt 2580
gcgggcatta gcctgagcgt ggcgagcggc gcggcgtggc atggcgcgac ccaggtgctg 2640
cagagcgcga ccctgggcaa aggcggcacc tgggtggtga acgcggatag ccgcgtgcag 2700
gatatgagca tgcgcggcgg ccgcgtgaaa tttcaggcgc cggcgccgga agcgagctat 2760
aaaacccgtga ccctgcagac cctgatggcc aacggcgtgt ttgtgctgaa caccaacgtg 2820
gcggcgggcc agaacgatca gctgcgcgtg accggccgcg gcgatggcca gcatcgcgtg 2880
ctggtgcgca acgcgggcgg cgaagcggat agccgcggcg cgcgcctggg cctggtgcat 2940
acccagggcc agggcaacgc gacctttcgc ctggcgaacg tgggcaaagc ggtggatctg 3000
ggcacctggc gctatagcct ggcggaagat ccgaaaaacc atgtgtggag cctgcagcgc 3060
gcgggccagg cgctgagccg cgcggcgaac gcgcggtga acgcggcgga tctgagcagc 3120
attgcgctgg cggaaagcaa cgcgctggat aaacgcctgg gcgaactgcg cctgcgcgcg 3180
gatgcgggcg cccgtgggc gcgcaccttt agcgaacgcc agcagattag caaccgccat 3240
gcgcgcgcgt atgatcagac cgtgagcggc ctggaaattg gcctggatcg cggctggagc 3300
gcgagcggcg gccgctggta tgccggcggc ctgctggcgt ataccatgc ggatcgcacc 3360
tatccgggcg atggcggcgg caaagtgaaa ggcctgcatg tgggcggcta tgcggcgtat 3420
gtgggcgatg gcggctatta tctggatacc gtgctgcgcc tgggccgcta tgatcagcag 3480
tataacattg cgggcaccga tggcggccgc gtgaccgcgg attatcgcac cagcggcgcg 3540
gcgtggagcc tggaaggcgg ccgccgcttt gaactgcgca acgattggtt tgcggaaccg 3600
caggcggaag tgatgctgtg gcgcaccagc ggcaaacgct atcgcgcgag caacggcctg 3660
cgcgtgaaag tggatgcgaa caccgcgacc ctgggccgcc tgggcctgcg ctttggccgc 3720
cgcattgcgc tggcgggcgg caacattgtg cagccgtatg cgcgcctggg ctggacccag 3780
gaatttaaaa gcaccggcga tgtgcgcacc aacggcatg cgcggcgcg cgcggggcgc 3840
catgccgcg tggaactggg cgcgggcgtg gatgcggcgc tgggcaaagg ccataacctg 3900
tatgcgagct atgaatatgc ggcgggcgat cgcattaaca ttccgtggag ctttcatgcg 3960
ggctatcgct atagcttttg a                                           3981

SEQ ID NO: 45          moltype = DNA   length = 8194
FEATURE                Location/Qualifiers
misc_feature           1..8194
                       note = pGEX-6P-1_Brk-ACC Deaminase vector
source                 1..8194
                       mol_type = other DNA
                       organism = synthetic construct
SEQUENCE: 45
acgttatcga ctgcacggtg caccaatgct tctggcgtca ggcagccatc ggaagctgtg 60
gtatggctgt gcaggtcgta aatcactgca taattcgtgt cgctcaaggc gcactcccgt 120
tctgataat gttttttgcg ccgacatcat aacggttctg gcaaatattc tgaaatgagc 180
tgttgacaat taatcatcgg ctcgtataat gtgtggaatt gtgagcggat aacaatttca 240
cacaggaaac agtattctcc cctatactag gttattgaaa aattaaggcc cttgtgcaac 300
ccactcgact tcttttggaa tatcttgaag aaaaatatga agagcattg tatgagcgcg 360
atgaaggtga taaatggcga acaaaaaagt ttgaattggg tttggagttt cccaatcttc 420
cttattatat tgatggtgat gttaaattaa cacagtctat ggccatcata cgttatatag 480
ctgacaagca caacatgttg ggtggttgtc caaaagagcg tgcagattt caatgcttg 540
aaggagcggt tttggatatt agatacggtg ttcgagaat tgcatatagt aaagactttg 600
aaactctcaa agttgatttt cttagcaagc tacctgaaat gctgaaaatg ttcgaagatc 660
gtttatgtca taaaacatat ttaaatggtg atcatgtaac catcctgac ttcatgttgt 720
atgacgctct tgatgttgtt ttatacatgg acccaatgtg cctggatgcg ttcccaaaat 780
tagtttgttt taaaaacgt attgaagcta tcccacaaat tgataagtac ttgaaatcca 840
gcaagtatat gcatgcct ttgcaggct gcaagcac gtttggtggt ggcgaccatc 900
ctccaaaatc ggatctggaa gttctgttcc aggggcccct gggatccatg tatctggatc 960
gctttcgcca gtgccgagc agcctgcaga ttccgcgcag cgctggcgc ctgcatcgc 1020
tggcggcggc gctggcgctg gcgggcatgg gcgcctggc gccggcggcg gcgcaggcgc 1080
cgcagccgcc ggtggcgggc gcgccgcatg cgcaggatgg gggccaccat caccatcacc 1140
atgttcagct ggttgaaagc ggtggtgcac tggttcagcc tggtggtagc ctgcgtctga 1200
```

```
gctgtgcagc aagcggtttt ccggttaatc gttatagcat gcgttggtat cgtcaggcac 1260
cgggtaaaga acgtgaatgg gttgcaggta tgagcagtgc cggtgatcgt agcagctacg 1320
aagatagcgt taaaggtcgt tttaccatca gccgtgatga tgcacgtaat accgtttatc 1380
tgcaaatgaa tagcctgaaa ccggaagata ccgcagtgta ttattgcaac gttaacgtgg 1440
gctttgaata ttggggtcag ggcacccagg ttaccgttag cagcaaactc gagcggccgc 1500
atcgtgacat gcgcggacgc tcactgacgc tgagccgcgt aaagttggaa ctggcccgcc 1560
gctccatgtc ggctacttca gtgcctagca tggcggactt cttgaccaag aaaccctatt 1620
cccctccctc atgggcatca cacttacgcc ctttacctag ccataccttc tcgctggccc 1680
atcttccgac cccgattcac cgctggaatc ttcccggtct gccgaatggg actgagttat 1740
ggattaagcg cgacgatttc acgggtatgg aattgtcggg taacaaagtt cgtaaattgg 1800
agtttcttat ggccgaagcg gtggaccaac atgccgacac agttatcacc atcggtggca 1860
ttcagagtaa tcactgccgt gctaccgcga cggcgtcgaa ttatcttaac ctgaattcgc 1920
acttgattct tcgcacatcc aaactgctgg ctgacgaaga tcctgggttg gttggcaacc 1980
ttctggtgga gcgcctggta ggggccaacg ttcatcttat ttcgaaggag gagtatagtt 2040
caattgggtc cgaagctttg accaacgcac tgaaagagaa gttagagaaa gagggaaaaa 2100
agccctatgt catcccgtc ggtggctcta actccctggg tacatggggt tatatcgaag 2160
ccgctcgtga gattgaagaa cagttgaact atcgcccgga tgacttaaaa tttgatgata 2220
ttgttgtggc ttgtggtagc ggtgcacta tcgcgggcat ttctctgttg tcatggttag 2280
gggcattgaa ggccaaagtc cacgcttttt ctgtatgtga tgacccggac tacttttacg 2340
atttcgtgca gggctgctt gacggttttgc atgcaggcgt gaattctcgt gacattgtta 2400
atattcacaa tgctaagggt aagggatacg ccatgaacac gagcgaagaa ttggagtttg 2460
tgaagaaggt ggcctcgtct actggagtga ttctggaatc agtttactcc ggtaaagcgg 2520
cttatggctt gattaacgaa atcaccaaag atcccaagtg ctgggagggg cgtaaaatcc 2580
ttttcattca tacgggcggt ttgcttggct tatatgataa agttgaccaa atggcatccc 2640
ttatgggaaa ctggagtcgc atggatgtca gcgaatccgt cccacgcaag gacggtgttg 2700
gcaagatgtt cgaacagaaa ctgattagcg aagaagatct ggaaaacctg tacttccagg 2760
gtgcgggcat tagcctgagc gtggcgagcg gcgcggcgtg gcatggcgcg acccaggtgc 2820
tgcagagcgc gaccctgggc aaaggcggca cctgggtggt gaacgcggat agccgcgtgc 2880
aggatatgag catgcgcggc ggccgcgtgg aatttcaggc gccggcgccg gaagcgagct 2940
ataaaaccct gaccctgcag accctggatg gcaacgcgcg gtttgtgctg aacaccaacg 3000
tggcggcggg ccagaacgat cagctgcgcg tgaccgcccg cgcggatggc cagcatcgcc 3060
tgctggtgcg caacgcgggc ggcgaagcgg atagccgcgg cgcgcgcctg ggcctggtgc 3120
ataccaggg ccagggcaac gcgacctttc gcctggcgaa cgtgggcaaa gcggtggatc 3180
tgggcacctg gcgctatagc ctggcggaag atccgaaaac ccatgtgtgg agcctgcagc 3240
gcgcgggcca ggcgctgagc ggcgcgggcg acgcggcggt gaacgcggcg gatctgagca 3300
gcattgcgct ggcggaaagc aacgcgctgg ataaacgcct gggcgaactg cgcctgcgca 3360
cggatgcggg cggcccgtgg gcgcgcacct ttagcgaacg ccagcagatt agcaaccgcc 3420
atgcgcgcgc gtatgatcag accgtgagcg gcctggaaat tggcctggat cgcggctgga 3480
gcgcgagcgg cggccgctgg tatgcgggcg gcctgctggg ctatacctat gcggatcgca 3540
cctatccggg cgatgcggc ggcaaagtga aaggcctgca tgtgggcggc tatgcggcgt 3600
atgtgggcga tggcggctat tatctggata ccgtgctgcg cctgggccgc tatgatcagc 3660
agtataacat tgcgggcacc gatggcggcc gcgtgaccgc ggattatcgc accagcggcg 3720
cggcgtggag cctggaaggc ggccgccgct ttgaactgcc gaacgattgg tttgcggaac 3780
cgcaggcgga agtgatgctg tggcgcacca gcggcaaacg ctatcgcgcg agcaacggcc 3840
tgcgcgtgaa agtggatgcg aacaccgcga ccctgggccg cctgggcctg cgctttggcc 3900
gccgcattgc gctggcgggc ggcaacattg tgcagccgta tgcgcgcctg ggctggaccc 3960
aggaatttaa aagcaccggc gatgtgcgca ccaacgcgat tggccatgcg ggcgcgggcc 4020
gccatgccg cgtggaactg ggcgcggggc tggatgcgcg gctgggcaaa ggccataacc 4080
tgtatgcgag ctatgaatat gcggcgggcg atcgcattaa cattccgtgg agctttcatg 4140
cgggctatcg ctatagcttt tgagaattcc cgggtcgact cgagcggccg catcgtgact 4200
gactgacgat ctgcctcgcg cgtttcggtg atgacggtga aaacctctga cacatgcagc 4260
tcccggagac ggtcacagct tgtctgtaag cggatgccgg gagcagacaa gcccgtcagg 4320
gcgcgtcagc gggtgttggc gggtgtcggg gcgcagccat gacccagtca cgtagcgata 4380
gcggagtgta taattcttga agacgaaagg gcctcgtgat acgcctattt ttataggtta 4440
atgtcatgat aataatggtt tcttagacgt caggtggcac ttttcgggga aatgtgcgcg 4500
gaacccctat ttgtttattt ttctaaaatac attcaaatat gtatccgctc atgagacaat 4560
aaccctgata aatgcttcaa taatattgaa aaaggaagag tatgagtatt caacatttcc 4620
gtgtcgccct tattccctt tttgcggcat tttgccttcc tgtttttgct cacccagaaa 4680
cgctggtgaa agtaaaagat gctgaagatc agttgggtgc acgagtgggt tacatcgaac 4740
tggatctcaa cagcggtaag atccttgaga gttttcgccc cgaagaacgt tttccaatga 4800
tgagcacttt taaagttctg ctatgtggcg cggtattatc ccgtgttgac gccgggcaag 4860
agcaactcgg tcgccgcata cactattctc agaatgactt ggttgagtac tcaccagtca 4920
cagaaaagca tcttacggat ggcatgacag taagagaatt atgcagtgct gccataacca 4980
tgagtgataa cactgcggcc aacttactt gacaacgat cggaggaccg aaggagctaa 5040
ccgctttttt gcacaacatg ggggatcatg taactcgcct tgatcgttgg aaccggagc 5100
tgaatgaagc cataccaaac gacgagcgtg acaccacgat gcctgcagca atggcaacaa 5160
cgttgcgcaa actattaact ggcgaactac ttactctagc ttcccggcaa caattaatag 5220
actggatgga ggcggataaa gttgcaggac cacttctgcg ctcggccctt ccggctggct 5280
ggtttattgc tgataaatct ggagccggtg agcgtgggtc tcgcggtatc attgcagcac 5340
tggggccaga tggtaagccc tcccgtatcg tagttatcta cacgacgggg agtcaggcaa 5400
ctatgatga acgaaataga cagatcgctg agataggtgc ctcactgatt aagcattggt 5460
aactgtcaga ccaagtttac tcatatatac tttagattga tttaaaactt cattttaat 5520
ttaaaaggat ctaggtgaag atcctttttg ataatctcat gaccaaaatc ccttaacgtg 5580
agttttcgtt ccactgagcg tcagacccc g tagaaaagat caaaggatct tcttgagatc 5640
cttttttct gcgcgtaatc tgctgcttgc aaacaaaaaa accaccgcta ccagcggtgg 5700
tttgtttgcc ggatcaagag ctaccaactc tttttccgaa ggtaactggc ttcagcagag 5760
cgcagatacc aaatactgtc cttctagtgt agccgtagtt aggccaccac ttcaagaact 5820
ctgtagcacc gcctacatac ctcgctctgc taatcctgtt accagtggct gctgccagtg 5880
gcgataagtc gtgtcttacc gggttggact caagacgata gttaccggat aaggcgcagc 5940
```

-continued

```
ggtcgggctg aacgggggt tcgtgcacac agcccagctt ggagcgaacg acctacaccg 6000
aactgagata cctacagcgt gagctatgag aaagcgccac gcttcccgaa gggagaaagg 6060
cggacaggta tccggtaagc ggcagggtcg gaacaggaga gcgcacgagg gagcttccag 6120
ggggaaacgc ctggtatctt tatagtcctg tcgggtttcg ccacctctga cttgagcgtc 6180
gatttttgtg atgctcgtca gggggcgga gcctatggaa aaacgccagc aacgcggcct 6240
ttttacggtt cctggccttt tgctggcctt ttgctcacat gttctttcct gcgttatccc 6300
ctgattctgt ggataaccgt attaccgcct ttgagtgagc tgataccgct cgccgcagcc 6360
gaacgaccga gcgcagcgag tcagtgagcg aggaagcgga agagcgcctg atgcggtatt 6420
ttctccttac gcatctgtgc ggtatttcac accgcataaa ttccgacacc atcgaatggt 6480
gcaaaacctt tcgcggtatg gcatgatagc gcccggaaga gagtcaattc agggtggtga 6540
atgtgaaacc agtaacgtta tacgatgtcg cagagtatgc cggtgtctct tatcagaccg 6600
tttcccgcgt ggtgaaccag gccagccacg tttctgcgaa aacgcgggaa aaagtggaag 6660
cggcgatggc ggagctgaat tacattccca accgcgtggc acaacaactg gcgggcaaac 6720
agtcgttgct gattggcgtt gccacctcca gtctggccct gcacgcgccg tcgcaaattg 6780
tcgcggcgat taaatctcgc gccgatcaac tgggtgccag cgtggtggtg tcgatggtag 6840
aacgaagcgg cgtcgaagcc tgtaaagcgg cggtgcacaa tcttctcgcg caacgcgtca 6900
gtgggctgat cattaactat ccgctggatg accaggatgc cattgctgtg gaagctgcct 6960
gcactaatgt tccggcgtta tttcttgatg tctctgacca gacacccatc aacagtatta 7020
ttttctccca tgaagacggt acgcgactgg gcgtggagca tctggtcgca ttgggtcacc 7080
agcaaatcgc gctgttagcg ggcccattaa gttctgtctc ggcgcgtctg cgtctggctg 7140
gctggcataa atatctcact cgcaatcaaa ttcagccgat agcggaacgg gaaggcgact 7200
ggagtgccat gtccggtttt caacaaacca tgcaaatgct gaatgagggc atcgttccca 7260
ctgcgatgct ggttgccaac gatcagatgg cgctgggcgc aatgcgcgcc attaccgagt 7320
ccgggctgcg cgttggtgcg gatatctcgg tagtgggata cgacgatacc gaagacagct 7380
catgttatat cccgccgtca accaccatca aacaggattt tcgcctgctg gggcaaacca 7440
gcgtggaccg cttgctgcaa ctctctcagg gccaggcggt gaagggcaat cagctgttgc 7500
ccgtctcact ggtgaaaaga aaaaccaccc tggcgcccaa tacgcaaacc gcctctcccc 7560
gcgcgttggc cgattcatta atgcagctgg cacgacaggt ttcccgactg gaaagcgggc 7620
agtgagcgca acgcaattaa tgtgagttag ctcactcatt aggcacccca ggctttacac 7680
tttatgcttc cggctcgtat gttgtgtgga atttgtgagcg gataacaatt tcacacagga 7740
aacagctatg accatgatta cggattcact ggccgtcgtt ttacaacgtc gtgactggga 7800
aaaccctggc gttacccaac ttaatcgcct tgcagcacat ccccctttcg ccagctggcg 7860
taatagcgaa gaggcccgca ccgatcgccc ttcccaacag ttgcgcagcc tgaatggcga 7920
atggcgcttt gcctggtttc cggcaccaga agcggtgccg gaaagctggc tggagtgcga 7980
tcttcctgag gccgatactg tcgtcgtccc ctcaaactgg cagatgcacg gttacgatgc 8040
gcccatctac accaacgtaa cctatcccat tacggtcaat ccgccgtttg ttcccacgga 8100
gaatccgacg ggttgttact cgctcacatt taatgttgat gaaagctggc tacaggaagg 8160
ccagacgcga attatttttg atggcgttgg aatt                          8194
```

COMPOSITIONS AND METHODS FOR SCALABLE PRODUCTION AND DELIVERY OF BIOLOGICALS

CROSS-REFERENCE TO RELATED APPLICATIONS

This application is a continuation of U.S. application Ser. No. 16/649,857, filed Mar. 23, 2020, now U.S. Pat. No. 11,812,743, which is a national phase of International Application No. PCT/US2018/052690, filed Sep. 25, 2018, which claims the benefit of priority to U.S. provisional application No. 62/666,981 filed on May 4, 2018 and U.S. provisional application No. 62/562,723 filed on Sep. 25, 2017, the contents of each of which are hereby incorporated by reference in their entirety for all purposes.

FIELD

The present disclosure is generally directed to formulations, platforms, compositions and methods for encapsulating biologically active compounds within achromosomal and/or anucleated cells. The present disclosure provides scalable delivery of biologically active compounds encapsulated in achromosomal and/or anucleated cells to a desired target. Also, disclosed herein are methods for encapsulating and delivering biologically active compounds onto and/or into a target in a stable and scalable manner.

STATEMENT REGARDING SEQUENCE LISTING

The contents of the electronic sequence listing (AGRO_004_04US_SeqList_ST26.xml; Size: 120,553 bytes; and Date of Creation: Aug. 16, 2023) are herein incorporated by reference in its entirety.

BACKGROUND

With expected growth of world population to over 9 billion by 2050, human society will face the biggest challenges of being able to feed the people. The Food and Agriculture Organization of the United Nations (FAO) estimates that 80% of the necessary increases in food production keep pace with population growth are projected to come from increases in yields and the number of times per year crops can be grown on the same land. Only 20% of new food production is expected to come from expansion of farming land. Global efforts to increase future crop harvest and food production is required to meet future challenges. Pesticides play a significant role in agriculture and food production to prevent large crop losses. Pesticides can help producing food by controlling pest such as insects, rodents, weeds, bacteria, mold and fungus and by increasing yields and the number of times per year a crop can be grown on the same land.

However, there are a continuing concern about the negative effects of pesticides on human health and the surrounding environment. Pesticides are potentially toxic to humans and can have both acute and chronic health effects, depending on the quantity and ways in which a person is exposed. Some pesticides can remain for years in soil and water, which can make environment more contaminated and harmful. People who face the greatest health risks from exposure to pesticides are those who come into contact with them at work, in their home or garden. Due to the unintended consequences that conventional pesticides pose on society, applications for alternative ways to prevent pests from destroying crops without the detrimental effects of pesticides is of utmost importance.

On the other hand, fertilizers have been important to increase crop yields as a growth stimulant. However, chemically-based conventional fertilizers make people suffered from similar negative impacts that the pesticides possess. Not only pesticides as a controlling agent, but also fertilizer as a stimulating agent, have issues on reduced efficacy of the chemicals and losses of chemicals into the soil due to dripping off from a target while spraying or due to wash-out during rainfall, which may result in groundwater contamination, environmental damage, loss of functional activity, and human and animal health problems.

Thus, there is an unmet need to develop a new delivery system to ensure the targeted delivery of biologically active compounds such as biocontrols and/or biostimulants. Also, there is a great need for an efficient encapsulation and delivery platform for sustaining bioactivity of the biocontrols and/or biostimulants until the biologically active compounds are delivered to their intended targets in a scalable, targeted, cost-effective manner.

SUMMARY OF THE DISCLOSURE

The present disclosure is directed to an agricultural formulation comprising an intact minicell for encapsulation and delivery of biologically active compounds and application of the agricultural formulation to a desired locus such as a plant or a pest. The present disclosure is also directed to an anucleated minicell for encapsulation and delivery of biologically active compounds and application of the platform to a desired locus such as a plant or a pest. The present disclosure is provided to platforms, compositions, formulations and methods for encapsulating biologically active compounds within achromosomal and/or anucleated minicells. The present disclosure provides scalable delivery of biologically active compounds encapsulated in achromosomal and/or anucleated minicells to a desired target. Also, disclosed herein are methods for encapsulating and delivering biologically active compounds onto and/or into a target in a stable and scalable manner.

In some embodiments, an agricultural formulation is provided, which comprises a) an intact minicell comprising at least one biologically active compound within said minicell, wherein said biologically active compound is selected from the group consisting of i) a nucleic acid, wherein the nucleic acid targets a transcript encoding a polypeptide within a cell of a target, ii) a biocontrol compound, wherein the biocontrol compound is active against a pest, and iii) a biostimulant compound, wherein the biostimulant compound stimulates growth or health of a plant. In some embodiments, said target is a plant or a pest. In some embodiments, said minicell is applied with at least one agricultural suitable additive or adjuvant. In some embodiments, said minicell is derived from a prokaryotic cell, a gram-negative bacterial cell, a gram-positive bacterial cell, or an eukaryotic cell. In other embodiments, said minicell is derived from endophytes or plant pathogenic bacteria.

In some embodiments, said minicell is protease deficient or ribonuclease deficient. In some embodiments, said minicell is protease deficient. In some embodiments, said minicell is ribonuclease deficient. In some embodiments, said minicell is protease deficient and ribonuclease deficient. In some embodiments, said minicell is protease-deficient, and wherein said biologically active compound is a protein. In some embodiments, said minicell is ribonuclease-deficient, and wherein said biologically active compound is a nucleic acid. In some embodiments, said biologically active compound is said nucleic acid that is selected from the group consisting of an antisense nucleic acid, a double-stranded RNA (dsRNA), a short-hairpin RNA (shRNA), a small-interfering RNA (siRNA), a microRNA (miRNA), a ribozyme, an aptamer, and combination thereof.

In some embodiments, said biologically active compound is inert to a cell other than a cell of said target.

In some embodiments, said biocontrol compound is a peptide, a polypeptide, a fermentation product, a metabolite, an antibody, a semiochemical, or a micronutrient. In some embodiments, said biostimulant compound is a peptide, polypeptide, fermentation product, metabolite, antibody, semiochemical, or micronutrient. In some embodiments, said target comprises a plant, an insect, a worm, a bacterium, a fungus, a virus and an aquatic animal, wherein said aquatic animal comprises a fish, a shellfish, and a crustacean.

In some embodiments, said agricultural formulation further comprises a polypeptide within said minicell, wherein said polypeptide is expressed within said minicell, wherein said polypeptide binds to said nucleic acid. In some embodiments, said polypeptide is a dsRNA binding protein, and wherein said dsRNA binding protein increases loading and enhances the stability of dsRNA.

In some embodiments, said minicell further comprises at least one fusion protein, and wherein said fusion protein is expressed on a surface of said minicell. In other embodiments, said fusion protein comprises at least one surface expressing moiety and at least one target cell adhesion moiety, and wherein said target cell adhesion moiety comprises a carbohydrate binding module consisting of a cellulose binding domain, a xylan binding domain, a chitin binding domain, and a lignin binding domain.

In some embodiments, said minicell is treated with a solvent, agent, fixative, preservative, or cross-linking agent for better solubility, increased stability, or enhanced integrity. In some embodiments, said minicell exhibits a controlled release rate of said biologically active compound, wherein the release can be a steady release or an initial burst followed by steady release.

In some embodiments, a method of delivering at least one biologically active compound is provided, which comprises: applying said minicell to a target cell. In some embodiments, said minicell is applied to a target and delivered into a cell of said target by endocytosis. In other embodiments, a method of delivering at least one biologically active compound is provided, further comprises: applying said minicell to said target cell with an agent, wherein said agent is an adjuvant for improving penetration of said minicell into said target cell. In some embodiments, a method of delivering at least one biologically active compound is provided, said agent is a surfactant, an emulsifier, a crop oil concentrate, a penetrant, a salt or combination thereof.

In some embodiments, a method of delivering at least one biologically active compound is provided, which comprises: applying an agricultural formulation to a target cell, wherein said agricultural formulation comprises: a) an intact anucleated cell derived from a bacterial parental cell, comprising said biologically active compound within said cell, wherein said biologically active compound is selected from the group consisting of i) a nucleic acid, wherein the nucleic acid targets a transcript encoding a polypeptide within said target cell, ii) a biocontrol compound, and iii) a biostimulant compound. In some embodiments, said biologically active compound is said nucleic acid selected from the group consisting of an antisense nucleic acid, a double-stranded RNA (dsRNA), a short-hairpin RNA (shRNA), a small-interfering RNA (siRNA), a microRNA (miRNA), a ribozyme, an aptamer, and combination thereof. In some embodiments, said biocontrol compound is a peptide, a polypeptide, a fermentation product, a metabolite, an antibody, a semiochemical, or a micronutrient. In some embodiments, said biostimulant compound is a peptide, a polypeptide, a fermentation product, a metabolite, an antibody, a semiochemical, or a micronutrient. In some embodiments, said target cell comprises a plant cell, an insect cell, a worm cell, a bacterial cell, a fungal cell, a virus and a cell of an aquatic animal, wherein said aquatic animal comprises a fish, a shellfish, and a crustacean. In some embodiments, said anucleated cell further comprises at least one fusion protein, and wherein said fusion protein is expressed on a surface of said cell. In some embodiments, said fusion protein comprises at least one surface expressing moiety and at least one target cell adhesion moiety, and wherein said target cell adhesion moiety comprises a carbohydrate binding module consisting of a cellulose binding domain, a xylan binding domain, a chitin binding domain, and a lignin binding domain.

BRIEF DESCRIPTION OF THE FIGURES

FIG. 8A shows His-Tag staining of CBM expressed from non-permeabilized protease-deficient minicells. FIG. 8B shows His-Tag staining of CBM expressed from permeabilized protease-deficient minicells. FIG. 8C shows no or little CBM expression from non-permeabilized control minicells. FIG. 8D also shows no or little CBM expression from permeabilized control minicells. Arrow points out the expressed CBMs.

FIG. 9A illustrates that minicells are treated with 1% (v/v) Glutaraldehyde and untreated (0% (v/v) Glutaraldehyde) at 25° C. for 15 days. FIG. 9B illustrates that minicells are treated with three different concentrations of Glutaraldehyde (5%, 1%, and 0.25% (v/v), compared to an untreated control at 37° C. for 15 days.

FIG. 15A illustrates that the anucleate cells and the dsRNA are produced from different host cells and are incubated together after the independent productions have been completed. The anucleate cell lacks Ribonuclease III, ensuring that the dsRNA will not be broken down once encapsulated. FIG. 15B illustrates our anucleate cell platform is utilized to internally express dsRNA and encapsulate one or more sequences of dsRNA for the purposes of targeting one or multiple different pests. This entails encapsulating dsRNA that is either homologous or heterologous to the internally expressed dsRNA sequence in the anucleate cell. The anucleate cell lacks Ribonuclease III, ensuring that the dsRNA will not be broken down once encapsulated.

FIG. 24A shows His-Tag staining of ACC deaminase expressed from non-permeabilized protease-deficient minicells. FIG. 24B shows His-Tag staining of ACC deaminase expressed from permeabilized protease-deficient minicells. FIG. 24C shows no ACC deaminase expression from non-permeabilized control minicells. FIG. 24D also shows no ACC deaminase expression from permeabilized control minicells. Arrow points out the expressed ACC deaminases.

FIG. 25A shows activity of lipase purified from protease-deficient minicells expressing the recombinant AIDA-1 lipase fusion expression vector. FIG. 25B shows activity of lipase purified from protease-deficient minicells expressing the recombinant Brk-lipase fusion expression vector. FIG. 25C shows that activity of lipase purified from protease-deficient minicells expressing the recombinant InaK-lipase fusion expression vector. (Protease Deficient control: protease-deficient B8 strain without fusion lipase, Wild Strain Control: wild type p678-54 strain without fusion lipase, Fusion Protein Control: his-tag purified CBM protein without lipase activity)

FIG. 26A shows activity of surface-expressed lipase that is fused to AIDA-1. FIG. 26B shows activity of surface-expressed lipase that is fused to BRK. FIG. 26C shows activity of surface-expressed lipase that is fused to InaK.

DETAILED DESCRIPTION

Figure 1:
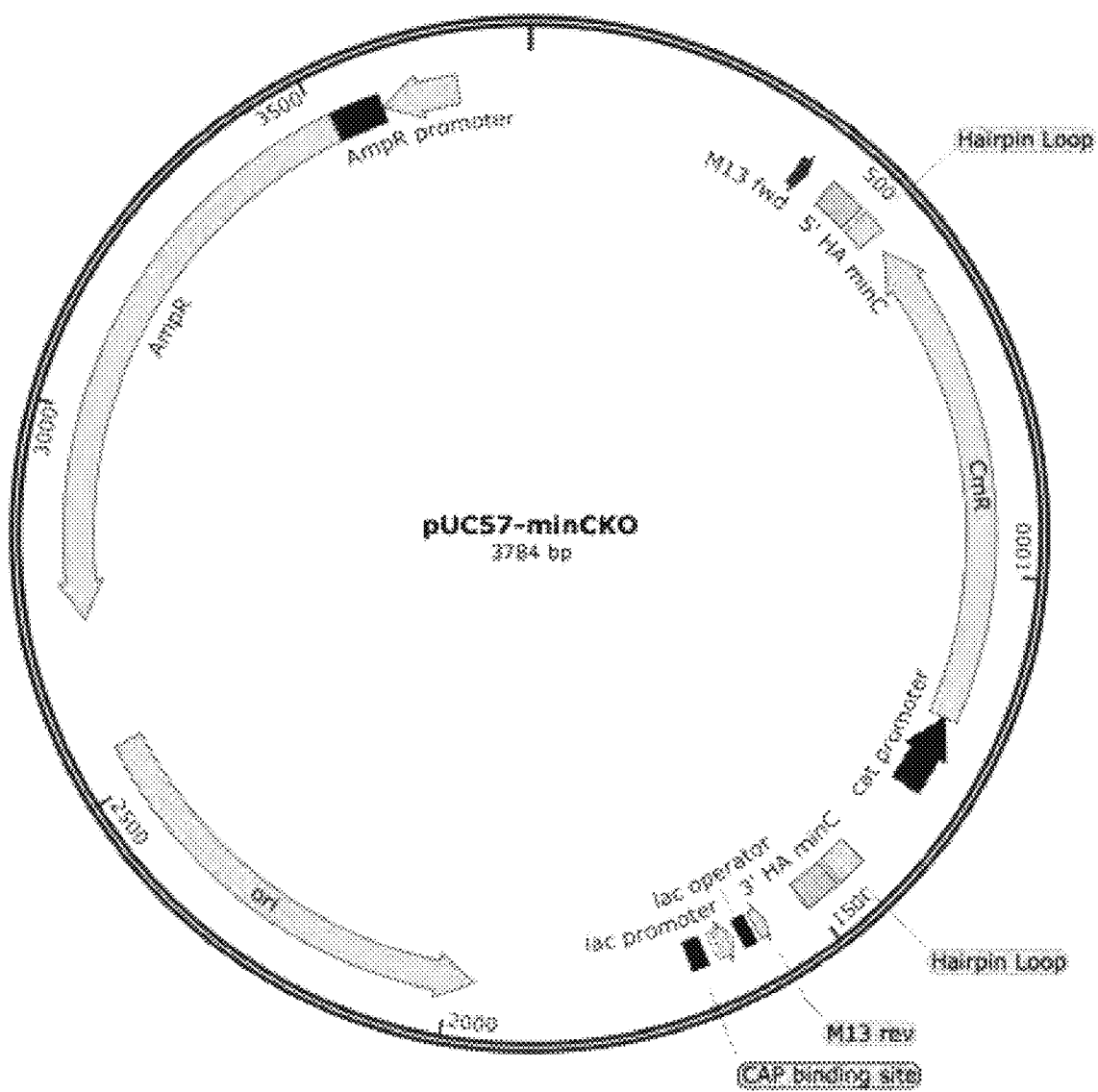
FIG. 1 illustrates an exemplary bacterial minicell-inducing vector for a minC knockout to produce ribonuclease-deficient and/or protease-deficient minicells. The pUC57 vector was inserted with a recombinant DNA insert comprising 5' end nucleotide sequence of minC gene, a chloramphenicol resistant gene (CmR) with cat promoter, and 3' end nucleotide sequence of minC gene. The hairpin loops flanked by 5' and 3' ends of minC gene are inserted into the insert to stop transcriptional regulation of other neighboring genes in the genome where the insert is integrated.

The present disclosure relates generally to development of a new delivery system to ensure an targeted delivery of biologically active compounds such as biocontrols and/or biostimulants and give intended effects upon a target in a specific way. Also, the present disclosure relates to an efficient encapsulation and delivery platform for sustaining bioactivity of the biocontrols and/or biostimulants until the biologically active compounds are delivered to their intended targets in a scalable, targeted, cost-effective manner.

The present disclosure is generally directed to an anucleated cell-based platforms for encapsulation and scalable delivery of biologically active compounds to targets with increased specificity. Also, disclosed are compositions for the stable and targeted delivery of biologically active compounds within achromosomal and/or anucleated cells onto and/or into a target cell. The present disclosure also provides an anucleated cell-based platforms having immobilized enzymatically active polypeptides on their surface and uses thereof in addition to features of encapsulation and scalable delivery of biologically active compounds to targets. Furthermore, the present disclosure provides methods of improving encapsulation and retention of biologically active compounds in achromosomal and/or anucleated cells and topically delivering biologically active compounds into a target cell.

Definitions

While the following terms are believed to be well understood by one of ordinary skill in the art, the following definitions are set forth to facilitate explanation of the presently disclosed subject matter.

The term "a" or "an" refers to one or more of that entity, i.e. can refer to a plural referents. As such, the terms "a" or "an", "one or more" and "at least one" are used interchangeably herein. In addition, reference to "an element" by the indefinite article "a" or "an" does not exclude the possibility that more than one of the elements is present, unless the context clearly requires that there is one and only one of the elements.

As used herein, "industrially suitable" refers to utilization, and applications, of the anucleated cell-based delivery platform, in contexts outside of internally administered animal host applications, e.g. outside of administered human therapeutics.

The term "biologically active" (synonymous with "bioactive") indicates that a composition or compound itself has a biological effect, or that it modifies, causes, promotes, enhances, blocks, reduces, limits the production or activity of, or reacts with or binds to an endogenous molecule that has a biological effect. A "biological effect" may be but is not limited to one that impacts a biological process in an plant; one that impacts a biological process in a pest, pathogen or parasite; one that generates or causes to be generated a detectable signal; and the like. Biologically active compositions, complexes or compounds may be used in agricultural applications and compositions. Biologically active compositions, complexes or compounds act to cause or stimulate a desired effect upon a plant, an insect, a worm, bacteria, fungi, or virus. Non-limiting examples of desired effects include, for example, preventing, treating or curing a disease or condition in a plant suffering therefrom; limiting the growth of or killing a pest, a pathogen or a parasite that infects a plant; augmenting the phenotype or genotype of a plant; stimulating a positive response in a plant to germinate, grow vegetatively, bloom, fertilize, produce fruits and/or seeds, and harvest; controlling a pest to cause a disease or disorder.

In the context of agricultural applications of the present disclosure, the term "biologically active" indicates that the composition, complex or compound has an activity that impacts vegetative and reproductive growth of a plant in a positive sense, impacts a plant suffering from a disease or disorder in a positive sense and/or impacts a pest, pathogen or parasite in a negative sense. Thus, a biologically active composition, complex or compound may cause or promote a biological or biochemical activity within a plant that is detrimental to the growth and/or maintenance of a pest, pathogen or parasite; or of cells, tissues or organs of a plant that have abnormal growth or biochemical characteristics and/or a pest, a pathogen or a parasite that causes a disease or disorder within a host such as a plant.

As used herein the term "biocontrol" or "biological control" refers to control of pests by interference with their ecological status, as by introducing a natural enemy or a pathogen into the environment. "Biocontrols" are interchangeably used with 'biocontrol agents" and "biological control agents", which are most often referred to as antagonists. Successful biological control reduces the population density of the target species. The term "biocontrol" as a biocontrol agent refers to a compound or composition which originates in a biological matter and is effective in the treatment, prevention, amelioration, inhibition, elimination or delaying the onset of at least one of bacterial, fungal, viral, insect, or any other plant pest infections or infestations and inhibition of spore germination and hyphae growth. It is appreciated that any biocontrol agent is environmentally safe, that it, it is detrimental to the target species, but does not substantially damage other species in a nonspecific manner. Furthermore, it is understood that the term "biocontrol agent" or "biocontrol compound" also encompasses the term "biochemical control agent" or "biochemical control compound". Biochemical control agents are semichemicals for example, plant-growth regulators, hormones, enzymes, pheromones, allomones and kairomones, which are either naturally occurring or identical to a natural product, that attract, retard, destroy or otherwise exert a pesticidal activity. In the some embodiments, biocontrols refer to biologically active compounds a polypeptide, a metabolite, a semiochemical, a hormone, a pheromone, and a nucleic acid such as RNA biomolecule including antisense nucleic acid, dsRNA, shRNA, siRNA, miRNA, ribozyme, and aptamer.

As used herein the terms "biostimulant", "biostimulants" or "biostimulant compound" refers to any microorganism or substance based on natural resources, in the form in which it is supplied to the user, applied to plants, seeds or the root environment soil and any other substrate with the intention to stimulate natural processes of plants to benefit their nutrient use efficiency and/or their tolerance to stress, regardless of its nutrients content, or any combination of such substances and/or microorganisms intended for this use. In the some embodiments, biostimulants refer to biologically active compounds a polypeptide, a metabolite, a semiochemical, a hormone, a pheromone, a micronutrient and a nucleic acid such as RNA biomolecule including antisense nucleic acid, dsRNA, shRNA, siRNA, miRNA, ribozyme, and aptamer.

As used herein the terms "biopesticide" or "biopesticides" refers to a substance or mixture of substances intended for preventing, destroying or controlling any pest. Specifically, the term relates to substances or mixtures which are effective for treating, preventing, ameliorating, inhibiting, eliminating or delaying the onset of bacterial, fungal, viral, insect- or other pest-related infection or infestation, spore germination and hyphae growth. Also used as substances applied to crops either before or after harvest to protect the commodity from deterioration during storage and transport. As a contraction of 'biological pesticides', biopesticides include several types of pest management intervention through predatory, parasitic, or chemical relationships. The term has been associated historically with biological control—and by implication—the manipulation of living organisms. In the some embodiments, biopesticides refer to biologically active compounds a polypeptide, a metabolite, a semiochemical, a hormone, a pheromone, a macronutrient, a micronutrient and a nucleic acid such as RNA biomolecule including antisense nucleic acid, dsRNA, shRNA, siRNA, miRNA, ribozyme, and aptamer.

The term "pest" is defined herein as encompassing vectors of plant, humans or livestock disease, unwanted species of bacteria, fungi, viruses, insects, nematodes mites, ticks or any organism causing harm during or otherwise interfering with the production, processing, storage, transport or marketing of food, agricultural commodities, wood and wood products or animal feedstuffs. Insect pests include insects selected from the orders *coleoptera, diptera, hymenoptera, lepidoptera, mallophaga, homoptera, hemiptera orthroptera, thysanoptera, dermaptera, isoptera, anoplura, siphonaptera, trichoptera*, etc., particularly Lepidoptera and Coleoptera. Those skilled in the art will recognize that not all compounds are equally effective against all pests. Compounds of the embodiments display activity against insect pests, which may include economically important agronomic, forest, greenhouse, nursery ornamentals, food and fiber, public and animal health, domestic and commercial structure, household and stored product pests.

As used herein the terms "cellular organism" "microorganism" or "microbe" should be taken broadly. These terms are used interchangeably and include, but are not limited to, the two prokaryotic domains, Bacteria and Archaea, as well as certain eukaryotic fungi and protists.

The term "prokaryotes" is art recognized and refers to cells that contain no nucleus or other cell organelles. The prokaryotes are generally classified in one of two domains, the Bacteria and the Archaea. The definitive difference between organisms of the Archaea and Bacteria domains is based on fundamental differences in the nucleotide base sequence in the 16S ribosomal RNA.

The term "Archaea" refers to a categorization of organisms of the division Mendosicutes, typically found in unusual environments and distinguished from the rest of the prokaryotes by several criteria, including the number of ribosomal proteins and the lack of muramic acid in cell walls. On the basis of ssrRNA analysis, the Archaea consist of two phylogenetically-distinct groups: Crenarchaeota and Euryarchaeota. On the basis of their physiology, the Archaea can be organized into three types: methanogens (prokaryotes that produce methane); extreme halophiles (prokaryotes that live at very high concentrations of salt (NaCl); and extreme (hyper) *thermophilus* (prokaryotes that live at very high temperatures). Besides the unifying archaeal features that distinguish them from Bacteria (i.e., no murein in cell wall, ester-linked membrane lipids, etc.), these prokaryotes exhibit unique structural or biochemical attributes which adapt them to their particular habitats. The Crenarchaeota consists mainly of hyperthermophilic sulfur-dependent prokaryotes and the Euryarchaeota contains the methanogens and extreme halophiles.

"Bacteria" or "eubacteria" refers to a domain of prokaryotic organisms. Bacteria include at least 11 distinct groups as follows: (1) Gram-positive (gram+) bacteria, of which there are two major subdivisions: (1) high G+C group (Actinomycetes, Mycobacteria, *Micrococcus*, others) (2) low G+C group (*Bacillus, Clostridia, Lactobacillus*, Staphylococci, Streptococci, Mycoplasmas); (2) Proteobacteria, e.g., Purple photosynthetic+non-photosynthetic Gram-negative bacteria (includes most "common" Gram-negative bacteria); (3) Cyanobacteria, e.g., oxygenic phototrophs; (4) Spirochetes and related species; (5) *Planctomyces*; (6) *Bacteroides*, Flavobacteria; (7) *Chlamydia*; (8) Green sulfur bacteria; (9) Green non-sulfur bacteria (also anaerobic phototrophs); (10) Radioresistant micrococci and relatives; (11) *Thermotoga* and *Thermosipho* thermophiles.

A "eukaryote" is any organism whose cells contain a nucleus and other organelles enclosed within membranes. Eukaryotes belong to the taxon Eukarya or Eukaryota. The defining feature that sets eukaryotic cells apart from prokaryotic cells (the aforementioned Bacteria and Archaea) is that they have membrane-bound organelles, especially the nucleus, which contains the genetic material, and is enclosed by the nuclear envelope.

The terms "genetically modified host cell," "recombinant host cell," and "recombinant strain" are used interchangeably herein and refer to host cells that have been genetically modified by the cloning and transformation methods of the present disclosure. Thus, the terms include a host cell (e.g., bacteria, yeast cell, fungal cell, CHO, human cell, etc.) that has been genetically altered, modified, or engineered, such that it exhibits an altered, modified, or different genotype and/or phenotype (e.g., when the genetic modification affects coding nucleic acid sequences of the microorganism), as compared to the naturally-occurring organism from which it was derived. It is understood that in some embodiments, the terms refer not only to the particular recombinant host cell in question, but also to the progeny or potential progeny of such a host cell.

The term "wild-type microorganism" or "wild-type host cell" describes a cell that occurs in nature, i.e. a cell that has not been genetically modified. In the disclosure, "wild type strain" or "wild strain" or "wild type cell line" refers to a cell strain/line that can produce minicells. In some embodiments, wild type bacterial strains and/or cell lines such as *E. coli* strain p678-54 and *B. subtilis* strain CU403 can make miniature cells deficient in DNA. Methods for producing such minicells are known in the art. See, for example, Adler et al., 1967, *Proc. Natl. Acad. Sci. USA* 57:321-326; Inselburg J, 1970 *J. Bacteriol.* 102(3):642-647; Frazer 1975, *Curr. Topics Microbiol. Immunol.* 69:1-84, Reeve et al 1973, *J. Bacteriol.* 114(2):860-873; and Mendelson et al 1974 *J. Bacteriol.* 117(3):1312-1319.

The term "genetically engineered" may refer to any manipulation of a host cell's genome (e.g. by insertion, deletion, mutation, or replacement of nucleic acids).

The term "control" or "control host cell" refers to an appropriate comparator host cell for determining the effect of a genetic modification or experimental treatment. In some embodiments, the control host cell is a wild type cell. In other embodiments, a control host cell is genetically identical to the genetically modified host cell, save for the genetic modification(s) differentiating the treatment host cell.

As used herein, the term "genetically linked" refers to two or more traits that are co-inherited at a high rate during breeding such that they are difficult to separate through crossing.

A "recombination" or "recombination event" as used herein refers to a chromosomal crossing over or independent assortment.

As used herein, the term "phenotype" refers to the observable characteristics of an individual cell, cell culture, organism, or group of organisms which results from the interaction between that individual's genetic makeup (i.e., genotype) and the environment.

As used herein, the term "chimeric" or "recombinant" when describing a nucleic acid sequence or a protein sequence refers to a nucleic acid, or a protein sequence, that links at least two heterologous polynucleotides, or two heterologous polypeptides, into a single macromolecule, or that rearranges one or more elements of at least one natural nucleic acid or protein sequence. For example, the term "recombinant" can refer to an artificial combination of two otherwise separated segments of sequence, e.g., by chemical synthesis or by the manipulation of isolated segments of nucleic acids by genetic engineering techniques.

As used herein, a "synthetic nucleotide sequence" or "synthetic polynucleotide sequence" is a nucleotide sequence that is not known to occur in nature or that is not naturally occurring. Generally, such a synthetic nucleotide sequence will comprise at least one nucleotide difference when compared to any other naturally occurring nucleotide sequence.

As used herein, a "synthetic amino acid sequence" or "synthetic peptide" or "synthetic protein" is an amino acid sequence that is not known to occur in nature or that is not naturally occurring. Generally, such a synthetic protein sequence will comprise at least one amino acid difference when compared to any other naturally occurring protein sequence.

As used herein, the term "nucleic acid" refers to a polymeric form of nucleotides of any length, either ribonucleotides or deoxyribonucleotides, or analogs thereof. This term refers to the primary structure of the molecule, and thus includes double- and single-stranded DNA, as well as double- and single-stranded RNA. It also includes modified nucleic acids such as methylated and/or capped nucleic acids, nucleic acids containing modified bases, backbone modifications, and the like. The terms "nucleic acid" and "nucleotide sequence" are used interchangeably.

As used herein, the term "gene" refers to any segment of DNA associated with a biological function. Thus, genes include, but are not limited to, coding sequences and/or the regulatory sequences required for their expression. Genes can also include non-expressed DNA segments that, for example, form recognition sequences for other proteins. Genes can be obtained from a variety of sources, including cloning from a source of interest or synthesizing from known or predicted sequence information, and may include sequences designed to have desired parameters.

As used herein, the term "homologous" or "homologue" or "ortholog" is known in the art and refers to related sequences that share a common ancestor or family member and are determined based on the degree of sequence identity.

The terms "homology," "homologous," "substantially similar" and "corresponding substantially" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant disclosure such as deletion or insertion of one or more nucleotides that do not substantially alter the functional properties of the resulting nucleic acid fragment relative to the initial, unmodified fragment. It is therefore understood, as those skilled in the art will appreciate, that the disclosure encompasses more than the specific exemplary sequences. These terms describe the relationship between a gene found in one species, subspecies, variety, cultivar or strain and the corresponding or equivalent gene in another species, subspecies, variety, cultivar or strain. For purposes of this disclosure homologous sequences are compared. "Homologous sequences" or "homologues" or "orthologs" are thought, believed, or known to be functionally related. A functional relationship may be indicated in any one of a number of ways, including, but not limited to: (a) degree of sequence identity and/or (b) the same or similar biological function. Preferably, both (a) and (b) are indicated. Homology can be determined using software programs readily available in the art, such as those discussed in Current Protocols in Molecular Biology (F. M. Ausubel et al., eds., 1987) Supplement 30, section 7.718, Table 7.71. Some alignment programs are MacVector (Oxford Molecular Ltd, Oxford, U.K.), ALIGN Plus (Scientific and Educational Software, Pennsylvania) and AlignX (Vector NTI, Invitrogen, Carlsbad, CA). Another alignment program is Sequencher (Gene Codes, Ann Arbor, Michigan), using default parameters.

As used herein, the term "endogenous" or "endogenous gene," refers to the naturally occurring gene, in the location in which it is naturally found within the host cell genome. In the context of the present disclosure, operably linking a heterologous promoter to an endogenous gene means genetically inserting a heterologous promoter sequence in front of an existing gene, in the location where that gene is naturally present. An endogenous gene as described herein can include alleles of naturally occurring genes that have been mutated according to any of the methods of the present disclosure.

As used herein, the term "exogenous" is used interchangeably with the term "heterologous," and refers to a substance coming from some source other than its native source. For example, the terms "exogenous protein," or "exogenous gene" refer to a protein or gene from a non-native source or location, and that have been artificially supplied to a biological system.

As used herein, the term "nucleotide change" refers to, e.g., nucleotide substitution, deletion, and/or insertion, as is well understood in the art. For example, mutations contain alterations that produce silent substitutions, additions, or deletions, but do not alter the properties or activities of the encoded protein or how the proteins are made.

As used herein, the term "protein modification" refers to, e.g., amino acid substitution, amino acid modification, deletion, and/or insertion, as is well understood in the art.

As used herein, the term "at least a portion" or "fragment" of a nucleic acid or polypeptide means a portion having the minimal size characteristics of such sequences, or any larger fragment of the full length molecule, up to and including the full length molecule. A fragment of a polynucleotide of the disclosure may encode an enzymatically active portion of a genetic regulatory element. An enzymatically active portion of a genetic regulatory element can be prepared by isolating a portion of one of the polynucleotides of the disclosure that comprises the genetic regulatory element and assessing activity as described herein. Similarly, a portion of a polypeptide may be 4 amino acids, 5 amino acids, 6 amino acids, 7 amino acids, and so on, going up to the full length polypeptide. The length of the portion to be used will depend on the particular application. A portion of a nucleic acid useful as a hybridization probe may be as short as 12 nucleotides; in some embodiments, it is 20 nucleotides. A portion of a polypeptide useful as an epitope may be as short as 4 amino acids. A portion of a polypeptide that performs the function of the full-length polypeptide would generally be longer than 4 amino acids.

Variant polynucleotides also encompass sequences derived from a mutagenic and recombinogenic procedure such as DNA shuffling. Strategies for such DNA shuffling are known in the art. See, for example, Stemmer (1994) PNAS 91:10747-10751; Stemmer (1994) Nature 370:389-391; Crameri et al. (1997) Nature Biotech. 15:436-438; Moore et al. (1997) J. Mol. Biol. 272:336-347; Zhang et al. (1997) PNAS 94:4504-4509; Crameri et al. (1998) Nature 391:288-291; and U.S. Pat. Nos. 5,605,793 and 5,837,458.

For PCR amplifications of the polynucleotides disclosed herein, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (2001) Molecular Cloning: A Laboratory Manual ($3^{rd}$ ed., Cold Spring Harbor Laboratory Press, Plainview, New York). See also Innis et al., eds. (1990) PCR Protocols: A Guide to Methods and Applications (Academic Press, New York); Innis and Gelfand, eds. (1995) PCR Strategies (Academic Press, New York); and Innis and Gelfand, eds. (1999) PCR Methods Manual (Academic Press, New York). Known methods of PCR include, but are not limited to, methods using paired primers, nested primers, single specific primers, degenerate primers, gene-specific primers, vector-specific primers, partially-mismatched primers, and the like.

The term "primer" as used herein refers to an oligonucleotide which is capable of annealing to the amplification target allowing a DNA polymerase to attach, thereby serving as a point of initiation of DNA synthesis when placed under conditions in which synthesis of primer extension product is induced, i.e., in the presence of nucleotides and an agent for polymerization such as DNA polymerase and at a suitable temperature and pH. The (amplification) primer is preferably single stranded for maximum efficiency in amplification. Preferably, the primer is an oligodeoxyribonucleotide. The primer must be sufficiently long to prime the synthesis of extension products in the presence of the agent for polymerization. The exact lengths of the primers will depend on many factors, including temperature and composition (A/T vs. G/C content) of primer. A pair of bi-directional primers consists of one forward and one reverse primer as commonly used in the art of DNA amplification such as in PCR amplification.

As used herein, "promoter" refers to a DNA sequence capable of controlling the expression of a coding sequence or functional RNA. In some embodiments, the promoter sequence consists of proximal and more distal upstream elements, the latter elements often referred to as enhancers. Accordingly, an "enhancer" is a DNA sequence that can stimulate promoter activity, and may be an innate element of the promoter or a heterologous element inserted to enhance the level or tissue specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity.

As used herein, the phrases "recombinant construct", "expression construct", "chimeric construct", "construct", and "recombinant DNA construct" are used interchangeably herein. Also, "construct", "vector", and "plasmid" are used interchangeably herein. A recombinant construct comprises an artificial combination of nucleic acid fragments, e.g., regulatory and coding sequences that are not found together in nature. For example, a chimeric construct may comprise regulatory sequences and coding sequences that are derived from different sources, or regulatory sequences and coding sequences derived from the same source, but arranged in a manner different than that found in nature. Such construct may be used by itself or may be used in conjunction with a vector. If a vector is used then the choice of vector is dependent upon the method that will be used to transform host cells. For example, a plasmid vector can be used. The skilled artisan is well aware of the genetic elements that must be present on the vector in order to successfully transform, select and propagate host cells comprising any of the isolated nucleic acid fragments of the disclosure. The skilled artisan will also recognize that different independent transformation events will result in different levels and patterns of expression (Jones et al., (1985) EMBO J. 4:2411-2418; De Almeida et al., (1989) Mol. Gen. Genetics 218: 78-86), and thus that multiple events must be screened in order to obtain lines displaying the desired expression level and pattern. Such screening may be accomplished by Southern analysis of DNA, Northern analysis of mRNA expression, immunoblotting analysis of protein expression, or phenotypic analysis, among others. Vectors can be plasmids, viruses, bacteriophages, pro-viruses, phagemids, transposons, artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that is not autonomously replicating. As used herein, the term "expression" refers to the production of a functional end-product e.g., an mRNA or a protein (precursor or mature).

"Operably linked" means in this context the sequential arrangement of the promoter polynucleotide according to the disclosure with a further oligo- or polynucleotide, resulting in transcription of said further polynucleotide.

As used herein, the term "display" refers to the exposure of the polypeptide of interest on the outer surface of the minicell. By way of non-limiting example, the displayed polypeptide may be a protein or a protein domain which is either expressed on the minicell membrane or is associated with the minicell membrane such that the extracellular domain or domain of interest is exposed on the outer surface of the minicell (expressed and displayed on the surface of the minicell or expressed in the parental cell to be displayed on the surface of the segregated/budded minicell). In all instances, the "displayed" protein or protein domain is available for interaction with extracellular components. A membrane-associated protein may have more than one extracellular domain, and a minicell of the disclosure may display more than one membrane-associated protein.

As used herein, the terms "polypeptide", "protein" and "protein domain" refer to a macromolecule made up of a single chain of amino acids joined by peptide bonds. Polypeptides of the invention may comprise naturally occurring amino acids, synthetic amino acids, genetically encoded amino acids, non-genetically encoded amino acids, and combinations thereof. Polypeptides may include both L-form and D-form amino acids.

As used herein, the term "enzymatically active polypeptide" refers to a polypeptide which encodes an enzymatically functional protein. The term "enzymatically active polypeptide" includes but not limited to fusion proteins which perform a biological function. Exemplary enzymatically active polypeptides, include but not limited to enzymes/enzyme moiety (e.g. wild type, variants, or engineered variants) that specifically bind to certain receptors or biological/chemical substrates to effect a biological function such as biological signal transduction or chemical inactivation.

As used herein, the term "protease-deficient strain" refers to a strain that is deficient in one or more endogenous proteases. For example, protease deficiency can be created by deleting, removing, knock-out, silencing, suppressing, or otherwise downregulating at lease on endogenous protease. Said proteases can include catastrophic proteases. For example, BL21 (DE3) *E. coli* strain is deficient in proteases Lon and OmpT. *E. coli* strain has cytoplasmic proteases and membrane proteases that can significantly decrease protein production and localization to the membrane. In some embodiments, a protease-deficient strain can maximize production and localization of a protein of interest to the membrane of the cell. "Protease-deficient" can be interchangeably used as "protease-free" in the present disclosure.

As used herein, the term "ribonuclease-deficient strain" refers to a strain that is deficient in one or more endogenous ribonuclease. For example, ribonuclease deficiency can be created by deleting, removing, knock-out, silencing, suppressing, or otherwise downregulating at lease on endogenous ribonuclease. Said ribonuclease can include ribonuclease III. For example, HT115 *E. coli* strain is deficient in RNase III. In some embodiments, a ribonuclease-deficient strain is unable to and/or has a reduced capability of recognizing dsRNA and cleaving it at specific targeted locations. "Ribonuclease-deficient" can be interchangeably used as "ribonuclease-free" in the present disclosure.

As used herein, the term "anucleated cell" refers to a cell that lacks a nucleus and also lacks chromosomal DNA and which can also be termed as an "anucleate cell". Because eubacterial and archaebacterial cells, unlike eukaryotic cells, naturally do not have a nucleus (a distinct organelle that contains chromosomes), these non-eukaryotic cells are of course more accurately described as being "without chromosomes" or "achromosomal." Nonetheless, those skilled in the art often use the term "anucleated" when referring to bacterial minicells in addition to other eukaryotic minicells. Accordingly, in the present disclosure, the term "minicells" encompasses derivatives of eubacterial cells that lack a chromosome; derivatives of archaebacterial cells that lack their chromosome(s), and anucleate derivatives of eukaryotic cells that lack a nucleus and consequently a chromosome. Thus, in the present disclosure, "anucleated cell" or "anucleate cell" can be interchangeably used with the term "achromosomal cell."

As used herein, the term "binding site," means a molecular structure or compound, such as a protein, a polypeptide, a polysaccharide, a glycoprotein, a lipoprotein, a fatty acid, a lipid or a nucleic acid or a particular region in such molecular structure or compound or a particular conformation of such molecular structure or compound, or a combination or complex of such molecular structures or compounds. In certain embodiments, at least one binding site is on an intact living plant. An "intact living plant," as used herein, means a plant as it grows, whether it grows in soil, in water or in artificial substrate, and whether it grows in the field, in a greenhouse, in a yard, in a garden, in a pot or in hydroponic culture systems. An intact living plant preferably comprises all plant parts (roots, stem, branches, leaves, needles, thorns, flowers, seeds etc.) that are normally present on such plant in nature, although some plant parts, such as, e.g., flowers, may be absent during certain periods in the plant's life cycle.

A "binding domain," as used herein, means the whole or part of a proteinaceous (protein, protein-like or protein containing) molecule that is capable of binding using specific intermolecular interactions to a target molecule. A binding domain can be a naturally occurring molecule, it can be derived from a naturally occurring molecule, or it can be entirely artificially designed. A binding domain can be based on domains present in proteins, including but not limited to microbial proteins, antibodies, enzymes, protease inhibitors, protein toxins, fibronectin, lipocalins, single-chain antiparallel coiled coil proteins or repeat motif proteins. Non-limiting examples of such binding domains are carbohydrate binding modules (CBM) such as cellulose binding domain to be targeted to plants, ACC-deaminase, cutinase, cellulose and the like. In some embodiments, a cell adhesion moiety comprises a binding domain. In other embodiments, a cell stimulation moiety comprises a binding domain. In further embodiments, a cell degradation moiety comprises a binding domain.

As used herein, "carrier," "acceptable carrier," or "biologically actively acceptable carrier" refers to a diluent, adjuvant, excipient, or vehicle with which a composition can be administered to its target, which does not detrimentally effect the composition.

In some embodiments, biologically active compounds can be used as biocontrols and biostimulants that have become the new age of crop protection and enhancement.

An example of a biocontrol is RNAi, or RNA interference, which is used to silence genes in target pests, killing them while leaving the non targeted pests unharmed. In invertebrates, long dsRNA can be efficiently used to silence gene expression without activation of dsRNA-activated protein kinase (PKR) or the interferon response that has been shown to occur in mammalian cell systems.

Another example is delivering protein toxins to combat pests. One example of protein toxin is orally active insecticidal peptide-1 (OAIP-1), which is to be highly toxic to insects with potency similar to that of the synthetic insecticide imidacloprid. This OAIP-1 toxin can be isolated from the Venom of an Australian Tarantula, which can be used as one of biologically active compounds taught in this disclosure.

Chitinases can be delivered to plants as a fungicide.

Plant antibodies are another form of biocontrols that can be used to specifically target pests. Immunoglobulin domains, light chain, heavy chain, and CDRs, Fv, Fab, and Fc regions can be encapsulated as active compounds and be delivered to a target. The present disclosure provides fungicidal antibodies such as those generated from glucosylceramide.

Plant-growth regulators, hormones, enzymes, pheromones, allomones and kairomones are also biocontrols. A pheromone can act as a biocontrol to prevent bugs and/or insects from mating.

Biostimulants foster plant development in a number of demonstrated ways throughout the crop lifecycle, from seed germination to plant maturity. They can be applied to plant, seed, soil or other growing media that may enhance the plant's ability to assimilate nutrients and properly develop. By fostering complementary soil microbes and improving metabolic efficiency, root development and nutrient delivery, biostimulants can increase yield in terms of weight, seed and fruit set, enhance quality, affecting sugar content, color and shelf life, improve the efficiency of water usage, and strengthen stress tolerance and recovery. These biostimulants can include pheromones or enzymes like ACC-Deaminase.

Biostimulants are compounds that produce non-nutritional plant growth responses and reduce stress by enhancing stress tolerance. Fertilizers, which produce a nutritional response can be considered as biostimulants. Many important benefits of biostimulants are based on their ability to influence hormonal activity. Hormones in plants (phytohormones) are chemical messengers regulating normal plant development as well as responses to the environment. Root and shoot growth, as well as other growth responses are regulated by phytohormones. Compounds in biostimulants can alter the hormonal status of a plant and exert large influences over its growth and health. Sea kelp, humic acids and B Vitamins are common components of biostimulants that are important sources of compounds that influence plant growth and hormonal activity. Antioxidants are another group of plant chemicals that are important in regulating the plants response to environmental and chemical stress (drought, heat, UV light and herbicides). When plants come under stress, "free radicals" or reactive oxygen molecules (e.g., hydrogen peroxide) damage the plants cells. Antioxidants suppress free radical toxicity. Plants with the high levels of antioxidants produce better root and shoot growth, maintain higher leaf-moisture content and lower disease incidence in both normal and stressful environments. Applying a biostimulant enhances antioxidant activity, which increases the plant's defensive system. Vitamin C, Vitamin E, and amino acids such as glycine are antioxidants contained in biostimulants.

Biostimulants may act to stimulate the growth of microorganisms that are present in soil or other plant growing medium. Biostimulants are capable of stimulating growth of microbes included in the microbial inoculant. Thus, it is desirable to obtain a biostimulant, that, when used with a microbial inoculant, is capable of enhancing the population of both native microbes and inoculant microbes.

In some embodiments, the present disclosure provides an industrially suitable anucleated cell-based platform and/or an industrial formulation that can deliver biocontrols and biostimulants topically in a scalable, cost-effective manor by using the anucleated cell-based platform and/or an industrial formulation described herein. This anucleated cell-based platform and/or an industrial formulation can also be modified to invasively deliver biocontrols and biostimulants to plants including plants in aquaculture.

In one aspect, the anucleated cell-based platform and/or an industrial formulation uses bacterial cells lacking ribonucleases (ribonuclease III) and has T7, T3 or Sp6 RNA polymerase promoters to produce dsRNA used for RNA interference (RNAi) of a target. This bacterial cell is then modified to produce minicells with the dsRNA encapsulated within them. This helps simplify and cheapen purification and encapsulation. By encapsulating dsRNA, the dsRNA molecules are protected from environmental RNases. For examples, pests including insects orally consume the minicells for the delivery of the dsRNA. Once inside the insects, dsRNAs are a substrate for RNase III-like proteins referred to as Dicer or Dicer-like proteins. Dicer appears to preferentially initiate dsRNA cleavage at the ends of the dsRNA, making successive cleavages to generate 21- to 24-bp small-interfering (si) RNA duplexes to silence and/or suppress their target transcripts and inhibit translations of the transcripts. The resulting siRNA duplexes are loaded into a multiprotein complex called the RNA-induced silencing complex (RISC) where the passenger (sense) strand is removed and the guide (antisense) strand remains to target mRNA for silencing. The guide strand in the RISC enables base pairing of the complex to complementary mRNA transcripts and enzymatic cleavage of the target mRNA by a class of proteins referred to as Argonaute proteins, thereby preventing translation of the target mRNA. This is what causes the death of the targeted pest, while leaving untargeted pests unharmed. Also, the anucleated cell-based platform and/or an industrial formulation can be utilized to encapsulate dsRNA, siRNA shRNA, or miRNA. In other aspects, antisense nucleic acid, ribozyme, or aptamer can be encapsulated within the platform.

In some embodiments, the anucleated cell-based platform and the dsRNA are produced from different host cells and are incubated together after the independent productions have been completed. In some embodiments, the anucleated cell-based platforms can be utilized to internally express dsRNA from a recombinant plasmid capable of producing dsRNA inside of the anucleate minicell. Then, the internally produced dsRNA is delivered to its target within the anucleate minicell. In other embodiments, the anucleated cell-based platforms can be utilized to encapsulate externally and/or exogenously produced dsRNA that is first produced outside of the anucleate minicell. Then, the externally-produced dsRNA encapsulated into the minicell is delivered to its target within the anucleate minicell. In further embodiments, the anucleated cell-based platforms can be utilized to internally express dsRNA within the platform and encapsulate one or more sequences of exogenously-produced dsRNA into the platform for the purposes of targeting one or multiple different pests. This entails encapsulating dsRNA that is either homologous or heterologous to the internally expressed dsRNA sequence in the anucleate cell. Thus, the anucleated cell-based platform can carry both internally-expressed dsRNA and externally-expressed, but encapsulated dsRNA over to its intended target.

The present disclosure teaches that the anucleated cell-based platforms and/or an industrial formulation can deliver internally-produced dsRNA and externally/exogenously-produced dsRNA individually, or together to a target cell. The target cell is not a mammalian cell.

The present disclosure teaches that an industrially suitable anucleated cell-based platform and/or an industrial formulation for encapsulation and delivery of at least one biologically active compound, comprising: an intact anucleated cell derived from a ribonuclease deficient parental cell, comprising at least one biologically active compound within said cell, wherein said biologically active compound is a nucleic acid, wherein the nucleic acid targets a transcript encoding a polypeptide within a target cell, and wherein the target cell is not a mammalian cell. The anucleated cell-based platform and/or an industrial formulation further comprises at least one biologically acceptable carrier.

In some embodiments, for protein-mediated biocontrols, the present disclosure uses bacterial cells lacking proteases and has T7, T3, or Sp6 polymerase promoters to produce a significant amount of proteins. This bacterial cell is then modified to produce minicells with the proteins immobilized to their surface or encapsulated within them. A protein-expressing plasmid is integrated into the nucleoid DNA of the bacteria to safely and efficiently produce proteins. Insects then interact with or orally consume the minicells that express or retain the desired proteins. For antibody-mediated biocontrols, minicells can express or encapsulate antibodies to specifically target unwanted pests. Minicells can deliver antibodies or recombinant antibodies that serve as highly specific biopesticides against insects or fungal pathogens (Raymond et al., Fungal Biology Review 25(2): 84-88, 2011).

In some embodiments, for biostimulants, the present disclosure teaches that minicells can deliver a wide range of plant-growth promoting biomolecules to the surface of the plant, its seeds, and its root system. Many of these biomolecules occur as a result of a dynamic, symbiotic relationship that some microorganisms have with plants and are produced naturally in response to certain environmental cues or stresses. The minicell can be engineered to deliver a high-payload capacity of these plant growth promoting biomolecules, either immobilized extracellularly on their surface or encapsulated intracellularly, without relying on microorganism or plants to naturally produce them. This enables a higher effective concentration of these biomolecules to be delivered to the plant microenvironment while also allowing for a more controlled, adaptive response to agricultural input needs. Many of these biomolecules are enzymes that bacteria produce, either intracellularly or extracellularly, that play an important role in promoting soil fertility and providing defense against plant pathogens (Jog et al, Journal of Applied Microbiology 113:1154-1164, 2012; Sathya et al. 3 Biotech 7:102, 2017). Others, like 1-aminocyclopropane-1-carboxylate (ACC) Deaminase, can regulate plant growth on a hormonal level by lowering ethylene levels in the plant microenvironment (Souza et al., Genet. Mol. Biol. 38(4): 401-419, 2015).

In some embodiments, the biologically active compound are valuable enzymes that could be produced and delivered to the plant or its root system using the minicell, which include, but are not limited to cellulase, phytase, chitinase, protease, phosphatase, nucleases, lipases, glucanases, xylanases, amylases, peptidases, peroxidases, ligninases, pectinases, hemicellulases, and keratinases. Beyond being able to effectively deliver enzymes to promote the growth of plants, the minicell described herein can deliver other high-value biomolecules that play a role in promoting the growth of plants. These biomolecules include, but are not limited to plant hormones, such as the auxin IAA, peptides, primary metabolites, and secondary metabolites.

In some embodiments, the biologically active compounds are pheromones to improve and modify chemical reactions to help the plants grow and fight stresses as biostimulants.

In other embodiments, the delivery of biocontrols and biostimulants can be assisted through binding domains expressed on a surface of minicells. For example, minicells can express a binding domain such as a carbohydrate binding module (CBM) to be targeted to plants. These domains allow for better retention on plant surfaces, preventing runoff or drift. In some embodiments, minicells express a fusion protein comprising at least one surface expressing moiety and at least one target cell adhesion moiety, wherein said target cell adhesion moiety comprises a carbohydrate binding module. The target cell adhesion moiety comprises a carbohydrate binding module selected from the group consisting of: a cellulose binding domain, a xylan binding domain, a chitin binding domain, and a lignin binding domain.

In other embodiments, minicells can also express various proteins that encourage them to be uptaken by plants for invasive delivery through the leaf surface or roots. In some embodiments, minicells can express and display biologically active compound such as polypeptide and/or proteins on their surface. In other embodiments, minicells can express and display both surface expressed binding proteins and biologically active compound such as polypeptide and/or proteins on their surface.

The surface expressed binding proteins are as a carbohydrate binding module (CBM) described above. The biologically/enzymatically active polypeptide/proteins, which are surface-expressed, comprise cell stimulation moiety and/or cell degradation moiety. Non-limiting examples of such active proteins include, but are not limited to, ACC-deaminase, chitinase, cellulase, phytase, chitinase, protease, phosphatase, nucleases, lipases, glucanases, xylanases, amylases, peptidases, peroxidases, ligninases, pectinases, hemicellulases, and keratinases.

In some embodiments, these proteins are expressed exogenously and encapsulated into the minicells. In other embodiments, these proteins are internally expressed and immobilized on the surface of the minicells. The biologically active compounds such as such proteins are either encapsulated within the minicells after being expressed outside of the minicells or internally expressed within the minicells and displayed on the surface of the minicells. In further embodiments, the minicells express at least one biologically active compound on its surface and encapsulate another biologically active compound at the same time. So, the minicell can carry at least two biologically active compounds within the minicells and on the surface of the minicells. Non-limiting examples of such proteins include, but are not limited to ACC-deaminase, cellulase, phytase, chitinase, protease, phosphatase, nucleases, lipases, glucanases, xylanases, amylases, peptidases, peroxidases, ligninases, pectinases, hemicellulases, and keratinases.

In some embodiments, the protein is lipase used as a biocontrol compound. In other embodiments, the protein is lipase used as a biostimulant compound. In further embodiments, the protein is ACC deaminase used as a biostimulant compound. In some embodiments, the protein is lipase used as a biocontrol compound. In other embodiments, the protein is lipase used as a biostimulant compound. In further embodiments, the protein is ACC deaminase used as a biostimulant compound.

In some embodiments, minicells express a fusion protein comprising at least one surface expressing moiety and at least one target cell degradation moiety, wherein said target cell degradation moiety comprises an cutinase and cellulose.

The present disclosure teaches production and encapsulation of the RNA biomolecule including antisense nucleic acid, dsRNA, shRNA, siRNA, miRNA, ribozyme, or aptamer during the fermentation cycle by utilizing the microorganism's RNA synthesis and asymmetric division capabilities. This anucleated cell-based platform and/or an industrial formulation addresses three critical issues that have posed a great challenge to the delivery of ribonucleic acid (RNA) to a system: (1) the scalable synthesis and encapsulation of RNA (2) the synthesized/encapsulated oligonucleotide payload must survive the process; (3) the targeted delivery of this RNA biomolecule such that it reaches the tissue or cells of interest and invokes the desired phenotypic response. Current forms of RNA delivery are direct coupling of siRNA to N-acetylgalactosamine (GalNAc), formulating the RNA (often chemically modified) with cationic lipids and other excipients protects the oligonucleotide from the environment to compact its size, making chemical modifications to stabilize oligonucleotides for RNAi applications such as replacing the 2'-hydroxyl group on the ribose ring with 2'-methoxy and 2'-fluoro moieties. For dsRNA production, in vitro transcription is incredibly expensive compared to in vivo bacterial production of dsRNA. There are also Cell-Free and protein capsid processes for the production of dsRNA. The bacterial model is accompanied with the risk of environmental contamination due to proliferation of the modified species. This proliferation can have adverse and unforeseen consequences on the naturally existing species in the environment. Minicells result from naturally occurring mutations. The use of minicells for the purification and delivery of RNA allow for use the benefits of fermentation to scale the dsRNA production, without the risks associated with using genetically-modified bacteria. The use of minicells is also better for the delivery of protoxins and enzymes than using genetically-modified bacteria as biopesticides.

Biologically Active Compounds

The present disclosure provides a new anucleated cell-based platform and/or an industrial formulation for the encapsulation and delivery of biologically active compounds. In some embodiments, the anucleated cell-based platform and/or an industrial formulation comprises an intact anucleated cell, which comprises at least one biologically active compounds. By way of non-limiting example, the biologically active compound is a nucleic acid, a polypeptide, a metabolite, a semiochemical or a micronutrient. There is currently great interest in the agricultural industry to begin replacing some of these synthetic compounds with their biologically derived counterparts. These biologically active compounds can be broadly categorized as biocontrols and biostimulants.

Biocontrols

The present disclosure teaches the biologically active compounds as a biocontrol including, but are not limited to, RNAi, protoxins, metabolites, antibodies, fermentation products, hormones, pheromones, and semiochemicals. In some embodiments, the biologically active compound is the polypeptide. In other embodiments, the polypeptide is a protein toxin including a Bt toxin. In further embodiments, the polypeptide is not a Bt toxin.

RNAi related nucleic acids, RNAi biomolecule, including dsRNA, miRNA, siRNA, and miRNA. These RNAi biomolecules can be achieved via internal production within the minicells or via external production and loading of the RNA into the minicells. The RNAi biomolecules are applied for i) biotic stress by controlling insects, weeds, fungi, viruses, or parasites by targeted delivery of RNAi biomolecules to a target transcript within a target cell and release over time, ii) abiotic stress such as drought by targeted delivery of RNAi biomolecules to enhance drought tolerance of the plant (also can be used as a biostimulant), and iii) aquaculture by preventing, treating, controlling diseases in fish, shellfish, crustaceans. In some embodiments, a biologically active compound as a biocontrol is a nucleic acid that is selected from the group consisting of an antisense nucleic acid, a double-stranded RNA (dsRNA), a short-hairpin RNA (shRNA), a small-interfering RNA (siRNA), a microRNA (miRNA), a ribozyme, an aptamer, and combination thereof.

Protoxins can be achieved via internal production within the minicells or via surface expression of the protein/protoxin on a surface of minicell. For example, lipases secreted by *Metarhizium anisopliae* can be delivered to a target via minicells and works as, an important biological control agent to be involved in the host infection process (Beys da Silva et al, Fungal Biol. 114(1):10-15, 2010). In some embodiments, the biologically active compound is the polypeptide. In other embodiments, the polypeptide is a protein toxin. In further embodiments, the polypeptide is not a Bt toxin. In some embodiments, the polypeptide is lipase used as a biocontrol compound.

Metabolites can be internally expressed within the minicells or encapsulated into the minicells. Microbial volatile organic compounds can be used as both biocontrols and bio stimulants.

Antibodies can be internally expressed within the minicells or encapsulated into the minicells. Highly specific biological agents can be surface expressed or expressed internally. For example, nanobodies, which has heavy-chain antibodies and its antigen binding fragment, but lack of light chains, have higher stability due to smaller size, lower toxicity due to more rapid clearance of unbound antibodies, additional routes of administration, and increased manufacturing production efficiency. Nanobodies can be delivered via minicells to act as biocontrols for crops.

Fermentation products such as spinosad can be internally expressed within the minicells or encapsulated into the minicells.

Semiochemicals such as pheromones, allomones, kairomones, and synomones, can be internally expressed within the minicells or encapsulated into the minicells. Pheromones, a class of microbial volatile organic compounds, can act as attractants and repellents to insects and other invertebrates. They can be used as biocontrol agents to control various pathogens as well as biofertilizers used for plant growth promotion. They are even used postharvest to prevent plant disease (Kanchiswamy et al., Trends Plant Sci. 40(4):206-211, 2015). Pheromones can be naturally produced or synthetically produced. Pheromones can be used for plant growth promotion. Some pheromones, derived from microorganisms, are able to promote the growth of some plants under various stressful conditions. For example, 2,3 butanediol, which is derived from the genus *Bacillus*) has been shown to induce systemic resistance and promote the growth of plants under stressful conditions like high salinity (Ryu et al., Plant Physiol. 134(3):1017-1026, 2004; Ryu et al., PNAS 100(8):4927-2932, 2003).

Pheromones can be also used for pest management. Certain pheromones, usually derived from insects, are able to be used as biocontrol agents. They can be a part of a formulation that can attract and kill the target pest or they can be used for "mass-trapping of pest populations (Witzgall et al., J Chem Ecol. 36(1):80-100, 2010). For example, pheromones ((Z)-9-hexadecenal, (Z)-11-hexadecenal and (Z)-9-octadecenal, components of the *S. incertulas* pheromone) have been demonstrated to be able to control the population of yellow stem borer (*Scirpophaga incertulas*) on rice (Cork et al., Bulletin of Entomological Research, 86(5): 515-524).

There are types of pheromones as follows; i) Aggregation pheromones function in mate selection, overcoming host resistance by mass attack, and defense against predators. A group of individuals at one location is referred to as an aggregation, whether consisting of one sex or both sexes, ii) Alarm pheromones function in some species to release a volatile substance when attacked by a predator that can trigger flight (in aphids) or aggression (in ants, bees, termites) in members of the same species, iii) Epideictic pheromones are used for territory marking, in regards to laying eggs, iv) Releaser pheromones are pheromones that cause an alteration in the behavior of the recipient. For example, some organisms use powerful attractant molecules to attract mates from a distance of two miles or more, v) Signal pheromones cause short-term changes, such as the neurotransmitter release that activates a response, vi) Primer pheromones trigger a change of developmental events, vii) Territorial pheromones mark the boundaries and identity of an organism's territory, viii) trail pheromones are commonly used by insects. For example, ants mark their paths with pheromones consisting of volatile hydrocarbons. Certain ants lay down an initial trail of pheromones as they return to the nest with food, ix) sex pheromones indicate the availability of the female for breeding. Male animals may also emit pheromones that convey information about their species and genotype, and other pheromones such as nasonov pheromones (worker bees), royal pheromones (bees), calming (appeasement) pheromones (mammals), necromones consisting of oleic and linoleic acids, which are given off by a deceased and decomposing organism. Also, Z-9-Tetradecenyl Acetate is used as an attractant.

In some embodiments, pheromones can be used as a form of a biocontrol. Pheromones present new environmentally safe strategies used for insect control. Pheromones follow the process of mating disruption through chemical communication inhibitors, pheromones, and plant-based volatiles, and attractant-and-kill and push-pull strategies.

In some embodiments, an anucleated cell-based platform and/or an industrial formulation disclosed herein can encapsulate biologically active compounds as biocontrols and deliver them in a scalable, targeted, cost-effective manner.

In some embodiments, the biocontrol compound is a peptide, polypeptide, fermentation product, metabolite, antibody, semiochemical, or micronutrient. In some embodiments, the polypeptide is lipase used as a biocontrol compound.

Biostimulants

The present disclosure teaches the biologically active compounds as a biostimulant. Non-limiting examples of these biostimulants include hormones and biochemical growth agents. These actives include abscisic acid (involved in dormancy mechanisms under stress), auxins (positively influence plant growth), cytokinins (influence cell division and shoot formation), ACC Deaminase (lowers inhibitory growth effects of ethylene), gibberellins (positively influence plant growth by elongating stems and stimulating pollen tube growth), and many others (brassinosteroids, salicylic acid, jasmonates, plant peptide hormones, polyamines, nitric oxide, strigolactones, karrikins, and triacontanol), which are used to both positively and negatively regulate the growth of plants. In some embodiments, an anucleated cell-based platform and/or an industrial formulation disclosed herein can encapsulate biologically active compounds as biostimulants and deliver them in a scalable, targeted, cost-effective manner.

In some embodiments, the biologically active compounds are pheromones to improve and modify chemical reactions to help the plants grow and fight stresses as biostimulants.

In some embodiments, the biologically active compounds are fertilizers, plant micronutrients and plant macro-nutrients, which include, but are not limited to, nitrogen, potassium, and phosphorous, and trace nutrients such as iron, copper, zinc, boron, manganese, calcium, molybdenum, and magnesium.

In some embodiments, biostimulants comprises microbial properties such as *rhizobium* (PGPRs) properties, fungal properties, cytokinins, phytohormones, peptides, and ACC-Deaminase. For example, nitrogen fixation can be achieved by delivering deliver ureases and/or nitrogenases via minicells to assist with nitrogen fixation.

In some embodiments, biostimulants comprises acids (such as humic substances, humin, fulvic acids, B vitamins, amino acids, fatty acids/lipids), extracts (such as carboxyls, botanicals, allelochemicals, betaines, polyamines, polyphenols, chitosan and other biopolymers), phosphites, phosphate solubilizers, nitrogenous compounds, inorganic salts, protein hydrolysates, and beneficial elements.

As one example, chitosan is a linear polysaccharide that is composed of randomly distributed (1-4)-linked D-glucosamine and N-acetyl-D-glucosamine. It is commercially produced by deacetylation of chitin, which is the second abundant polysaccharide in nature and is usually found in the cell wall of fungi and exoskeletons of arthropods. It is formed from chitin, co-polymer of N-acetyl-D-glucosamine and D-glucosamine. Chitosan-based materials induce several defensive genes in plants such as pathogenesis-related genes (i.e. glucanase and chitinase). Chitosan induces enzymes in reactive oxygen species scavenging system, such as superoxide dismutase, catalase and peroxidase. Signal transduction pathway from chitosan that elicits its responses involves hydrogen peroxide and nitric oxide signals, and may also directly control gene expression by interacting with chromatin. Chitosan can be used to stimulate plant growth and abiotic stress tolerance, and to induce pathogen resistance (Pichyangkura et al, Scientia Horticulturae 196(30:49-65, 2015).

As another example, protein hydrolysates have potential to increase germination, productivity and quality of wide range of crops. Protein hydrolysates can also alleviate negative effects of salinity, drought, and heavy metals. Protein hydrolysates can stimulate carbon and nitrogen metabolism, and interfering with hormonal activity. Protein hydrolysates can enhance nutrient availability in plant growth substrates and increase nutrient uptake and use efficiency in plants. Protein hydrolysates can also stimulate plant microbiomes; substrates such as amino acids provided by protein hydrolysates could provide food source for plant-associated microbes.

In some embodiments, said biostimulant compound is a peptide, polypeptide, fermentation product, metabolite, antibody, semiochemical, or micronutrient. In some embodiments, the polypeptide is lipase used as a biostimulant compound. In some embodiments, the polypeptide is ACC deaminase used as a biostimulant compound.

Minicells

Minicells are the result of aberrant, asymmetric cell division, and contain membranes, peptidoglycan, ribosomes, RNA, protein, and often plasmids but no chromosome. (Frazer A C and Curtiss III, Production, Properties and Utility of Bacterial Minicells, Curr. Top. Microbial. Immunol. 69:1-84 (1975)). Because minicells lack chromosomal DNA, minicells cannot divide or grow, but they can continue other cellular processes, such as ATP synthesis, replication and transcription of plasmid DNA, and translation of mRNA. Although chromosomes do not segregate into minicells, extrachromosomal and/or episomal genetic expression elements may segregate, or may be introduced into minicells after segregation from parent cells.

In embodiments, the minicells described herein are non-naturally occurring.

In some embodiments, the disclosure provides a composition comprising a plurality of minicells. In some embodiments, the disclosure provides a composition comprising a plurality of minicells comprising at least one biologically active compound within said cell. In some embodiments, the disclosure provides a composition comprising a plurality of minicells, wherein each minicell of said plurality comprises an enzymatically active polypeptide displayed on the surface of the minicell, wherein said enzymatically active polypeptide has enzymatic activity. The enzymatic activity is derived from enzymatically active polypeptides disclosed in the present disclosure.

In some embodiments, the invention provides a composition comprising a plurality of intact, bacterially-derived minicells. In some embodiments, the disclosure provides a composition comprising a plurality of intact, bacterially-derived minicells comprising at least one biologically active compound within said cell. In some embodiments, the invention provides a composition comprising a plurality of intact, bacterially-derived minicells, wherein each minicell of said plurality comprises an enzymatically active polypeptide displayed on the surface of the bacterial minicell, wherein said enzymatically active polypeptide has enzymatic activity. In some embodiments, the composition comprises minicells which further comprise a second polypeptide displayed on the surface of the bacterial minicell, to increase adhesion to a subject and/or subjects including, but are not limited to substrates of enzymes, receptors, metal, plastic, soil, bacteria, fungi, pathogens, germs, plants, animals, human, and the like. In some embodiments, the composition comprises a mixture of minicells, wherein certain minicells within the mixed minicell population display the enzymatically active polypeptide or display the second polypeptide including subject adhesion increasing polypeptide or display both.

Eubacterial Minicells

One type of minicell is a eubacterial minicell. For reviews of eubacterial cell cycle and division processes, see Rothfield et al., *Annu. Rev. Genet.,* 33:423-48, 1999; Jacobs et al., *Proc. Natl. Acad. Sci. USA,* 96:5891-5893, May, 1999; Koch, *Appl. and Envir. Microb.,* Vol. 66, No. 9, pp. 3657-3663; Bouche and Pichoff, *Mol Microbiol,* 1998. 29: 19-26; Khachatourians et al., *J Bacteriol,* 1973. 116: 226-229; Cooper, *Res Microbiol,* 1990. 141: 17-29; and Danachie and Robinson, "Cell Division: Parameter Values and the Process," in: *Escherichia Coli* and *Salmonella Typhimurium: Cellular and Molecular Biology,* Neidhardt, Frederick C., Editor in Chief, American Society for Microbiology, Washington, D.C., 1987, Volume 2, pages 1578-1592, and references cited therein; and Lutkenhaus et al., "Cell Division," Chapter 101 in: *Escherichia coli and Salmonella typhimurium: Cellular and Molecular Biology,* $2^{nd}$ Ed., Neidhardt, Frederick C., Editor in Chief, American Society for Microbiology, Washington, D.C., 1996, Volume 2, pages 1615-1626, and references cited therein. When DNA replication and/or chromosomal partitioning is altered, membrane-bounded vesicles "pinch off" from parent cells before transfer of chromosomal DNA is completed. As a result of this type of dysfunctional division, minicells are produced which contain an intact outer membrane, inner membrane, cell wall, and all of the cytoplasm components but do not contain chromosomal DNA.

In some embodiments, the bacterially-derived minicells are produced from a strain, including, but are not limited to a strain of *Escherichia coli, Bacillus* spp., *Salmonella* spp.,

*Listeria* spp., *Mycobacterium* spp., *Shigella* spp., or *Yersinia* spp. In some embodiments, the bacterially-derived minicells are produced from a strain that naturally produces minicells. Such natural minicell producing strains produce minicells, for example, at a 2:1 ratio (2 bacterial cells for every one minicell). In certain embodiments, exemplary bacterial strains that naturally produce minicells include, but are not limited to *E. coli* strain number P678-54, *Coli* Genetic Stock Center (CGSC) number: 4928 and *B. subtilis* strain CU403.

As one example, mutations in *B. subtilis* smc genes result in the production of minicells (Britton et al., 1998, *Genes and Dev.* 12:1254-1259; Moriya et al., 1998, *Mol Microbiol* 29:179-87). Disruption of smc genes in various cells is predicted to result in minicell production therefrom.

As another example, mutations in the divIVA gene of *Bacillus subtilis* results in minicell production. When expressed in *E. coli, B. subtilis* or yeast *Schizosaccharomyces pombe*, a DivIVA-GFP protein is targeted to cell division sites therein, even though clear homologs of DivIVA do not seem to exist in *E. coli, B. subtilis* or *S. pombe* (David et al., 2000, EMBO J. 19:2719-2727. Over- or under-expression of *B. subtilis* DivIVA or a homolog thereof may be used to reduce minicell production in a variety of cells.

In some embodiments, the minicell-producing bacteria is a Gram-negative bacteria. The Gram-negative bacteria includes, but is not limited to, *Escherichia coli, Salmonella* spp. including *Salmonella typhimurium, Shigella* spp. including *Shigella flexneri, Pseudomonas aeruginosa, Agrobacterium, Campylobacter jejuni, Lactobacillus* spp., *Neisseria gonorrhoeae*, and *Legionella pneumophila*. In some embodiments, the minicell-producing gram-negative bacteria can produce minicells naturally caused by endogenous or exogenous mutation(s) associated with cell division and/or chromosomal partitioning. In some embodiments, the minicell-producing bacteria comprises endogenous or exogenous gene(s) that is involved in cell division and/or chromosomal partitioning, where the gene is genetically modified such as by homologous recombination, compared to a corresponding wild-type gene. In some embodiments, the minicell-producing gram-negative bacteria is deficient in protease and/or its activity naturally and/or by genetic engineering techniques disclosed herein. In some embodiments, the protease-deficient minicell-producing gram-negative bacteria comprises a recombinant expression vector comprising a gene or genes that is involved in a protein of interest disclosed in the present disclosure.

In some embodiments, the minicell-producing bacteria can be a Gram-positive bacteria. The Gram-positive bacteria includes, but is not limited to, *Bacillus subtilis, Bacillus cereus, Corynebacterium Glutamicum, Lactobacillus acidophilus, Staphylococcus* spp., or *Streptococcus* spp. In some embodiments, the minicell-producing gram-positive bacteria can produce minicells naturally caused by endogenous or exogenous mutation(s) associated with cell division and/or chromosomal partitioning. In some embodiments, the minicell-producing gram-positive bacteria comprises endogenous or exogenous gene(s) that is involved in cell division and/or chromosomal partitioning, where the gene is genetically modified such as by homologous recombination, compared to a corresponding wild-type gene. In some embodiments, the minicell-producing gram-positive bacteria is deficient in protease and/or its activity naturally and/or by genetic engineering techniques disclosed herein. In some embodiments, the protease-deficient minicell-producing gram-positive bacteria comprises a recombinant expression vector comprising a gene or genes that is involved in a protein of interest disclosed in the present disclosure.

The minicell-producing bacteria can be a Extremophilic bacteria. The Extremophilic bacteria includes, but is not limited to, Thermophiles including *Thermus aquaticus*, Psychrophiles, Piezophiles, Halophilic bacteria, Acidophile, Alkaliphile, Anaerobe, Lithoautotroph, Oligotroph, Metallotolerant, Oligotroph, Xerophil or Polyextremophile. In some embodiments, the minicell-producing Extremophilic bacteria can produce minicells naturally caused by endogenous or exogenous mutation(s) associated with cell division and/or chromosomal partitioning. In some embodiments, the minicell-producing Extremophilic bacteria comprises endogenous or exogenous gene(s) that is involved in cell division and/or chromosomal partitioning, where the gene is genetically modified such as by homologous recombination, compared to a corresponding wild-type gene. In some embodiments, the minicell-producing Extremophilic bacteria is deficient in protease and/or its activity naturally and/or by genetic engineering techniques disclosed herein. In some embodiments, the protease-deficient minicell-producing Extremophilic bacteria comprises a recombinant expression vector comprising a gene or genes that is involved in a protein of interest disclosed in the present disclosure.

Eukaryotic Minicells

Achromosomal eukaryotic minicells (i.e., anucleate cells) are within the scope of the disclosure. Yeast cells are used to generate fungal minicells. See, e.g., Lee et al., Ibd1p, a possible spindle pole body associated protein, regulates nuclear division and bud separation in *Saccharomyces cerevisiae*, Biochim Biophys Acta 3:239-253, 1999; Kopecka et al., A method of isolating anucleate yeast protoplasts unable to synthesize the glucan fibrillar component of the wall J Gen Microbiol 81:111-120, 1974; and Yoo et al., Fission yeast Hrp1, a chromodomain ATPase, is required for proper chromosome segregation and its overexpression interferes with chromatin condensation, Nucl Acids Res 28:2004-2011, 2000. Cell division in yeast is reviewed by Gould and Simanis, The control of septum formation in fission yeast, Genes & Dev 11:2939-51, 1997).

In some embodiments, the eukaryotic minicells can be produced from yeast cells, such as *Saccharomyces cerevisiae, Pichia pastoris* and/or *Schizosaccharomyces pombe*.

As one example, mutations in the yeast genes encoding TRF topoisomerases result in the production of minicells, and a human homolog of yeast TRF genes has been stated to exist (Castano et al., 1996, *Nucleic Acids Res* 24:2404-10). Mutations in a yeast chromodomain ATPase, Hrp1, result in abnormal chromosomal segregation; (Yoo et al., 2000 *Nuc. Acids Res.* 28:2004-2011). Disruption of TRF and/or Hrp1 function is predicted to cause minicell production in various cells. Genes involved in septum formation in fission yeast (see, e.g., Gould et al., 1997 *Genes and Dev.* 11:2939-2951) can be used in like fashion.

Platelets are a non-limiting example of eukaryotic minicells. Platelets are anucleate cells with little or no capacity for de novo protein synthesis. The tight regulation of protein synthesis in platelets (Smith et al., 1999, Vasc Med 4:165-72) may allow for the overproduction of exogenous proteins and, at the same time, under-production of endogenous proteins. Thrombin-activated expression elements such as those that are associated with Bcl-3 (Weyrich et al., Signal-dependent translation of a regulatory protein, Bcl-3, in activated human platelets, Cell Biology 95:5556-5561, 1998) may be used to modulate the expression of exogenous genes in platelets.

As another non-limiting example, eukaryotic minicells are generated from tumor cell lines (Gyongyossy-Issa and Khachatourians, Tumour minicells: single, large vesicles released from cultured mastocytoma cells (1985) Tissue Cell 17:801-809; Melton, Cell fusion-induced mouse neuroblastomas HPRT revertants with variant enzyme and elevated HPRT protein levels (1981) *Somatic Cell Genet.* 7: 331-344).

Yeast cells are used to generate fungal minicells. See, e.g., Lee et al., Ibd1p, a possible spindle pole body associated protein, regulates nuclear division and bud separation in *Saccharomyces cerevisiae*, Biochim Biophys Acta 3:239-253, 1999; Kopecka et al., A method of isolating anucleate yeast protoplasts unable to synthesize the glucan fibrillar component of the wall J Gen Microbiol 81:111-120, 1974; and Yoo et al., Fission yeast Hrp1, a chromodomain ATPase, is required for proper chromosome segregation and its overexpression interferes with chromatin condensation, Nucl Acids Res 28:2004-2011, 2000. Cell division in yeast is reviewed by Gould and Simanis, The control of septum formation in fission yeast, Genes & Dev 11:2939-51, 1997). In some embodiments, the present disclosure teaches production of yeast minicells.

Archaebacterial Minicells

The term "archaebacterium" is defined as is used in the art and includes extreme thermophiles and other Archaea (Woese, C. R., L. Magrum. G. Fox. 1978. Archaebacteria. *Journal of Molecular Evolution.* 11:245-252). Three types of Archaebacteria are halophiles, thermophiles and methanogens. By physiological definition, the Archaea (informally, archaes) are single-cell extreme thermophiles (including thermoacidophiles), sulfate reducers, methanogens, and extreme halophiles. The thermophilic members of the Archaea include the most thermophilic organisms cultivated in the laboratory. The aerobic thermophiles are also acidophilic; they oxidize sulfur in their environment to sulfuric acid. The extreme halophiles are aerobic or microaerophilic and include the most salt tolerant organisms known. The sulfate-reducing Archaea reduce sulfate to sulfide in extreme environment. Methanogens are strict anaerobes, yet they gave rise to at least two separate aerobic groups: the halophiles and a thermoacidophilic lineage. Non-limiting examples of halophiles include *Halobacterium cutirubrum* and *Halogerax mediterranei*. Non-limiting examples of methanogens include *Methanococcus voltae; Methanococcus vanniela; Methanobacterium thermoautotrophicum; Methanococcus voltae; Methanothermus fervidus; and Methanosarcina barkeri*. Non-limiting examples of thermophiles include *Azotobacter vinelandii; Thermoplasma acidophilum; Pyrococcus horikoshii; Pyrococcus furiosus*; and Crenarchaeota (extremely thermophilic archaebacteria) species such as *Sulfolobus solfataricus* and *Sulfolobus acidocaldarius*.

Archaebacterial minicells are within the scope of the invention. Archaebacteria have homologs of eubacterial minicell genes and proteins, such as the MinD polypeptide from *Pyrococcus furiosus* (Hayashi et al., *EMBO J.* 20:1819-28, 2001). It is thus possible to create Archaebacterial minicells by methods such as, by way of non-limiting example, overexpressing the product of a min gene isolated from a prokaryote or an archaebacterium; or by disrupting expression of a min gene in an archaebacterium of interest by, e.g., the introduction of mutations thereof or antisense molecules thereto. See, e.g., Laurence et al., *Genetics* 152: 1315-1323, 1999.

By physiological definition, the Archaea (informally, archaes) are single-cell extreme thermophiles (including thermoacidophiles), sulfate reducers, methanogens, and extreme halophiles. The thermophilic members of the Archaea include the most thermophilic organisms cultivated in the laboratory. The aerobic thermophiles are also acidophilic; they oxidize sulfur in their environment to sulfuric acid. The extreme halophiles are aerobic or microaerophilic and include the most salt tolerant organisms known. The sulfate-reducing Archaea reduce sulfate to sulfide in extreme environment. Methanogens are strict anaerobes, yet they gave rise to at least two separate aerobic groups: the halophiles and a thermoacidophilic lineage. In some embodiments, the present disclosure teaches production of archaeal minicells.

Minicells Derived from Endophytes

An endophyte is an endosymbiont, often a bacterium or fungus, that lives within a plant for at least part of its life cycle. The endophyte can transport itself from the environment to internal organs of plants. Non-limiting examples of endophytes include *Acidovorax facilis, Bradyrhizobium, Rhizobium, Rhodococcus rhodochrous, Colletotrichum, Curvularia, epichloe, Fusarium, Mycosphaerella, Neotyphodium, Piriformospora,* and *Serendipita*. In some embodiments, the present disclosure teaches production of endophyte-derived minicells. In other embodiments, endophyte-derived minicells can enter into internal plant cell, tissues, or organs, and function as an invasive minicell.

Fungal endophytes have the ability to colonize inter- or intra-cellularly. The colonization process involves several steps, including host recognition, spore germination, penetration of the epidermis and tissue multiplication. Once the endophytes are successfully colonized in the host tissue, the endophytic niche becomes established. In the endophytic niche, endophytes will obtain a reliable source of nutrition from the plant fragment, exudates and leachates and protect the host against other microorganisms (Gao et al., 2010). In some embodiments, minicells produced from fungal endophytes can transmit the active compounds within and/or on their surface to a target using their invasive capability.

Minicells Derived from Plant Pathogen Bacteria

The present disclosure provides plant pathogen bacteria, which can be utilized for minicell production, including but are not limited to (1) *Pseudomonas syringae* pathovars; (2) *Ralstonia solanacearum*; (3) *Agrobacterium tumefaciens*; (4) *Xanthomonas oryzae* pv. *oryzae*; (5) *Xanthomonas campestris* pathovars; (6) *Xanthomonas axonopodis* pathovars; (7) *Erwinia amylovora*; (8) *Xylella fastidiosa*; (9) *Dickeya* (*dadantii* and *solani*); (10) *Pectobacterium carotovorum* (and *Pectobacterium atrosepticum*), (11) *Clavibacter michiganensis* (*michiganensis* and *sepedonicus*), (12) *Pseudomonas savastanoi*, and (13) *Candidatus liberibacter asiaticus*. Such plant pathogen bacteria natively have the capacity to penetrate and invade into internal host tissues in their natural state. In some embodiments, minicells derived from plant pathogen bacteria described above can naturally deliver biologically active compounds disclosed herein into internal cells, tissues, and/or organs of a target host in their natural ability of invasion, penetration, and/or transmission into internal parts of a target.

From example, some pathogen bacteria are found to secrete cell wall-degrading endoglucanase and endopolygalacturonase, potentially explaining penetration into the root endosphere. Other pathogen bacteria can penetrate through the stomata into the substomatal chamber, and colonization of the intercellular spaces of the leaf mesophyll. The minicells produced from these pathogen bacteria possess and utilize natural ability of invading, penetrating and/or transmitting for scalable and targeted delivery of active compounds disclosed herein.

Bacterial Minicell Production

Minicells are produced by parent cells having a mutation in, and/or overexpressing, or under expressing a gene involved in cell division and/or chromosomal partitioning, or from parent cells that have been exposed to certain conditions, that result in aberrant fission of bacterial cells and/or partitioning in abnormal chromosomal segregation during cellular fission (division). The term "parent cells" or "parental cells" refers to the cells from which minicells are produced. Minicells, most of which lack chromosomal DNA (Mulder et al., *Mol Gen Genet,* 221: 87-93, 1990), are generally, but need not be, smaller than their parent cells.

Minicells are achromosomal, membrane-encapsulated biological nanoparticles (≤400 nm) that are formed by bacteria following a disruption in the normal division apparatus of bacterial cells. Minicells can also be 400 nm to 650 nm in size. In essence, minicells are small, metabolically active replicas of normal bacterial cells with the exception that they contain no chromosomal DNA and as such, are non-dividing and non-viable. Although minicells do not contain chromosomal DNA, the ability of plasmids, RNA, native and/or recombinantly expressed proteins, and other metabolites have all been shown to segregate into minicells. Some methods of construction of minicell-producing bacterial strains are discussed in detail in U.S. patent application Ser. No. 10/154,951 (US Publication No. US/2003/0194798 A1), which is hereby incorporated by reference in its entirety.

Disruptions in the coordination between chromosome replication and cell division lead to minicell formation from the polar region of most rod-shaped prokaryotes. Disruption of the coordination between chromosome replication and cell division can be facilitated through the overexpression of some of the genes involved in septum formation and binary fission. Alternatively, minicells can be produced in strains that harbor mutations in genes that modulate septum formation and binary fission. Impaired chromosome segregation mechanisms can also lead to minicell formation as has been shown in many different prokaryotes.

Plasmid Based Methods of Minicell Production

In some embodiments, minicell production can be achieved by the overexpression or mutation of genes involved in the segregation of nascent chromosomes into daughter cells. For example, mutations in the parC or mukB loci of *E. coli* have been demonstrated to produce minicells. The overexpression or mutation of a cell division gene capable of driving minicell production in one family member, can be used to produce minicells in another. For example, it has been shown that the overexpression *E. coli* ftsZ gene in other Enterobacteriacea family members such as *Salmonella* spp. and *Shigella* spp as well as other class members such as *Pseudomonas* spp. will result in similar levels of minicell production.

In some embodiments, minicells can be produced in *E. coli* by the overproduction of the protein FtsZ which is an essential component of the Min division system by which *E. coli* operates. Overproduction of this protein in *E. coli* results in the inability for this ring to be spatially restricted to the midsection of the cell, thus resulting in production of minicells upon cell division. Because the overproduction of FtsZ can create minicells, it can be overexpressed using a plasmid based system.

The same can be demonstrated in the mutation-based minicell producing bacterial strains. For example, deletion of the Min locus in any of bacterial strains results in minicell production. Cell division genes in which mutation can lead to minicell formation include but are not limited to the min genes (such as minC, minD, and minE).

In some embodiments, *E. coli* rely on the min system in order to ensure proper replication of parent cells into daughter cells. This min system (known as the minB operon) consists of 3 parts, minD, minC, and minE. These genes work together in order to control the placement of the Z-ring which is comprised of polymerized FtsZ protein. MinC consists of two distinct domains, both of which interact directly with the FtsZ protein in order to inhibit polymerization (Z-ring formation). MinD is a protein that is associated with the membrane that forms at one of the cell's poles and polymerizes toward the cell's mid-point. It binds MinC which is distributed throughout the cytoplasm. MinE is a protein that binds to MinD as well and releases MinC. It polymerizes into a ring like shape and oscillates from pole to pole in the cell.

In some embodiments, this system can be manipulated in order to shift the Z-ring to a polar end of the cell which excludes the nucleoid DNA upon completion of replication. The Z-ring can be shifted by not allowing the cell to sequester MinC to the polar ends of the cell. In the absence of MinC or MinD, or overexpression of MinE, *E. coli* cells will form achromosomal and/or anucleate cells. The FtsZ and the Min systems for causing asymmetrical cell division are exemplified by Piet et al, 1990, *Proc. Natl. Acad. Sci. USA* 87:1129-1133 and Xuan-Chuan et al, 2000, *J. Bacteriol.* 182(21):6203-62138, each of which is incorporated herein by reference.

Genes can be introduced in a site directed fashion using homologous recombination. Homologous recombination permits site specific modifications in endogenous genes and thus inherited or acquired mutations may be corrected, and/or novel alterations may be engineered into the genome. Homologous recombination and site-directed integration in plants are discussed in, for example, U.S. Pat. Nos. 5,451, 513; 5,501,967 and 5,527,695.

In some embodiments, minicells are produced by deleting, mutating, knocking out, or disrupting minC, minD, and/or minC and minD gene(s) in bacteria by traditional gene engineering techniques including homologous recombination. In other embodiments, minicells are produced by overexpressing certain genes such as ftsZ and/or minE in bacteria.

Controlled Production of Minicells

In some embodiments, the present disclosure teaches mutating cell populations by introducing, deleting, or replacing selected portions of genomic DNA. Thus, in some embodiments, the present disclosure teaches methods for targeting mutations to a specific locus such as ftsZ, minC, minD, minC/D, and minE. In other embodiments, the present disclosure teaches the use of gene editing technologies such as ZFNs, TALENS, CRISPR or homing endonucleases, to selectively edit target DNA regions. In aspects, the targeted DNA regions is ftsZ, minC, minD, minC/D, and minE.

Engineered nucleases such as zinc finger nucleases (ZFNs), Transcription Activator Like Effector Nucleases (TALENs), engineered homing endonucleases, and RNA or DNA guided endonucleases, such as CRISPR/Cas such as Cas9 or CPF1, are particularly appropriate to carry out some of the methods of the present disclosure. Additionally or alternatively, RNA targeting systems can use used, such as CRISPR/Cas systems have RNA targeting nucleases.

In some embodiments, one skilled in the art can appreciate that the Cas9 disclosed herein can be any variant described in the literature, including but not limited to the functional mutations described in: Fonfara et al. Nucleic Acids Res. 2014 February; 42(4):2577-90; Nishimasu H. et al. Cell. 2014 Feb. 27; 156(5):935-49; Jinek M. et al. Science. 2012 337:816-21; and Jinek M. et al. Science. 2014 Mar. 14; 343(6176); see also U.S. patent application Ser. No. 13/842,859 filed Mar. 15, 2013, which is hereby incorporated by reference; further, see U.S. Pat. Nos. 8,697,359; 8,771,945; 8,795,965; 8,865,406; 8,871,445; 8,889,356; 8,895,308; 8,906,616; 8,932,814; 8,945,839; 8,993,233; and 8,999,641, which are all hereby incorporated by reference. Thus, in some embodiments, the systems and methods disclosed herein can be used with the wild type Cas9 protein having double-stranded nuclease activity, Cas9 mutants that act as single stranded nickases, deactivated Cas9 (dCas9) that has no nuclease activity, or other mutants with modified nuclease activity.

In some examples, a Type II nuclease may be catalytically dead (e.g. dCas9, "dead Cas9," "deactivated Cas9") such that it binds to a target sequence, but does not cleave. dCAS9 is a variant of the CAS9 protein (CRISPR) that has had its active site altered to no longer be able to edit genomes, but can still bind to highly specific segments of the genome using a guide RNA. This protein can stop transcription of the gene if bound. In some embodiments, the dCAS9 gene can be placed under inducible control so that its expression would be controlled. The guide RNA corresponding to the knockout within the Min system could be included on a plasmid or cut into the genome and placed under inducible control. Upon induction with this system, the guide RNA would direct the dCAS9 protein to the gene within the Min system in order to stop its expression. The stopping of expression of this gene such as minC, minD, and minC/D would result in the formation of minicells.

Antibiotic Resistance Knock In-Knock Out

In some embodiments, the present disclosure teaches uses of the genetic manipulation technique using Lambda-Red recombination system in order to edit genome integrated with exogenous expression cassette such as an selectable marker such as antibiotic resistant gene. In some embodiments, an selectable marker such as antibiotic resistant gene is integrated into the host genome (e.g. bacteria) in order to knockout minC/D/CD gene for inducing minicell production. If the marker with antibiotic resistance is no longer desired after successfully selecting the minicells in which the target gene (such as minC/D/CD) is knocked out, the flippase can be used to remove the integrated antibiotic resistant gene cassette from the host genome. A fragment of linear DNA is inserted into the genome directed by that fragment homology to the genome. This can be used to knock in genes of interest or to knockout genes of interest by replacing them with an antibiotic resistance cassette such as Chloramphenicol-resistant gene, kanamycin-resistant gene, spectinomycin-resistant gene, streptomycin-resistant gene, ampicillin-resistant gene, tetracycline-resistant gene, erythromycin-resistant gene, bleomycin-resistant gene, and bleomycin-resistant gene. A successful genetic manipulation is then selected for using this antibiotic resistance cassette. If a flippase recombination target (FRT) site is included within the resistance cassette for further genetic manipulations, it can be used for removing the antibiotic resistant gene integrated into the genome in vivo after selection of target minicells. The enzyme used for this is recombinase flippase and is often expressed from a plasmid that can be removed from the cell line using a temperature sensitive origin of replication. Recombinase flippase recognizes two identical FRT sites on both the 5' and 3' ends of the antibiotic resistance cassette and removes the DNA between the two sites. In some embodiments, the FRT site can be included within an antibiotic resistance cassette to remove the antibiotic resistance cassette after its use.

Strains for Minicell Production

A E. coli P678-54 strain is obtained from Coli Genetic Stock Center (CGSC), and is used to produce minicells (Adler et al., 1967, Proc. Natl. Acad. Sci. USA 57:321-326; Inselburg J, 1970 J. Bacteriol. 102(3):642-647; Frazer 1975, Curr. Topics Microbiol. Immunol. 69:1-84).

In some embodiments, an anucleated cell is produced from a P678-54 E. coli parental strain. The anucleated cell produced from P678-54 parental bacterial strain is used as an anucleated cell-based platform and/or an industrial formulation for the encapsulation and delivery of biologically active compounds.

Protease-Deficient Bacterial Strains

The present disclosure provides the production of minicells from B strains using genetically-engineering techniques including B strains including BL21, BL21 (DE3), and BL21-AI are deficient in Lon protease (cytoplasm) and OmpT protease (outer membrane). Accordingly, B strains as protease-deficient strains can be utilized to create protease-deficient and/or protease-deficient minicells. The DE3 designation means that respective strains contain the λDE3 lysogen that carries the gene for T7 RNA polymerase under control of the lacUV5 promoter. IPTG is required to maximally induce expression of the T7 RNA polymerase in order to express recombinant genes cloned downstream of a T7 promoter. BL21(DE3) is suitable for expression from a T7 or T7-lac promoter or promoters recognized by the E. coli RNA polymerase: e.g. lac, tac, trc, ParaBAD, PrhaBAD and also the T5 promoter. The genotype of BL21 (DE3) is: fhuA2 [lon] ompT gal (λ DE3) [dcm] ΔhsdS λ DE3=λ sBamHIo ΔEcoRI-B int::(lacI::PlacUV5::T7 gene1) i21 Δnin5.

BL21-AI E. coli contains a chromosomal insertion of the gene encoding T7 RNA polymerase (RNAP) into the araB locus of the araBAD operon, placing regulation of T7 RNAP under the control of the arabinose-inducible araBAD promoter. Therefore, this strain is especially useful for the expression of genes that may be toxic to other BL21 strains where basal expression of T7 RNAP is leaky. The BL21-AI strain does not contain the lon protease and is deficient in the outer membrane protease, OmpT. The genotype of BL21-AI is F$^-$ ompT hsdS$_B$ (r$_B^-$ m$_B^-$) gal dcm araB::T7RNAP-tetA. The BL21-AI has an arabinose promoter that controls the production T7 RNA Polymerase, while the BL21 (DE3) has a lac promoter that controls the production of the T7 RNA Polymerase. This is significant because the lac promotion system is leaky. Therefore, the BL21-AI protein production is more tightly regulated due to the arabinose promotion system.

The present disclosure teaches that LPS (Lipopolysaccharide) modified BL21 (DE3) cells can be used. The LPS of the E. coli is modified to be significantly less toxic. This LPS modified BL21 (DE3) cells if necessary. This could also be branched out to other gram-negative bacterial cells. Safe usage of gram-negative cells can be beneficial for anucleated cell-based platform and/or an industrial formulation.

ClearColi® BL21(DE3) cells are the commercially available competent cells with a modified LPS (Lipid IVA) that does not trigger the endotoxic response in diverse cells. For example, ClearColi cells lack outer membrane agonists for hTLR4/MD-2 activation; therefore, activation of hTLR4/MD-2 signaling by ClearColi® is several orders of magnitude lower as compared with E. coli wild-type cells. Heterologous proteins prepared from ClearColi® are virtually free of endotoxic activity. After minimal purification from ClearColi cells, proteins or plasmids (which may contain Lipid IVA) can be used in most applications without eliciting an endotoxic response in human cells. In ClearColi cells, two of the secondary acyl chains of the normally hexa-acylated LPS have been deleted, eliminating a key determinant of endotoxicity in eukaryotic cells. The six acyl chains of the LPS are the trigger which is recognized by the Toll-like receptor 4 (TLR4) in complex with myeloid differentiation factor 2 (MD-2), causing activation of NF-κB and production of proinflammatory cytokines. The deletion of the two secondary acyl chains results in lipid IVA, which does not induce the formation of the activated heterotetrameric TLR4/MD-2 complex and thus does not trigger the endotoxic response. In ClearColi® BL21(DE3) Electrocompetent Cells 4 MA145 Rev. 31 Oct. 2016 addition, the oligosaccharide chain is deleted, making it easier to remove the resulting lipid IVA from any downstream product.

In some embodiments, protease-deficient minicells disclosed herein are produced from protease-deficient parental strains including, but are not limited to, BL21 (DE3), BL21-AI and LPS-modified BL21 (DE3). In other embodiments, BL21 (DE3), BL21-AI and LPS-modified BL21 (DE3) strains are genetically engineered by deleting, mutating, knocking out, or disrupting minC, minD, and/or minC and minD gene(s) to induce minicell production. In other embodiments, BL21 (DE3), BL21-AI and LPS-modified BL21 (DE3) strains are genetically engineered by overexpressing ftsZ and/or minE genes to induce minicell production.

In further embodiments, the present disclosure provides a new minicell-producing strain named as B8. This strain is the protease-deficient minicell-producing strain without the T7 RNA Polymerase. This minicell strain is produced from the BL21 (DE3) strain. While knocking out minC/D/CD, the T7 RNA Polymerase was silenced due to the homology of the introduced knockout via Lambda Red Transformation. This strain can be used for a need of a protease-deficient minicell, but not having the T7 RNA Polymerase. In some embodiments, minicells displayed an enzymatically active polypeptide such as complicated or toxic proteins on their surface, need to be more controlled and slower expression of the desired but complicated or toxic proteins.

The present disclosure teaches genotypes of newly-generated protease-deficient minicell strains comprising i) minC-deleted BL21(DE3); fhuA2 [lon] ompT gal (λ DE3) [dcm] ΔhsdS λ DE3=λ sBamHIo ΔEcoRI-B int::(lacI::PlacUV5::T7 gene1) i21 Δnin5 ΔminC, ii) minD-deleted BL21(DE3); fhuA2 [lon] ompT gal (λ DE3) [dcm] ΔhsdS λ DE3=λ sBamHIo ΔEcoRI-B int::(lacI::PlacUV5::T7 gene1) i21 Δnin5 ΔminD, iii) minC/D-deleted BL21(DE3); fhuA2 [lon] ompT gal (λ DE3) [dcm] ΔhsdS λ DE3=λ sBamHIo ΔEcoRI-B int::(lacI::PlacUV5::T7 gene1) i21 Δnin5 ΔminC ΔminD; iv) minC-deleted BL21-AI; F⁻ ompT hsdS$_B$ (r$_B^-$ m$_B^-$) gal dcm araB::T7RNAP-tetA ΔminC, v) minD-deleted BL21-AI; F⁻ ompT hsdS$_B$ (r$_B^-$ m$_B^-$) gal dcm araB::T7RNAP-tetA ΔminD, vi) minC/D-deleted BL21-AI; F⁻ ompT hsdS$_B$ (r$_B^-$ m$_B^-$) gal dcm araB::T7RNAP-tetA ΔminC ΔminD; vii) minC-deleted LPS-modified BL21(DE3); msbA148 ΔgutQ ΔkdsD ΔlpxL ΔlpxM ΔpagP ΔlpxP ΔeptA ΔminC, viii) minD-deleted LPS-modified BL21(DE3); msbA148 ΔgutQ ΔkdsD ΔlpxL ΔlpxM ΔpagP ΔlpxP ΔeptA ΔminD, ix) minC/D-deleted LPS-modified BL21(DE3); msbA148 ΔgutQ ΔkdsD ΔlpxL ΔlpxM ΔpagP ΔlpxP ΔeptA ΔminC, ΔminD, x) minC-deleted B8 with suppression on T7 RNA polymerase activity; fhuA2 [lon] ompT gal (λ DE3) [dcm] ΔhsdS λ DE3=λ sBamHIo ΔEcoRI-B int::(lacI:: PlacUV5::T7 gene1) i21 Δnin5 ΔminC; xi) minD-deleted B8 with suppression on T7 RNA polymerase activity; fhuA2 [lon] ompT gal (λ DE3) [dcm] ΔhsdS λ DE3=λ sBamHIo ΔEcoRI-B int::(lacI::PlacUV5::T7 gene1) i21 Δnin5 ΔminD; and xii) minC/D-deleted B8 with suppression on T7 RNA polymerase activity; fhuA2 [lon] ompT gal (λ DE3) [dcm] ΔhsdS λ DE3=λ sBamHIo ΔEcoRI-B int::(lacI:: PlacUV5::T7 gene1) i21 Δnin5 ΔminC ΔminD.

Minicells that have segregated from parent cells lack chromosomal and/or nuclear components, but retain the cytoplasm and its contents, including the cellular machinery required for protein expression. In some embodiments, minicells are protease-deficient because the parent cells are protease-deficient strains. Although chromosomes do not segregate into minicells, extrachromosomal and/or episomal genetic expression elements may segregate, or may be introduced into minicells after segregation from parent cells. In some embodiments, the disclosure is drawn to protease-deficient minicells comprising an expression element, which may be an inducible expression element. The inducible expression element such as an inducible promoter can be introduced to a recombinant plasmid used for homologous recombination to knock out and/or delete gene(s) involved to cell division and/or chromosomal partitioning such as minC, minD, and minC/D, a recombinant expression vector to overexpress gene(s) involved to cell division and/or chromosomal partitioning such as ftsZ and minE, and a recombinant expression vector for expressing an enzymatically active polypeptide including a protein of interest disclosed herein. In further embodiments, the inducible expression element comprises expression sequences operably linked to an open reading frame (ORF) that encodes proteins of interest disclosed herein. Optionally, at any point in the method, an inducing agent is provided in order to induce expression of an ORF that encodes proteins of interest disclosed herein.

In some embodiments, the disclosure teaches methods of making a protease-deficient bacterial minicell comprising a recombinant fusion protein that is not naturally found in parental cells. In some embodiment, the disclosure teaches method of preparing protease-deficient minicells from the host cells.

Figure 16:
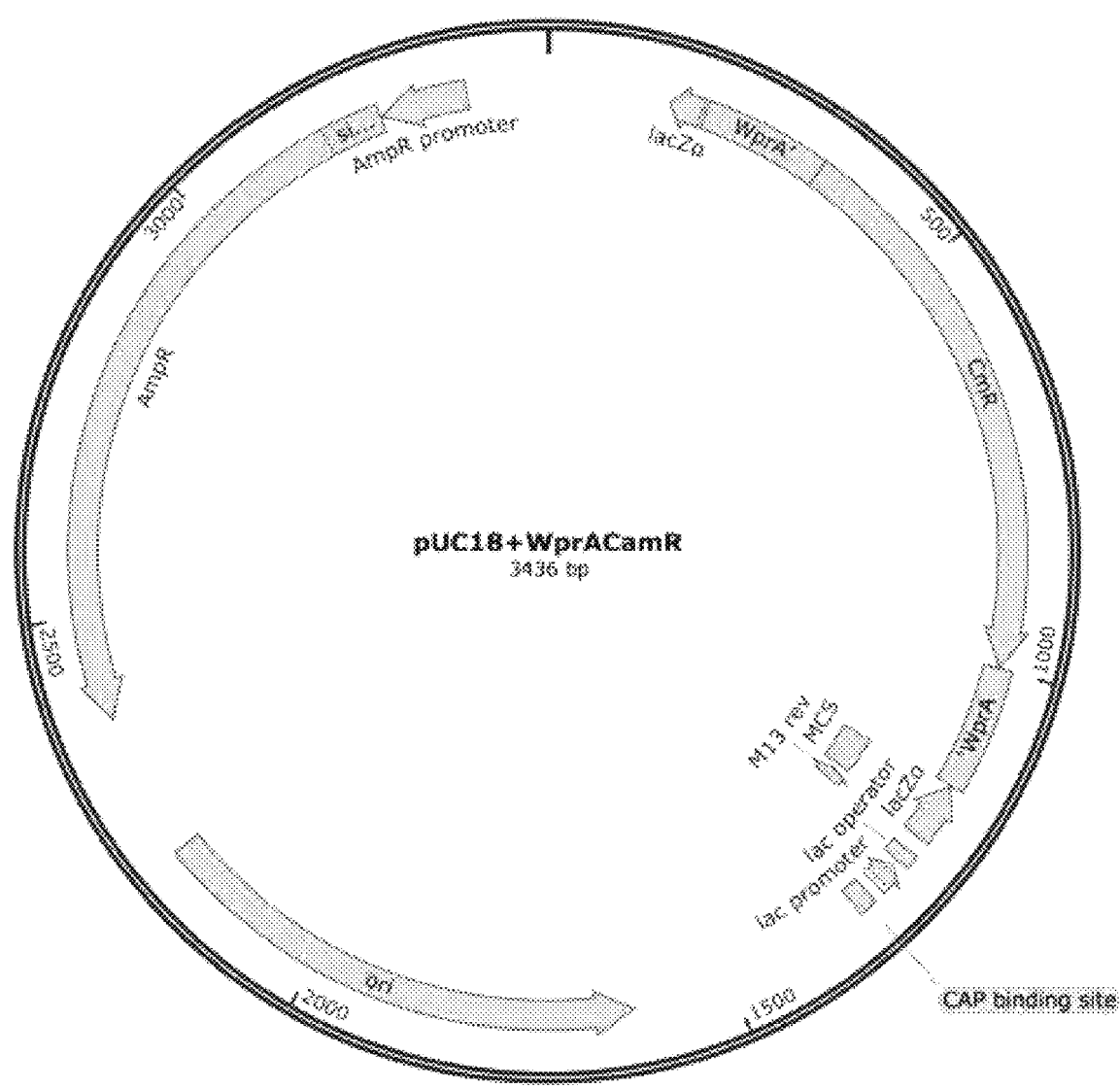
FIG. 16 illustrates an exemplary pUC18 vector for a protease WprA knockout to produce protease-deficient minicells from bacterial strains with WprA protease. The pUC18 vector was inserted with a recombinant DNA insert comprising 5' end nucleotide sequence of WprA nucleotide sequence gene, a chloramphenicol resistant gene (CmR) with cat promoter, and 3' end of WprA gene. The hairpin loops flanked by 5' and 3' ends of wprA gene are inserted into the insert to stop transcriptional regulation of other neighboring genes in the genome where the insert is integrated.

In other embodiments, the present disclosure teaches production of protease-deficient minicells from B. subtilis strains such as CU403 DIVIVA, CU403,DIVIVB,SPO–, CU403,DIVIVB and CU403,DIVIVB1 using by deleting, mutating, knocking out, or disrupting gene encoding WprA protease. FIG. 16 illustrate an exemplary recombinant vector for this purpose of suppressing and/or removing WprA protease activity to make protease-deficient condition in B. subtilis.

B. subtilis genetic manipulations work slightly differently than genetic manipulations in E. coli. B. subtilis is known to readily undergo homologous recombination if DNA containing homology to the existing genome is inserted. This is unlike E. coli; E. coli has mechanisms in place to degrade any non-natural linear DNA present. This difference can be utilized in order to knockout genes by designing an antibiotic resistance cassette flanked by homologous arms which correspond to the start and end of the gene that is desired to be knockout out.

The present disclosure provides the production of minicells from B. subtilis using genetically-engineering techniques. In some embodiments, B. subtilis strains including, but are not limited to CU403 DIVIVA (BGSC No. 1A196), CU403,DIVIVB,SPO– (BGSC No. 1A197), CU403,DIVIVB (BGSC No. 1A292), CU403,DIVIVB1 (BGSC No.

1A513), KO7 can be used as parental bacterial cells to produce minicells. *B. subtilis* strains are the commercially available and can be obtained from *Bacillus* Genetic Stock Center (BGSC). The catalog of strains is available on the document provided by publicly accessible BGSC webpage (www.bgsc.org/_catalogs/Catpart1.pdf).

In some embodiments, *Bacillus Subtilis* stains including, but are not limited to CU403 DIVIVA, CU403,DIVIVB, SPO−, CU403,DIVIVB and CU403,DIVIVB1 can be genetically modified by knocking out gene encoding WprA Protease in these strains. WprA protease is known as one of the harshest proteases.

In order to knock out, delete, and or remove WprA-encoding gene from *B. subtilis* strains, the pUC18 WprA-CamR vector is used as illustrated in FIG. 16. This vector has the homologous arms corresponding to the gene coding for WprA cell wall protease that naturally occurs in *B. subtilis* which is undesirable for protein surface expression. These homologous arms flank a chloramphenicol resistance cassette in order to allow for selection. After the homologous recombination via the homologous arms within the host cells, the WprA-encoding nucleotide except the homologous arm is replaced with the chloramphenicol selection marker gene. This plasmid can replicate within *E. coli* due to its origin of replication, thus when transformed into *B. subtilis* it cannot replicate. After transformation, colonies are selected for using chloramphenicol in order to isolate the colonies in which the knockout of WprA successfully occurs. Because the plasmid cannot replicate in *B. subtilis*, only the cells can survive against the presence of chloramphenicol if the recombinant cassette having the chloramphenicol resistant marker gene is integrated to the genome of the *B. subtilis* cell by homologous recombination.

*B. subtilis* secretes no fewer than seven proteases during vegetative growth and stationary phase. Strains in which multiple protease genes have been inactivated have proved to be superior to wild type strains in production of foreign proteins. The KO7 is prototrophic, free of secreted proteases, and have marker-free deletions in PY79 genetic background. This KO7 is available from the BGSC as accession number 1A1133. KO7 Genotype: ΔnprE ΔaprE Δepr Δmpr ΔnprB Δvpr Δbpr.

In some embodiments, a seven-protease deletion strain, *B. subtilis* KO7, can be used for *B. subtilis* minicell production by knocking out DIV-IVA and DIV-IVB using genetic engineering techniques described in the present disclosure.

In some embodiments, an anucleated cell is produced from a P678-54 *E. coli* wild strain. In other embodiments, an anucleated cell is produced from a protease-deficient *E. coli* strain including BL21, BL21(DE3), BL21-AI, LPS-modified BL21 (DE3) and B8. In some embodiments, an anucleated cell is produced from a parental bacterial cell deficient in WprA protease. In some embodiments, an anucleated cell is produced from a protease deficient *B. subtilis* parental bacterial cell. In some embodiments, an anucleated cell is produced from produced from a protease deficient KO7 *B. subtilis* parental bacterial cell. In other embodiments, an anucleated cell is produced from a protease deficient *B. subtilis* parental bacterial cell selected from the group consisting of: (1) CU403,DIVIVA; (2) CU403,DIVIVB,SPO−; (3) CU403,DIVIVB; and (4) CU403,DIVIVB1, wherein at least one protease encoding gene has been repressed, deleted, or silenced. In further embodiments, an anucleated cell is produced from an eukaryotic cell. In further embodiments, the anucleated cell produced as described above is used as an anucleated cell-based platform and/or an industrial formulation for the encapsulation and delivery of biologically active compounds.

In some embodiments, minicells taught in the present disclosure is protease deficient or ribonuclease deficient. In some embodiments, said minicell is protease deficient. In some embodiments, said minicell is ribonuclease deficient. In some embodiments, said minicell is protease deficient and ribonuclease deficient.

Ribonuclease-Deficient Bacterial Strains

The present disclosure provides the production of minicells from HT115 (DE3) using genetically-engineering techniques. HT115 (DE3) is a RNAi Feeding strain, which is an Rnase III-deficient *E. coli* strain with IPTG-inducible T7 Polymerase activity. To induce dsRNA production from these plasmids, the HT115 bacteria is grown on special RNAi NGM feeding plates that contain IPTG and the ampicillin analog carbenicillin. Carbenicillin is preferred over ampicillin because it tends to be more stable. Accordingly, HT115 strain as a ribonuclease-deficient strains can be utilized to create ribonuclease-deficient and/or ribonuclease-free minicells. The DE3 designation means that respective strains contain the λDE3 lysogen that carries the gene for T7 RNA polymerase under control of the lacUV5 promoter. IPTG is required to maximally induce expression of the T7 RNA polymerase in order to express recombinant genes cloned downstream of a T7 promoter. HT115 (DE3) is suitable for expression from a T7 or T7-lac promoter or promoters recognized by the *E. coli* RNA polymerase: e.g. lac, tac, trc, ParaBAD, PrhaBAD and also the T5 promoter. The genotype of HT115 (DE3) is: F−, mcrA, mcrB, IN(rrnD-rrnE)1, rnc14::Tn10(DE3 lysogen: lavUV5 promoter—T7 polymerase) (IPTG-inducible T7 polymerase) (RNAse III minus). This strain grows on LB or 2XYT plates. This strain is tetracycline resistant. Researchers using this strain can test for expression by transforming in one of the plasmids from the Fire Vector Kit (1999) (pLT76, e.g.) using standard $CaCl_2$ transformation techniques. This strain is resistant to tetracycline, and can be cultivated at 37° C., LB, and aerobic. Researchers also use this strain to test the interference experiment of nematodes.

In some embodiments, ribonuclease-deficient minicells disclosed herein are produced from ribonuclease-deficient parental strains including, but are not limited to, HT115 (DE3). In other embodiments, HT115 (DE3) strain is genetically engineered by deleting, mutating, knocking out, or disrupting minC, minD, and/or minC and minD gene(s) to induce minicell production. In other embodiments, HT115 (DE3) strain is genetically engineered by overexpressing ftsZ and/or minE genes to induce minicell production.

In some embodiments, ribonuclease-deficient minicells disclosed herein can be produced from protease-deficient parental strains including, but are not limited to, BL21 (DE3), BL21-AI and LPS-modified BL21 (DE3), genetically engineered by deleting, mutating, knocking out, or disrupting gene(s) encoding ribonuclease III. In other embodiments, BL21 (DE3), BL21-AI and LPS-modified BL21 (DE3) strains, in which ribonuclease III expression is suppressed, disrupted and/or nullified, are further genetically engineered by deleting, mutating, knocking out, or disrupting minC, minD, and/or minC and minD gene(s) to induce minicell production. In other embodiments, BL21 (DE3), BL21-AI and LPS-modified BL21 (DE3) strains, in which ribonuclease III expression is suppressed, disrupted and/or nullified, are also genetically engineered by overexpressing ftsZ and/or minE genes to induce minicell production.

The present disclosure teaches genotypes of newly-generated ribonuclease-deficient minicell strains comprising i) minC-deleted and ribonuclease III-deleted BL21(DE3); fhuA2 [lon] ompT gal (λ DE3) [dcm] ΔhsdS λ DE3=λ sBamHIo ΔEcoRI-B int::(lacI::PlacUV5::T7 gene1) i21 Δnin5 ΔminC rnc14::Tn10, ii) minD-deleted and ribonuclease III-deleted BL21(DE3); fhuA2 [lon] ompT gal (λ DE3) [dcm] ΔhsdS λ DE3=λ sBamHIo ΔEcoRI-B int::(lacI::PlacUV5::T7 gene1) i21 Δnin5 ΔminD rnc14::Tn10, iii) minC/D-deleted and ribonuclease III-deleted BL21(DE3); fhuA2 [lon] ompT gal (λ DE3) [dcm] ΔhsdS λ DE3=λ sBamHIo ΔEcoRI-B int::(lacI::PlacUV5::T7 gene1) i21 Δnin5 ΔminC ΔminD rnc14::Tn10, iv) minC-deleted and ribonuclease III-deleted BL21-AI; F$^-$ ompT hsdS$_B$ (r$_B^-$ m$_B^-$) gal dcm araB::T7RNAP-tetA ΔminC rnc14::Tn10, v) minD-deleted and ribonuclease III-deleted BL21-AI; F$^-$ ompT hsdS$_B$ (r$_B^-$ m$_B^-$) gal dcm araB::T7RNAP-tetA ΔminD rnc14::Tn10, vi) minC/D-deleted and ribonuclease III-deleted BL21-AI; F$^-$ ompT hsdS$_B$ (r$_B^-$ m$_B^-$) gal dcm araB::T7RNAP-tetA ΔminC ΔminD rnc14::Tn10; vii) minC-deleted LPS-modified and ribonuclease III-deleted BL21 (DE3); msbA148 ΔgutQ ΔkdsD ΔlpxL ΔlpxM ΔpagP ΔlpxP ΔeptA ΔminC rnc14::Tn10, viii) minD-deleted LPS-modified and ribonuclease III-deleted BL21(DE3); msbA148 ΔgutQ ΔkdsD ΔlpxL ΔlpxM ΔpagP ΔlpxP ΔeptA ΔminD rnc14::Tn10, ix) minC/D-deleted LPS-modified and ribonuclease III-deleted BL21(DE3); msbA148 ΔgutQ ΔkdsD ΔlpxL ΔlpxM ΔpagP ΔlpxP ΔeptA ΔminC, ΔminD rnc14::Tn10, x) minC-deleted and ribonuclease III-deleted B8 with suppression on T7 RNA polymerase activity; fhuA2 [lon] ompT gal (λ DE3) [dcm] ΔhsdS λ DE3=λ sBamHIo ΔEcoRI-B int::(lacI::PlacUV5::T7 gene1) i21 Δnin5 ΔminC rnc14::Tn10; xi) minD-deleted and ribonuclease III-deleted B8 with suppression on T7 RNA polymerase activity; fhuA2 [lon] ompT gal (λ DE3) [dcm] ΔhsdS λ DE3=λ sBamHIo ΔEcoRI-B int::(lacI::PlacUV5::T7 gene1) i21 Δnin5 ΔminD rnc14::Tn10; xii) minC/D-deleted and ribonuclease III-deleted B8 with suppression on T7 RNA polymerase activity; fhuA2 [lon] ompT gal (λ DE3) [dcm] ΔhsdS λ DE3=λ sBamHIo ΔEcoRI-B int::(lacI::PlacUV5::T7 gene1) i21 Δnin5 ΔminC ΔminD rnc14::Tn10; xiii) minC-deleted HT115 (DE3); F-, mcrA, mcrB, IN(rrnD-rrnE)1, rnc14::Tn10(DE3 lysogen: lavUV5 promoter-T7 polymerase) ΔminC, xiv) minD-deleted HT115 (DE3); F-, mcrA, mcrB, IN(rrnD-rrnE)1, rnc14::Tn10(DE3 lysogen: lavUV5 promoter-T7 polymerase) ΔminD, and xv) minC/D-deleted HT115 (DE3); F-, mcrA, mcrB, IN(rrnD-rrnE)1, rnc14::Tn10(DE3 lysogen: lavUV5 promoter-T7 polymerase) ΔminC ΔminD.

Minicells that have segregated from parent cells lack chromosomal and/or nuclear components, but retain the cytoplasm and its contents, including the cellular machinery required for protein expression. In some embodiments, minicells are ribonuclease-deficient because the parent cells are ribonuclease-deficient strains. Although chromosomes do not segregate into minicells, extrachromosomal and/or episomal genetic expression elements may segregate, or may be introduced into minicells after segregation from parent cells. In some embodiments, the disclosure is drawn to ribonuclease-deficient minicells comprising an expression element, which may be an inducible expression element. The inducible expression element such as an inducible promoter can be introduced to a recombinant plasmid used for homologous recombination to knock out and/or delete gene(s) involved to cell division and/or chromosomal partitioning such as minC, minD, and minC/D, a recombinant expression vector to overexpress gene(s) involved to cell division and/or chromosomal partitioning such as ftsZ and minE, and a recombinant expression vector for expressing an enzymatically active polypeptide including a protein of interest disclosed herein. In further embodiments, the inducible expression element comprises expression sequences operably linked to an open reading frame (ORF) that encodes proteins of interest disclosed herein. Optionally, at any point in the method, an inducing agent is provided in order to induce expression of an ORF that encodes proteins of interest disclosed herein.

In some embodiments, the disclosure teaches methods of making a ribonuclease-deficient bacterial minicell comprising a recombinant fusion protein that is not naturally found in parental cells. In some embodiment, the disclosure teaches method of preparing ribonuclease-deficient minicells from the host cells.

In further embodiments, an anucleated cell is produced from an eukaryotic cell. In further embodiments, the anucleated cell produced as described above is used as an anucleated cell-based platform and/or an industrial formulation for the encapsulation and delivery of biologically active compounds.

In some embodiments, minicells taught in the present disclosure is protease deficient or ribonuclease deficient. In some embodiments, said minicell is protease deficient. In some embodiments, said minicell is ribonuclease deficient. In some embodiments, said minicell is protease deficient and ribonuclease deficient. In some embodiments, said minicell is ribonuclease-deficient, and wherein said biologically active compound is a nucleic acid. In some embodiments, said biologically active compound is said nucleic acid is selected from the group consisting of an antisense nucleic acid, a double-stranded RNA (dsRNA), a short-hairpin RNA (shRNA), a small-interfering RNA (siRNA), a microRNA (miRNA), a ribozyme, an aptamer, and combination thereof.

Minicell Separation and Purification

A variety of methods are used to separate minicells from parent cells (i.e., the cells from which the minicells are produced) in a mixture of parent cells and minicells. In general, such methods are physical, biochemical and genetic, and can be used in combination.

Physical Separation of Minicells from Parent Cells

By way of non-limiting example, minicells are separated from parent cells glass-fiber filtration (Christen et al., Gene 23:195-198, 1983), and differential and zonal centrifugation (Barker et al., J. Gen. Microbiol. 111:387-396, 1979), size-exclusion chromatography, e.g. gel-filtration, differential sonication (Reeve, J. N., and N. H. Mendelson. 1973. Biochem. Biophys. Res. Commun. 53:1325-1330), and UV-irradiation (Tankersley, W. G., and J. M. Woodward. 1973. Proc Soc Exp Biol Med. 1974 March; 145(3):802-805).

Some techniques involve different centrifugation techniques, e.g., differential and zonal centrifugation. By way of non-limiting example, minicells may be purified by the double sucrose gradient purification technique described by Frazer and Curtiss, Curr Topics Microbiol. Immunol. 69:1-84, 1975.

Other physical methods may also be used to remove parent cells from minicell preparations. By way of non-limiting example, mixtures of parent cells and minicells are frozen to −20° C. and then thawed slowly (Frazer and Curtiss, Curr. Topics Microbiol. Immunol. 69:1-84, 1975).

Biochemical Separation of Minicells from Parent Cells

Contaminating parental cells may be eliminated from minicell preparations by incubation in the presence of an agent, or under a set of conditions, that selectively kills dividing cells. Because minicells can neither grow nor divide, they are resistant to such treatments.

Examples of biochemical conditions that prevent or kill dividing parental cells is treatment with an antibacterial agent, such as penicillin or derivatives of penicillin. Penicillin has two potential affects. First, penicillin prevent cell wall formation and leads to lysis of dividing cells. Second, prior to lysis dividing cells form filaments that may assist in the physical separation steps described above. In addition to penicillin and its derivatives, other agents may be used to prevent division of parental cells. Such agents may include azide. Azide is a reversible inhibitor of electron transport, and thus prevents cell division. As another example, D-cycloserine or phage MS2 lysis protein may also serve as a biochemical approach to eliminate or inhibit dividing parental cells. (Markiewicz et al., FEMS Microbiol. Lett. 70:119-123, 1992). Khachatourians (U.S. Pat. No. 4,311,797) states that it may be desirable to incubate minicell/parent cell mixtures in brain heart infusion broth at 36° C. to 38° C. prior to the addition of penicillin G and further incubations.

Genetic Separation of Minicells from Parent Cells

Alternatively or additionally, various techniques may be used to selectively kill, preferably lyse, parent cells. For example, although minicells can internally retain M13 phage in the plasmid stage of the M13 life cycle, they are refractory to infection and lysis by M13 phage (Staudenbauer et al., Mol. Gen. Genet. 138:203-212, 1975). In contrast, parent cells are infected and lysed by M13 and are thus are selectively removed from a mixture comprising parent cells and minicells. A mixture comprising parent cells and minicells is treated with M13 phage at an M.O.I.=5 (phage cells). The infection is allowed to continue to a point where ≥50% of the parent cells are lysed, preferably ≥75%, more preferably ≥95% most preferably ≥99%; and ≤25% of the minicells are lysed or killed, preferably ≤15%, most preferably ≤1%.

As another non-limiting example of a method by which parent cells can be selectively killed, and preferably lysed, a chromosome of a parent cell may include a conditionally lethal gene. The induction of the chromosomal lethal gene will result in the destruction of parent cells, but will not affect minicells as they lack the chromosome harboring the conditionally lethal gene. As one example, a parent cell may contain a chromosomal integrated bacteriophage comprising a conditionally lethal gene. One example of such a bacteriophage is an integrated lambda phage that has a temperature sensitive repressor gene (e.g., lambda cI857). Induction of this phage, which results in the destruction of the parent cells but not of the achromosomal minicells, is achieved by simply raising the temperature of the growth media. A preferred bacteriophage to be used in this method is one that kills and/or lyses the parent cells but does not produce infective particles. One non-limiting example of this type of phage is one that lyses a cell but which has been engineered to as to not produce capsid proteins that are surround and protect phage DNA in infective particles. That is, capsid proteins are required for the production of infective particles.

As another non-limiting example of a method by which parent cells can be selectively killed or lysed, toxic proteins may be expressed that lead to parental cell lysis. By way of non-limiting example, these inducible constructs may employ a system to control the expression of a phage holing gene. Holin genes fall with in at least 35 different families with no detectable orthologous relationships (Grundling, A., et al. 2001. Proc. Natl. Acad. Sci. 98:9348-9352) of which each and any may be used to lyse parental cells to improve the purity of minicell preparations.

In some embodiments, minicells are substantially separated from the minicell-producing parent cells in a composition comprising minicells. After separation, the compositions comprising the minicells is at least about 99.9%, about 99.8%, about 99.7%, about 99.6%, about 99.5%, about 99.4%, about 99.3%, about 99.2%, about 99.1%, about 99%, about 98%, about 97%, about 96%, about 95%, about 94%, about 93%, about 92%, about 91%, about 90%, about 89%, about 88%, about 87%, about 86%, about 85%, about 84%, about 83%, about 82%, about 81%, about 80%, about 79%, about 78%, about 77%, about 76%, about 75%, about 74%, about 73%, about 72%, about 71%, about 70%, about 65%, about 60%, about 55%, about 50%, about 45%, about 40%, about 35%, about 30%, about 25% or about 20% free of minicell-producing parent cells. Thus, the compositions of the disclosure can comprise minicells that are substantially free of the parental cell.

In some aspects, the present invention provides a method for making minicells, the method comprising (a) culturing a minicell-producing parent cell, wherein the parent cell comprises an recombinant construct, wherein the recombinant construct comprises a nucleotide sequence homologous to a target gene associated with regulating cell division, and (b) separating the minicells from the parent cell, thereby generating a composition comprising minicells. In some embodiments, the method further comprises (c) purifying the minicells from the composition by centrifugation and/or filtration. In some embodiments, one or more additional expression constructs can be introduced into the minicell-producing parent cell which comprise genes associated with cell division. In such instances, the expression constructs may be simultaneously or sequentially introduced into the parent cell prior to induction for minicell formation, and can comprise one or more selection markers (e.g., antibiotic resistance genes) and/or reporter genes to allow for selection and/or visualization of minicells expressing the protein(s) of interest. In other embodiments, the expression construct can express one or more additional proteins, which are driven by the same or different promoters, including inducible promoters. In further embodiments, genes associated with cell division are minC, minD, and/or both minC and minD.

Encapsulation

Encapsulation is a process of enclosing the substances within an inert material, which protects from environment as well as control release of active compounds. Two type of encapsulation has been well studies; 1) Nanoencapsulation that is the coating of various substances within another material at sizes on the nano scale, and 2) Microencapsulation that is similar to nanoencapsulation aside from it involving larger particles and having been done for a greater period of time than nanoencapsulation. Encapsulation is a new technology that has wide applications in pharmaceutical industries, agrochemical, food industries and cosmetics. In some embodiments, at least one biologically active compound described herein is inert to a cell other than a cell of a target.

In some embodiments, an anucleated cell-based platform and/or an industrial formulation comprising eubacterial, archaebacterial, and eukaryotic cells is utilized to produce to encapsulate biologically active compounds. The bacterial cells including gram-negative bacteria, gram-negative bacteria, and Extremophilic bacteria, can produce the platform, which can encapsulate the desired biologically active compounds. The anucleated cells comprises minicells that are produced from parental bacterial cells disclosed herein naturally and/or by genetic engineering techniques taught herein.

The present disclosure teaches the benefit of using bacterial minicells which simplify purification of anucleated cell-based platform and reduce costs of encapsulation thereof. By employing encapsulation to biologically active compounds, the compounds are protected from external factors that causes degradation of the compounds and reduces life cycle of the compounds.

Current encapsulation techniques include oils, invert suspensions, polymer-based nanomaterials, lipid-based nanomaterials, porous inorganic nanomaterials, and clay-based nanomaterials.

COC (Crop Oil Concentrate) and MSO (Methylated Seed Oil) technologies are used for oil encapsulation. They act as humectants to move the active ingredient droplets through the spray nozzle and reconfigure the droplets on the outside to keep the active ingredients from evaporating.

Invert suspension is an oil sub-category providing either a suspension of water encapsulated within an oil shell or water surrounded by an oil coating used to minimize the creation of driftable fines (sub 105 microns) after being sprayed through a nozzle tip. This technology works on reducing driftable fines for the active ingredients.

Polymer-based nanomaterials consist of a polymer that has nanoparticles or nanofillers dispersed within the polymer matrix. Typically, the polymers are contrasting (one hydrophobic, one hydrophilic) to sustain amphiphilic properties. Either synthetic or natural polymers (guar gum) act to increase the viscosity of the spray solution and affect the rheological profile by producing larger spray particles. Polymer-based adjuvants increase the possibility of spray particles shattering, increasing drift. However, use of polymer-based drift reduction technology adjuvants for aerial applications of active ingredients is not recommend. Although they have an efficient loading capacity, the necessary polymers are expensive, limiting scalability.

Lipid-based nanomaterials have great potential to encapsulate hydrophilic, hydrophobic, and lipophilic active ingredients, and are commonly used in the pharmaceutical field. However, scalable production is significantly limited by cost.

Porous inorganic nanomaterials, such as silica nanoparticles, are effective at encapsulating bioactive molecules, but face limitations in biodegradability and scalability. These polymer-coated nanoparticles suffer from various limitations such as poor thermal and chemical stability, rapid elimination by the plant enzyme system, and degradation of some polymers, resulting in the formation of acidic monomers and decreased pH value within the polymer matrix. Clay nanoparticles are economically viable and provide great opportunities for developing multifunctional nanocarrier materials, but are energy intensive, requiring high heat for production. These alternatives cannot be modified as easily to provide targeted delivery to plants.

In some embodiments, an anucleated cell-based minicell platform and/or an industrial formulation has advantages in cost and biodegradability. The minicell platforms are easily scaled through common, industrial fermentation practices. Once scaled, they can be purified through a series of centrifugation and/or filtration steps. The self-assembly of the carbohydrate-binding modules to the surface of minicells significantly cuts the cost of making a targeting bioparticle. Additionally, an anucleated cell-based minicell platform is advantageous compared to other encapsulation technologies in terms of biocompatibility for plant and environmental use; this is because the anucleated cell-based minicell platform is derived by safe, commonly found microbes that are native to the applied areas and can safely biodegrade to be reused by the ecosystem. This platform suitable for scalable, non-toxic delivery can play an significant role in the field of agriculture.

In order to solve problems of conventional agrochemicals that are easily degraded or evaporated before they reach their intended target, the present disclosure provides an anucleated cell-based platform and/or an industrial formulation for the encapsulation and delivery of biologically active compounds aims to protect the bioactivity from external factors until the compounds are applied to a target and to be slowly released to the intended target. The various mechanisms by which biologically active compounds are typically lost to the environment are averted using the disclosed minicell-based encapsulation and delivery platform. This is because the lipid-bilayer of the minicell acts as an effective layer of protection against harsh environmental conditions. Specifically, the internalization of the active inside of the minicell protects the compounds against sharp changes in temperature, pH, or strong exposure to light. In other words, the minicell protects the compounds against volatilization, photolytic degradation, and hydrolysis. Therefore, the biologically active compounds can remain protected from adverse external factors and is allowed for gradual and/or controlled release to intended targets via minicell-based platform that encapsulates the biologically active compound of interest.

Furthermore, the other benefit of the present disclosure provides an anucleated cell-based platform and/or an industrial formulation for the encapsulation and delivery of biologically active compounds is that this platform offers the improved and enhanced targeting capability to the plant and its microenvironment. The inherent surface chemistry of the outer membrane of the minicell-based bioparticle naturally mimics that of bacteria. This is significant because there are many types of bacteria that live symbiotically in a microbiome on the surface of plant leaves, stems, and in their root system. By using the minicell-based platform, biological membrane of the minicell has natural adherence to the various surfaces of plants. This feature allows for delivering encapsulated biologically-active compounds including biocontrols and biostimulants in the minicell chassis that is targeted to adhere to plant surfaces and the soil microenvironment around the plant's root system as well as to other targets such as pests, insects, bugs, weeds, worms, bacteria, viruses, pathogens, and parasites. In addition to relying on the natural adherence of the minicell-based bioparticle to plants, the present disclosure teaches uses of genetic engineering to give rise to surface-expressing moiety fused with specific binding domain on the membrane of the minicell. In this way its ability to target the plant or the pest is significantly enhanced.

In some embodiments, the present disclosure provides the genetic engineering techniques to make minicell-based platform with binding domains/motifs that functionalize the surface of the minicell. Proteins including specific binding domains and/or motifs are expressed on the surface of the minicells and specifically target binding sites that are present on the surface of plants or pests.

In some embodiments, minicell-based platform can be functionalized by proteins with carbohydrate binding modules (CBMs) that can target and bind to carbohydrates such as cellulose, xylan, chitin, and lignin, which are important and ubiquitous structural components of plant cell walls. Because CBMs can recognize their binding site present on a subject such as a plant or a pest, the minicell-based platform comprising the functionalized binding domain allows for targeting with high specificity.

In some embodiments, the use of CBMs is not limited to agriculture uses. CBMs can be used for the purification of active ingredients or biomolecules through the means of cellulose columns. Supplementary to the surface chemistry of the minicell-based platform, the relative mass of the bioparticle can also significantly mitigate the off-target exposure of active compounds due to aerosolization and leaching. By concentrating and encapsulating actives in the relatively large chassis of the minicell before being sprayed, the compound is less susceptible to aerosolization or drift caused by wind when compared to spraying free-floating compounds. Furthermore, the larger size of the minicell encapsulation and delivery platform can mitigate the leaching of actives through the soil and into groundwater supplies.

Agriculturally Acceptable Carrier

Compositions described herein can comprise an agriculturally acceptable carrier. The composition useful for these embodiments may include at least one member selected from the group consisting of a tackifier, a microbial stabilizer, a fungicide, an antibacterial agent, a preservative, a stabilizer, a surfactant, an anti-complex agent, an herbicide, a nematicide, an insecticide, a plant growth regulator, a fertilizer, a rodenticide, a desiccant, a bactericide, a nutrient, or any combination thereof. In some examples, compositions may be shelf-stable. For example, any of the compositions described herein can include an agriculturally acceptable carrier (e.g., one or more of a fertilizer such as a non-naturally occurring fertilizer, an adhesion agent such as a non-naturally occurring adhesion agent, and a pesticide such as a non-naturally occurring pesticide). A non-naturally occurring adhesion agent can be, for example, a polymer, copolymer, or synthetic wax. For example, any of the coated seeds, seedlings, or plants described herein can contain such an agriculturally acceptable carrier in the seed coating. In any of the compositions or methods described herein, an agriculturally acceptable carrier can be or can include a non-naturally occurring compound (e.g., a non-naturally occurring fertilizer, a non-naturally occurring adhesion agent such as a polymer, copolymer, or synthetic wax, or a non-naturally occurring pesticide).

In some embodiments, an anucleated cell-based platform described herein can be mixed with an agriculturally acceptable carrier. The carrier can be a solid carrier or liquid carrier, and in various forms including microspheres, powders, emulsions and the like. The carrier may be any one or more of a number of carriers that confer a variety of properties, such as increased stability, wettability, or dispersability. Wetting agents such as natural or synthetic surfactants, which can be nonionic or ionic surfactants, or a combination thereof can be included in the composition. Water-in-oil emulsions can also be used to formulate a composition that includes the isolated bacteria (see, for example, U.S. Pat. No. 7,485,451). Suitable formulations that may be prepared include wettable powders, granules, gels, agar strips or pellets, thickeners, liquids such as aqueous flowables, aqueous suspensions, water-in-oil emulsions, etc. The formulation may include grain or legume products, for example, ground grain or beans, broth or flour derived from grain or beans, starch, sugar, or oil.

In some embodiments, the agricultural carrier may be soil or a plant growth medium. Other agricultural carriers that may be used include water, fertilizers, plant-based oils, humectants, or combinations thereof. Alternatively, the agricultural carrier may be a solid, such as diatomaceous earth, loam, silica, alginate, clay, bentonite, vermiculite, seed cases, other plant and animal products, or combinations, including granules, pellets, or suspensions. Mixtures of any of the aforementioned ingredients are also contemplated as carriers, such as but not limited to, pesta (flour and kaolin clay), agar or flour-based pellets in loam, sand, or clay, etc. Formulations may include food sources for the bacteria, such as barley, rice, or other biological materials such as seed, plant parts, sugar cane bagasse, hulls or stalks from grain processing, ground plant material or wood from building site refuse, sawdust or small fibers from recycling of paper, fabric, or wood.

Additional examples of agriculturally acceptable carriers include dispersants (e.g., polyvinylpyrrolidone/vinyl acetate PVPIVA S-630), surfactants, binders, and filler agents.

Persons having skill in the art will appreciate that, unless otherwise noted, all references to an anucleated cell-based platform in the present disclosure can be read as referring to an agricultural formulation. Therefore, embodiments described in the present disclosure which refer to an anucleated cell-based platform will also be understood to refer to an agricultural formulation.

Binding Domain for Cell Adhesion

In some embodiments, the anucleated cell-based platform described herewith express binding domains. These domains allow for better retention of the minicells on plant surfaces, which prevents runoff or drift of biologically active compounds encapsulated within the minicells. They can also improve adhesion to the targeted pests to ensure the administration of an effective dose of the biologically active compounds. Once the minicells are on the plant, the chemical will slowly release into the environment.

In some embodiments, the anucleated cell described herewith expresses a fusion protein, which comprises at least one surface expressing moiety and at least one plant cell adhesion moiety. The plant cell adhesion moiety comprises a carbohydrate binding module comprising a carbohydrate binding module selected from the group consisting of: a cellulose binding domain, a xylan binding domain, a chitin binding domain, and a lignin binding domain.

In some embodiments, the anucleated cell expresses a polypeptide on its surface that increases adhesion to a plant surface. The polypeptide is a plant adhesion polypeptide on its surface. In some embodiments, the polypeptide is a carbohydrate binding module that is displayed on its surface. In other embodiments, the polypeptide is a cellulose binding domain that is displayed on its surface. In other embodiments, the polypeptide is a chitin binding domain that is displayed on its surface.

A carbohydrate-binding module (CBM) is a protein domain found in carbohydrate-active enzymes (for example glycoside hydrolases). The majority of these domains have carbohydrate-binding activity. Some of these domains are found on cellulosomal scaffoldin proteins. CBMs are also known as cellulose-binding domains. CBMs are classified into numerous families, based on amino acid sequence similarity. CBMs of microbial glycoside hydrolases play a central role in the recycling of photosynthetically fixed carbon through their binding to specific plant structural polysaccharides. CBMs can recognize both crystalline and amorphous cellulose forms. CBMs are the most common non-catalytic modules associated with enzymes active in plant cell-wall hydrolysis. Many putative CBMs have been identified by amino acid sequence alignments but only a few representatives have been shown experimentally to have a carbohydrate-binding function. By binding to polysaccharides, CBMs bring appended catalytic domains into intimate contact with target substrates and thus potentiate catalysis. CBMs with the capacity to bind cellulose are associated with enzymes that hydrolyze both cellulose and other cell wall polymers such as xylan, mannan, pectin, and noncellulosic β-glucans.

Cellulose binding domains (CBDs) have been described as useful agents for attachment of molecular species to cellulose (U.S. Pat. Nos. 5,738,984 and 6,124,117). Indeed, as cotton is made up of 90% cellulose, CBDs have proved useful for delivery of so called "benefit agents" onto cotton fabrics, as is disclosed in WO9800500 where direct fusions between a CBD and an enzyme were used utilizing the affinity of the CBD to bind to cotton fabric. The use of similar multifunctional fusion proteins for delivery of encapsulated benefit agents was claimed in WO03031477, wherein the multifunctional fusion proteins consist of a first binding domain which is a cellulose binding domain and a second binding domain, wherein either the first binding domain or the second binding domain can bind to a microparticle. WO03031477 is exemplified using a bifunctional fusion protein consisting of a CBD and an anti-RR6 antibody fragment binding to a microparticle, which complex is deposited onto cotton treads or cut grass.

In some embodiments, the enzymatically active polypeptide displayed by the minicells of the invention comprises a CBM. Exemplary CBM from *Cellulomonas fimi* that is within the scope of the disclosure is used. In some embodiments, the cell adhesion moiety is fused to surface-expressing moiety. In other embodiments, the CBM is fused to surface-expressing moiety and is displayed on the surface of the minicells.

Surface Expression System

In some embodiments, the present disclosure teaches surface-expressing moiety that is fused to cell adhesion moiety. The surface-expressing moiety can be transmembrane protein and/or transmembrane domains that function as a linker protein to display the enzymatically active polypeptides having cell adhesion moiety on the surface of cells.

In some embodiments, surface-expressing moiety can be membrane-associated proteins including, but not limited to, transmembrane protein, membrane-anchoring protein, linker protein and/or domain thereof.

In some embodiments, the invention is drawn to display produced membrane-associated protein(s) fused to proteins of interest disclosed herein on the surface of the minicell. By way of non-limiting example, this structure may be an internally expressed membrane protein or chimeric construct to be inserted in or associated with the minicell membrane such that the extracellular domain or domain of interest is exposed on the outer surface of the minicell (expressed and displayed on the surface of the minicell or expressed in the parental cell to be displayed on the surface of the segregated minicell).

The displayed domain fused to a membrane-associated linker protein may be an cell adhesion domain including carbohydrate binding modules. In other embodiments.

Contacting such minicells with the appropriate substrate of the enzyme allows the substrate to be converted to reactant. When either the substrate or reactant is detectable, the reaction catalyzed by the membrane-bound enzyme may be quantified. In the latter instance, the minicells may be used to identify and isolate, from a pool of compounds, one or more compounds that inhibit or stimulate the activity of the enzyme represented by the displayed enzymatic moiety.

In some embodiments, the membrane-associated protein can be a fusion protein, i.e., a protein that comprises a first polypeptide having a first amino acid sequence and a second polypeptide having a second amino acid sequence, wherein the first and second amino acid sequences are not naturally present in the same polypeptide. At least one polypeptide in a membrane fusion protein is a "transmembrane protein/domain" "membrane-anchoring protein/domain" or "linker protein/domain". The transmembrane and membrane-anchoring domains of a fusion protein may be selected from membrane proteins that naturally occur in a prokaryote such as bacteria, a eukaryote, such as a fungus, a unicellular eukaryote, a plant and an animal, such as a mammal including a human. Such domains may be from a viral membrane protein naturally found in a virus such as a bacteriophage or a eukaryotic virus, e.g., an adenovirus or a retrovirus. Such domains may be from a membrane protein naturally found in an archaebacterium such as a thermophile.

Exemplary surface-expressing moieties include but are not limited to ice nucleation protein (INP) *Bordetella* serum-resistance killing protein (BRK), Adhesin Involved in Diffuse Adherence protein (AIDA) and/or an exported bacterial protein. "Exported bacterial proteins," generally refers to bacterial proteins that are transported across the plasma membrane and function as an anchor for membrane proteins. Exemplary exported bacterial proteins encompassed by the present invention, include, but are not limited to LamB (GenBank Accession No. AMC96895), OprF (GenBank Accession No. NP_792118), OmpA (GenBank Accession No. AIZ93785), Lpp (GenBank Accession No. P69776), MalE (GenBank Accession No. P0AEX9), PhoA (GenBank Accession No. AIZ92470.1), Bla (GenBank Accession No. P62593), F1 or M13 major coat (J7I0P6—Uniprot No.), and F1 or M13 minor coat (P69168—Uniprot No.).

In some embodiments, for gram negative bacterial expression systems, enzymes of interest disclosed herein are immobilized to the surface of the minicells via wild type or mutant versions of the exported bacterial proteins such as LamB (lambda receptor), OprF (*P. aeruginosa* outer membrane protein F), OmpA (outer membrane protein A), Lpp (Lipoprotein), MalE (Maltose binding protein), PhoA (Alkaline phosphatase), Bla (TEM-1 B-lactamase), F1 or M13 major coat (derived from Gene VIII), F1 or M13 minor coat (Gene III).

In other embodiments, a wild type and/or truncated version of the Ice Nucleation Protein (INP) can be used to immobilize enzymes on the surface of bacteria.

Surface Display System

Bacterial surface display technique enables the exogenous proteins or polypeptides displayed on the bacterial surface, while maintaining their relatively independent spatial structures and biological activities. The technique makes recombinant bacteria possess the expectant functions, subsequently, directly used for many applications. Many proteins could be used to achieve bacterial surface display, among them, autotransporter, a member of the type V secretion system of gram-negative bacteria, has been extensively studied because of its modular structure and apparent simplicity. However, autotransporter has not been widely used at present due to lack of a convenient genetic vector system.

The present disclosure teaches that autodisplay of an protein/polypeptide of interest requires an autotransporter protein in order to surface display a protein or peptide in a gram negative bacteria. The autotransporter proteins are broken down into 3 different subgroups, classical autotransporters (type Va), trimeric autotransporters adhesins (type Vb), and two partner secretion systems (type Vc).

Classic autotransporters (type Va) are thought to all share a common general structure which consists of a N-terminus signal peptide fused to the passenger protein that takes place of autotransport precursor protein, which provides transport across the cytoplasmic membrane. The N-terminus signal peptide normally utilizes the Secretion machinery in order to provide transport. This signal peptide is cleaved once the protein crosses the inner membrane. Outer membrane translocation is facilitated by the C-terminal domain of the autotransporter. This domain, known as the translocator domain, forms a β-barrel within the outer membrane. This autotransporter requires an additional linker domain due to the β-strand that closes barrel is directed towards the periplasm. Over 30 different proteins have been expressed as the passenger protein using this mechanism.

The trimeric autotransporters (type Vb) are similar to the classical autotransporters except that they cannot transport just one protein to the surface, they transport 3 (trimeric) proteins to the surface.

Type Vc autotransporters consist of a passenger and translocation domain, however both domains are expressed in separate genes. Both domains are transported across the inner membrane by the Secretion machinery, but interact with the periplasm via the polypeptide transport associated domain (POTRA). Due to the similarities between this mechanism of transport and the systems of transport that exist in chloroplasts and mitochondria, this system is expected to be able to transport extremely complex protein structures, but Vb or Vc systems of autotransport have been rarely used.

Enzymes are immobilized to the surface of the minicell by means of protein mediated membrane localization mechanisms including, but are not limited to the following linking proteins and mechanisms. In some embodiments, these systems include the BrkA protein, and AIDA-1 protein. The comparison of autotransporter and Ice Nucleation Protein as carrier proteins for protein display on the cell surface of *E. coli* is reported by Yang et al. 2013, Progress in Biochemistry and Biophysics 40(12):1209-1219, which is herein incorporated by reference in its entirety.

AIDA-I Autotransporter System

One of the most widely studied autotransporters is AIDA-1 which naturally occurs in *E. coli*. It was originally discovered in a pathogenic strain of *E. coli* but was subsequently transferred to laboratory *E. coli* strains using both the pAIDA-1 plasmid and the pDT1 plasmids.

Figure 4A:
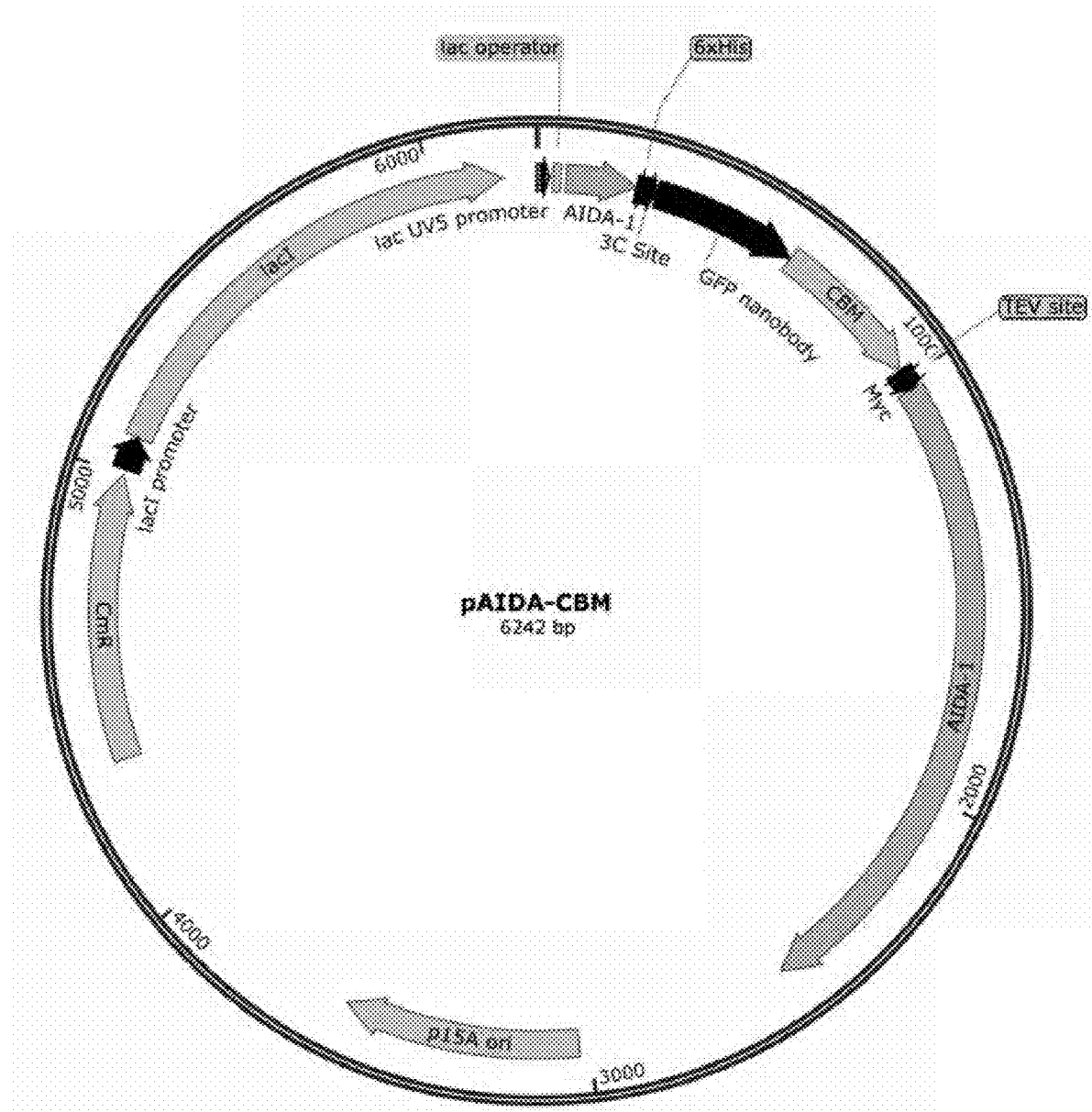
FIG. 4A illustrates an exemplary pAIDA-1-CBM vector with an AIDA-1 surface expression system for display of a CBM (Carbohydrate binding module) protein flanked by 6×His, GFP nanobody and Myc tags on the surface of minicells.
Figure 4B:
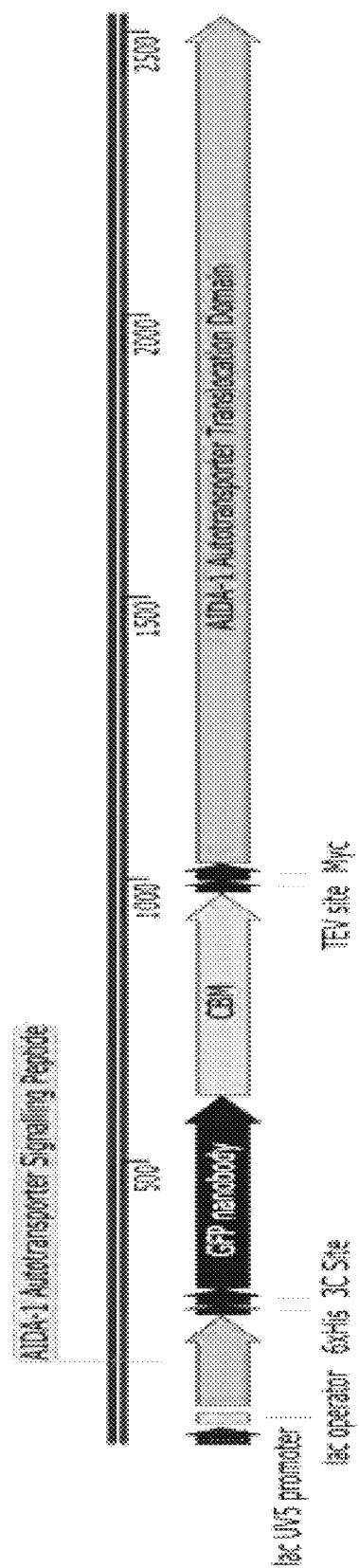
FIG. 4B illustrates an exemplary pAIDA-1 CBM surface expression cassette, comprising nucleotide sequences encoding AIDA-1 Autotransporter signal peptide, GFP nanobody, CBM, and AIDA-1 autotransporter translocation domain with tags including 6×His Tag and Myc Tag as well as two protease cleavage sites including HRV3C and TEV.

In some embodiments, the present disclosure provides the pAIDA-1 expression vector in which a polynucleotide sequence encoding a protein of interest including CBM. For example, the recombinant pAIDA-1 expression vector with CBM-encoding gene is illustrated in FIGS. 4A and 4B. The AIDA-I autotransport system consists of an N-terminus 5 kDa signaling peptide, a 5 kDa linker region, and a 47 kDa C-terminus translocation unit. The passenger domain is located between the signaling peptide and the linker domain. This autotransporter with no protein in its passenger domain is a total of 63 kDa. The protein of interest is inserted into the passenger domain in order to enable surface expression. This corresponds genetically to the signaling peptide region of the protein being located between the NdeI and SalI, the passenger domain between KpnI and SacI, the linker region of the peptide between the XbaI and NotI restriction sites, and the rest of the protein corresponding to the C-terminus translocation unit.

The pAIDA-1-CBM expression vector contains the AIDA-I gene under inducible control with a lacUV5 promoter and includes 2 protein tags (6×His Tag and Myc Tag) and 2 protease cleavage sites (HRV3C and TEV) in order to enable surface expression analysis. FIGS. 4A and 4B illustrates the pAIDA-1 CBM expression vector. The TEV site is an amino acid sequence recognized by the tobacco etch virus. It is a well-known, highly specific protease. The HRV3C site is another highly specific protease cleavage site located C-terminus to the 6×His tag. Both of these protease cleavage sites are used for protein tag removal for analytical purposes if desired. The 6×His tag is located between the SalI and the KpnI site. This 6×his tag was used for immunofluorescent staining with THE™ His Tag antibody [FITC] from Genscript® as well as used for Cobalt Immobilized Metal Affinity Chromatography for purification of the protein for assay confirmation of presence. The TEV site is N-terminus of the Myc tag and located between SacI and XbaI restriction site within the AIDA-I gene located in the pAIDA-I plasmid. The Myc tag present on the plasmid can be used for immunofluorescent staining, however this capability was not utilized.

Further components of the plasmid include a lac operator and a lad repressor gene placed under control of the lad promoter. These three components work in conjunction with the lacUV promoter in order to regulate expression of the AIDA-I gene. The pAIDA-1 plasmid maintained in vivo by the p15a origin of replication which is a medium copy origin of replication. This differs from a low copy or high copy origin of replication simply by the relative number of copies of the plasmid maintained within the cell. The antibiotic resistance gene for this plasmid is chloramphenicol (CmR) under control of its own promoter.

Brk Auto Display

The Brk has been recently discovered as autotransporter (autodisplay) protein. An autotransporter domain is a structural domain found in some bacterial outer membrane proteins. The domain is located at the C-terminal end of the protein and forms a beta-barrel structure. The barrel is oriented in the membrane such that the N-terminal portion of the protein, termed the passenger domain, is presented on the cell surface. With recently characterized autotransporter BrkA (*Bordetella* serum-resistance killing protein A) from *Bordetella pertussis*, BrkAutoDisplay system works better for surface display compared to other systems such as using the Ice Nucleation Protein (INP). The BrkAutoDisplay system for functional display of multiple exogenous proteins on the *E. coli* surface using BrkA autotransporter is exemplified by Sun et al. 2015, Microb. Cell Fact. 14:129, which is herein incorporated by reference in its entirety.

The BrkA protein (GenBank WP_010931506.1) is found as a 1010 amino acid chain length protein in its native form. The first 59 amino acids represent the signal peptide and the Beta barrel is formed between amino acids 693-1010. The Translocation domain corresponds to amino acids 545-1010. The passenger domain corresponds to amino acids 60-544, which is replaced with the proteins of interest such as CBM. The first 59 amino acids and the Beta barrel region, 693-1010, represent the minimal translocation domain.

Figure 6A:
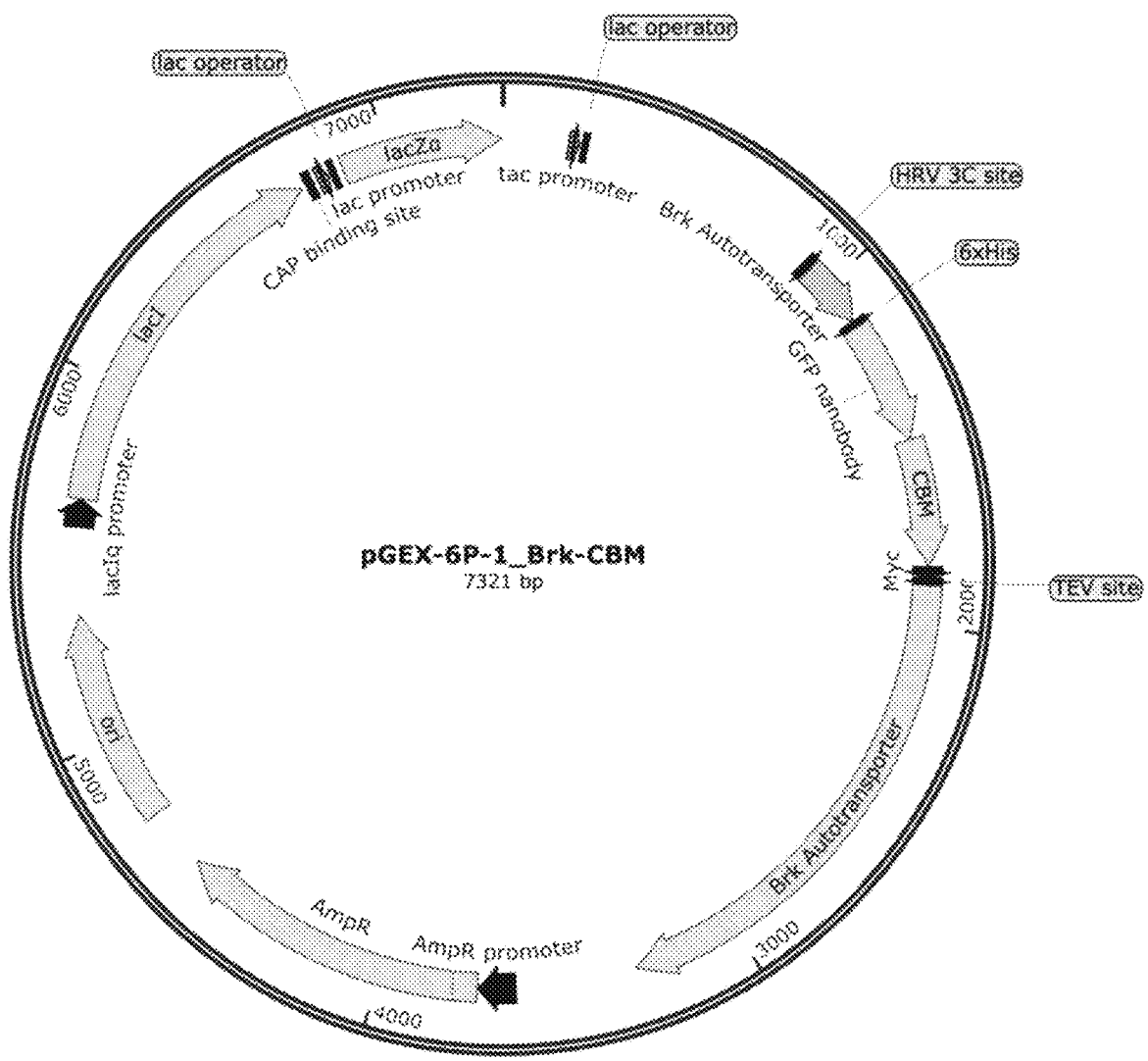
FIG. 6A illustrates an exemplary pGEX-6P-1 Brk-CBM vector with a serum resistance autotransporter BrkA surface expression system for display of a CBM protein flanked by 6×His, GFP nanobody and Myc tags on the surface of minicells.
Figure 6B:
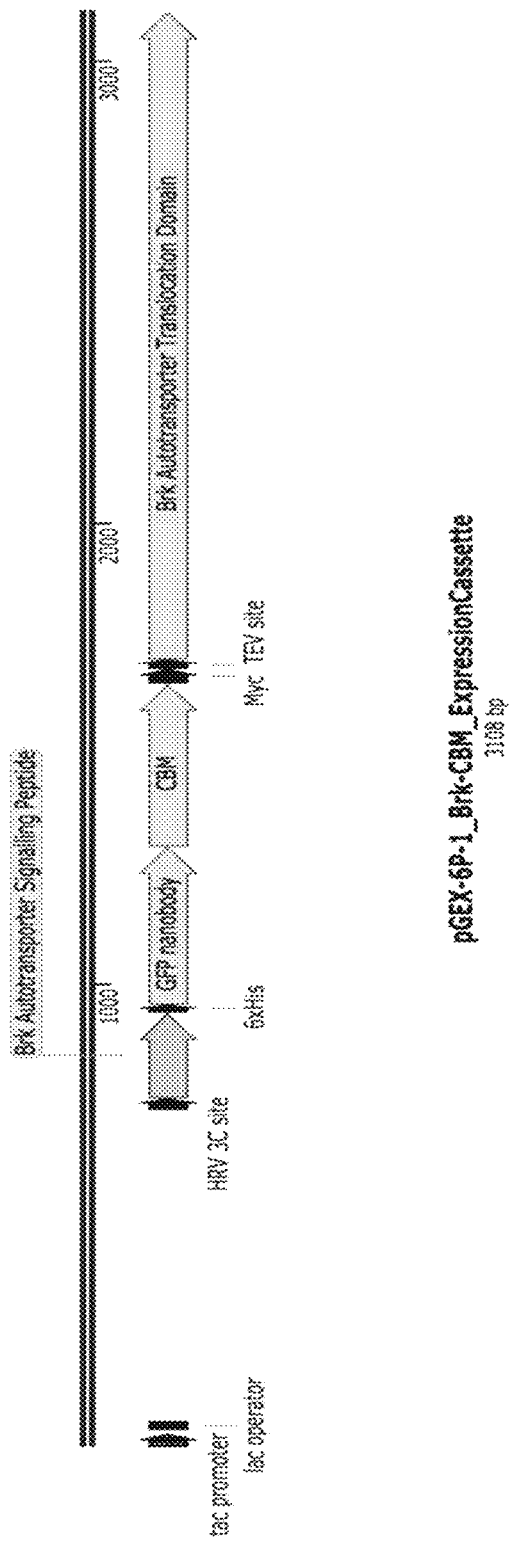
FIG. 6B illustrates an exemplary Brk-CBM surface expression cassette, comprising nucleotide sequences encoding Brk Autotransporter signal peptide, GFP nanobody, CBM, and Brk autotransporter translocation domain with tags including 6×His Tag and Myc Tag as well as two protease cleavage sites including HRV3C and TEV.

The present disclosure teaches a recombinant expression vector/construct for expression a fusion protein possesses two polynucleotide sequences encoding i) the first 228 amino acids (signal peptide and 5' partial passenger domain) and ii) the 694-1010 amino acid (Beta barrel domain) sequence of the BrkA protein. In this recombinant expression vector, polynucleotide sequences encoding protein of interest such as CBM are inserted between these two segments (i) one for the signal peptide and 5' partial passenger domain, and ii) the other for the Beta barrel domain) of the BrkA protein. Once the fusion protein is trafficked to the membrane, it is cleaved between the Asn731 and Ala732 residues corresponding to location of the wild-type BrkA protein, upon which the protein of interest including CBM located between the signal peptide and the B-barrel translocation domain, adopts its mature conformation and is displayed externally on the surface of the cells. The recombinant expression vector used herein is illustrated in FIGS. 6A and 6B. The pGEX-6P-1 Brk-CBM expression vector contains the AIDA-I gene under control with a tac promoter and includes protein tags (6×His Tag and Myc Tag) and two protease cleavage sites (HRV3C and TEV) in order to enable surface expression analysis. The uses of 6×His tag and Myc tag are well described above.

Figure 10A:
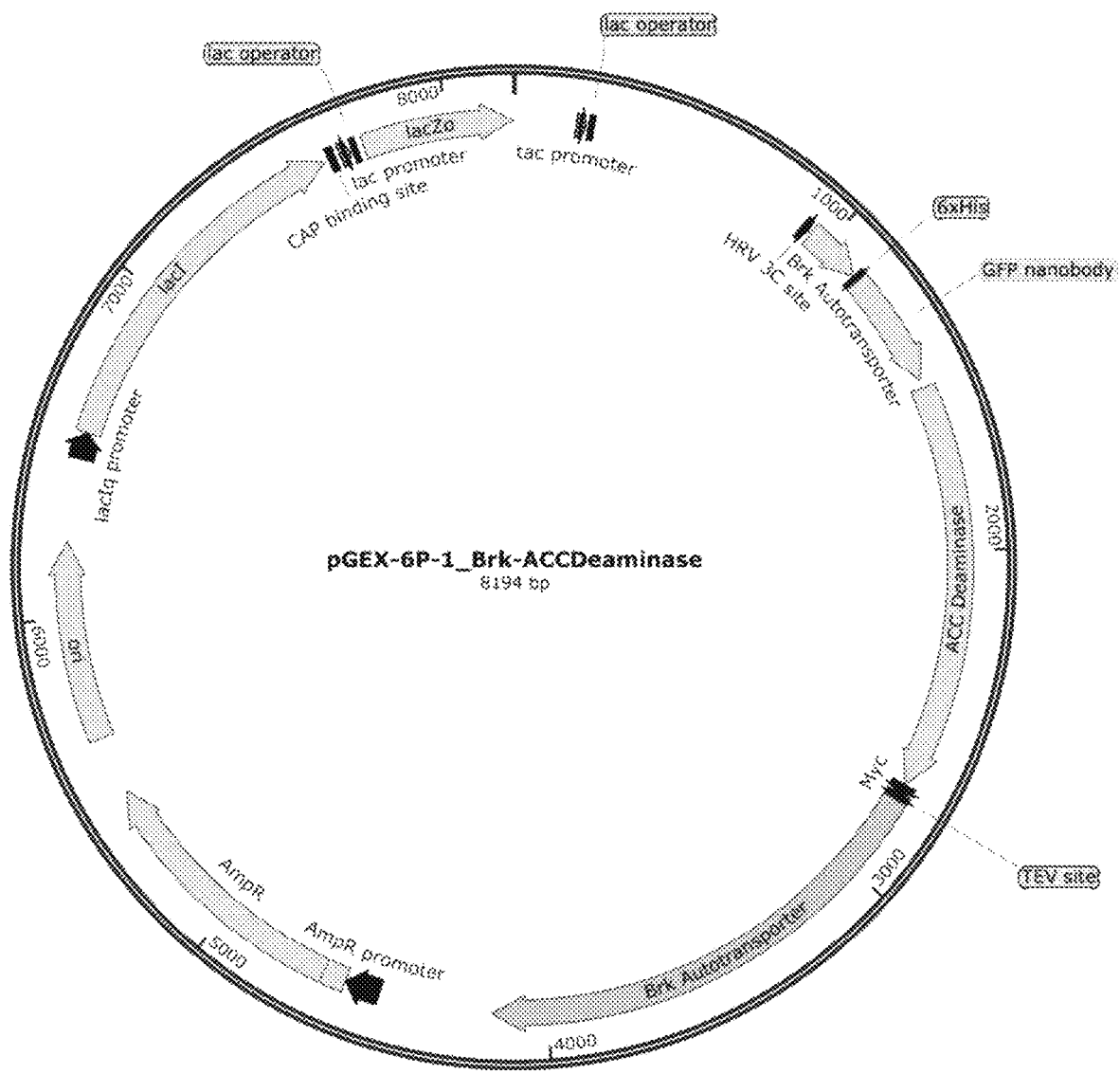
FIG. 10A illustrates an exemplary pGEX-6P-1 Brk-ACC_Deaminase vector with a serum resistance autotransporter BrkA surface expression system for display of a ACC-Deaminase protein flanked by 6×His, GFP nanobody and Myc tags on the surface of minicells.
Figure 10B:
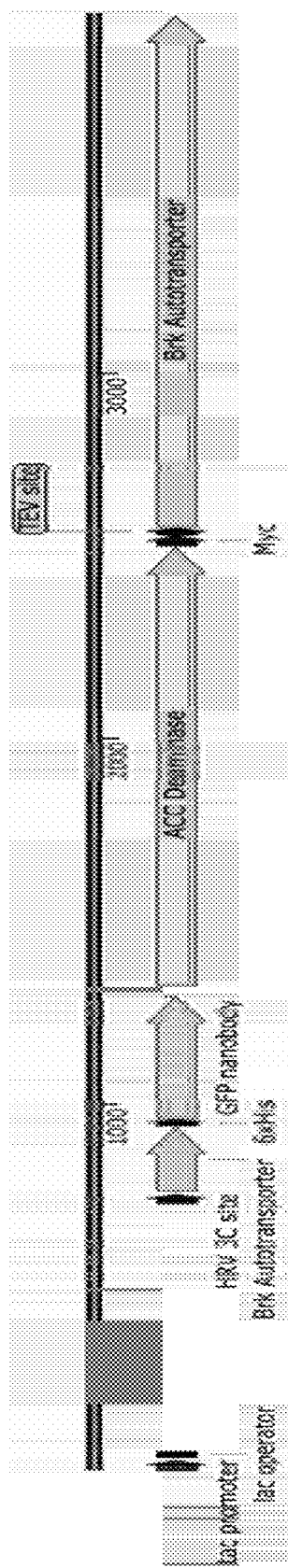
FIG. 10B illustrates an exemplary Brk-ACC_Deaminase surface expression cassette, comprising nucleotide sequences encoding Brk Autotransporter signal peptide, GFP nanobody, ACC-Deaminase, and Brk autotransporter translocation domain with tags including 6×His Tag and Myc Tag as well as two protease cleavage sites including HRV3C and TEV.

Similar to FIGS. 6A and 6B, the present disclosure teaches a recombinant expression vector/construct for expression a fusion protein ACC deaminase, located between the signal peptide and the B-barrel translocation domain, which adopts its mature conformation and is displayed externally on the surface of the cells. The recombinant expression vector used herein is illustrated in FIGS. 10A and 10B. The first 177 nucleotides (encoding 59 amino acids) of BrK gene correspond to the signaling peptide portion of the Brk autotransporter. This is the most N-terminus region of the fusion protein. This portion is cleaved during the translocation process. Immediately C-terminus of the signaling peptide is the 6×His tag used for purification and staining mentioned above. This is the surface expressed end of the protein (N-terminus). C-terminus to the His tag is the protein of interest (ACC Deaminase). C-terminus to that is the Myc tag followed by the TEV site. Immediately C-terminus to the TEV site is the translocation domain. This region of the protein is the most C-terminus region of the protein and the part of the protein that is embedded in the membrane.

Vectors

In some embodiments, pUC-57 vector is used for knocking out a gene of target including minC, minD, and minC/D for including the production of minicells from the protease-deficient strain. From the 5' and 3' ends of the gene of target, about 50 base pairs of nucleotide sequence (homologous arms) corresponding to the gene of target within the genome are used for homologous recombination to knock out the gene of target. This directs the gene of interest to the place in the genome to replace the gene of target that are aimed to be knocked out. Just inside of the homologous arms, hairpin loops were inserted. These hairpin loops, when transcribed to mRNA, do not allow for any translation of what is contained between the loops in which the translation starts outside of the hairpin loops. These hairpin loops are formed upon translation of DNA to RNA and are also known as stem loops. This allows for the insert to not interfere with the native promotion of the other genes in the min system. Due to the hairpin loops, the chloramphenicol cassette (CmR) that was contained within the insert was placed under control of its own promoter, the cat promoter. By including the hairpin loops, this promoter would also not affect the regulation of any genes.

Figure 18A:
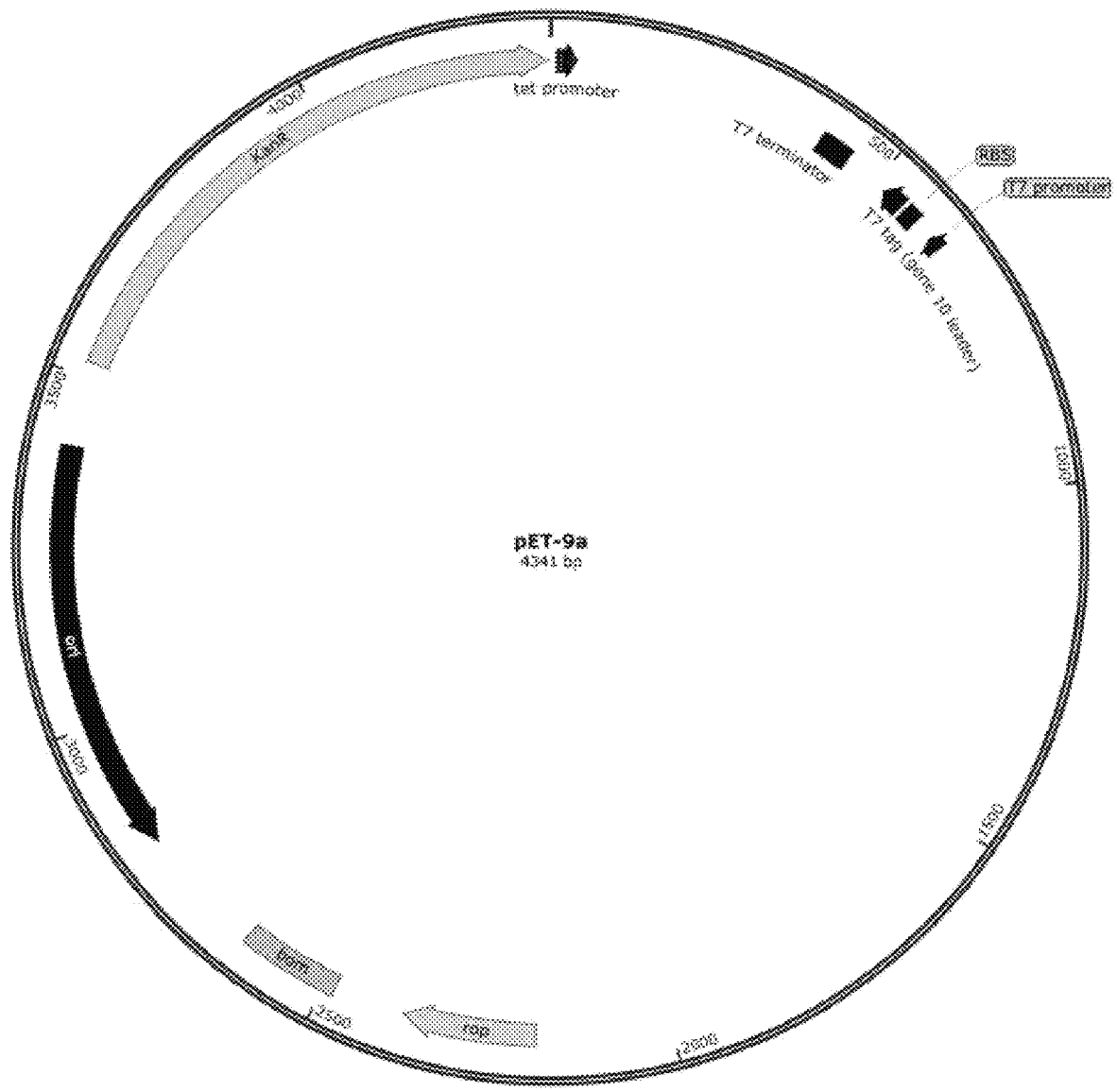
FIG. 18A illustrates an exemplary pET-9a vector for expression of a protein of interest in the ribonuclease-deficient strain with T7 RNA polymerase.

In some embodiments, the pET-9a plasmid can be used for expressing a protein of interest when the protease-deficient and/or ribonuclease-deficient strains in which the protein of interest can be expressed has its own T7 RNA polymerase activity. The pEF-9a expression vector is illustrated in FIG. 18A. This plasmid is operated under the T7 promotion system which includes a promoter region upstream of the gene of interest. This promoter sequence is essentially a recognition site of the T7 RNA polymerase located under inducible control within the genome of the cell line in which the vector is transformed. Thus, production of the protein of interest is controlled by the promoter that controls the T7 rather than a promoter present on the plasmid. Because the plasmid is under control of the T7 promoter, directly after the gene is a T7 terminator region. This is to ensure that only the gene of interest is overexpressed. C-terminus to the protein of interest is the T7 epitope tag which can be used for immunofluorescent staining purposes. This plasmid is maintained in vivo by the pBR322 origin of replication which is normally a high copy origin of replication. However, T7 promotion with a high copy origin of replication is undesirable (toxic levels of protein) so the rop gene was also included in order to keep the copy number low. This plasmid contains a kanamycin resistance cassette (KanR) under control of its own promoter and thus is selected for with kanamycin.

Figure 18B:
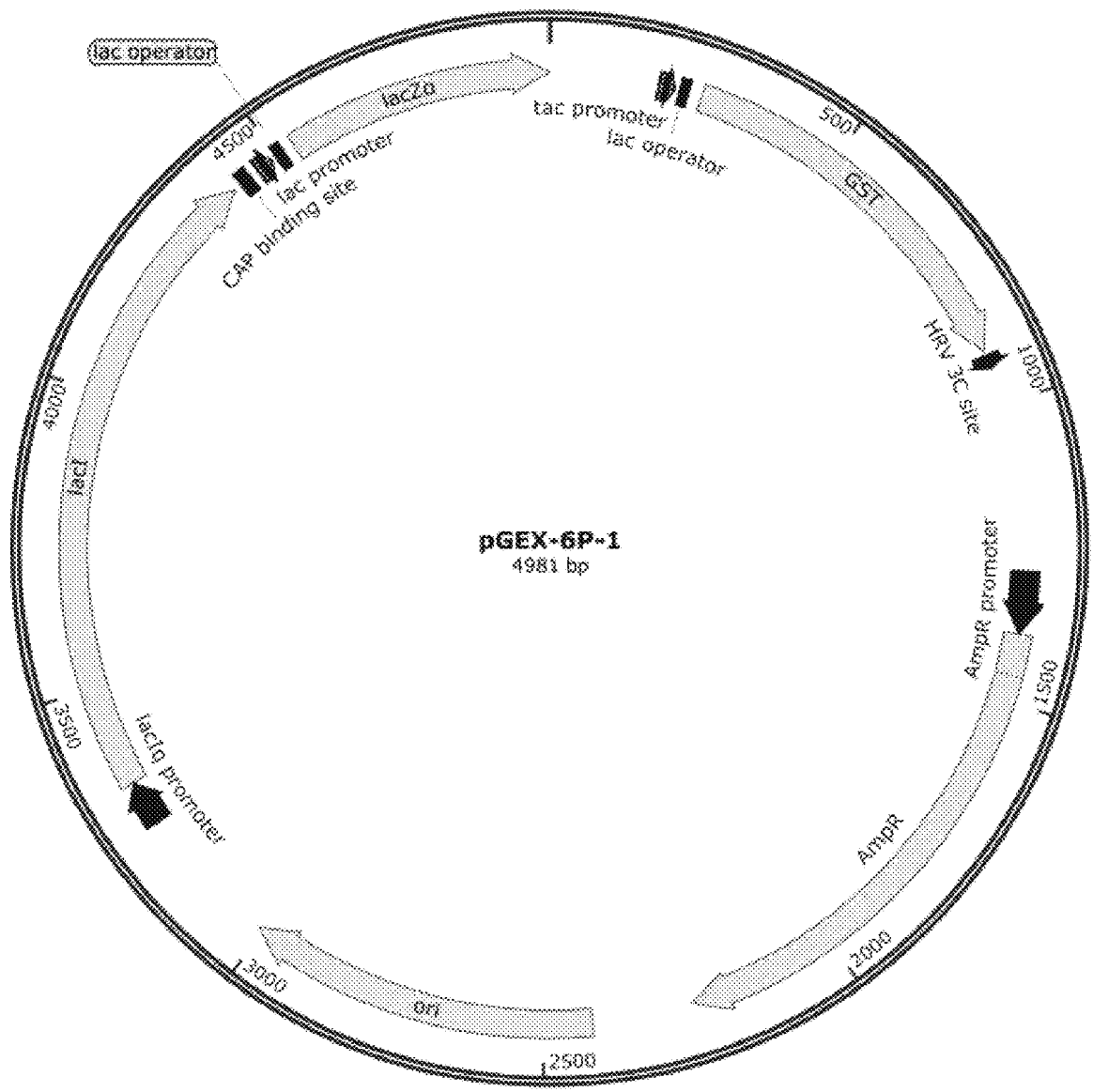
FIG. 18B illustrates an exemplary pGEX-6P-1 vector for expression of a protein of interest in the ribonuclease-deficient strain without T7 RNA polymerase.

In some embodiments, the pGEX-6P-1 plasmid can be used for expressing a protein of interest when the protease-deficient and/or ribonuclease-deficient strains in which the protein of interest can be expressed does not have a T7 RNA polymerase activity. The pGEX-6P-1 expression vector is illustrated in FIG. 18B. The pGEX-6P-1 is operated under the tac promotion system. The tac promotion system is a hybrid promotion system between the trp promoter and the lac promoter. By hybridizing the promotion system, the binding/release lad protein (inhibitor) is the mechanism of modulation of the promotion system, but it allows for tunable expression levels by varying the concentration of the induction agent (normally IPTG). This lad gene and its promoter are included on the plasmid in order to mitigate any basal level of gene expression thus enhancing the degree of expression control resulting from the tac promoter. pGEX-6P-1, pGEX-6P-2, and pGEX-6P-3 each encodes the recognition sequence for site-specific cleavage by PreScission Protease, between the GST domain and the multiple cloning site. According to the need of experiments of the present disclosure, each vector can be used interchangeably for recombinant vector construction.

This pGEX plasmid normally contains a glutathione S-transferase tag (GST) which enables for protein purification or immunochemical applications. However, given the purpose of the present disclosure, the start codon (ATG) for the GST tag was removed from the pGEX-6P-1 plasmid in order to decrease the size of the overall protein of interest to ensure adequate overexpression. This plasmid also contains an HRV3C cleavage site C-terminus of the GST tag for removal of the tag post purification.

This plasmid is maintained in vivo by the pBR322 origin of replication which is a high copy origin of replication. Unlike the T7 promotion system, the level of protein accumulated using the tac promotion system with a high copy plasmid is not toxic due to the use of the native RNA polymerase for mRNA production. This pGEX plasmid contains an ampicillin resistance cassette (AmpR) under the control of its own promoter.

Figure 21A:
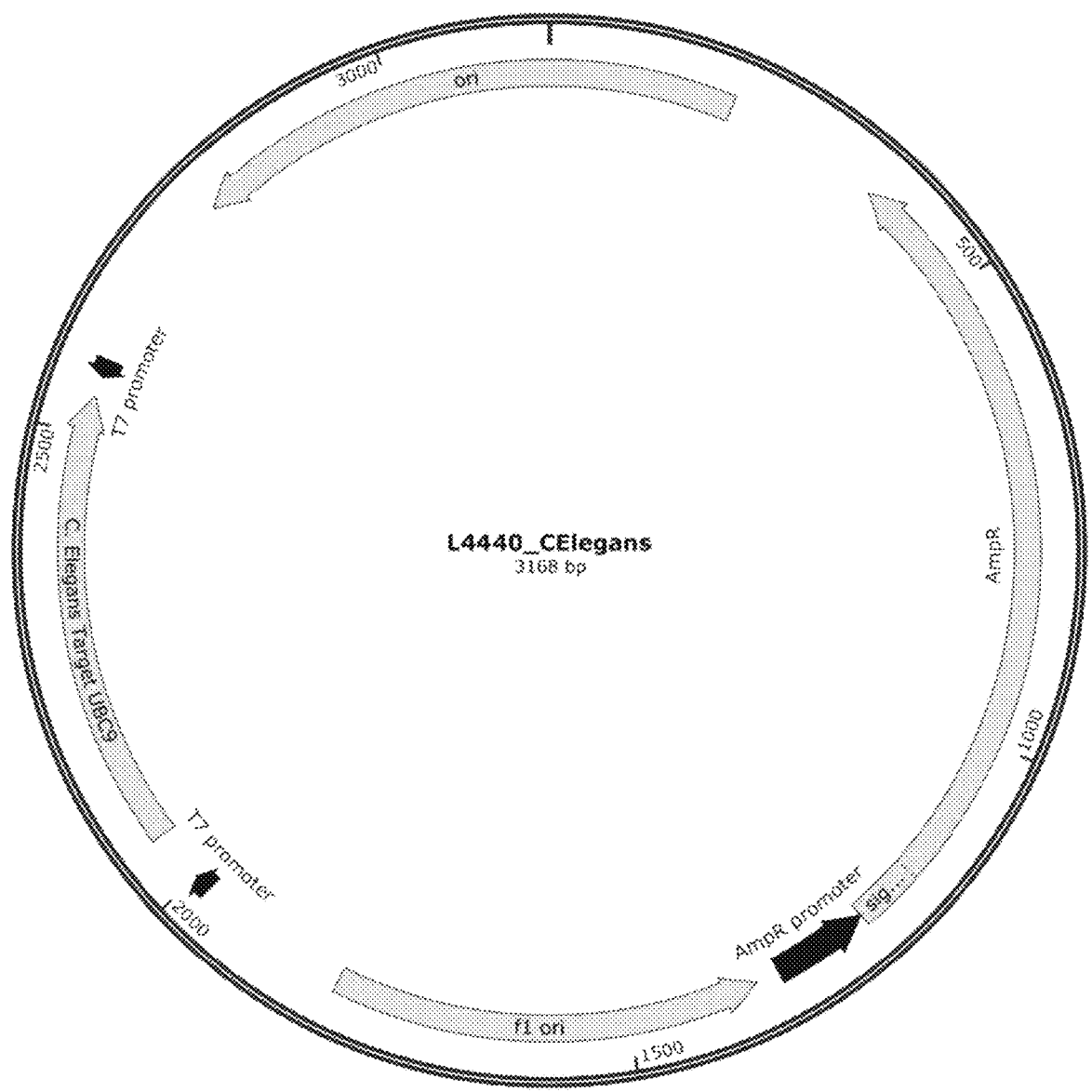
FIG. 21A illustrates an exemplary L4440 dsRNA vector with an insert of *C. elegans* UBC9 target gene for production of UBC9 dsRNA.
Figure 21B:
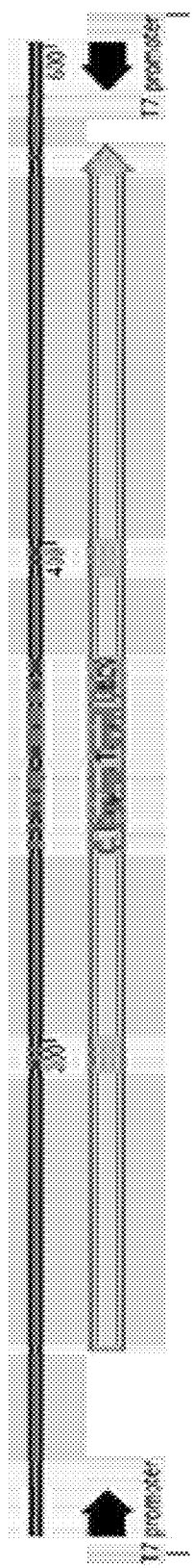
FIG. 21B illustrates an exemplar insert of insert of *C. elegans* UBC9 target gene, which is fused to an L4440 dsRNA vector.
Figure 22A:
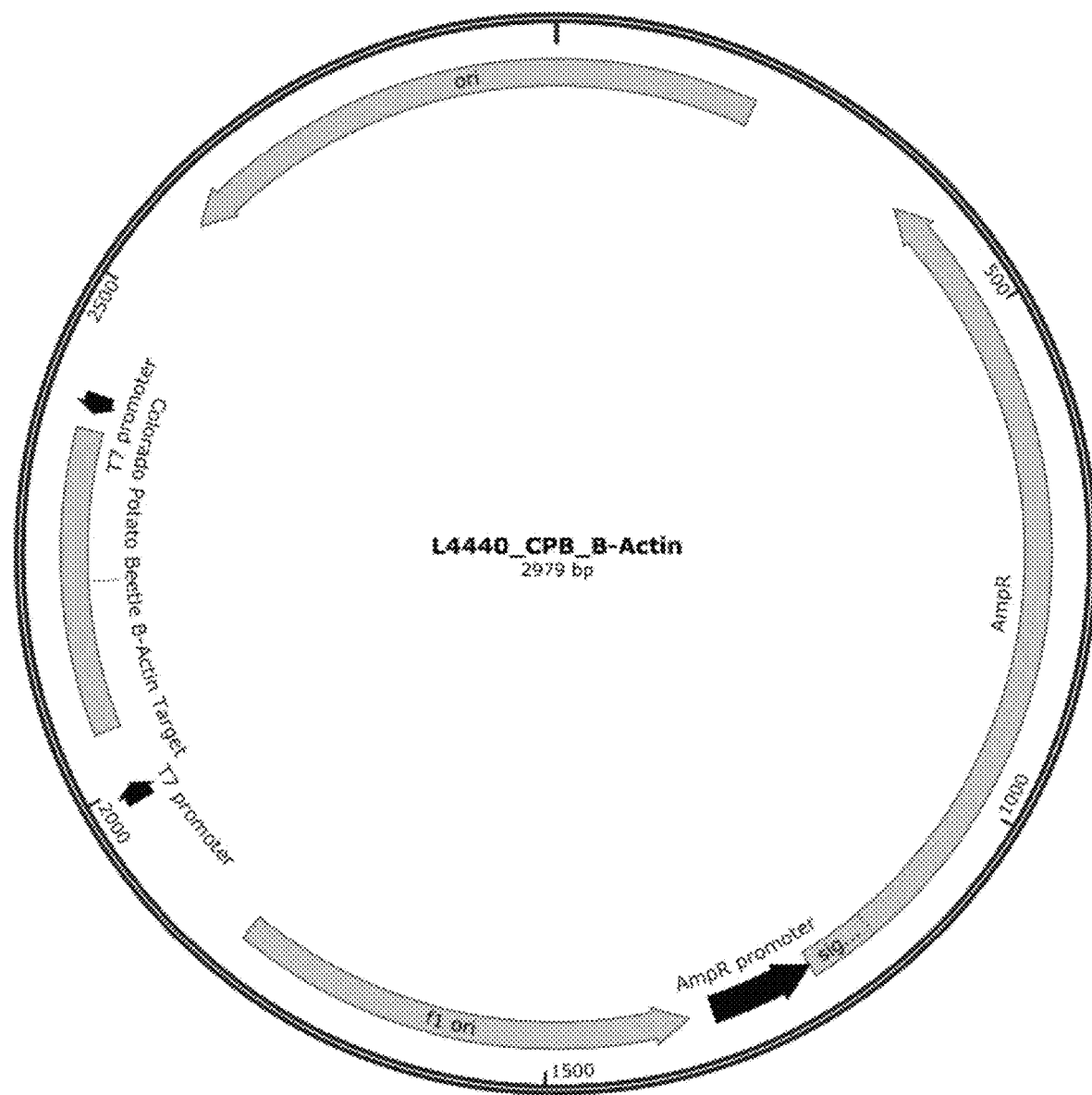
FIG. 22A illustrates an exemplary L4440 dsRNA vector with an insert of Colorado Potato Beetle B-Actin target gene for production of UBC9 dsRNA.
Figure 22B:
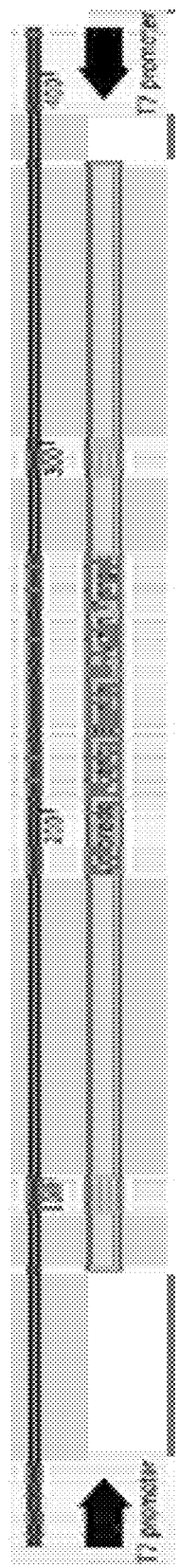
FIG. 22B illustrates an exemplar insert of insert of Colorado Potato Beetle B-Actin, which is fused to an L4440 dsRNA vector.
Figure 23:
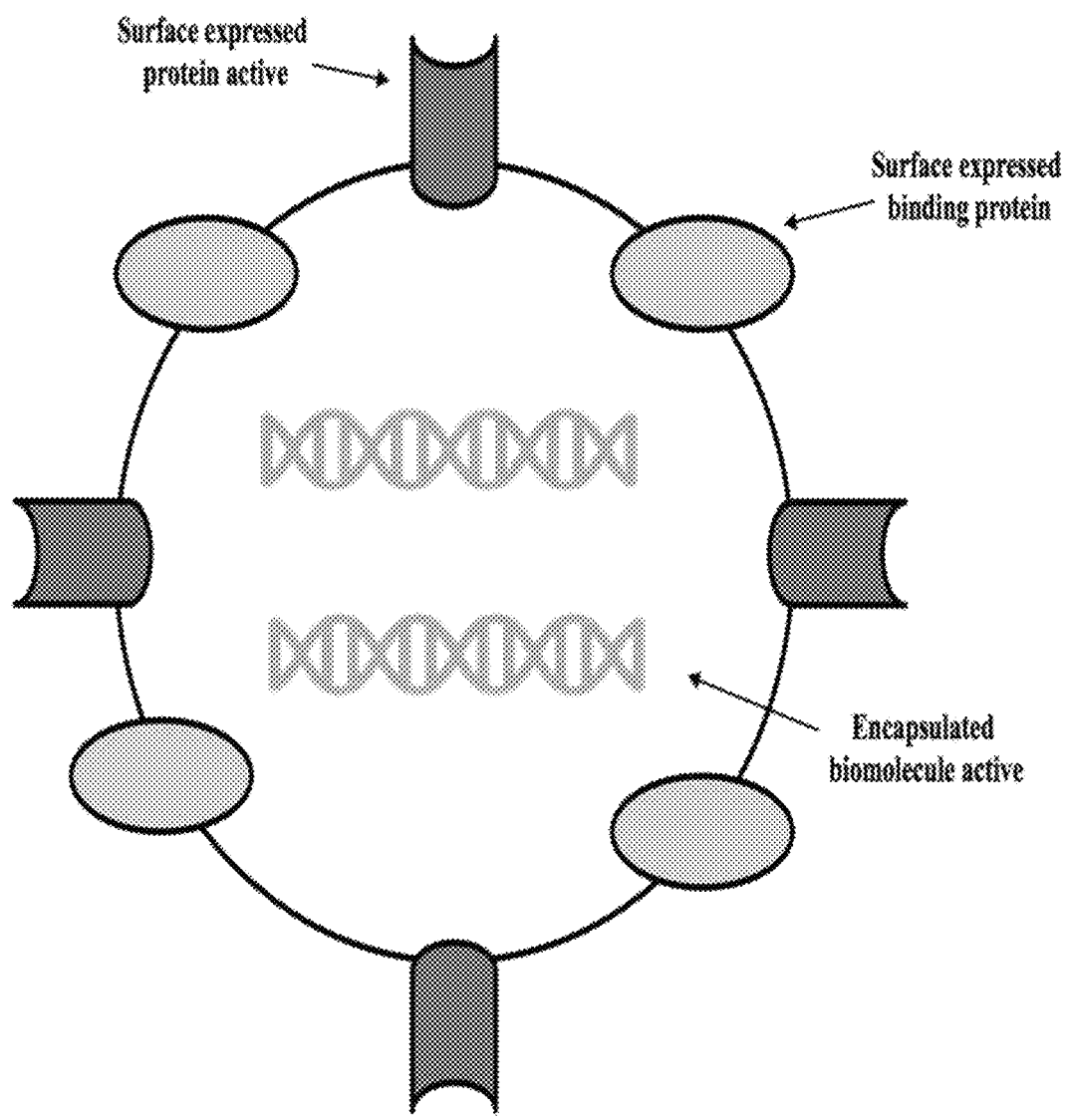
FIG. 23 illustrates an anucleated cell-based platform for encapsulation and delivery of biologically active compounds such as a nucleic acid and a polypeptide. As an example, a nucleic acid including dsRNA can be encapsulated within the anucleated cell-based platform. The anucleated cell-based platform can capture and deliver either internally produced or externally produced dsRNA, or both to a target. Also, the anucleated cell-based platform can have one or more surface-expressed fusion protein on its surface. One of surface-expressed fusion proteins can be a surface-expressed binding protein such as CBM. On the other hand, surface-expressed fusion protein can be a surface-expressed active protein/polypeptide, which is one of the biologically active compounds. Therefore, the anucleated cell-based platform has a capability of expressing at least two different surface-expressed fusion proteins on its surface and carry other biologically active compounds within the platform at the same time in order to deliver them to a target.

In some embodiments, the L4440 plasmid is used for RNAi that involves double-stranded RNA (dsRNA) interfering with the expression of genes with sequences complementary to the dsRNA. In some embodiments, a specific dsRNA is internally expressed from the recombinant L4440 plasmid within minicells derived from ribonuclease-deficient strains. In other embodiments, a specific dsRNA is produced from the recombinant L4440 plasmid and encapsulated into minicells derived from ribonuclease-deficient strains. In further embodiments, minicells derived from ribonuclease-deficient strains encapsulate the internally-expressed dsRNA and/or the exogenously-produced dsRNA. RNAi plasmids such as L4440 plasmid typically consist of DNA coding sequence from the intended target gene cloned between two T7lac promoters. The L4440 plasmid also has a selectable marker that confers resistance to an antibiotic, in this case ampicillin. In some embodiments, the E. coli strain HT115 carrying various L4440 plasmids is used, each containing a different cloned gene sequence. HT115 is an RNase III-deficient E. coli strain with IPTG-inducible T7 polymerase activity. To induce dsRNA production from these plasmids, the HT115 bacteria is grown on special RNAi NGM feeding plates that contain IPTG and the ampicillin or the ampicillin analog carbenicillin. In some cases, carbenicillin is preferred over ampicillin because it tends to be more stable. An example of the recombinant L4440 vector with an insert sequence from C. elegans UBC9 gene is illustrated in FIG. 21A. This plasmid is operated under the T7 promotion system which includes two T7 promoters located in opposite direction. As a result, the bidirectional transcript of the gene of interest, such as C. elegans UBC9 gene (FIG. 21B) produces dsRNA for the silencing of a target gene. The sequence information of the recombinant L4440 plasmid inserted with C. elegans UBC9 target gene is provided in SEQ ID No. 42. The sequence information of C. elegans UBC9 target gene is provided in SEQ ID No. 40. This promoter sequence is essentially a recognition site of the T7 RNA polymerase located under inducible control within the genome of the cell line in which the vector is transformed. HT115 (DE3) has a modified lac promoter controlling the transcript of T7 RNA polymerase. This allows transcription of two strands of RNA from the insert between the promoter and form dsRNA that is carried by minicells to a target cell. FIG. 22A illustrates another example of the recombinant L4440 vector with an insert sequence, B-Actin gene from Colorado potato beetle, which is shown in FIG. 22B. The sequence information of the recombinant L4440 plasmid inserted with Colorado potato beetle B-Actin target gene is provided in SEQ ID No. 43. The sequence information of Colorado potato beetle B-Actin target gene is provided in SEQ ID No. 41.

Enzyme Expression on Surface of Gram Positive Bacterial Derivatives

Enzymes are immobilized to the surface of the minicell by means of protein mediated membrane localization mechanisms including but not limited to the following linking proteins and mechanisms: Sortase linking mechanism. Sortase is one of autotransporters for enzyme immobilization that specifically works in gram positive bacteria cells like *Bacillus Subtilis*. This sortase is induced with D (+) xylose. Sortase is a transpeptidase that attaches surface proteins to the cell wall; it cleaves between the Gly and Thr of the LPXTG motif and catalyzes the formation of an amide bond between the carboxyl-group of threonine and the amino-group of the cell-wall peptidoglycan. In some embodiments, the LPXTG motif can be inserted into the end of the C-terminus of the enzymatically active polypeptide of interest to express on the surface of gram positive bacterial cell. The Sortase can recognize this motif and covalently bind the enzymatically active polypeptide to the surface of the gram positive bacterial cell.

Likewise, minicells can be engineered from Extremophiles such that they retain the resilient physical and chemical properties of the parent species. For instance minicells from thermophiles would retain the resistance to high temperatures. Fluorescent protein fusions, ATP synthase mediated protein localization, Succinate dehydrogenase mediated protein localization. The focalization of membrane proteins and linking mechanisms in Gram-Positive Bacteria is reported by Mitra S D et al 2016, Trends in Microbiology, 24 (8):611-621, which is herein incorporated by reference in its entirety.

Enzyme Expression on the Surface of Yeast Derivatives

Enzymes can be immobilized to the surface of the yeast minicell via surface display proteins. Minicells can be produced from yeast strains, including but not limited to *Saccharomyes cervisiae, Pichia pastoris* and *Schizosaccharomyces pombe*.

The crystal structures of mammalian membrane proteins derived from recombinant sources were solved from protein expressed in yeast cells: the $Ca^{2+}$-ATPase (SERCA1a) from rabbit. This protein was overexpressed in *Saccharomyces cerevisiae*. Also, the rat voltage-dependent potassium ion channel, Kv1.2 was produced in *Pichia pastoris* to understand its structure. Since then, several other host cells have been used for eukaryotic membrane protein production including *Escherichia coli*, baculovirus-infected insect cells and mammalian cell-lines. Whilst all host systems have advantages and disadvantages, yeasts have remained a consistently-popular choice in the eukaryotic membrane protein field. As microbes, they are quick, easy and cheap to culture; as eukaryotes they are able to post-translationally process eukaryotic membrane proteins. Very recent crystal structures of recombinant transmembrane proteins produced in yeast include those of human aquaporin 2, chicken bestrophin-1, the human TRAAK channel, human leukotriene C4 synthase, an algal P-glycoprotein homologue and mouse P-glycoprotein using *P. pastoris*-derived samples; the structures of the *Arabidopsis thaliana* NRT1.1 nitrate transporter, a fungal plant pathogen TMEM16 lipid scramblase and the yeast mitochondrial ADP/ATP carrier were solved using recombinant protein produced in *S. cerevisiae*. Due to its features as an eukaryotic cells, yeast cells can be used for the purpose of enzyme-immobilized minicell production.

The yeast membrane differs in composition from that of mammalian membranes. This is relevant to subsequent structural and functional studies of recombinant membrane proteins produced in yeast because lipids have a particularly important role in the normal function of membrane proteins by contributing to membrane fluidity and may directly interact with membrane proteins.

In an attempt to "humanize" the yeast membrane, yeast strains have been developed that synthesize cholesterol rather than the native yeast sterol, ergosterol. This was achieved by replacing the ERG5 and ERG6 genes of the ergosterol biosynthetic pathway with the mammalian genes DHRC24 and DHRC7 and, respectively. The gene products of DHRC7 and DHRC24 were identified as key enzymes that saturate sterol intermediates at positions C7 and C24 in cholesterol (but not ergosterol) synthesis. Erg5p introduces a double bond at position C22 and Erg6p adds a methyl group at position C24 in the ergosterol biosynthetic pathway and therefore competes with the gene product of DHRC24 for its substrate.

In addition to the open reading frame (ORF) of the gene of interest, a typical expression plasmid usually incorporate a number of other sequences in its expression cassette. The *S. cerevisiae* α-mating factor signal sequence is a common addition to commercial expression plasmids because it is believed to correctly-target recombinant membrane proteins to the yeast membrane. For example, its presence had a positive impact on the yield of the mouse 5-HT5A serotonin receptor but dramatically reduced expression of the histamine Hi receptor. Alternative signal sequences have been used (albeit much less frequently) such as the STE2 leader sequence of the fungal GPCR, Ste2p. The known signal sequences in yeast can be another advantage for trafficking a protein of interest fused to membrane-associated protein/domain and immobilizing the protein of interest on the surface of yeast cell.

Release of Biologically Active Compounds Encapsulated by Minicell

The present disclosure teaches that biologically active compounds is retained within the minicell and be released over time. The disclosure teaches a high value, low volume product of an anucleated minicell encapsulating at least one biologically active compounds and/or expressing a fusion protein. In some embodiments, the fusion protein has at least one surface expressing moiety and at least one cell adhesion moiety. In some embodiments, the fusion protein has at least one surface expressing moiety and at least one cell stimulation moiety. In some embodiments, the fusion protein has at least one surface expressing moiety and at least one cell degrading moiety. In some embodiments, the anucleated cell-based product can be sprayed much less than other commercially available agrochemical products and also retain the desired effects of the active compounds over a longer period of time.

The term "controlled release" as used herein means that one or more agrochemicals encapsulated by an anucleated cell described in the present disclosed is released over time in a controlled manner. The controlled release is meant for purposes of the present disclosure that, once the biologically active compound is released from the formulation, it is released at a controlled rate such that levels and/or concentrations of the compounds are sustained and/or delayed over an extended period of time from the start of compound release, e.g., providing a release over a time period with a prolonged interval.

Current controlled release mechanism of agrochemical is based mainly on fully encapsulation of fertilizer (e.g. Agrium, ICL, Kingenta and Ekompany) or pesticides (e.g. Adama, Syngenta, Bayer). Fully encapsulation of fertilizer is usually based on resins (e.g. polyurethanes) or sulfur base mixture. Pesticides are loaded into micro polymeric capsules. Products of encapsulated fertilizer are limited to milligrams scale of dry fertilizer, due to the need of thick wall opposing the high inner pressure. This pressure is build up due to water entering the capsule driven by the negative osmotic potential of the dissolve fertilizer. As more fertilizer is encapsulated, more pressure will build up and a thicker wall is required. The feasible ratio between fertilizer amounts to wall thickness is in the tens of milligrams scale. Nevertheless encapsulated fertilizer is still very expensive and costs up to four times over the fertilizer price.

Moreover, the release mechanism is based on transport through faults and cracks distributed in the casing. Meaning, coating must be uniform throughout the all surface area, which is in turn a manufacturing challenge. On top of that, the materials being used for coating are temperature sensitive and change their structural properties extremely in small temperature range (17° C.-25° C.), leading to radical changes in release rates (up to double the rate). Thus, conventional encapsulation of agrochemicals has challenges of uniform coating and temperature dependent.

If it is desired to permit fast release of the encapsulated composition during drying of the formulation on a leaf, or similar, surface it is necessary to have thin walled microcapsules. Typically microcapsules with a mean diameter of about 2 microns require a polymer wall concentration in the formulation of about 3% by weight. Greater quantities of polymer will slow the release rate. The diameter of the capsules and the quantity of wall forming polymer can be used to tune the performance of the capsules, depending on the required pesticide and the conditions of use.

The increasing use of agrochemicals such as pesticides, herbicides, fungicides, insecticides, nematicides, fertilizer and the like, poses serious health and environmental problems which must be controlled in order to minimize the harmful effects of those products. One problem frequently encountered with herbicides, such as alachlor, metolachlor, norflurazon and sulfometuron is leaching and migration, which results in loss of herbicidal efficiency and can cause damage to other crops and contaminate water.

The present disclosure teaches that biologically active compounds encapsulated by minicells disclosed herein can be released in a controlled manner. In some embodiments, the controlled release of the compounds are determined by a treatment of an agent such as glutaraldehyde, formaldehyde, as well as natural compounds, such as genipin, and epigallocatechin gallat, derivatives of ethylene glycol di(meth)acrylate, derivatives of methylenebisacrylamide, and formaldehyde-free crosslinking agent DVB (Divinyl Benzene). In some embodiments, a varying concentration of the agent (e.g. glutaraldehyde) can prevent the degradation of minicells encapsulating the biologically active compounds in different degrees.

In other embodiments, the agent includes, but is not limited to glutaraldehyde, formaldehyde, as well as natural compounds, such as genipin, and epigallocatechin gallat, derivatives of ethylene glycol di(meth)acrylate, derivatives of methylenebisacrylamide, and formaldehyde-free crosslinking agent DVB (Divinyl Benzene).

In some embodiments, biologically active compounds encapsulated by minicells disclosed herein can be released at a rate of 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 55%, 60%, 65%, 70%, 75%, 80%, 85%, 90%, 95%, or 100% of a desired minicell unit/input per day. In other embodiments, an amount of the desired minicell unit/input accounts for encapsulated biologically active compounds. Encapsulation amount of biologically active compounds can calculate encapsulation fraction and mass fraction, which determines the desired minicell unit and/or input per day.

In some embodiments, minicells without treatment of an agent (e.g. glutaraldehyde) may have an initial fast release of 10%, 20%, 30%, 40%, 50%, 60%, 70%, or 80% of their desired unit/input per day and are followed by a controlled release of minicells treated with a varying concentration of the agent (e.g. glutaraldehyde), which give rise to a controlled release of 1%, 2%, 3%, 4%, 5%, 6%, 7%, 8%, 9%, 10%, 11%, 12%, 13%, 14%, 15%, 16%, 17%, 18%, 19%, or 20% of the desired input per day. In some embodiments, a varying concentration of the agent (e.g. glutaraldehyde) can prevent the degradation of minicells encapsulating the biologically active compounds in different degrees. In some embodiments, the agent includes, but is not limited to glutaraldehyde, formaldehyde, as well as natural compounds, such as genipin, and epigallocatechin gallat, derivatives of ethylene glycol di(meth)acrylate, derivatives of methylenebisacrylamide, and formaldehyde-free crosslinking agent DVB (Divinyl Benzene).

Improved Encapsulation and Retention

In order to improve encapsulation and retention, the present disclosure teaches that solvents can be used in the encapsulation solution to increase the solubility of the biologically active compounds in the minicells. These solvents include, but are not limited to, CaCl$_2$ solution, ethanol, DMSO, polyethylene glycol, and glycerol. Not only can these solvents be used to increase the solubility of certain active compounds, but they may be used to increase the diffusion of the active compounds into the cell through certain protein channels or through the lipid bilayer of the outer membrane. In addition to the use of solvents to enhance the encapsulation process of the anucleated cell-based platform, certain fixatives, preservatives, and cross-linking agents can be used to trap the active ingredient within the membrane of the minicell, cross-link certain active compounds to the minicell itself, and improve the stability of the minicell. The relative concentration of these stabilizing/cross-linking agents can be tuned to achieve the required loading capacity for the active ingredient as well as the release kinetics of the active ingredient from the cell. These agents include, but are not limited to synthetic compounds, such as glutaraldehyde, formaldehyde, as well as natural compounds, such as genipin, and epigallocatechin gallat.

In some embodiments, minicells described herein are treated with a solvent, agent, fixative, preservative, or cross-linking agent for better solubility, increased stability, or enhanced integrity. In some embodiments, said minicell exhibits a controlled release rate of said biologically active compound, wherein the release can be a steady release or an initial burst followed by steady release.

In other embodiments, minicells can show their innate and modified stability and can withstand various environmental conditions and changes in temperature, pH, and/or shear stress.

In further embodiments, the present disclosure teaches that the anucleated minicell can be derived from ribonuclease-deficient cell strains and/or protease-deficient cell strains. Also, the minicell can be generated from cell strains genetically engineered to disrupt structure/function of ribonuclease and/or protease. The ribonuclease-deficient minicell can capture and deliver dsRNAs to a target disclosed herein. In order to enhance encapsulation and retention of dsRNAs, the present disclosure teaches expression of dsRNA binding protein internally and/or externally. Once the dsRNA binding protein recognizes and binds to the dsRNA within the minicells, the dsRNA cannot flow back across the membrane. Also, the dsRNA binding protein can aid in dsRNA encapsulation and retention as well as protect dsRNA from degradation by RNase. On the other hand, the protease-deficient minicell can better encapsulate and retain dsRNA within the minicells when the dsRNA binding protein is expressed to protect dsRNA from RNase activity. RNase cannot have an easy access to the dsRNA bound to the dsRNA binding protein for degradation. The dsRNA binding protein can also be expressed in conjunction with internal dsRNA production to ensure better retention.

In some embodiments, the minicell expresses a polypeptide within the cell, and wherein the polypeptide binds to said at least one biologically active compound such as dsRNA within the cell. In other embodiments, said at least one biologically active compound is a dsRNA and wherein said polypeptide is a dsRNA binding protein. The dsRNA binding protein increases stability of said dsRNA and protects said dsRNA from degradation. In further embodiments, the dsRNA binding protein is DRB4 protein. In some embodiments, an agricultural formulation comprises a polypeptide within minicells, wherein said polypeptide is expressed within said minicell, wherein said polypeptide binds to said nucleic acid. In some embodiments, said polypeptide is a dsRNA binding protein, and wherein said dsRNA binding protein increases loading and enhances the stability of dsRNA.

Invasive Delivery

The present disclosure teaches an invasive delivery method of biologically active compounds into a target cell, which is not a mammalian cell by application of an agent that can help improve penetration of the minicell into targets such as plants, pests, insects, bugs, worms, pathogens and parasites. The anucleated minicells encapsulating the biologically active compounds described herein is applied to a target cell with an agent. In some embodiments, the agent is an adjuvant for improving penetration of the anucleated minicell into the target cell and invasively delivering the biologically active compounds within the target cell. The agent is a surfactant, an emulsifier, a crop oil concentrate, a penetrant, a salt or combination thereof. Not-limiting examples of the agent are methylated seed oil, N,N-dimethyldecanamide, and N-decyl-N-methyl formamide. In some embodiments, a method of delivering at least one biologically active compound is provided, comprising: applying said minicell to said target cell with an agent, wherein said agent is an adjuvant for improving penetration of minicells into a target cell. In further embodiments, a method of delivering at least one biologically active compound is provided, said agent is a surfactant, an emulsifier, a crop oil concentrate, a penetrant, a salt or combination thereof.

Various surfactants and other formulation additives can be used to enhance the uptake/invasiveness of nanoparticles or compounds into plants through the roots and leaves. Silicone surfactants can enhance the uptake of compounds and nanoparticles through the stomata, cuticle, and root system. Lipid-based liquid crystalline nanoparticles can be used as a surfactant to improve delivery of biologically active compounds through the cuticle layer.

In other embodiments, the present disclosure teaches an invasive delivery method of biologically active compounds into a target cell by expressing proteins that improve penetration of plant surface or increase uptake through the roots or stomata. In some embodiments, the minicells express at least one fusion protein comprises at least one surface expressing moiety and at least one target cell degradation moiety. The target cell degradation moiety comprises an cutinase and cellulose, which can facilitate minicells to pass through plant surface and deliver biologically active compounds into a target cell, tissue or organ.

In some embodiments, the intact anucleated cell expresses a cutinase on its surface that facilitate said anucleated cell to penetrate through a plant cuticle into the target cell. The intact anucleated cell expresses a heterologous cutinase that is displayed on its surface. The intact anucleated cell expresses a cellulase on its surface that breaks down a target cell wall and facilitate said anucleated cell to penetrate into the target cell. The intact anucleated cell expresses a heterologous cellulase that is displayed on its surface.

In further embodiments, the present disclosure teaches an invasive delivery method of biologically active compounds into a target cell, which is not a mammalian cell, by generating minicells from plant invasive species such as *Agrobacterium* and Endophytes.

The present disclosure provides compositions and methods of producing minicells from plant pathogenic bacteria and fungi such as endophytes. The bacterial and/or yeast species has mechanisms to transport itself from the environment to the cells, internal tissues or organs of target plants. In some embodiments, minicells from these bacterial and yeast endophytes are produced. The endophytes used for minicell production include, but are not limited to *Acidovorax facilis, Bradyrhizobium, Rhizobium, Rhodococcus rhodochrous, Colletotrichum, Curvularia, Epichloë, Fusarium, Mycosphaerella, Neotyphodium, Piriformospora, Serendipita*. The minicells derived from endophytes can encapsulate biologically active compounds described herein and deliver them into the internal parts of target plants by invasion/penetration mechanisms.

There are several pathways by which biologically active compounds or particles are able to be uptaken through the leaf. These pathways include through trichomes, stomata, plant wounds, root junctions, stigma, and the cuticle (Alshaal et al., Env. Biodiv. Soil Security 1:71-83, 2017). Due to the extensive presence of the cuticle at the outermost layer of plant leaves, a primary manner in which foliar uptake occurs is through the cuticle layer. Various compounds, both lipophilic and hydrophilic, are able to transport across the cuticle through aqueous pores (for polar compounds) or cutin matrices (for apolar compounds) (Wang et al., Pesticide Biochemistry and Physiology, 87(1):1-8, 2007). It has been reported that all kinds of nanoparticles, from negatively charged silica nanoparticles (20 nm) to lipid-based liquid crystalline NPs (150-300 nm), have been shown to accumulate above actinal cell walls and in the cuticle (Schwab et al., J of Nanotoxicology 10(3):257-278, 2016). There are permeable regions of the cuticle, such as trichomes, hydathodes, or cell junctions, in plant tissue that have also have uptake functions.

On the other hand, plants are able to uptake compounds and nanoparticles through the stomata. The ability for uptake through the stomata varies for each plant species, but the stomata has generally shown to have a high transport velocity into the leaf, especially for particles or compounds less than 10 nm. However, it is also the case that larger nanoparticles have been able to enter the plant through stomata openings. Foliar application of nanoparticles has been shown to lead to translocation of nanoparticle from stomatal cavities to plant tissues, the vasculature, and roots cuticle (Schwab et al., J of Nanotoxicology 10(3):257-278, 2016). Bacteria (which are larger than minicells) are also able to invade plants through stomata openings, often times regulating their openings using virulence factors (Zeng et al., Curr. Opin. Biotechnol. 21(5):599-603, 2010). In some embodiments, minicells disclosed herein can be uptaken to target plants and translocated to target cells when the minicells encapsulating biologically active compounds are applied to leaves of target plants.

Agricultural applications of agrochemicals or nanoparticles in soil can be very effective since nanoparticles generally accumulate in the first few meters or centimeters of the soil and therefore, interact closely with the rhizosphere. Many studies have shown that nanoparticles are able to accumulate and aggregate near the roots, root tips, root caps, and mucilage of plants. It has also been shown that the mucilage, exudates, and exDNA of plants around its root system serves as a "trap" that immobilizes some nanoparticles and bacteria. Furthermore, plant roots have been shown to be able to uptake and absorb a variety of compounds and nanoparticles into the plant vasculature and tissue (Schwab et al., J of Nanotoxicology 10(3):257-278, 2016). In some embodiments, minicells disclosed herein can be uptaken to target plants and translocated to target cells when the minicells encapsulating biologically active compounds are applied to soil and/or roots of target plants.

Once these compounds and/or nanomaterials have successfully invaded the plant and are in proximity to the plant cell membranes, they can undergo a process of endocytosis. The plant cell membrane uptakes extracellular material, including nanoparticles, through endocytosis. Nanoparticles, up to 500 nm and regardless of charge, can enter the plant cell through endocytosis. Alternative pathways for nanoparticles and other compounds into plant cells are through the permeable pathways of the cell membrane themselves. One of these pathways, aquaporins, allows for non-ionic, solutes to be non-selectively be uptaken into plant cells. In some embodiments, at least one biologically active compound is delivered into a target cell, which is not a mammalian cell, when the anucleated minicell described herein is applied by endocytosis. In some embodiments, minicells descried herein are applied to a target and delivered into a cell of a target by endocytosis.

Target

As used herein, the term "target" is intended to include any target surface to which a compound, a minicell, an industrial formulation or an anucleated cell-based platform of the present disclosure may be applied to a plant or a pest. For example to a plant, plant material including roots, bulbs, tubers, corms, leaves, flowers, seeds, stems, callus tissue, nuts, grains, fruit, cuttings, root stock, scions, harvested crops including roots, bulbs, tubers, corms, leaves, flowers, seeds, stems, callus tissue, nuts, grains, fruit, cuttings, root stock, scions, or any surface that may contact harvested crops including harvesting equipment, packaging equipment and packaging material.

The term "target cell" refers to cells that is a component of each target.

In some embodiments, exemplary crops, according to certain embodiments of the present disclosures, include but not limited to Row crops, specialty crops, commodity crops, and ornamental crops. Examples of row crops include sunflower, potato, canola, dry bean, field pea, flax, safflower, buckwheat, cotton, maize, soybeans, and sugar beets. Examples of commodity crops include maize, soybean and cotton. Examples of ornamental crops include boxwood, christmas trees, greenhouse grown decorative plants The present disclosure also teaches exemplary crops as a target, according to certain embodiments of the present disclosure, including vegetables such as broccoli, cauliflower, globe artichoke, peas, beans, kale, collard greens, spinach, arugula, beet greens, bok choy, chard, choi sum, turnip greens, endive, lettuce, mustard, greens, watercress, garlic chives, gai lan, leeks, Brussels sprouts, capers, kohlrabi, celery, rhubarb, cardoon, Chinese celery, lemon gass, asparagus, bamboo shoots, galangal, ginger, soybean, mung beans, urad, carrots parsnips, beets, radishes, rutabagas, turnips, burdocks, onions, shallots, leeks, garlic, green beans, lentils, and snow peas; fruits, such as tomatoes, cucumbers, squash, zucchinis, pumpkins, melons, peppers, eggplant, tomatillos, christophene, okra, breadfruit, avocado, blackcurrant, redcurrant, gooseberry, guava, lucuma, chili pepper, pomegranate, kiwifruit, grapes, cranberry, blueberry, orange, lemon, lime, grapefruit, blackberry, raspberry, boysenberry, pineapple, fig, mulberry, hedge apple, aplle, rose hip, and strawberry; nuts such as almonds, pecans, walnuts, brazil nuts, cnadlenuts, cahshew nuts, gevuinanuts, horse-chestnuts, macadamia nuts, Malabar chestnuts, mongongo, peanuts, pine nuts, and pistachios; tubers such as potatoes, sweet potatoes, cassava, yams, and dahlias; cereals or grains such as maize, rice, wheat, barley, sorghum, millet, oats, rye, triticale, fonio, buckwheat, and quinoa; fibers, including, for example, cotton, flax, hemp, kapok, jute, ramie, sisal, and other fibers from plants; stimulant crops, including, for example, coffee, cocoa bean, tea, mate, other plants; and pulses, including, for example, beans (including, for example, kidney, haricot, lima, butter, adzuki, mungo, golden, green gram, black gram, urd, scarlet runner, rice, moth, tepary, lablab, hyacinth, jack, winged, guar, velvet, yam, and other beans), horse-bean, broad bean, field bean, garden pea, chickpea, bengal gram, garbanzo, cowpea, blackeyed pea, pigeon pea, cajan pea, congo bean, lentil, bambara ground nut, earth pea, vetches, lupins, and other pulses.

In some embodiments, the present disclosure also teaches exemplary aquaculture targets including fish, shrimp, shellfish, and crustacean. The target can be viruses that cause diseases.

The present disclosure teaches that a target cell comprises a plant cell, an insect cell, a worm cell, a bacterial cell, a fungal cell, a virus and a cell of an aquatic animal, wherein said aquatic animal comprises a fish, a shellfish, and a crustacean.

It is appreciated that the anucleated cell-based platform and/or agricultural formulation as described herein is particularly useful within the fishing and aquaculture industries, primarily by causing a reduction in the harmful effects of microbial organisms exerted on shellfish, cartilaginous fish, fin fish or aquatic mammals. Shellfish may comprise the group of filter-feeding bivalves such as e.g. clams, oysters, scallops and mussels, and may in addition comprise lobsters, crabs and shrimps. Finfish include, but are not limited to the salmonid species including Atlantic salmon (*Salmo salar*), rainbow trout (*Oncorhynchus mykiss*). Further aquatic animal is a fish including a gadid species including *Gadus callarias*, sea trout (*Salmo trutta*) and sea bass (*Dicentrarchus labrax*) and cod, eel as well as fresh water finfish and carp. Further, an aquatic animal may be a dolphin or a whale.

Aquatic animals further encompass any of the broadly known ornamental fish widely used throughout the hobby of fish tank maintenance. Ornamental hobby fish include both fresh water and salt water fish. Representative species of ornamental fish are well known to enthusiasts of the hobby. Preferably the aquatic animal is an animal farmed in an aquaculture. The aquatic animal may be in an early developmental stage e.g., such as larvae and juvenile animals, or a later developmental stage subsequent to the juvenile stage.

The present disclosure provides that the anucleated cell-based platform and/or agricultural formulation as described herein, is targeted to a plant, an insect, a worm, a bacterium, a fungus, a virus and an aquatic animal, wherein said aquatic animal comprises a fish, a shellfish, and a crustacean.

In some embodiments, the target is agricultural pests such as mites, aphids, whiteflies and thrips among the agricultural pests. Examples of other agricultural insect pests than the mites, aphids, whiteflies and thrips include diamondback moth (*Plutella xylostella*), cabbage armyworm (*Mamestra brassicae*), common cutworm (*Spodoptera litura*), codling-moth (*Cydia pomonella*), bollworm (*Heliothis zea*), tobacco budworm (*Heliothis virescens*), gypsy moth (*Lymantria dispar*), rice leafroller (*Cnaphalocrocis medinalis*), smaller tea tortrix (*Adoxophyes* sp.), Colorado potato beetle (*Leptinotarsa decemlineata*), cucurbit leaf beetle (*Aulacophora femoralis*), boll weevil (*Anthonomus grandis*), planthoppers, leafhoppers, scales, bugs, grasshoppers, anthomyiid flies, scarabs, black cutworm (*Agrotis ipsilon*), cutworm (*Agrotis segetum*) and ants.

In addition, examples of other agricultural pests include soil pests, such as plant parasitic nematodes such as root-knot nematodes (Meloidogynidae), cyst nematodes (Heteroderidae), root-lesion nematodes (Pratylenchidae), white-tip nematode (*Aphelenchoi desbesseyi*), strawberry bud nematode (*Nothotylenchus acris*) and pine wood nematode (*Bursaphelenchus xylophilus*); gastropods such as slugs and snails; and isopods such as pill bugs (*Armadillidium vulgare*) and pill bugs (*Porcellio scaber*).

Examples of other insect pests include hygienic insect pests such as tropical rat mite (*Ornithonyssus bacoti*), cockroaches, housefly (*Musca domestica*) and house mosquito (*Culex pipiens pallens*); stored grain insect such as angoumois grain moth (*Sitotroga cerealella*), adzuki bean weevil (*Callosobruchus chinensis*), red flour beetle (*Tribolium castaneum*) and mealworms; clothes insect pests such as casemaking clothes moth (*Tinea translucens*) and black carpet beetle (*Attagenus unicolor japonicus*); house and household insect pests such as subterranean termites; domestic mites such a mold mite (*Tyrophaqus putrescentiae*), *Dermatophagoides farinae* and *Chelacaropsis moorei*; and hygienic insect pests such as tropical rat mite (*Ornithonyssus bacoti*).

Insect pests include insects selected from the orders *coleoptera, diptera, hymenoptera, lepidoptera, mallophaga, homoptera, hemiptera, orthoptera, thysanoptera, dermaptera, isoptera, anoplura, siphonaptera, trichoptera*, etc.

In some embodiments, the insects are selected from cotton bollworm, native budworm, green minds, aphids, green vegetable bugs, apple dimpling bugs, thrips (plaque thrips, tobacco thrips, onion thrips, western flower thrips), white flies and two spotted mites. In an embodiment the insect pests of animals include fleas, lice, mosquitoes, flies, tsetse flies, ants, ticks, mites, silverfish and chiggers. The above agricultural pests and insect pests are described, for example, in U.S. Patent Application Nos. 2012/0016022 and 2016/0174571, which are incorporated by reference herein in their entirety.

Biologically Active Compound Delivery Amounts

In some embodiments, biologically active compounds are encapsulated within the anucleated cells described herein and delivered to a desired target. Amounts of an biologically active compound of interest are provided herein with percent weight proportions of the various components used in the preparation of the anucleated cell for the encapsulation and deliver of biologically active compounds.

The percent weight proportions of the various components used in the preparation of the anucleated cell for the encapsulation and deliver of biologically active compounds can be varied as required to achieve optimal results. In some embodiments, the biologically active compounds including, but are not limited to a nucleic acid, a polypeptide, a metabolite, a semiochemical and a micronutrient polypeptide, are present in an amount of about 0.1 to about 90% by weight, is present in an amount of about 0.5 to about 80% by weight, 1 to about 70% by weight, 2 to about 60% by weight, 3 to about 55% by weight, 5 to about 50% by weight, 10 to about 45% by weight, and 15 to about 40% by weight, based on the total weight of the anucleated cell within which an active compound of interest is encapsulated. When a polymer is used in the preparation of the anucleated cell disclosed herein, according to one embodiment it is present in an amount of about 0.01 to about 10% by weight based on the total weight of the anucleated cell disclosed herein. When a co-solvent is used in the preparation of the anucleated cell disclosed herein, according to one embodiment it is present in an amount of about 0.1 to about 30% by weight based on the total weight of the anucleated cell disclosed herein. Alternate percent weight proportions are also envisioned. For example, the biologically active compound of interest can be present in an amount of up to about 50% by weight; the solvent can be present in an amount of up to about 70% by weight; the surfactant can be present in an amount of up to about 40% by weight and the water can be present in an amount of from about 1 to about 90% by weight, based on the total weight of the anucleated cell disclosed herein.

Among the various aspects of the present disclosure is an anucleated cell in the form of encapsulation of an biologically active compound of interest at least about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%, by weight of the biologically active compound within the anucleated cell.

In other embodiments, the biologically active compound within the anucleated cell is present in an amount of at least about 0.01, about 0.02, about 0.03, about 0.04, about 0.05, about 0.06, about 0.07, about 0.08, about 0.09, about 0.1, about 0.2, about 0.3, about 0.4, about 0.5, about 0.6, about 0.7, about 0.8, about 0.9, about 1, about 2, about 3, about 4, about 5, about 6, about 7, about 8, about 9, about 10, about 11, about 12, about 13, about 14, about 15, about 16, about 17, about 18, about 19, about 20, about 30, about 40, about 50, about 60, about 70, about 80, about 90, or about 100 g/L.

In another embodiment, the biologically active compound of interest and the anucleated cell are present in compositions of the disclosure in a weight ratio of at least 1:200, 1:195, 1:190, 1:185, 1:180, 1:175, 1:170, 1:165, 1:160, 1:155, 1:150, 1:145, 1:140, 1:135, 1:130, 1:125, 1:120, 1:115, 1:110, 1:105, 1:100, 1:95, 1:90, 1:85, 1:80, 1:75, 1:70, 1:65, 1:60, 1:55, 1:50, 1:45, 1:40, 1:35, 1:30, 1:25, 1:20, 1:15, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, 15:1, 20:1, 25:1, 30:1, 35:1, 40:1, 45:1, 50:1, 55:1, 60:1, 65:1, 70:1, 75:1, 80:1, 85:1, 90:1, 95:1, 100:1, 110:1, 120:1, 130:1, 140:1, 150:1, 160:1, 170:1, 180:1, 190:1 or 200:1. In another embodiment, the biologically active compound of interest and the anucleated cell are present in a weight ratio of from about 1:50 to about 50:1, from about 1:40 to about 40:1, from about 1:30 to about 30:1, from about 1:20 to about 20:1, from about 1:10 to about 10:1, or from about 1:5 to about 5:1.

In further embodiments, the density of the formulation of the anucleated cell encapsulating the biologically active compound is least 0.01, at least 0.02, at least 0.03, at least 0.04, at least 0.05, at least 0.06, at least 0.07, at least 0.08, at least 0.09, at least 0.1, at least about 0.2, at least about 0.3, at least about 0.4, at least about 0.5, at least about 0.6, at least about 0.7, at least about 0.8, at least about 0.9, at least about 1.0, at least 1.1, at least about 1.2, at least about 1.3, at least about 1.4, at least about 1.5, at least about 1.6, at least about 1.7, at least about 1.8, at least about 1.9, at least about 2.0, at least 2.1, at least about 2.2, at least about 2.3, at least about 2.4, at least about 2.5, at least about 2.6, at least about 2.7, at least about 2.8, at least about 2.9, at least about 3.0, at least 3.1, at least about 3.2, at least about 3.3, at least about 3.4, at least about 3.5, at least about 3.6, at least about 3.7, at least about 3.8, at least about 3.9, at least about 4.0, at least 4.1, at least about 4.2, at least about 4.3, at least about 4.4, at least about 4.5, at least about 4.6, at least about 4.7, at least about 4.8, at least about 4.9, at least about 5.0, at least about 5.5, at least about 6.0, at least about 6.5, at least about 7.0, at least about 7.5, at least about 8.0, at least about 8.5, at least about 9.0, at least about 9.5, or at least about 10.0 grams/liter.

In some embodiments, an biologically active compound of interest, for example, is present in at least about 20% of the total mass of the formulated product. In further embodiments, about 20 to 40% of the total mass of the formulated product is provided for the biologically active compound disclosed herein and the remaining about 60 to 80% of the mass is from the anucleated cell.

In some embodiments, more than one non-expressed biologically active compounds can be encapsulated within the anucleated cell. In another embodiment, the formulated product comprises two biologically active compounds that are present in compositions of the disclosure in a weight ratio of at least 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, or 10:1.

In terms of amounts of the biologically active compound, about a concentration of about 0.01-20, about 0.1-15, about 0.2-10, about 0.3-9, about 0.3-8, about 0.5-5, about 1-3 g/L is provided for the formulated product.

In some embodiments, the targeted delivery and controlled release disclosed herein can improve efficacy of the biologically active compounds so that the amounts of the biologically active compound can be used less. The formulation of the anucleated cell-based platform can be in a liquid or solid form. In some embodiments, the formulated product is a liquid form such as a solution. In some embodiments, the formulated product is a solid form such as a powder.

In some embodiments, the agricultural formulation further comprises an agricultural chemical that is useful for promoting plant growth, reducing weeds, or reducing pests. In some embodiments, the agricultural formulation further comprises at least one of a fungicide, an herbicide, a pesticide, a nematicide, an insecticide, a plant activator, a synergist, an herbicide safener, a plant growth regulator, an insect repellant, an acaricide, a molluscicide, or a fertilizer. In some embodiments, the agricultural formulation further comprises a surfactant. In some embodiments, the agricultural formulation further comprises a carrier. The present disclosure provides for agricultural formulations formulated for contacting to plants.

The formulations can be suitable for treating plants or plant propagation material, such as seeds, in accordance with the present disclosure, e.g., in a carrier. Suitable additives include buffering agents, wetting agents, coating agents, polysaccharides, and abrading agents. Exemplary carriers include water, aqueous solutions, slurries, solids and dry powders (e.g., peat, wheat, bran, vermiculite, clay, pasteurized soil, many forms of calcium carbonate, dolomite, various grades of gypsum, bentonite and other clay minerals, rock phosphates and other phosphorous compounds, titanium dioxide, humus, talc, alginate and activated charcoal. Any agriculturally suitable carrier known to one skilled in the art would be acceptable and is contemplated for use in the present invention). Optionally, the formulations can also include at least one surfactant, herbicide, fungicide, pesticide, or fertilizer.

In some embodiments, the agricultural formulation further comprises at least one of a surfactant, an herbicide, a pesticide, such as but not limited to a fungicide, a bactericide, an insecticide, an acaricide, and a nematicide, a plant activator, a synergist, an herbicide safener, a plant growth regulator, an insect repellant, or a fertilizer.

In some embodiments, exemplary herbicides includes, but are not limited to, paraquat, mesotrione, sulcotrione, clomazone, fentrazamide, mefenacet, oxaziclomefone, indanofan, glyphosate, prosulfocarb, molinate, triasulfuron, halosulfuron-methyl, pretilachlor, topramezone, tembotrione, isoxaflutole, fomesafen, clodinafop-propargyl, fluazifop-P-butyl, dicamba, 2,4-D, pinoxaden, bicyclopyrone, metolachlor, and pyroxasulfone. The above herbicidal active ingredients are described, for example, in "The Pesticide Manual", Editor C. D. S. Tomlin, 12th Edition, British Crop Protection Council, 2000, under the entry numbers added in parentheses; for example, mesotrione (500) is described therein. The above compounds are described, for example, in U.S. Pat. No. 7,338,920, which is incorporated by reference herein in its entirety.

In some embodiments, exemplary fungicides include, but are not limited to, sedaxane, fludioxonil, penthiopyrad, prothioconazole, flutriafol, difenoconazole, azoxystrobin, captan, cyproconazole, cyprodinil, boscalid, diniconazole, epoxiconazole, fluoxastrobin, trifloxystrobin, metalaxyl, metalaxyl-M (mefenoxam), fluquinconazole, fenarimol, nuarimol, pyrifenox, pyraclostrobin, thiabendazole, tebuconazole, triadimenol, benalaxyl, benalaxyl-M, benomyl, carbendazim, carboxin, flutolanil, fuberizadole, guazatine, myclobutanil, tetraconazole, imazalil, metconazole, bitertanol, cymoxanil, ipconazole, iprodione, prochloraz, pencycuron, propamocarb, silthiofam, thiram, triazoxide, triticonazole, tolylfluanid, isopyrazam, mandipropamid, thiabendazole, fluxapyroxad, and a manganese compound (such as mancozeb, maneb). In some embodiments, the agricultural chemical formulation comprises an effective amount of one or more of an insecticide, an acaricide and/or nematcide selected from the group consisting of: thiamethoxam, imidacloprid, clothianidin, lamda-cyhalothrin, tefluthrin, beta-cyfluthrin, permethrin, abamectin, fipronil, cyanotraniliprole, chlorantraniliprole, and spinosad. Details (e.g., structure, chemical name, commercial names, etc.) of each of the above pesticides with a common name can be found in the e-Pesticide Manual, version 3.1, 13th Edition, Ed. CDC Tomlin, British Crop Protection Council, 2004-05. The above compounds are described, for example, in U.S. Pat. No. 8,124,565, which is incorporated by reference herein in its entirety.

In some embodiments, further exemplary fungicides include, but are not limited to, Cyprodinil ((4-cyclopropyl-6-methyl-pyrimidin-2-yl)-phenyl-amine), Dodine, Chlorothalonil, Folpet, Prothioconazole, Boscalid, Proquinazid, Dithianon, Fluazinam, Ipconazole, and Metrafenone. Some of the above compounds are described, for example, in "The Pesticide Manual" [The Pesticide Manual—A World Compendium; Thirteenth Edition; Editor: C. D. S. Tomlin; The British Crop Protection Council, 2003]. The above compounds are described, for example, in U.S. Pat. No. 8,349,345, which is incorporated by reference herein in its entirety.

In some embodiments, other exemplary fungicides includes, but not limited to, fludioxonil, metalaxyl and a strobilurin fungicide, or a mixture thereof. In some embodiments, the strobilurin fungicide is azoxystrobin, picoxystrobin, kresoxim-methyl, or trifloxystrobin. In some embodiments, the agricultural chemical formulation comprises an effective amount of one or more of an insecticide selected from a phenylpyrazole and a neonicotinoid. In some embodiments, the phenylpyrazole is fipronil and the neonicotinoid is selected from thiamethoxam, imidacloprid, thiacloprid, clothianidin, nitenpyram and acetamiprid. The above compounds are described, for example, in U.S. Pat. No. 7,071,188, which is incorporated by reference herein in its entirety. In some embodiments, one or more biological pesticide, includes but not limited to, *Pasteuria* spp., *Paeciliomyces, Pochonia chlamydosporia, Myrothecium* metabolites, *Muscodor volatiles, Tagetes* spp., *Bacillus firmus*, including *Bacillus firmus* CNCM 1-1582.

EXAMPLES

The following examples are given for the purpose of illustrating various embodiments of the disclosure and are not meant to limit the present disclosure in any fashion. Changes therein and other uses which are encompassed within the spirit of the disclosure, as defined by the scope of the claims, will occur to those skilled in the art.

Figure 17A:
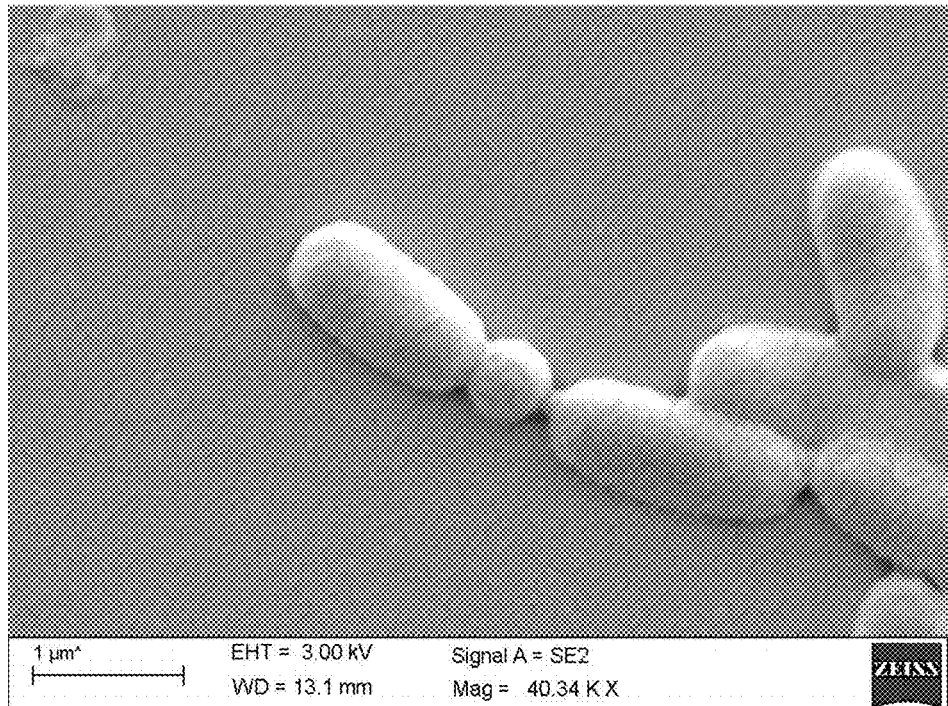
FIG. 17A-B shows scanning electron micrograph images of minicell formation in *E. coli* (FIG. 17A) and a ribonuclease-deficient anucleate minicell (white arrow) in which minC, minD, and/or minC/D gene is knocked out and/or removed (FIG. 17B). The size of exemplary minicells is less than one micrometer as shown in FIG. 17B.
Figure 17B:
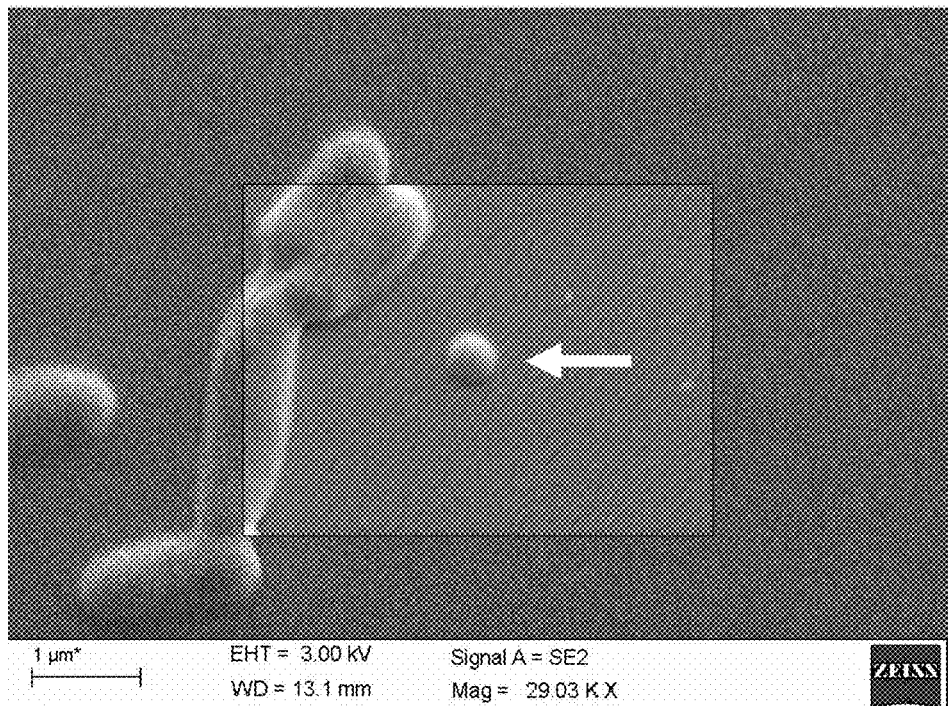

Example 1. Production of Ribonuclease-Deficient and/or Protease-Deficient Minicells The success of these knockouts was determined by PCR amplification (Eppendorf Mastercycler 5333) and morphological characterization using the Laxco LMC4000 microscope (40× Objective, brightfield and fluorescent LED light sources) in conjunction with the Zeiss Sigma VP HD field SEM (UVA Advanced Microscopy Core). Based on the results shown in FIGS. 17A and 17B, it was determined that the minC, minD, and/or minC/D knockouts produced the ribonuclease-deficient minicell closest in morphological characteristics to the original wild type P678-54 strain producing minicells (Adler et al., 1967, *Proc. Natl. Acad. Sci. USA* 57:321-326; Inselburg J, 1970 *J. Bacteriol.* 102 (3):642-647; Frazer 1975, *Curr. Topics Microbiol. Immunol.* 69:1-10). As an example, FIG. 17B shows the ribonuclease deficient minicell.

To further investigate which gene knockout was responsible for producing minicells closest to the minicell-producing wild type p678-54 strains, the Lambda Red homologous recombination system was used. This lambda red recombinant-engineering system relies on three different proteins (Beta, Gam, and Exo) required for facilitating insertion of double stranded linear DNA into the genome guided by homology to the already existing genome, as exemplified by Murphy K C, 2011 Methods Mol. Biol. 765:27-42. All of these proteins are expressed via a plasmid with the pSC101 origin of replication containing the RepA protein which only allows for plasmid replication at 30° C. Thus, once the genetic manipulation is complete, the plasmid is removed from the cell line by growth at 37° C.

The genes that were inserted into the genome were designed to have 50 base pairs of homology to both the 5' and 3' ends of a targeted gene to be knocked out. The homology corresponded to 50 base pairs at the 5' (SEQ ID NO:1) and 3' end (SEQ ID NO:2) of minC in order to knockout minC, at the 5' (SEQ ID NO:3) and 3' end (SEQ ID NO:4) of minD in order to knockout minD, or 5' end (SEQ ID NO:3) of minD and 3' end (SEQ ID NO:2) of minC in order to knockout minCD, respectively. A chloramphenicol cassette with its promoter flanked by two hairpin loops was inserted in place of either minC, minD, or minC/D. The hairpin loops were included in the insert in order to not interfere with the regulation of other genes in the same area of the genome, due to their ability to stop transcription.

Figure 2:
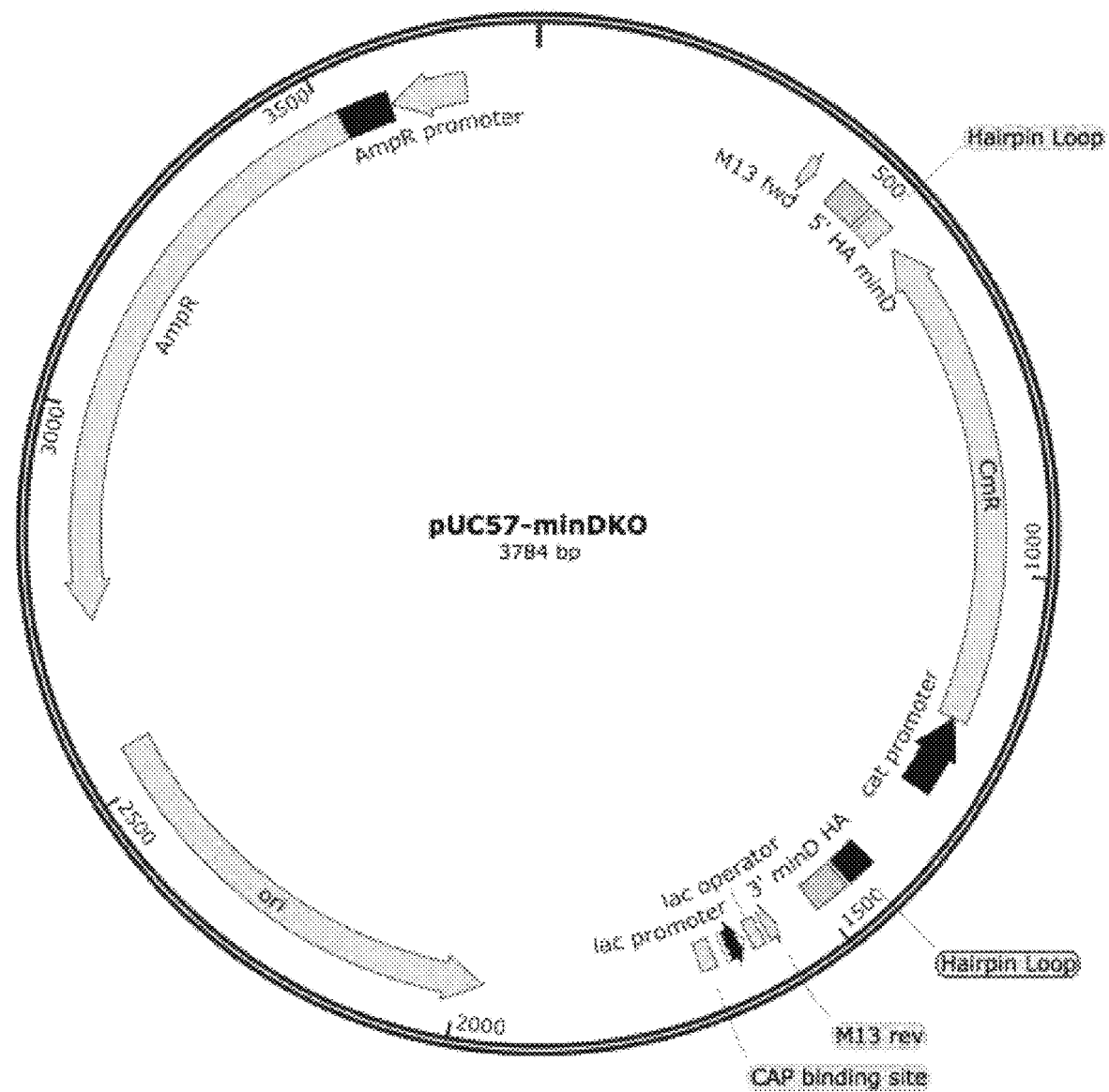
FIG. 2 illustrates an exemplary bacterial minicell-inducing vector for a minD knockout to produce ribonuclease-deficient and/or protease-deficient minicells. The pUC57 vector was inserted with a recombinant DNA insert comprising 5' end nucleotide sequence of minD gene, a chloramphenicol resistant gene (CmR) with cat promoter, and 3' end nucleotide sequence of minD gene. The hairpin loops flanked by 5' and 3' ends of minD gene are inserted into the insert to stop transcriptional regulation of other neighboring genes in the genome where the insert is integrated.
Figure 3:
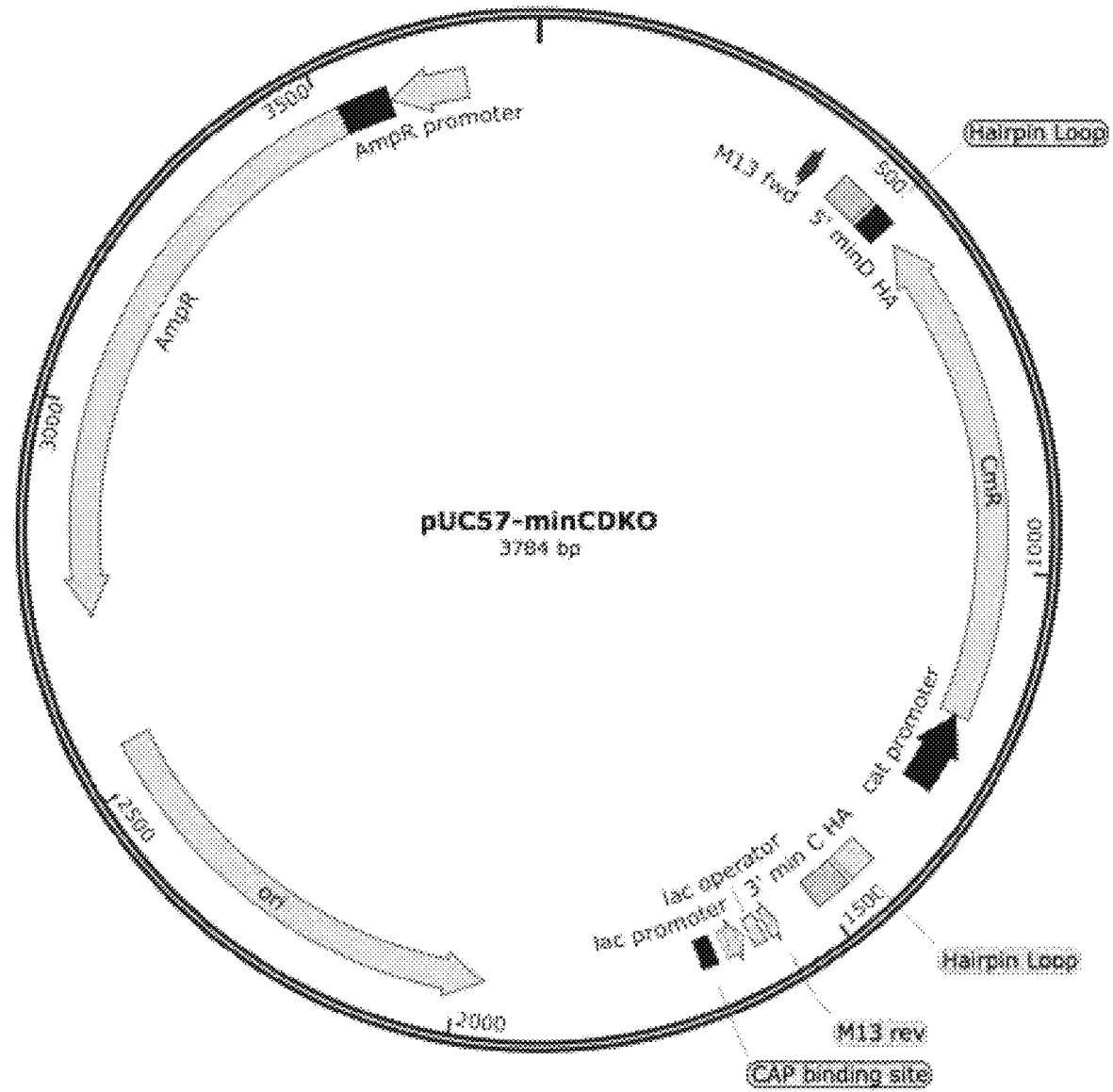
FIG. 3 illustrates an exemplary bacterial minicell-inducing vector for a minC/minD knockout to produce ribonuclease-deficient and/or protease-deficient minicells. The pUC57 vector was inserted with recombinant DNA insert comprising 5' end of minD gene, a chloramphenicol resistant gene (CmR) with cat promoter, and 3' end of minC gene. The hairpin loops, flanked by 5' end of minD gene and 3' ends of minC gene, are inserted into the insert to stop transcriptional regulation of other neighboring genes in the genome where the insert is integrated.

These genes were inserted into a pUC57 backbone as shown in FIGS. 1-3. This plasmid was used as a template to then amplify out the gene of interest to verify that the sequence information is accurate before integrate them into the host genome. All amplifications were run across 6 different annealing temperatures with the following components and conditions as shown in Tables 3 and 4. Table 2 displays that two different sets of primers were designed per each gene knockout amplification. All primers were synthesized by the service provider, Integrated DNA Technologies (IDT).

TABLE 2

Information on primer sets for testing min gene knockout

| Name | Sequence | Amplification Designation |
|---|---|---|
| F2 minCKO | AACAACAATAATGCGTGCCAT | A |
| R2 minCKO | GCGCTGGCGATGATTAATAG | A |
| F9 minCKO | AGTAACAACAATAATGCGTGCC | B |
| R9 minCKO | CGCGCTGGCGATGATT | B |
| F7 minDKO | TTCCGCGAGAGAAAGAAATCG | C |
| R7 minDKO | GACCGTTCAACCGTTAAATTGAT | C |
| F10 minDKO | CTGTGTTTTCTTCCGCGAG | D |
| R10 minDKO | TCAACCGTTAAATTGATCCCTTTTT | D |
| F6 minCDKO | TCCGCGAGAGAAAGAAATCG | E |
| R6 minCDKO | CGCGCTGGCGATGATTA | E |
| F9 minCDKO | CTGTGTTTTCTTCCGCGAG | F |
| R9 minCDKO | CGCGCTGGCGATGATT | F |

TABLE 3

Components for PCR reaction

| Contents Component | Volume (uL) | Final Concentration |
|---|---|---|
| Nuclease Free Water | 17.5 | N/A |
| Template DNA (5 ng/uL) | 1 | 5 ng |
| 10 uM Forward Primer | 2.5 | 500 nM |
| 10 uM Reverse Primer | 2.5 | 500 nM |
| DMSO | 1.5 | 3% |
| Phusion HF Master Mix | 25 | 1× |

TABLE 4

Conditions for PCR reaction

| Conditions | 55 Cycles | |
|---|---|---|
| Steps | Temperature (° C.) | Time (seconds) |
| Initial Denaturation | 98 | 30 |
| Cycle Denaturation | 98 | 10 |
| Cycle Annealing | 64, 4° Gradient | 30 |
| Cycle Extension | 72 | 30 |
| Final Extension | 72 | 600 |
| Hold | 4 | N/A |

Six series amplifications from A to F (Table 2) were run with each of the following annealing temperatures shown in Table 5. The number following the letter correspond to the position on the PCR plate with a gap between each well because of the slight increase in temperature from well to well. (example: well number A2 was the A series amplification run with Tm 1; A4—A series amplification run with Tm 2; A6—A series amplification run with Tm 3; A8—A series amplification run with Tm 4; A10—A series amplification run with Tm 5; A12—A series amplification run with Tm 6; and A1, A3, A5, A7, A9, and A11 are empty wells)

TABLE 5

Information on annealing temperatures for PCR reaction

| Annealing Temperatures Tm Number | Tm ° C. |
|---|---|
| 1 | 59.8 |
| 2 | 60.8 |
| 3 | 62.8 |
| 4 | 65.1 |
| 5 | 66.9 |
| 6 | 67.6 |

All amplifications were cleaned up using the Monarch® PCR and DNA Cleanup kit according to their standard protocol. All DNA was eluted with enough elution buffer in order to provide for adequate DNA quantification and quality determination. After cleanup, all amplifications were run on a gel against the 1 kB plus ladder from Invitrogen® to determine success of the PCR reaction. All amplifications run at all annealing temperatures were successful by visualization of a single band at about 1080 base pairs. All DNA visualization was accomplished using a 1% Agarose (w/v) gel prepared with 1×TAE and SYBR safe stain in conjunction with the Invitrogen Safe Imager 2.0.

These bands were extracted from the gel using the disposable scalpels and the Monarch® DNA gel extraction kit according to their standard protocol. After extraction the DNA was quantified, its quality was determined before sending off for sequencing from Eton Biosciences. Primers used for amplification (Table 2) were used for sequencing determination. All sequences came back with ~99% identity, thus they were deemed suitable for insertion into the genome.

The lambda red plasmid was transformed into a chemically competent ribonuclease-deficient E. coli strain via the heat shock method (see examples; Rahimzadeh et al. 2016, Mol. Boil. Res. Commun. 5(4):257-261). It was plated on a selective LB Agar plate, and re-streaked the following day in order to be sure that a single colony was isolated for lambda red recombination.

In order to introduce the PCR generated DNA into the genome, the TransformAid Bacterial Transformation Kit from Thermon Scientific™ was used with a modified protocol.

A single colony was grown in C-medium at 30° C. overnight. Next day, a 1:100 dilution of the cultured cells were inoculated into fresh C-medium. This was grown at 30° C. until it reached an optical density of about 0.2 (measured at 600 nm). This culture was induced with 1 mM IPTG for 20 minutes to allow for sufficient production and accumulation of the three proteins vital for this procedure (Beta, Gam, and Exo). After induction for every 1.5 mL of inoculated culture volume, the cells were pelleted for 1 minute at 10,000 rcf and resuspended in 300 uL of cold T-solution and incubated for 5 minutes. The cells were then pelleted again and resuspended in 120 uL of cold T-solution for 5 minutes. After the final incubation step, 50 uL of cells and 50 ng of PCR amplification were combined for each transformation and incubated on ice for 5 minutes. From here, 250 uL of SOC medium was added to each transformation and let grow for 90 minutes at 37° C. After the 90 minute outgrowth, all 300 uL of transformation was plated on Chloramphenicol LB Agar plates (10 ug/mL) and let the transformed cells grow overnight.

This protocol resulted in the successful transformation of almost all of the genes attempted (3 from each series). The morphology of the transformed cells was examined from each successful transformant on the Laxco LMC4000 (40× objective, brightfield) and it was determined that the minC knockouts (A and B) produced the most morphologically similar minicells to the control p678-54 strain from which minicells were discovered. The HT115 strain was the strain used for ribonuclease-deficient minicells and analyzed genetically. Also, BL21 and BL21-AI strains were used for protease-deficient minicells and analyzed genetically.

In order to confirm presence of the knockouts in the genome, primers were designed to amplify out specific parts of the knockouts of minC and/or minD. The 5' and 3' end of the insert was confirmed by having the primers span regions both inside and outside of the insert. The primers in Table 6 were used according to the following conditions in Tables 7-9.

TABLE 6

Information on primer sets for testing min gene knockout

| Name | Annealing Sequence | Designation |
|---|---|---|
| 3'minCKO_1 | GGCCGGATAAAACTTGTGCT | 1 |
| 3'minCKO_2 | AGTCTTCGGAACATCATCGC | 2 |
| 5'minCKO_1 | CCCTTTGCCCGAAGTAACAA | 3 |
| 5'minCKO_2 | ACGGTGAAAACCTGGCCTAT | 4 |
| minC_check_4_1 | TCAATTTAACGGTTGAACGGTCA | 5 |
| minC_check_4_2 | ATGTCAAACACGCCAATCGA | 6 |
| minD_check_2_1 | TTATCCTCCGAACAAGCGTTTGA | 7 |
| minD_check_2_2 | ATGGCACGCATTATTGTTGTTAC | 8 |

TABLE 7

Components for PCR reaction

| Component | 50 uL Reaction | Final Concentration |
|---|---|---|
| 10 uM Forward Primer | 2.5 uL | 0.5 uM |
| 10 uM Reverse Primer | 2.5 uL | 0.5 uM |
| DMSO | 1.5 uL | 3% |
| 2× Phusion Master Mix | 25 uL | 1× |
| Genomic DNA | 1 uL | 2 ng/uL |
| Nuclease Free Water | 17.5 uL | N/A |

TABLE 8

Conditions for PCR reaction

| Conditions | 55 Cycles | |
|---|---|---|
| Steps | Temperature (° C.) | Time (seconds) |
| Initial Denaturation | 98 | 30 |
| Cycle Denaturation | 98 | 10 |
| Cycle Annealing | 65.5° Gradient | 30 |
| Cycle Extension | 72 | 30 |
| Final Extension | 72 | 600 |
| Hold | 4 | N/A |

TABLE 9

Information on annealing temperatures for PCR reaction

| Annealing Temperatures Tm Number | Tm ° C. |
|---|---|
| 1 | 59.9 |
| 2 | 61.3 |
| 3 | 63.8 |
| 4 | 66.6 |
| 5 | 69.7 |
| 6 | 67.6 |

After PCR amplification, all products were cleaned up using either the Monarch® PCR and DNA Clean up Kit or the DNA Clean & Concentrator Kit™-5 with Zymo-Spin IC Columns. The purified PCR amplicants were then run in a DNA Agarose gel with the above conditions and visualized the same way. For both the A and B series, reactions using a pair of primers 1-2 and another pair of primers 3-4 produced primarily a single band at the appropriate size, respectively. Reaction with a set of primers 7-8 produced only a single band corresponding to the minD gene. Reaction using a set of primers 5-6 was run to check for presence of minC, and this reaction produced a stratification of bands indicating a nonspecific PCR product which is to be expected after knocking out minC. All of these reactions were also run on the wild type genome for comparison. Reactions using sets of primers 1-2 and 3-4 produced a stratification of bands which is to be expected from HT115 strain with the insert of min C and/or D knock-out system, but not in the wild type because the recombinant insert was not present in the wild type genome. Reactions using sets of primers 5-6 and 7-8 produced a single band indicating a specific PCR product, respectively.

All bands indicating a specific PCR product were extracted from the gel using the Monarch® gel extraction kit and the DNA sequences were analyzed by Eton Biosciences. All DNA sequencing results showed almost identical (99%) sequence homology to the expected sequence with min C and/or D knocked out.

To isolation minicells from parental cells, the entire culture including parent cells and minicells is spun down at 2,000 rcf for 10 minutes to pellet the parental cells. The supernatant is then collected and spun down again at 10,000 rcf for 10 minutes to pellet the minicells. The supernatant is discarded and the pelleted minicells are resuspended in PBS or any other buffer based on their intended use.

Example 2. Transformation of Fusion Protein Expression Cassette into Minicells The genetically modified minicell-producing bacterial strain was transformed with a linker protein fused CBM expression plasmid.

The CBM-encoding gene was inserted into the AIDA-1 surface expression cassette of the pAIDA-1 vector using KpnI and SacI restriction sites, which allows the CBM protein to be expressed and displayed by the fusion with the transmembrane autotransporter protein AIDA-1 (Adhesin Involved in Diffuse Adherence) as shown in FIG. 4B. This construction was conducted with primarily designed pAIDA-1 plasmid (from Addgene, Cambridge, MA) in which the CBM-encoding gene was ligated into the passenger domain within the AIDA-I autotransporter using KpnI and SacI sites as illustrated in FIG. 4A. The tags existed on the pAIDA-1 plasmid prior were used for further analysis on CBM expression. After the ligation is completed, the 6×His tag and HRV3C site are located at N-terminus of the CBM-encoding gene and the Myc tag and TEV site are placed at C-terminus of the CBM-encoding gene. The 6×His tag, which is the 5' end of the surface-expressed fusion CBM protein was used for Cobalt immobilized metal affinity chromatography (IMAC) and for immunofluorescent staining with THE His Tag antibody [FITC] from Genscript. The pAIDA-1 vector has a chloramphenicol resistant gene so that the recombinant pAIDA-CBM expression vector can be transformed into p567-48 wild type strain, and HT115 strain. In order to induce minicell production from HT115 strain, the present disclosure uses a minC, minD, and/or minC/D knockout system by replacing the min locus with a chloramphenicol resistant gene. In this case, the new ribonuclease-deficient minicell-producing strains (e.g. minC, D, or C/D-depleted HT115 strains) cannot be transformed with the recombinant pAIDA-1 CBM expression vector due to the presence of the same chloramphenicol resistant gene in both vector and the minicell-producing strains.

Figure 5A:
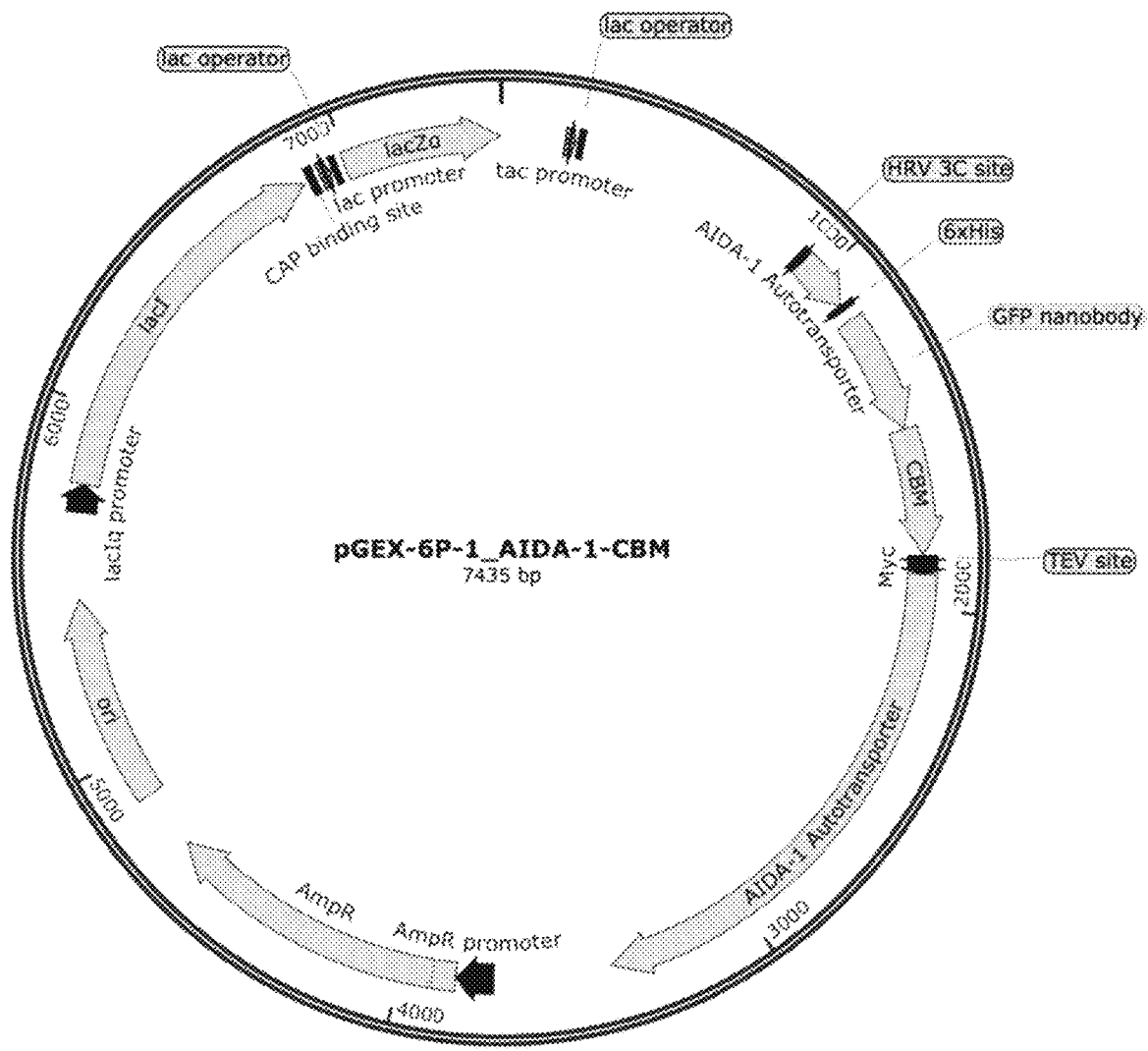
FIG. 5A illustrates an exemplary pGEX-6P-1 AIDA-1-CBM vector with AIDA-1 surface expression system for display of a CBM flanked by 6×His, GFP nanobody and Myc tags on the surface of minicells.
Figure 5B:
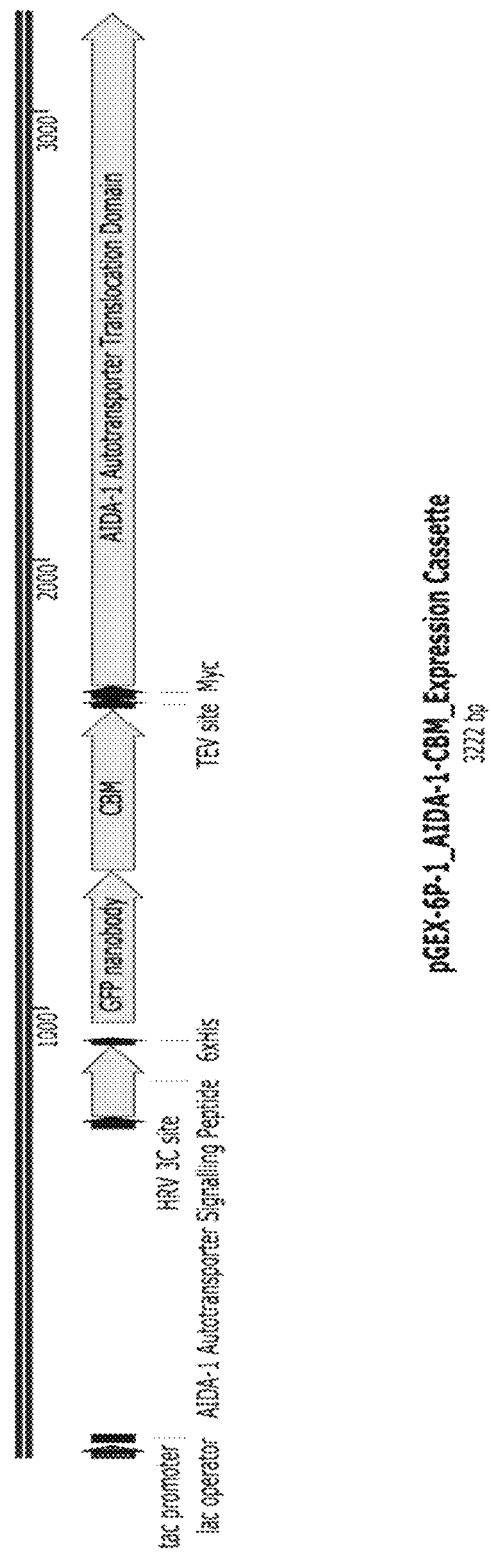
FIG. 5B illustrates an exemplary AIDA-1 CBM surface expression cassette, comprising nucleotide sequences encoding AIDA-1 Autotransporter signal peptide, GFP nanobody, CBM, and AIDA-1 autotransporter translocation domain with tags including 6×His Tag and Myc Tag as well as two protease cleavage sites including HRV3C and TEV.

In order to express the AIDA-1 CBM fusion protein, another recombinant AIDA-CBM expression plasmid was constructed in the backbone of pGEX-6P-1 vector. The AIDA-1 CBM surface expression cassette was cut from the pAIDA-1 CBM expression vector and cloned into the pGEX-6P-1 vector as illustrated in FIG. 5A. In this way, the new ribonuclease-deficient minicells, which has chloramphenicol resistant gene, can be selected with chloramphenicol because the pGEX-6P-1 AIDA-1-CBM vector possess Ampicillin-resistant gene.

For a bacterial surface display system named as BrkAutoDisplay based on the structure of autotransporter BrkA (*Bordetella* serum-resistance killing protein A) was used to host an exogenous gene encoding CBM. To construct a recombinant Brk-CBM expression vector, Brk autotransporter gene was first cloned into the pGEX-6P-1 plasmid. Using BamHI and EcoRI restriction sites, the CBM-encoding gene was ligated with the Brk autotransporter gene, as illustrated in FIG. 6A. As illustrated in FIG. 6B, the CBM-encoding gene was inserted into the passenger domain of BrkA autotransporter gene. The first 177 nucleotides of the expression cassette correspond to the signaling peptide portion of the Brk autotransporter. This is the most N-terminus region of the fusion protein. This portion is cleaved during the translocation process. Immediately at the end of C-terminus of the signaling peptide is located the 6×His tag used for purification and staining. This 6×His tag is the surface expressed N-terminus end of the fusion protein after the signal peptide is cut off. C-terminus to the His tag is fused to the CBM-encoding gene, which is followed by the Myc tag and the TEV site sequentially. Then, the translocation domain of the BrkA autotransporter is located right after the TEV site. This translocation domain of the fusion protein is the most C-terminus region of the protein that is embedded in the membrane.

Figure 7A:
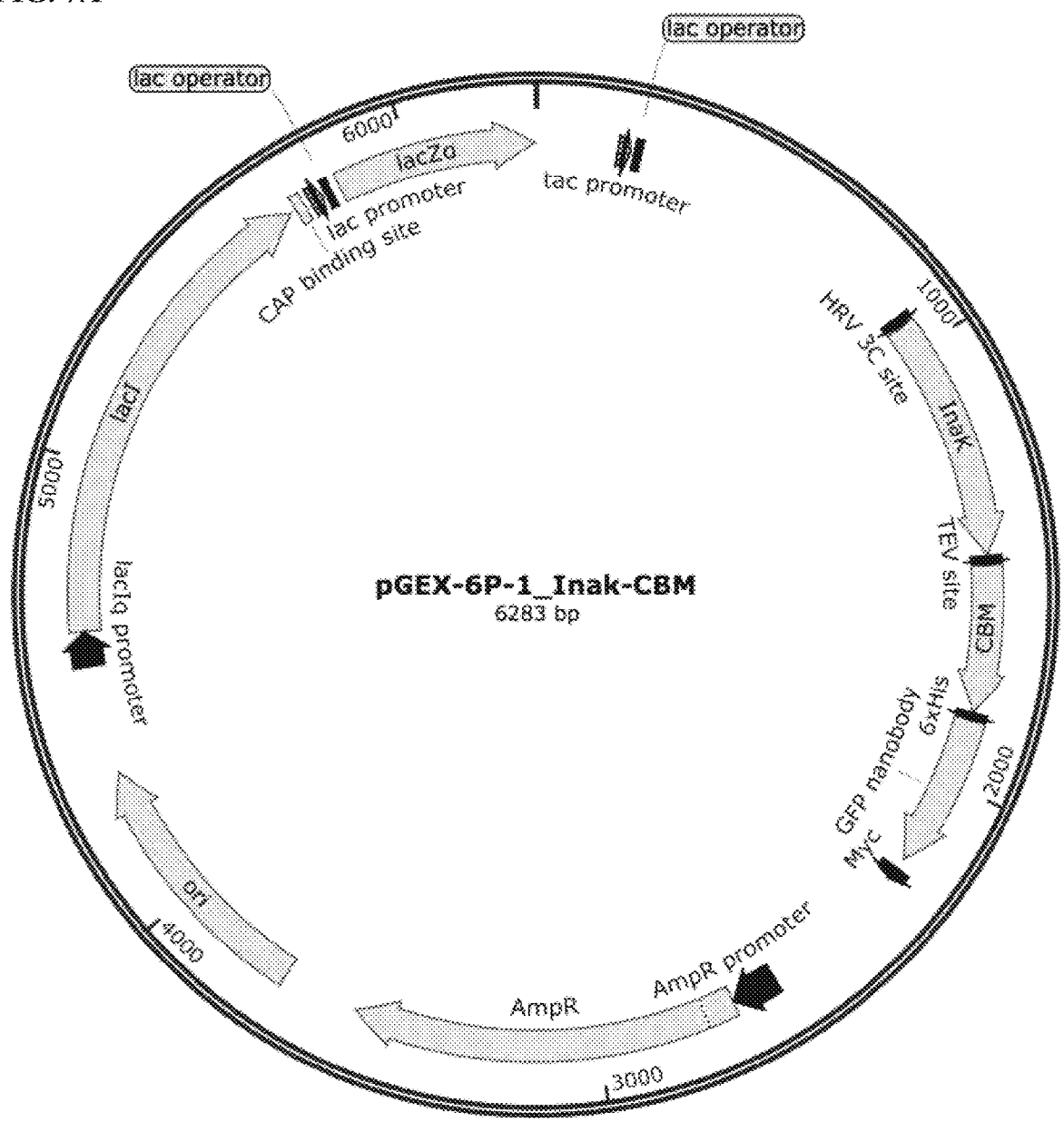
FIG. 7A illustrates an exemplary pGEX-6P-1 Inak-CBM vector with an Ice Nucleation Protein InaK surface expression system for display of a CBM protein on the surface of minicells. The CBM-encoding nucleotide sequence is ligated at its 5' end to Inak and at its 3' end to 6×His, GFP nanobody and Myc tags.
Figure 7B:
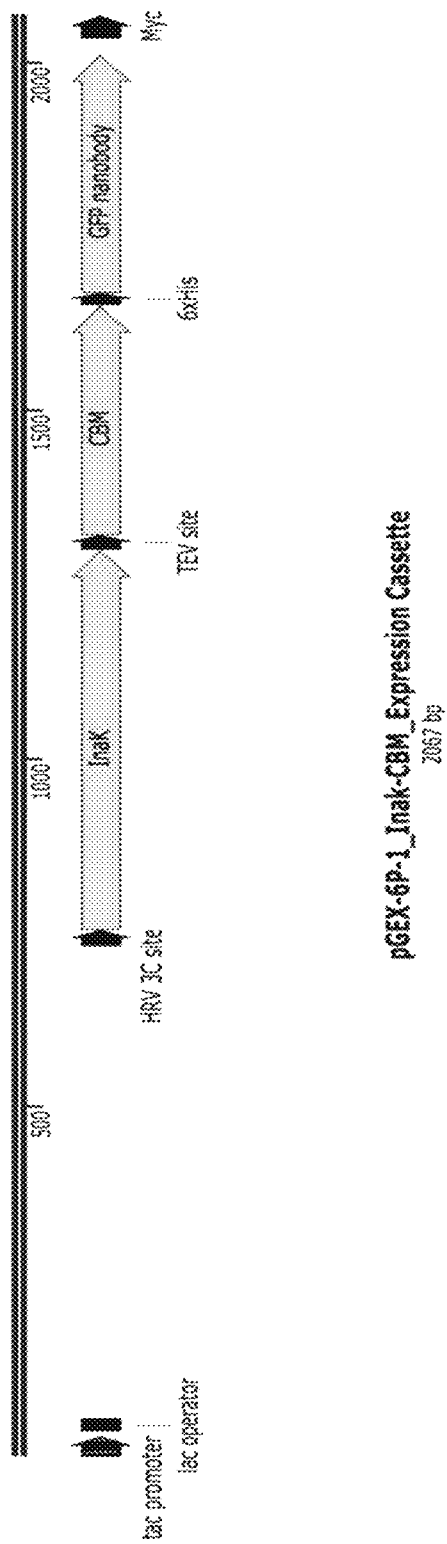
FIG. 7B illustrates an exemplary Inak-CBM surface expression cassette, comprising nucleotide sequences encoding Inak autotransporter translocation domain, CBM, and GFP nanobody, with tags including 6×His Tag and Myc Tag as well as two protease cleavage sites including HRV3C and TEV.

Another bacterial surface display protein, Ice Nucleation Protein K (InaK) was used for expressing recombinant CBM proteins fused to anchoring linker protein (motif) that direct the incorporated fusion protein on the surface of minicells. Like BrkAutoDisplay, polynucleotide encoding InaK transmembrane protein and the CBM-encoding gene were inserted into the pGEX-6P-1 vector for producing the bacterial surface display CBM protein as illustrated in FIG. 7A. For all InaK-CBM fusions, the CBM-encoding gene has a 6×His tag and an Myc tag at the C-terminus, while the TEV site is fused to N-terminus of the CBM-encoding gene. In this construct, the polynucleotide sequence encoding InaK is located before N-terminus of the TEV site. Since C-terminus of InaK protein is surface expressed and the N-terminus end becomes embedded in the membrane, the CBM-encoding gene is inserted after InaK-encoding polynucleotide sequence, which allows the CBM to be displayed on the surface while the InaK can function as a membrane anchor. The 6×His tag was used for the Cobalt immobilized metal affinity chromatography (IMAC) and for immunofluorescent staining with THE His Tag antibody [FITC] from Genscript®. The Myc tag can be used for immunofluorescent staining. The TEV site can be used for digesting off the protein of interest such as CBM for surface expression confirmation.

After construction of bacterial expression vectors for bacterial surface display fusion proteins using AIDA-1, BrkA, and InaK system was completed, transformation of each expression vector was conducted using the TransformAid Bacterial Transformation Kit (Thermo Scientific™) according to their standard protocol into the ribonuclease-deficient cell line, HT115 strain. The CBM was fused to each linker protein of AIDA-1, BrkA, and InaK to ensure surface-expression of the CBM. These expression plasmid can be transformed into the wild-type p678-54 strain and ribonuclease-deficient minicell-producing bacterial strains generated by the method taught in the present disclosure (e.g. minC, D, or C/D-depleted HT115 (DE3) strain). Also, BL21 and BL21-AI strains were used for protease-deficient minicells by the method taught in this example (e.g. minC, D, or C/D-depletion).

In order to confirm presence of plasmid in the transformed bacterial strains, a miniprep was done on a culture from the strains using GeneJet Plasmid MiniPrep Kit, and the purified plasmid was submitted for DNA sequencing analysis. All sequencing confirmed the presence of the surface expression CBM plasmids in the transformed bacterial strains.

Example 3. CBM Production

The transformed strain was grown overnight in a 5 mL culture with the appropriate antibiotic. The next day, 1:100 inoculation (4.5 mL of overnight culture in 550 mL of 2×YT media) was performed in 2×YT media plus appropriate antibiotic. The 2×YT media provided the surplus of nutrients necessary for efficient protein production. Once the culture reached the exponential growth stage (OD~0.4), it was induced with 1 mM IPTG and is incubated at 30° C. overnight. The culture was analyzed the next day for CBM production.

After overnight IPTG induction, the sample was removed from the incubator shaker and poured into three 250 mL centrifuge bottles, 150 mL of sample in each. The bottles were spun down at 2,000 rcf to pellet the bacterial cells. The supernatant was transferred to three clean 250 mL centrifuge bottles. The supernatant was spun down at 10,000 rcf to pellet the minicells. The minicells were resuspended in PBS. The volume depends on the number of encapsulation variables, 3 mL of minicells per variable and another 3 mL of minicells for the control. the OD of the minicells was measured around 1.0 for each Microcentrifuge tube. 3 mL of minicells was used in 3 microcentrifuge tubes (1 mL per tube at OD of 1.0) for one variable.

Example 4. CBM Staining

The cultured cells are subjected to staining in order to determine the presence surface-expressed CBM. Slides were developed for both the CBM-expressing minicell-producing bacterial BL21 and/or BL21-AI strain and the minicell-producing bacterial p678-54 strain that has not been transformed with the recombinant linker protein-fused CBM expression plasmid. 250 uL of poly-L-lysine was pipetted on slides for 15 minutes. After washing three times with 500 uL PBS, 500 uL of the correct cell type was pipetted on slides for 15 minutes. After washing three times with 500 uL PBS, 750 uL of 4% paraformaldehyde was pipetted on slides for 15 minutes in order to fix the cell samples to the slides. After washing three times with PBS, 500 uL of 0.1% triton x-100 PBS was added to slides allocated as permeabilized samples for 10 minutes. For non-permeabilized samples, 500 uL of PBS was added to slides during this step. After washing three times with PBS, 100 uL of 2% bovine serum albumin was pipetted on all slides as a blocking agent. After washing three times with PBS, on the slides it was pipetted 100 uL of 1 mg/mL GenScript® THE™ His Tag Antibody [FITC], mAb, Mouse antibody, which binds to the 6×-HIS tag component of the CBM fusion protein. Then, the slides were incubated with the antibody at room temperature for 1 hour while protected from light. After washing 5-10 times with PBS, 3-4 drops of Fluoroshield Mounting Medium with DAPI were added before mounting coverslips to the slides. Fluorescent microscopy can then be implemented to analyze localization between brightfield cells and fluorescent probes that are indicative of cell presence and surface-expressed protein presence.

Figure 8A:
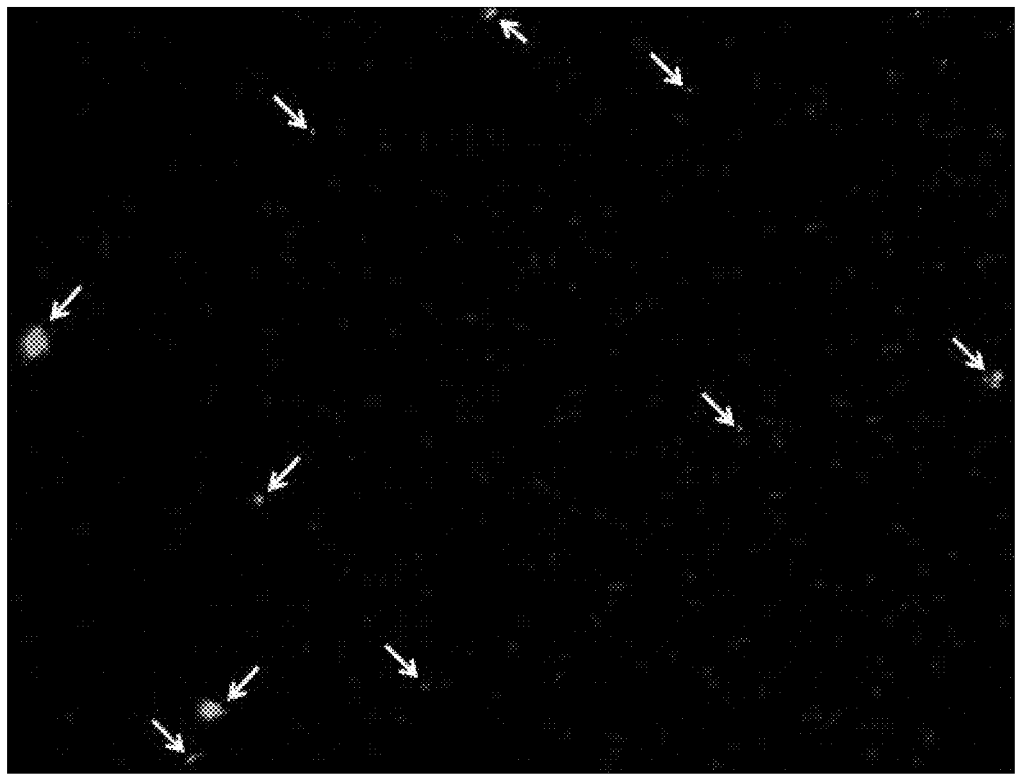
FIG. 8A-D shows His-Tag staining results of CBM protein fused with AIDA-1 linker protein on the surface of minicells. The minicells were either non-permeabilized (FIGS. 8A and 8C) or permeabilized (FIGS. 8B and 8D). The fusion CBMs were expressed from the recombinant fusion CBM expression vector on the surface of the transformed minicells (FIGS. 8A and 8B), compared to control minicells that did not have the recombinant AIDA-1 CBM expression vector (FIGS. 8C and 8D).
Figure 8B:
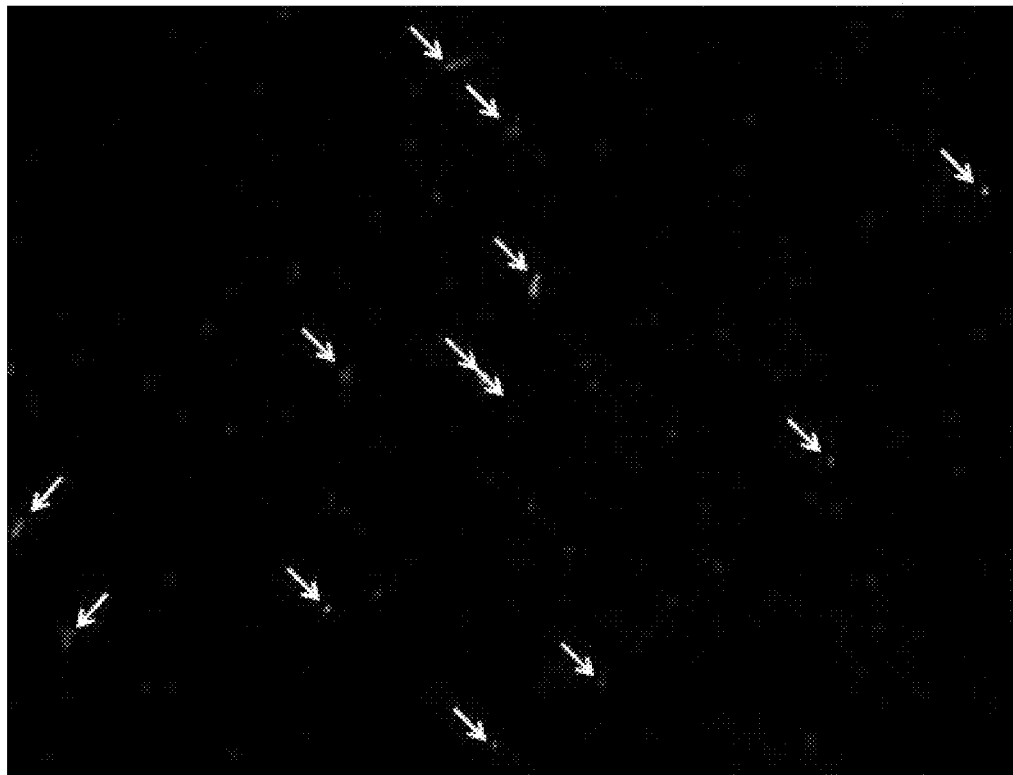
Figure 8C:
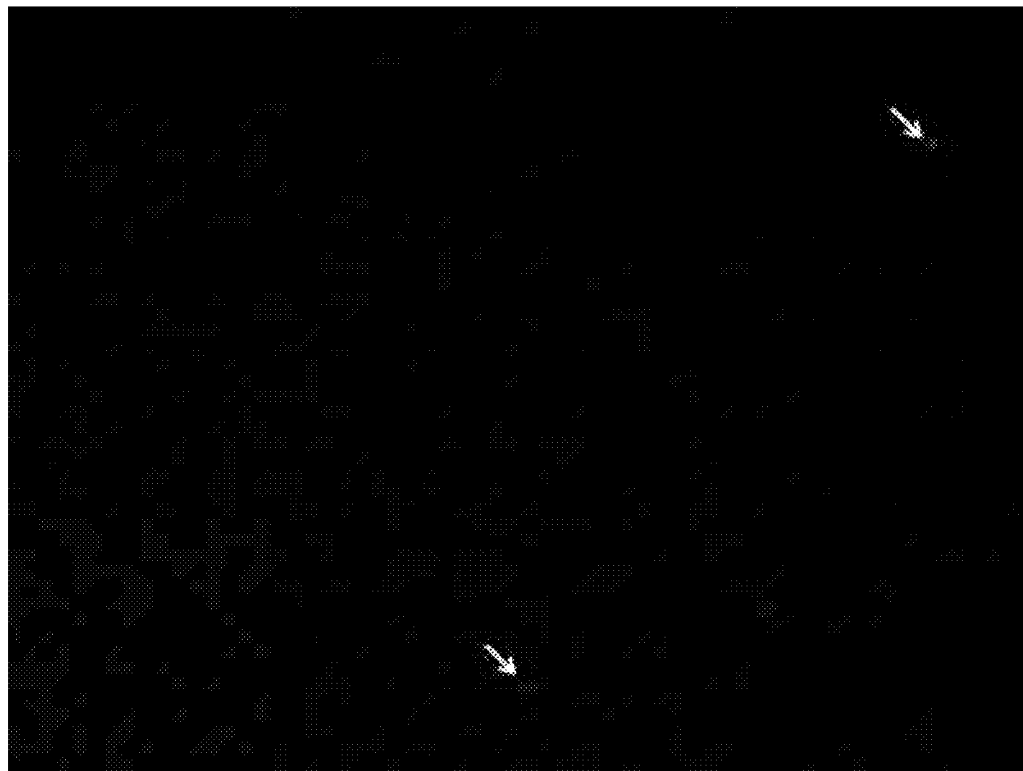
Figure 8D:
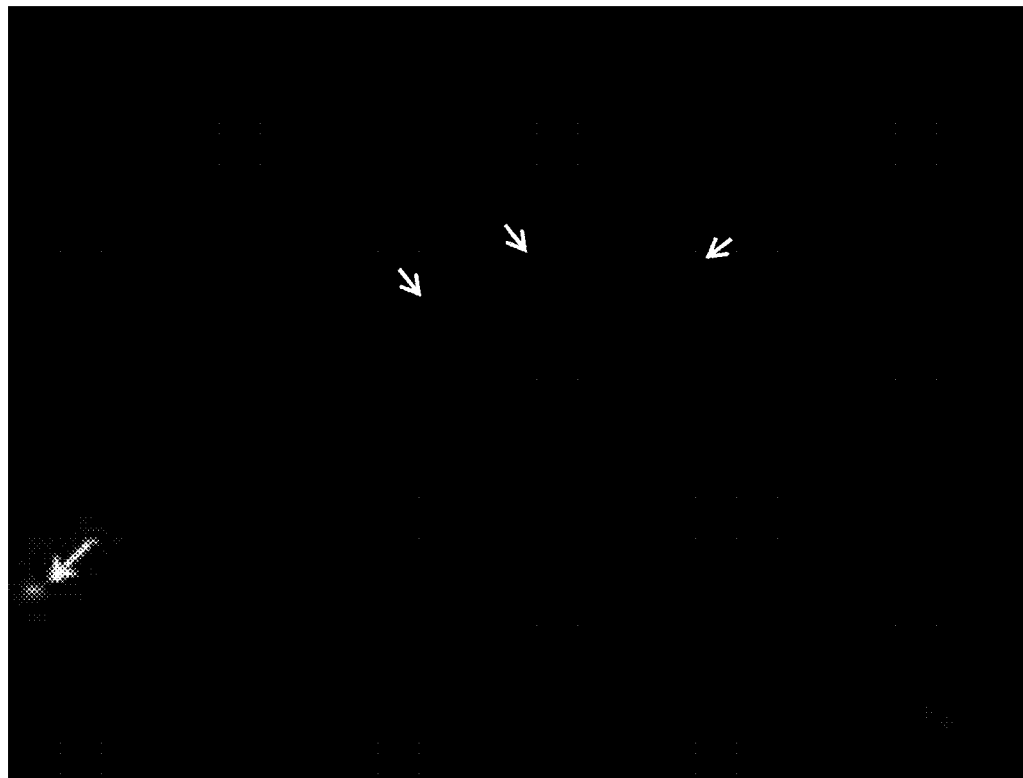

In both permeabilized and nonpermeabilized minicells, the staining with His-tag antibody showed a strong signal in a majority of the population of the cells that expressing AIDA-1-CBM fusion proteins (FIGS. 8A and 8B). However, the His-tag antibody detected little to no signal in the control samples (FIGS. 8C and 8D). The control samples are wild type p678-54 minicells that do not contain the recombinant CBM expressing plasmid so that the fusion protein cannot be detectable. Therefore, the His tag staining results indicate the expression of the fusion CBM from the minicells transformed with the recombinant CBM expression plasmid, but not the control cells. Non-permeabilized minicells (FIG. 8A) show the surface expressed CBM proteins, indicating that CBM is immobilized via the AIDA-1 linker protein on the surface of the minicells. However, the recombinant CBM is not all surface expressed from the comparison of non-permeabilized cells with permeabilized cells (FIG. 8B), indicating that endogenous CBMs and/or recombinant fusion CBM minicells can be also expressed within the minicells. On the other hand, a false positive by staining any endogenously produced CBMs within the transformed minicells can be detected as illustrated in in the control minicells (FIGS. 8C and 8D). The CBM surface expression can be similarly detected in the ribonuclease-deficient minicells as the CBM surface expression in the protease-deficient minicells shown in FIG. 8.

Example 5. Cell Retention Test

Figure 9A:
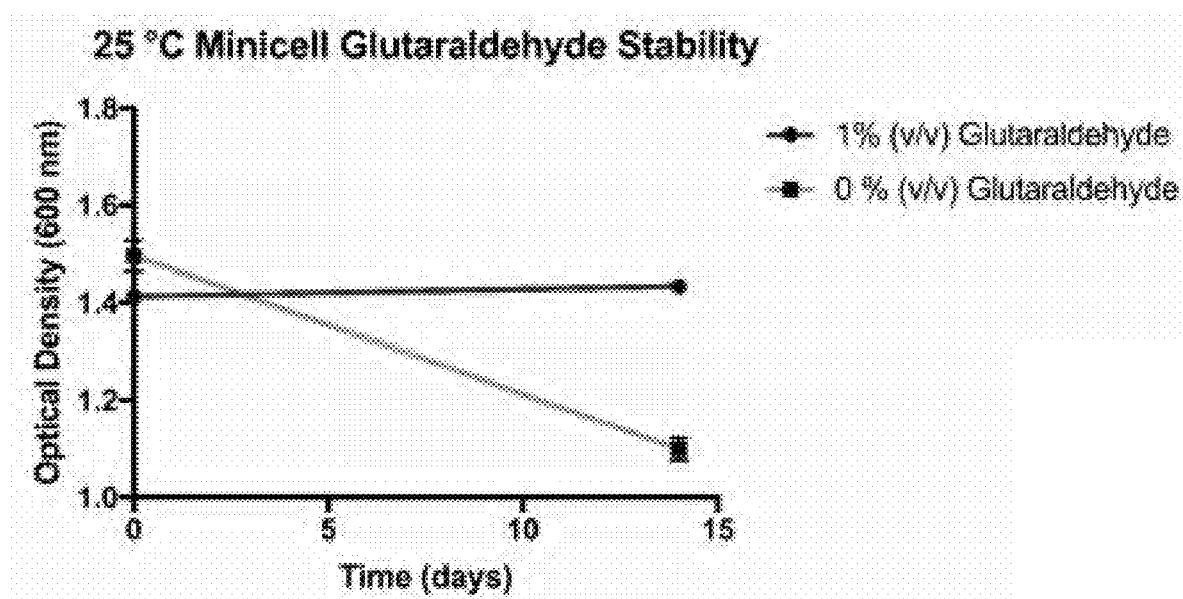
FIG. 9A-B shows optical density of minicells treated with glutaraldehyde at two different temperature to show cell retention for three weeks.
Figure 9B:
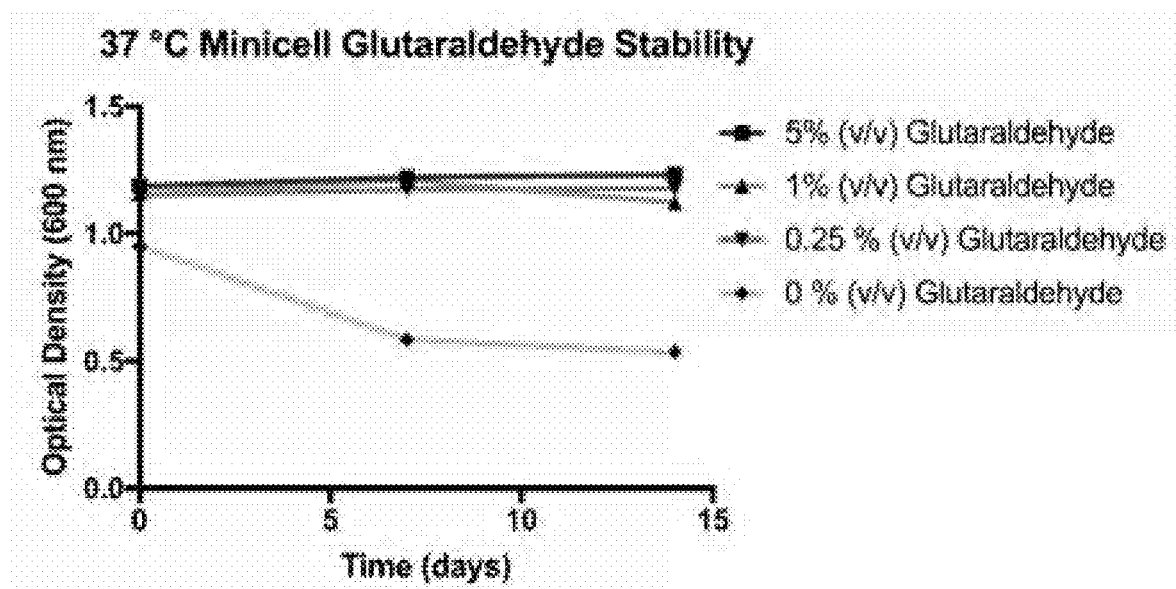

In order to test cell retention over two weeks with two variables; 1) temperature-dependent an 2) glutaraldehyde treatment. In one condition, wild-type minicells are treated with 1% (v/v) glutaraldehyde and untreated at room temperature for 15 days. In the other condition, wild-type minicells are treated with three varying concentrations of glutaraldehyde (5%, 1%, and 0.25% (v/v), compared to an untreated control at 37° C. for 15 days. As shown in FIG. 9A, the optical density of the untreated minicells drops more significantly than the optical density of the treated minicells. However, minicells treated with 1% (v/v) glutaraldehyde were not degraded and/or died. This indicates that glutaraldehyde helps prevent the early degradation of minicells at room temperature for 15 days, which ensures extended retention of active ingredients within the minicells. Also, optical density of the untreated minicells as illustrated in FIG. 9B, shows that at high temperate the glutaraldehyde-treated minicells maintained their viability without degradation. The stability of minicells treated with glutaraldehyde does not vary among wild-type minicells, protease-deficient minicells, and ribonuclease-deficient minicells. Thus, the application of glutaraldehyde can have very similar retention effects on various types of minicells including, but are not limited to wild-type minicells, ribonuclease-deficient minicells and protease-deficient minicells.

The results indicate that release of biologically active compounds from the minicells can be controlled by creating a formulation in which a certain portion of minicells are treated with glutaraldehyde and another portion of minicells are not. This would allow for the untreated minicells to break down much more quickly and initially release more of the active, while the treated cells will break down slower and release the active over time.

Example 6. Minicells Producing dsRNA Internally

The minicells derived from the HT115 cell line as described in Example 1 were transformed with an L4440 plasmid designed for double stranded RNA production. The L4440 plasmid with a gene of interest is illustrated in FIG. 21 and FIG. 22. The transformation was done using the TransformAid Bacterial Transformation Kit (Thermo Fisher Scientific). The synthesis of double stranded RNA (dsRNA) production was accomplished by the T7 promotion system inherent within the T7 cell line. The T7 RNA polymerase present in the HT115 cell line recognized the dual T7 promotion sites on the L4440 plasmid. One site was located on the coding strand with the other site located ~0.500 base pairs downstream of the coding site on the non-coding strand. The RNA was transcribed from the DNA via the T7 RNA polymerase, and by the nature of the DNA being complementary, this created two complementary strands of single stranded RNA of which a portion forms double stranded RNA due to the complementarity of the strands.

dsRNA of interest was produced in a similar fashion to protein production. An overnight culture of the HT115 minicell strain containing the plasmid was inoculated 1:100 into a volume of LB and grown at 37° C. until an OD600 of ~0.4. After this level of growth was achieved, expression of the T7, and thus the dsRNA, was induced using 1 mM IPTG for about 4 hours. After 4 hours of induction, the minicells were separated from the parent cells using differential centrifugation (10 minutes at 2000 rcf, then 10 minutes at 10000 rcf). The minicells were then subject to analysis.

The dsRNA content was analyzed via minicell lysis, total RNA extraction (including DNase Digest), and Ribonuclease T1 Digest (RNase T1) treatment. The minicell lysis and total RNA extraction was performed with a one step purification utilizing the Direct-Zol RNA Miniprep Plus with Zymo-Spin IICG (Zymo Research) and the Trizol Reagent (Thermo Fisher Scientific). This kit was run according to its standard protocol including the on-column DNase treatment designed to remove any DNA extracted together with RNA. After total RNA extraction, the RNA was quantified via nanodrop. 100 ug of total RNA was digested with the RNase T1 at a concentration of 1000 U/ug for 15 minutes in order to remove all single stranded RNA in the total RNA. After removal of all single stranded RNA (ssRNA), the digest was cleaned up using the EZ-10 Spin Column RNA Cleanup and Concentration (Biobasic). The presence of dsRNA was tested using 1% (w/v) agarose gel electrophoresis after digest/cleanup procedures. DsRNA can be confirmed by presence of a band at about 500 base pairs.

Figure 11:
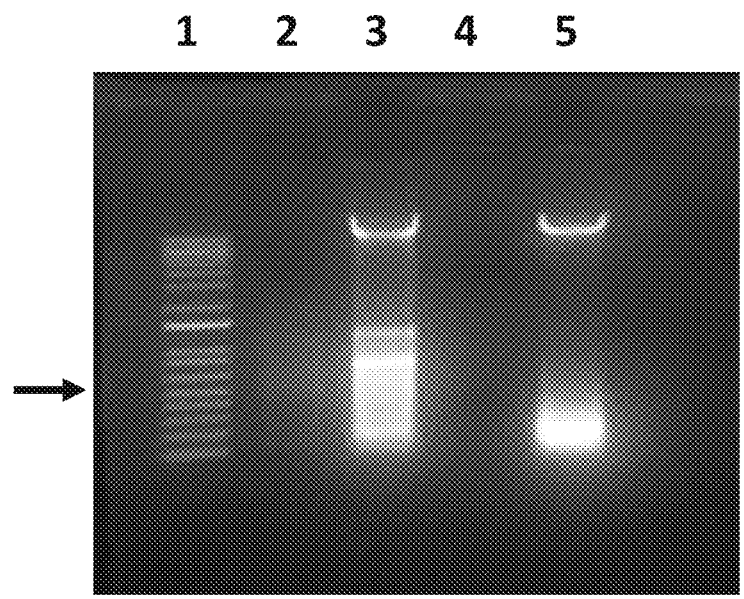
FIG. 11 shows RNA extracts from minicells producing dsRNA internally. RNA samples were loaded on a 1% agarose gel in TAE running buffer. Lane 1: 1 kb plus ladder from Invitrogen (Arrow signifies 500 bp mark). Lane 2: 100 ug of captured RNA from the dsRNA plasmid (L4440) containing minicells digested to remove any nucleic acids except for dsRNA. Lane 3: 10 ul of undigested experimental captured RNA, lane 4: 100 ug of captured RNA from non-plasmid containing minicells digested to remove any nucleic acids except for dsRNA. Lane 5: 10 ul of undigested control captured RNA.

FIG. 11 shows the presence of dsRNA that was internally expressed within the minicells. Arrow in lane 1 points about 500 bp size band. A band at about 500 bp, indicting the presence of dsRNA was observed in lane 2, which was loaded with 100 ug of captured RNA from the minicells containing dsRNA plasmid (L4440). As described above, the extracted total RNA was digested with DNase and RNase T1 to remove any nucleic acids except for dsRNA. Lanes 3 and 5 are undigested captured total. Lane 4 was a negative control, which was loaded with 100 ug of captured RNA from non-plasmid containing minicells with no dsRNA production.

Example 7. Minicells Encapsulating Exogenously Produced dsRNA

The same L4440 plasmid used from Example 6 was used in order to generate a PCR template for dsRNA production via the In Vitro Transcription method.

TABLE 10

Information on primer sets for generating PCR template for dsRNA production

| Name | Annealing Sequence (5'-3') |
|---|---|
| Amplification_dsRNACassette_1 | GTTTTCCCAGTCACGACGTT |
| Amplification_dsRNACassette_2 | AGCGAGTCAGTGAGCGAG |

TABLE 11

Components for PCR reaction

| Component | 50 uL Reaction | Final Concentration |
|---|---|---|
| 10 uM Forward Primer | 2.5 uL | 0.5 uM |
| 10 uM Reverse Primer | 2.5 uL | 0.5 uM |
| DMSO | 1.5 uL | 3% |

TABLE 11-continued

Components for PCR reaction

| Component | 50 uL Reaction | Final Concentration |
|---|---|---|
| 2× Phusion Master Mix | 25 uL | 1× |
| 5 ng/uL Template DNA | 1 uL | 2 ng/uL |
| Nuclease Free Water | 17.5 uL | N/A |

TABLE 12

Conditions for PCR reaction

| Step | Temp | Time |
|---|---|---|
| Initial Denaturation | 98° C. | 30 Seconds |
| 55 Cycles | 98° C. | 10 Seconds |
|  | 45-72° C. | 30 Seconds |
|  | 72° C. | 30 seconds |
| Final Extension | 72° C. | 10 minutes |
| Hold | 4° C. |  |

The PCR products were cleaned up using EZ-10 Spin Column DNA Cleanup Miniprep Kit and then analyzed via 1% (w/v) agarose gel electrophoresis. The bands of interest present at ~810 base pairs were purified using the Monarch DNA Gel Extraction Kit. This purified PCR product was used as the template from which the dsRNA was synthesized using the HiScribe T7 High Yield RNA Synthesis Kit according to its standard protocol. The nature of the template containing the dual T7 promotion system allowed for the production of dsRNA as opposed to solely ssRNA. The reaction was run at 37° C. in a dry air incubator for 2 hours prior to cleanup with the EZ-10 Spin Column RNA Cleanup and Concentration (Biobasic). After cleanup, the in vitro transcription product (IVT product) was quantified via nanodrop.

In brief, the encapsulation process utilized a $CaCl_2$ wash process in order to transport the IVT product across the membrane into the cytoplasm of the minicell. After the minicells were produced overnight and separated from their parent cells, they were resuspended in 1.6 mL of $CaCl_2$ solution at an OD600 of about 1.5 or less for 20 minutes on ice. After the 20 minute incubation, 40 ug of IVT product was added to the minicell-resuspended solution and let it incubate on ice for 1 hour. After incubation, the minicells were washed three times with 1.6 mL of cold PBS in order to remove any non-encapsulated IVT product from the cells. After washing, the loaded minicells were subject to analysis.

The 1.6 mL of washed minicells were lysed and the total RNA extracted as described in Example 6. This band was extracted and quantified using the Zymoclean Gel RNA Recovery Kit in combination with the nanodrop.

Provided herewith are more detailed protocols. 500 mL of B10:2 cells were grown overnight in a 2 L flask. After growth, one half of the culture was pelleted and resuspended in 10 mL of 1×PBS buffer in order to determine the expected cell count for the $CaCl_2$ resuspension. The average optical density measured at 600 nm is (OD600) was 0.356 which corresponded to $2.85 \times 10^9$ cells. Due to the small volume and the required number of aliquots of sample, the other pellet was resuspended in 5 mL of $CaCl_2$ solution. After incubation on ice for 20 minutes, the cells were pelleted at 10,000 rcf at RT for 1 minute. Experimental cells were resuspended in 2 mL of 0.1 M CaCl$_2$, while control cells were resuspended in 2 mL of 1×PBS. After competency treatment, the OD600 of the cells was 1.075. This created 10, 200 uL replicates of both the experimental and control cells. All cell suspensions were loaded with 1582.203 ng of 500 BP dsRNA (undigested after IVT generation) on ice for one hour.

After loading, all cells were spun down at 10,000 rcf for 1 minute and washed with 200 uL of 1×PBS. After washing, the cells were spun down at 10,000 rcf for 1 minute before lysing and total RNA extraction. The supernatant was drawn off and discarded. The cells were resuspended with Trizol and homogenized using a syringe. After homogenization, the solution was spun down at 12,000 rcf for 1 minutes and the supernatant extracted. This was done for all 20 samples, 10 from the experimental (E1-E10) and 10 from the control (C1-C10). The supernatant was diluted with 600 uL of 100% (v/v) EtOH, and was added to 20 separate Direct-zol RNA MiniPrep spin columns. The RNA was bound and washed according to the rest of the manufacturer protocol. No on-column digestions were done. The total RNA capture was eluted with 50 uL and quantified with 4 uL, leaving 46 uL remaining.

TABLE 13

Total RNA concentration and amount in Experimental and Control Samples

| Sample Name | [RNA] ng/uL | Elution Volume (uL) | Total RNA Present (ug) |
|---|---|---|---|
| E1 | 90.76 | 50 | 4.175 |
| E2 | 188.49 | 50 | 8.670 |
| E3 | 135.73 | 50 | 6.244 |
| E4 | 85.23 | 50 | 3.921 |
| E5 | 200.45 | 50 | 9.221 |
| E6 | 142.90 | 50 | 6.573 |
| E7 | 174.98 | 50 | 8.049 |
| E8 | 170.15 | 50 | 7.827 |
| E9 | 192.95 | 50 | 8.876 |
| E10 | 259.51 | 50 | 11.937 |
| C1 | 128.98 | 50 | 5.933 |
| C2 | 187.57 | 50 | 8.628 |
| C3 | 162.81 | 50 | 7.489 |
| C4 | 149.11 | 50 | 6.859 |
| C5 | 153.52 | 50 | 7.061 |
| C6 | 127.28 | 50 | 5.855 |
| C7 | 144.09 | 50 | 6.628 |
| C8 | 82.29 | 50 | 3.785 |
| C9 | 149.61 | 50 | 6.882 |
| C10 | 123.65 | 50 | 5.688 |

Figure 12:
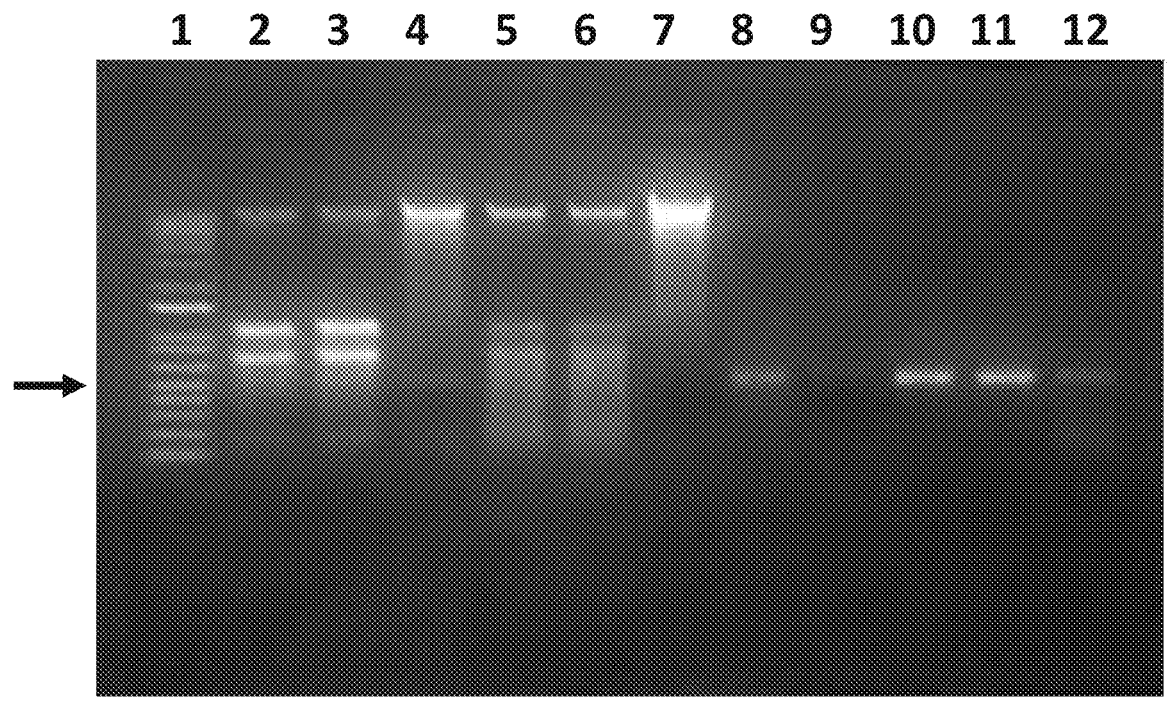
FIG. 12 shows RNA extracts from minicells encapsulating exogenously produced dsRNA. RNA samples were loaded on a 1% agarose gel in TAE running buffer. Lane 1: 1 kb plus ladder from Invitrogen (Arrow signifies 500 bp mark). Lane 2: E9 total RNA extract. Lane 3: E10 total RNA extract. Lane 4: total RNA extracts from samples E1-E8, which were combined and RNase T1 treated to remove any single stranded RNA. Lane 5: C9 total RNA extract. Lane 6: C10 total RNA extract. Lane 7: total RNA extracts from samples C1-C8, which were combined and RNase T1 treated to remove any single stranded RNA. Lane 8: $CaCl_2$ process controls in order to determine dsRNA losses through the procedure (1582 ng of 500 bp dsRNA undigested after IVT generation was loaded into 200 ul of the cold $CaCl_2$ for the duration of the experiment). Lane 9; A duplicate of lane 8. Lane 10: TE buffer controls in order to determine dsRNA losses through the procedure (1582 ng of 500 bp dsRNA undigested after generation of in vitro Transcription (IVT) product was loaded into 200 ul of the cold PBS for the duration of the experiment). Lane 11: A duplicate of lane 10. Lane 12: a control digest of the dsRNA in order to determine composition of dsRNA to ssRNA that was loaded for encapsulation (3 ug of the IVT product was digested to remove all DNA and single stranded RNA and to determine relative amounts of dsRNA within the IVT production after a T1 digestion)

In FIG. 12, E9 and E10 (lanes 2 and 3) were set aside along with C9 and C10 (Lanes 5 and 6) in order to demonstrate undigested total RNA extract after being loaded on the gel for imaging purposes.

The vast majority of RNA present in the cell is ssRNA. The RNase T1 was treated to the total RNA extracts in order to remove this vast majority of extracted ssRNA so that only the encapsulated dsRNA remained. These quantifications were used in order to calculate how much T1 enzyme with which to digest. The T1 enzyme concentration used for this experiment was 186,309.88 U/mL. 1000 U/ug for 15 minutes at 37° C. was the standard protocol, but, in order to conserve enzyme, 500 U/ug for 30 minutes was used. Samples E1-E8 (Lane 4) and C1-C8 (Lane 7) were digested with RNase T1, while the other samples (E9, E10, C9, and C10) were kept untreated with RNase to visualize the difference between T1-treated dsRNA samples and T1-untreated total RNA samples on the gel. After the digest, E1-E8 was cleaned up and combined in order to ensure that any band corresponding to the dsRNA would be able to be visualized given our limit of detection for dsRNA using the gel (~20 ng/band). C1-C8 were treated the same way. The cleanup was done according to the BioBasic Kit manufacturer's protocol. Each of the 8 aliquots of the T1 digested total RNA extracts from both the control cells and the experimental cells were diluted with 450 uL of RLT buffer. The experimental digested extracts were combined (lane 4), and the control extracts were combined (lane 7). The resulting solution was diluted with 1800 uL of 100% EtOH (v/v). The two solutions were passed through their respective control and experimental RNA spin columns. The columns were washed and eluted in 30 uL RNase free water. This resulted in a concentration of 70.2 ng/uL for the experimental and 101.5 ng/uL for the control. These numbers are heavily influenced by the presence of the genome as a result of not digesting it away. The T1-treated and purified experimental RNA sample was loaded into lane 4 and the T1-treated and purified control RNA sample was loaded into lane 7. As shown in FIG. 12, the band located at 500 bp was obviously detected in lane 4, indicating the presence of dsRNA. The dsRNA of the experimental samples E1-E8 (lane 4) was extracted using the ZymoResearch RNA Gel Extraction kit according to the manufacturer's protocol. As expected, no band was present in the negative control aliquots treated the same way (lane 7). The band from lane 4 was eluted in 8 uL of RNase free water. After quantification via nanodrop, the concentration was 7.2 ng/uL.

In order to arrive at the 172.8 ng of dsRNA loaded into the experimental minicells, the 7.2 ng/uL was multiplied by 8 given the assumption that the entire gel extraction elution fraction was homogenous in dsRNA. This results in 57.6 ng of dsRNA in 8 ul volume resulting from the extraction of that band from the gel. Only 10 out of the 30 uL of the T1 digested total RNA extract described above was run on the gel due to the volume constraints of the wells on the gel. The 30 uL of the T1 digested total RNA extract was also assumed to be homogenous for dsRNA content thus the 57.6 ng of dsRNA was multiplied by 3 in order to arrive at the 172.8 ng of total dsRNA loaded into the experimental minicells. From the quantification data and adjustment based on elution volume, at least 172.8 ng of dsRNA was loaded and/or encapsulated into the minicells if taken into account the loss of dsRNA during purification.

Example 8. dsRNA Retention with Glutaraldehyde Treatment

In order to demonstrate dsRNA retention over time, the minicells were loaded in the same method as described in Example 7. The step to be added in this example was to treat dsRNA-loaded minicells with glutaraldehyde at a concentration of 0.25% (v/v). After 5 days incubation at 4° C., the minicells were analyzed utilizing the same methods as described in Example 7.

Minicells were generated and made competent similarly described in Example 6. After competency treatment, the OD600 of the cells was 0.932. This created 5,200 uL replicates of the experimental cells. 200 uL of the control cells were also generated at roughly the same OD600. All cell suspensions were loaded with 1,500 ng of 500 bp dsRNA (undigested after IVT generation) on ice for one hour.

After loading, all cells were spun down at 10,000 rcf for 1 minute and washed with 200 uL of 1×PBS. After washing, the cells were spun down at 10,000 rcf for 1 minute before glutaraldehyde treatment (0.25%) overnight at 4° C. This solution remained at 4° C. for 5 days prior to analysis.

The cells were washed three times with 200 uL of PBS prior to Trizol extraction. The cells were resuspended with Trizol and homogenized using a syringe. After homogenization, the solution was spun down at 12,000 rcf for 1 minutes and the supernatant extracted. This was done for five experimental samples and one control. The supernatant was taken and diluted with 600 uL of 100% (v/v) EtOH, and was added to 6 separate Direct-zol RNA MiniPrep spin columns (five for experimental and one for control). The RNA was bound and washed according to the rest of the manufacturer protocol. The on-column DNA digestions were done for this experiment. The total RNA capture was eluted with 100 uL and quantified with 4 uL, leaving 96 uL remaining.

TABLE 14

Total RNA concentration and amount in Experimental and Control Samples

| Sample Name | [RNA] ng/uL | Elution Volume (uL) | Total RNA Present (ug) |
|---|---|---|---|
| E1 | 21.58 | 100 | 2.071 |
| E2 | 58.94 | 100 | 5.658 |
| E3 | 21.87 | 100 | 2.099 |
| E4 | 6.23 | 100 | 0.598 |
| E5 | 31.34 | 100 | 3.008 |
| Control | 0.988 | 100 | 0.095 |

Figure 13:
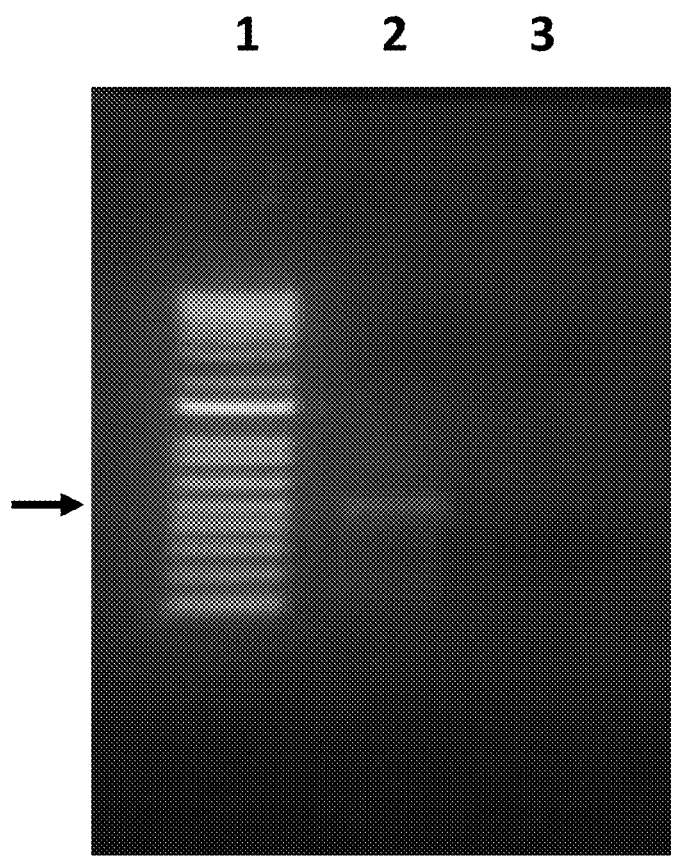
FIG. 13 shows RNA extracts from minicells encapsulating exogenously produced dsRNA after the minicells were treated with 0.25% glutaraldehyde for five days at 4° C. RNA samples were loaded on a 1% agarose gel in TAE running buffer. Lane 1: 1 kb plus ladder from Invitrogen (Arrow signifies 500 bp mark). Lane 2: T1 digested total RNA extract from minicells, resulting in only dsRNA present. Lane 3: T1 digested total RNA extract from control cells, which are HT115 B10 minicells.

The vast majority of RNA present in the cell is ssRNA. The RNase T1 was treated to the total RNA extracts in order to remove this vast majority of extracted ssRNA so that only the encapsulated dsRNA remained. These quantifications were used in order to calculate how much T1 enzyme with which to digest. The T1 enzyme concentration used for this experiment was 199,150.12 U/mL. The total RNA extracts were digested at a T1 concentration of 1000 U/ug for 15 minutes at 37° C. Samples E1-E5 (Lane 2) and Control (Lane 3) were digested with RNase T1. After the digest, E1-E5 were cleaned up and combined in order to ensure that any band corresponding to the dsRNA would be able to be visualized given our limit of detection for dsRNA using the gel (~20 ng/band). The control was treated in the same way. The cleanup was done according to the BioBasic Kit manufacturer's protocol. Each of the 5 aliquots of the T1 digested total RNA extracts from the experimental cells were diluted with ~900 uL of RLT buffer along with the control extract. The experimental digested extracts were combined. The resulting experimental solution was diluted with ~2500 uL of 100% EtOH (v/v) while the control solution was diluted with 500 uL of 100% EtOH (v/v) in accordance with the kit manufacturer's protocol. The two solutions were passed through their respective control and experimental RNA spin columns prior to washing and elution with 20 uL of RNase free water. After elution, 10 uL was run on the gel. The result is illustrated in FIG. 13. No signal was detected in the control in lane 3 as expected because most of the total RNA extracts were ssRNA that were removed by RNase T1 treatment. RNAs loaded into lane 3 were extracted from control cells, which were the HT115 B10 minicells. The 500 bp band of interest, indicating the presence of dsRNA, was extracted from the gel using the ZymoResearch RNA Gel Extraction kit according to the manufacturer's protocol. No band was present in the control aliquot treated in the same way (lane 3) as a control. The band shown in lane 2 was eluted in 8 uL of RNase free water. After quantification via nanodrop, the concentration was 6.23 ng/uL.

In order to arrive at least 99.68 ng of dsRNA loaded into the experimental minicells, the 6.23 ng/uL was multiplied by 8 given the assumption that the entire gel extraction elution fraction was homogenous in dsRNA. This results in 49.84 ng of dsRNA in 8 ul volume resulting from the extraction of that band from the gel. Only 10 out of the 20 uL of the T1 digested total RNA extract described above was run on the gel due to the volume constraints of the wells on the gel. The 20 uL of the T1 digested total RNA extract was also assumed to be homogenous for dsRNA content thus the 49.84 ng of dsRNA was multiplied by 2 in order to arrive at the 99.68 ng of total dsRNA loaded into the experimental minicells after 5 days of incubation at 4° C.

From the quantification data and adjustment based on elution volume, at least 99.68 ng of dsRNA were kept encapsulated in the minicells after 5 days of incubation/encapsulation.

Example 9. dsRNA Protection from RNaseA Treatment

Figure 14:
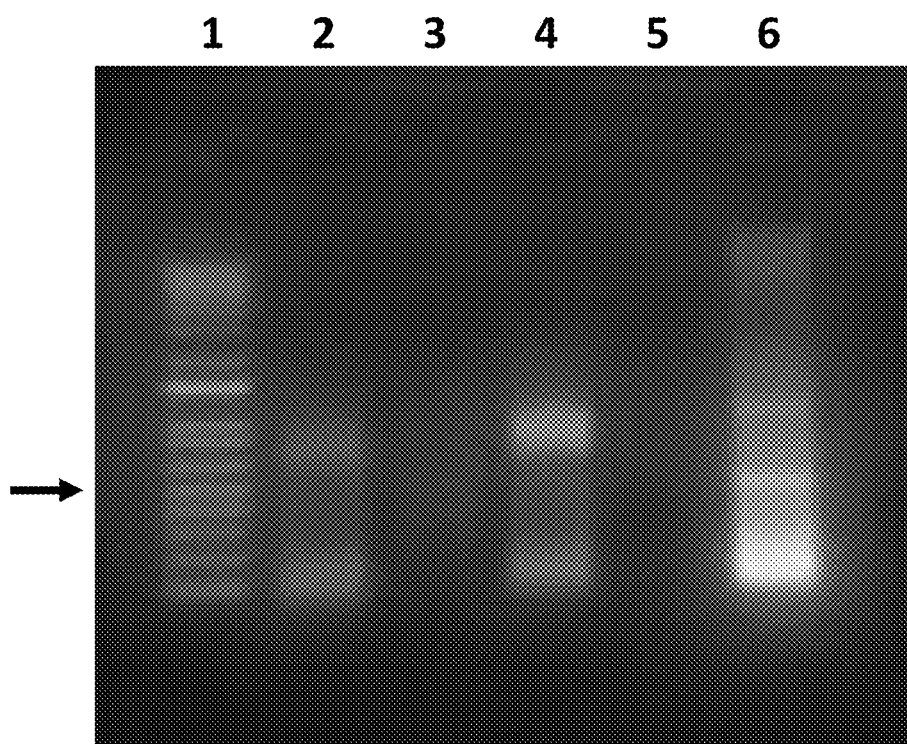
FIG. 14 shows RNA extracts from minicells encapsulating exogenously produced dsRNA after the minicells were treated with RNaseA (50 ug/ml) for 30 minutes at room temperature. RNA samples were loaded on a 1% agarose gel in TAE running buffer. Lane 1: 1 kb plus ladder from Invitrogen (Arrow signifies 500 bp mark). Lane 2: total RNA extract from minicells treated with $CaCl_2$ and loaded with 80 ug of IVT product, but not exposed to RNaseA. Lane 3: total RNA extract from minicells treated with PBS, and loaded with 80 ug of IVT product with being exposed to RNaseA (50 ug/ml). Lane 4: total RNA extract from minicells treated with $CaCl_2$ and loaded with 80 ug of IVT product with being exposed to RNaseA. Lane 5: 80 ug of IVT product exposed to RNaseA (50 ug/ml). Lane 6: internally produced dsRNA from the same number of cells (parents and minicells) exposed to RNaseA.
Figure 15A:
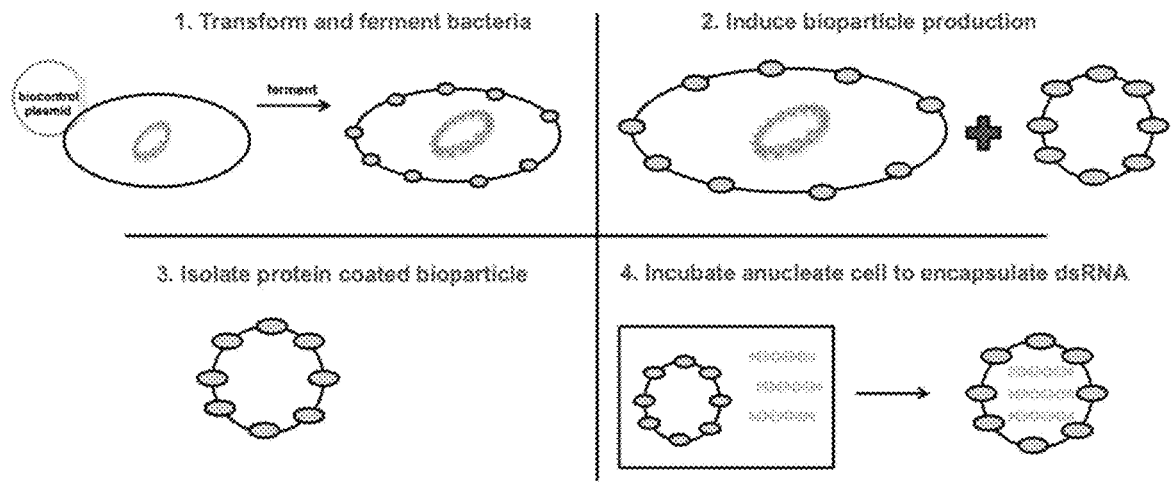
FIG. 15A and FIG. 15B illustrates a process of creation of an anucleated cell-based platform for encapsulation and delivery of biologically active compounds such as dsRNA, siRNA or shRNA.
Figure 15B:
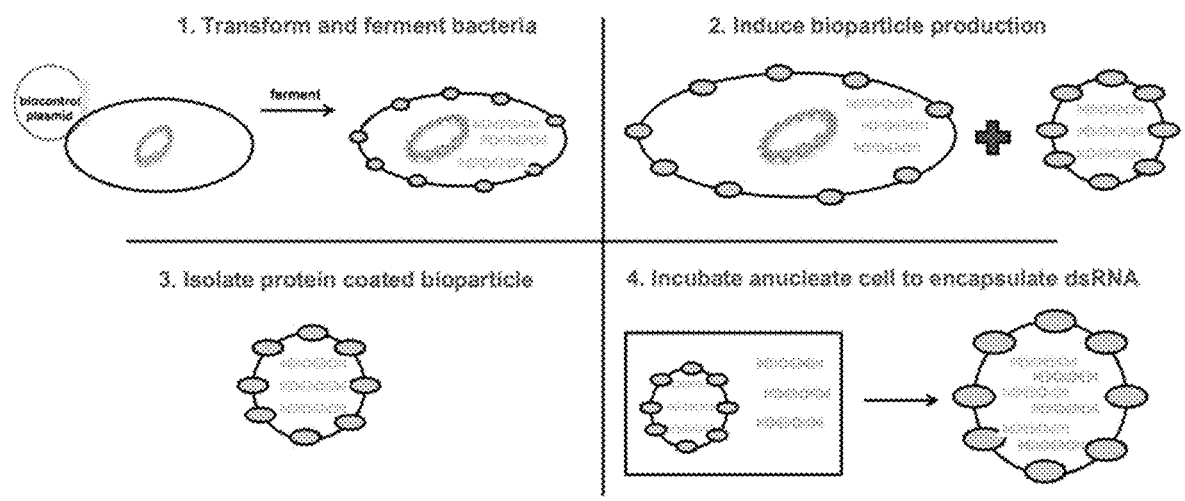

In order to demonstrate dsRNA encapsulation and retention, the minicells were loaded with IVT product as described in Examples 7 and 8. Unlike the above described examples, total 80 ug of dsRNA (IVT product) was added to either the PBS solution or the $CaCl_2$ solution instead of using 40 ug of dsRNA. After loading, incubating, and washing of dsRNA, the minicells were incubated with RNaseA at a concentration of 50 ug/mL for 30 minutes at room temperature. RNaseA activity was stopped via minicell pelleting in combination with resuspension in the Trizol reagent. The RNA extraction, confirmation of dsRNA on a 1% agarose gel, and quantification of the loaded dsRNA were performed as described in Examples 7 and 8. As shown in FIG. 14, Lane 2 displays total RNA extract from minicells treated with $CaCl_2$ and loaded with 80 ug of IVT product, but not exposed to RNaseA. Lane 3 displays total RNA extract from minicells treated with PBS, and loaded with 80 ug of IVT product with being exposed to RNaseA (50 ug/ml). Lane 4 displays total RNA extract from minicells treated with $CaCl_2$ and loaded with 80 ug of IVT product with being exposed to RNaseA. Lane 5 displays 80 ug of IVT product exposed to RNaseA (50 ug/ml). Lane 6 displays internally produced dsRNA from the same number of cells (parents and minicells) exposed to RNaseA. The quantification data adjusted for elution volumes resulted in 210 ng from the band in lane 4 and 631 ng from the band in lane 6.

The faintly visible band was extracted using the ZymoResearch RNA Gel Extraction kit according to the manufacturer's protocol. The band of interest in lane 4 was eluted in 14 uL of RNase free water. After quantification via nanodrop, the concentration was 6.26 ng/uL. The band of interest in lane 6 was eluted in 14 uL of RNase free water. After quantification via nanodrop, the concentration was 18.77 ng/uL.

In order to arrive at the 210.44 ng of dsRNA loaded into the experimental minicells in lane 4, the 6.26 ng/uL was multiplied by 14 given the assumption that the entire gel extraction elution fraction was homogenous in dsRNA. This results in 87.64 ng of dsRNA in 14 ul volume resulting from the extraction of that band from the gel. Only 10 out of the 24 uL of the T1 digested total RNA extract described above was run on the gel due to the volume constraints of the wells on the gel. The 24 uL of the T1 digested total RNA extract was also assumed to be homogenous for dsRNA content thus the 87.64 ng was multiplied by 2.4 in order to arrive at the 210.44 ng of total dsRNA loaded into the experimental minicells and incubated with RNase A. In lane 6, the 630.67 ng of dsRNA of the appropriate size was calculated in the same way. 18.77 ng/uL was multiplied by 14 to account for the entire elution fraction resulting in 262.78 ng in 14 ul volume. This was multiplied up to account for the gel volume constraint (multiplied by 2.4) in order to arrive at the 630.67 ng of dsRNA remaining after RNase A incubation. These results indicate that dsRNA encapsulated by minicells are preserved and protected from environments in which RNase is present, and can be delivered to its target in a stable and safe way.

Example 10. DRB4 Expression in Minicells

In order to improve dsRNA encapsulation and retention, 1) a dsRNA binding protein is produced inside of the minicell followed by the loading of the IVT product (DRB4*+externally-produced dsRNA), 2) a dsRNA binding protein is co-expressed together with dsRNA inside of the minicell (DRB4*+internally-produced dsRNA) or 3) a dsRNA binding protein is co-expressed together with dsRNA inside of the minicell followed by the loading of the IVT product (DRB4*+internally-produced dsRNA additionally supplemented with externally-produced dsRNA). The IVT (in vitro transcription) product described in Example 7 is externally-produced dsRNA. This protein can be, but is not limited to, DRB4* protein from *Arabidopsis thaliana*. This DRB4* protein is able to recognize and purify dsRNA from cell lysates as well as to bind non-specifically to dsRNA.

Colonies for both HT115-B10 (control) and HT115-B10_pGEX-6P-2_DRB4_Cal_T7 (experimental) were picked in 5 mL LB and let them grow overnight at 37° C. in order to generate seed cultures. A 150 mL volume of selective 2xYT media was inoculated with 1.5 mL of the seed culture for both the control and experimental cultures. These cultures were let grow until an OD600 (optical density measured at 600 nm) of ~0.4 prior to induction with 1 mM Isopropyl β-D-1-thiogalactopyranoside (IPTG). After addition of the IPTG, the cultures were allowed to induce overnight at 37° C.

Induction was stopped by centrifugation at 10,000 rcf for 10 minutes the following day and the pellets were frozen prior to lysis. The experimental and control cells were homogenized utilizing a syringe and lysed using P Buffer, EDTA negative with the addition of MgCl2 (2 mM) and lysozyme (10 mg/mL). 8 mL of lysis buffer was used for each cell pellet (~1/20th culture volume) and incubated at 37° C. for 1 hour prior to a second freeze thaw cycle. P Buffer was the principle buffer for the GST-purification and contains 0.1 M Tris-HCl (pH 8.0), 500 mM NaCl, and 5 mM EDTA (except for lysis due to the MgCl2 presence). P Buffer was prepared fresh from concentrates of all of its components prior to use. While thawing the lysate, 1.2 mL (1 mL bed volume) of the Glutathione Sepharose 4B GST-tagged Protein Purification Resin (GE Healthcare) was added to the 20 mL Econo-Pac® Chromatography Columns (Bio-Rad) and equilibrated using 10-column volumes of P Buffer, EDTA positive. The lysates (experimental and control) were clarified by centrifugation at 10,000 rcf at 4° C. for 10 minutes prior to being transferred to the columns containing the resin. The clarified lysate was incubated in a tube revolver for 1 hour in order to allow the protein of interest (DRB4*) to bind to the resin.

After the protein had been given sufficient time to bind to the resin, a sample of each lysate was taken for SDS-PAGE analysis. The lysates were allowed to flow through their respective columns (experimental and control) generating their respective flow through fractions saved for SDS-PAGE analysis. The resin was washed with 5 fractions, 5 mL each of P Buffer EDTA positive while monitoring the protein concentration present in each wash fraction via quantification using Nanodrop (1 ABS=1 mg/mL protein). The washing was stopped when the protein concentration of the 5th wash fraction was approaching 0, thus ensuring the resin had been effectively washed of non-specifically bound proteins. Wash fractions 3-5 were saved from both the control and experimental resins for SDS-PAGE analysis. The protein was eluted from the resin in 10, 0.5 mL fractions of elution buffer (50 mM Tris-HCl (pH 8.0) and 50 mM reduced Glutathione) for both the control and experimental resins. Elution buffer was prepared just prior to use. Elution fractions 1 and 2 were analyzed via SDS-PAGE for presence of the protein of interest DRB4* at its approximate expected size of 62 kDa.

All fractions analyzed via SDS-PAGE were prepared in the same fashion. 19.5 uL of sample was added to 7.5 uL of NuPAGE™ LDS Sample Buffer (ThermoFisher Scientific) and 3 uL of 2-Mercaptoethanol. The ladder was prepared by the addition of 10 uL of the PageRuler™ Plus Prestained Protein Ladder, 10 to 250 kDa to 7.5 uL of LDS sample buffer above and 12.5 uL of water. These solutions were incubated at 70° C. for 10 minutes prior to loading to ensure linearization of proteins in solution. After heating, 15 uL of each of the samples including ladder were loaded onto the NuPAGE™ 4-12% Bis-Tris Protein Gels, 1.5 mm, 15-well (ThermoFisher Scientific). The gel was run in MES running buffer for 35 minutes at 200 volts to ensure proper electrophoretic separation.

Figure 19:
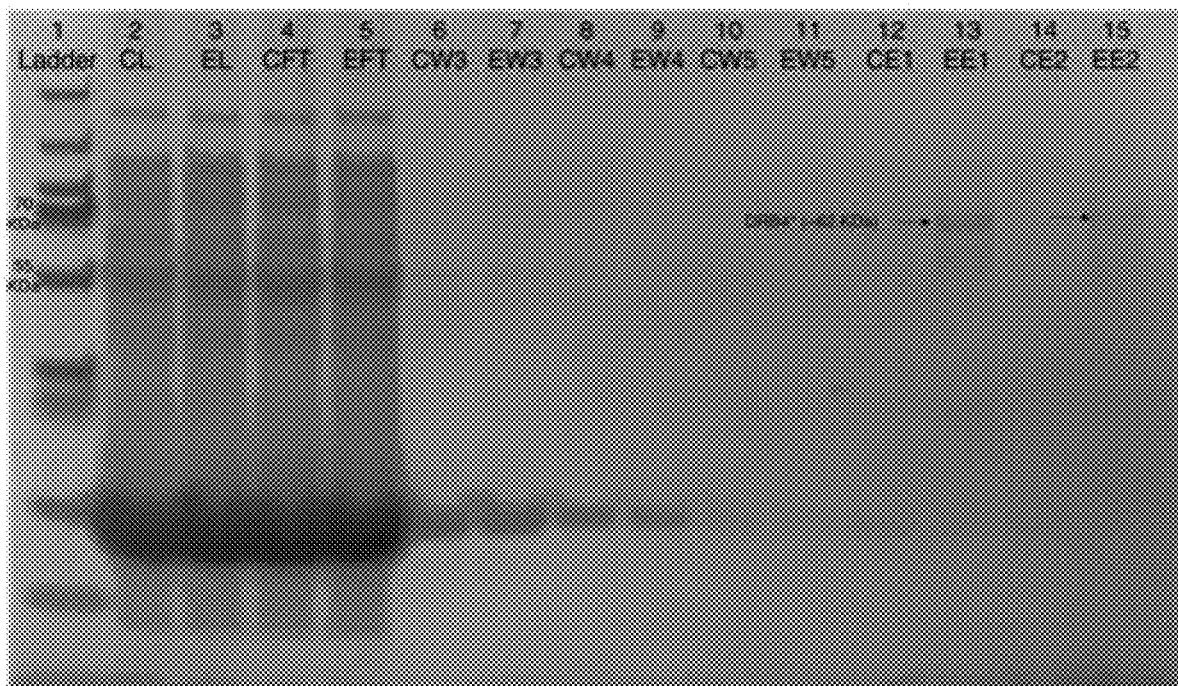
FIG. 19 shows the resulting fractions from the GST-Purification that were run on a 1.5 mm, 4-12% NuPAGE Bis-Tris Gel in order to electrophoretically separate proteins based on size in SDS-MES running buffer. The protein within the gel were visualized using the SimplyBlu™ SafeStain. The GST-Purification was done on clarified cell lysate generated from the HT115-B10 cell line designed to produce the GST-fused DRB4 protein using the pGEX-6P-2_DRB4_Cal_T7 plasmid. All fractions generated by this cell line were designated experimental, while the entire purification procedure was controlled for using the non-plasmid containing cell line HT115-B10 which could not produce any GST-tagged proteins. Lane 1: PageRuler Plus prestained protein ladder, 10 to 250 kDa. Lanes 2 and 3: the clarified lysates from the control and experimental lysates. Lanes 4 and 5: the flow through fractions generated by passing the lysates through the Glutathione Sepharose 4B GST-tagged Protein Purification Resin. Lanes 6-11 (CW3: control wash fraction 3 and E the later wash fractions (starting on wash fraction 3) generated from both the control and experimental lysates demonstrating that the resin was sufficiently washed to removed almost all non-specifically bound proteins prior to elution of the protein of interest (DRB4*). Lanes 12 and 13: the first elution fraction generated from the respective control lysate and experimental lysate. As is evident, a protein is present at the approximate expected size of the protein of interest (DRB4*, ~62 kDa) in the first elution fraction resulting from the experimental lysate, but not in the first control fraction. This same band was seen again in the second experimental elution fraction (lane 15) and again not in the control elution fraction (lane 14). From these results, it was determined that the DRB4* protein had been successfully produced and purified in its entirety. (CL: control lysate, EL: experimental lysate, CFT: control flow through, EFT: experimental flow through, CW3: control wash fraction 3, EW3: experimental wash 3, CW4: control wash 4, EW4: experimental wash 4, CW5: control wash 5, EW5: experimental wash 5, CE1: control elution 1; EE1: experimental elution 1; CE2: control elution 2; EE2: experimental elution 3)

After running, the protein within the gel were visualized using the SimplyBlue™ SafeStain for in gel detection of proteins using the microwave protocol. The gel was washed in ultra-pure water by microwaving the gel/water solution until almost boiling followed by a 2 minute shaking step. This was done 3 times prior to the addition of the stain. The stain was microwaved with the gel until almost boiling, then shaken with gel for 10 minutes. The gel was destained in ultra-pure water (no heating) for 10 minutes prior to a final destaining (5 minutes) in a 20% (w/v) NaCl solution for maximum sensitivity (5 ng/band). This result is illustrated in FIG. 19.

As can be clearly seen, a protein at the approximate expected weight of 62 kDa can be seen in elution fractions 1 and 2 of the experimental cell line (Lanes 13 and 15, respectively), which was expected to produce the GST-fused DRB4* protein. No bands of this size can be detected in the elution fractions from the control cell line which should not have been able to produce any GST-tagged proteins, but all other proteins native to the cell line. This control was designed to account for any non-specifically captured proteins unrelated to the DRB4* protein.

From this result, it was concluded that the full length DRB4* protein had been successfully produced and purified.

Example 11. Enhanced Encapsulation and Retention of Internally-Produced dsRNA and Externally-Produced dsRNA Colonies for HT115-B10 (wild type), HT115-B10_pGEX-6P-2_DRB4_Cal_T7 (DRB4*), and HT115-B10_L4440_CElegans (CElegans) were picked in 5 mL LB and let them grow overnight at 37° C. in order to generate seed cultures. A 450 mL volume of selective 2xYT media was inoculated with 4.5 mL of the seed culture for all cultures. These cultures were let grow until an OD600 (optical density measured at 600 nm) of ~0.4 prior to induction with 1 mM Isopropyl β-D-1-thiogalactopyranoside (IPTG). After addition of the IPTG, the cultures were allowed to induce overnight at 37° C.

The minicells were separated from the parent cells utilizing a 2000 rcf spin down for 10 minutes. The minicells were collected from that supernatant by a subsequent 10000 rcf spin down for 10 minutes. Each 450 mL culture was spun down using 2 bottles. In one of two bottles for each culture, the pellet resulting from the final spin down was resuspended in 3 mL of PBS in order to gauge the OD600 for the CaCl$_2$ suspension in order to make minicells competent. This resulted in the following OD600's.

TABLE 15

OD600 Results of Minicells

| Culture | OD600 1 | OD600 2 | OD600 3 | Average OD600 |
|---|---|---|---|---|
| Wild Type | 0.962 | 0.946 | 0.963 | 0.957 |
| DRB4* | 1.263 | 1.255 | 1.253 | 1.257 |
| CElegans | 1.087 | 1.097 | 1.097 | 1.094 |

Wild Type: Minicells not carrying heterologous recombinant vector(s)
DRB4*: Minicells internally expressing DRB4 protein from HT115-B10_pGEX-6P-2_DRB4_Cal_T7
Celegans: Minicells internally expressing dsRNA that targets C. elegans UBC9 from HT115-B10_L4440_CElegans The minicells were treated with CaCl$_2$ solution to make minicells competent. The CaCl$_2$-treated cells were resuspended in 3 mL of 0.1 M CaCl$_2$ and 15% Glycerol solution while the PBS treated cells were resuspended in 3 mL of PBS.

The OD600 of the cells was measured at this point as the pre-load OD600.

TABLE 16

OD600 Results of Minicells after CaCl2 and PBS treatment

| Culture | PBS OD600 | CaCl2 OD600 |
|---|---|---|
| Wild Type | 0.984 (A) | 1.023 (B) |
| CElegans | 1.277 (C) | 1.054 (D) |
| DRB4* | 1.189 (E) | 1.032 (F) |

Each solution (A-F) had 30 ug of dsRNA (10 ug/mL) loaded into it and was incubated on ice for 1 hour. After incubation, each solution was washed twice utilizing a 10000 rcf centrifugation for 1 minute and resuspension in 3 mL of PBS. After washing, all cells were pelleted and resuspended in 4.8 mL of TRI reagent for lysis and total RNA extraction via the Direct-zol RNA MiniPrep Plus with Zymo-Spin IICG Columns (Zymo Research) kit.

The 4.8 mL suspensions in TRI reagent were homogenized via syringe before the cell debris was spun away at 10000 rcf for 5 minutes. The supernatant was added to 4.8 mL of 100% (v/v) ethanol (EtOH). Each TRI reagent, EtOH solution was passed through 4 columns in order to ensure collection of all RNA present. The DNA collected in the columns was digested away using the kit provided on-column DNase I digest protocol. After the digest, the columns were washed as directed by the manufacturer before elution. Each column was eluted with 125 uL of RNase free water. After elution, the four fractions from each condition were combined and quantified via Nanodrop prior to the digest using the T1 ribonuclease from Aspergillus oryzae. 4 uL was used to quantify. The quantification results and corresponding volume of T1 (500 U/ug RNA) are as follows.

TABLE 17

Quantification results and corresponding volume of T1 (500 U/ug RNA)

| Sample | [RNA] ng/uL | Volume Remaining (uL) | RNA (ng) | Volume T1 (uL) |
|---|---|---|---|---|
| A | 50.5 | 496 | 25045 | 13 |
| B | 117.1 | 496 | 58081 | 29 |
| C | 123.7 | 496 | 61370 | 31 |
| D | 168.1 | 496 | 83383 | 42 |
| E | 50.7 | 496 | 25131 | 13 |
| F | 143.0 | 496 | 70948 | 36 |

Each solution was digested for 30 minutes at 37° C. After digest, each solution was cleaned up utilizing the Direct-zol RNA MiniPrep Plus with Zymo-Spin IIICG Columns (Zymo Research) kit. The volume of TRI reagent used was 3 uL per 1 uL of solution volume. An equal volume of ethanol was added prior to passing each solution through 1 column. The DNase digest was not performed, and the column was washed using the manufacturer's protocol. After washing, each column was eluted in three fractions of 24 uL each of RNase free water. 10 uL from each fraction was run on the gel after being combined with 2×RNA loading dye (New England Biolabs).

Figure 20A:
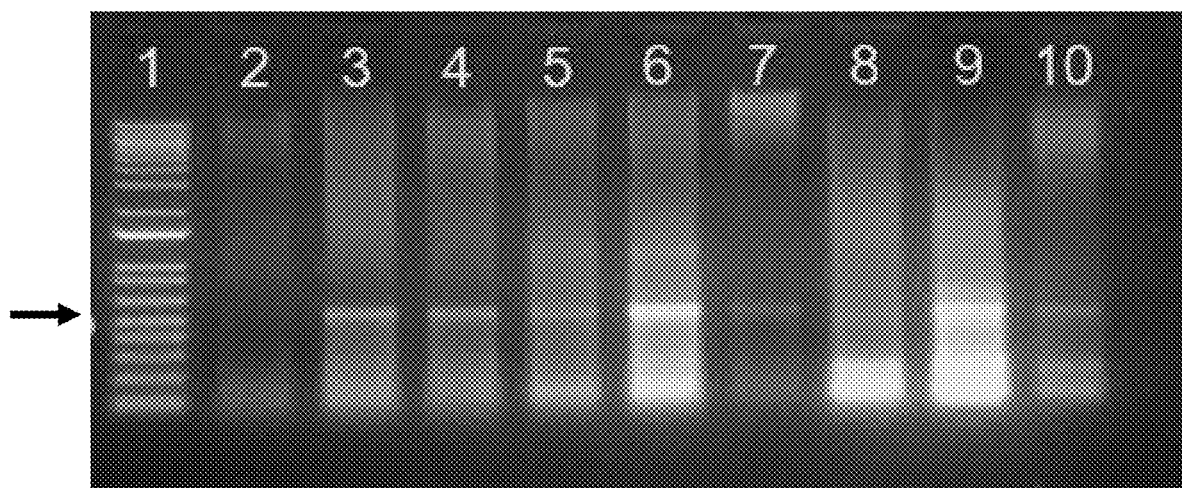
FIG. 20A shows increased dsRNA encapsulation and retention in minicells encapsulating both internally-produced dsRNA internally and exogenously produced dsRNA in the treatment of $CaCl_2$ solution with the presence of DRB4 protein. RNA samples were loaded on a 1% agarose gel in TAE running buffer. Lane 1: 1 kb plus ladder from Invitrogen (Arrow signifies 500 bp mark). Lane 2: total RNA extract from the HT115 wild type minicells incubated with dsRNA in PBS which does not allow the dsRNA to enter the cells due to the lack of electrostatic attraction of the $Ca^{2+}$ cations, but controls for presence of dsRNA due to incomplete washing. Lane 3: total RNA extract from the HT115 wild type minicells incubated with dsRNA in a $CaCl_2$ solution which allows dsRNA to enter the cells. As was evident the band was present at the 500 bp mark according to the ladder demonstrating successful encapsulation. Lane 4: the second elution fraction of the T1 ribonuclease digest for the first RNA elution of Lane 3. Lane 5: total RNA extract from the HT115 minicells containing a plasmid designed to produce 500 bp dsRNA internally incubated in PBS solution having externally-produced dsRNA. This dsRNA was expressed overnight prior to loading. Lane 6: the same condition as lane 5, but incubated with dsRNA in a $CaCl_2$ solution which allowed the dsRNA to enter the cell. As was evident, the $CaCl_2$ solution resulted in a much stronger band present at 500 bp demonstrating that production of the dsRNA and loading with dsRNA results in more encapsulated dsRNA. Lane 7: the second elution fraction of the T1 ribonuclease digest for the first RNA elution of lane 6. Lane 8: total RNA extract from the HT115 minicells containing a plasmid designed to produce the DRB4* protein which binds dsRNA within the cell and does not allow it to leave. The minicells were incubated in PBS solution having externally-produced dsRNA. This protein was expressed overnight prior to loading. The presence of this protein and resulting band present at the 500 bp mark demonstrated that the electrostatic attraction of the dsRNA to the $Ca^{2+}$ cations can be replaced in some capacity with the presence of the protein in order to encapsulate the dsRNA within the minicell. Lane 9: the same condition as lane 8, but the minicells having DRB4 protein were incubated with externally-produced dsRNA in a $CaCl_2$ solution, which resulted in a much stronger band present at the 500 bp mark. Lane 10: the second elution fraction of the T1 ribonuclease digest for the first RNA elution of lane 9.
Figure 20B:
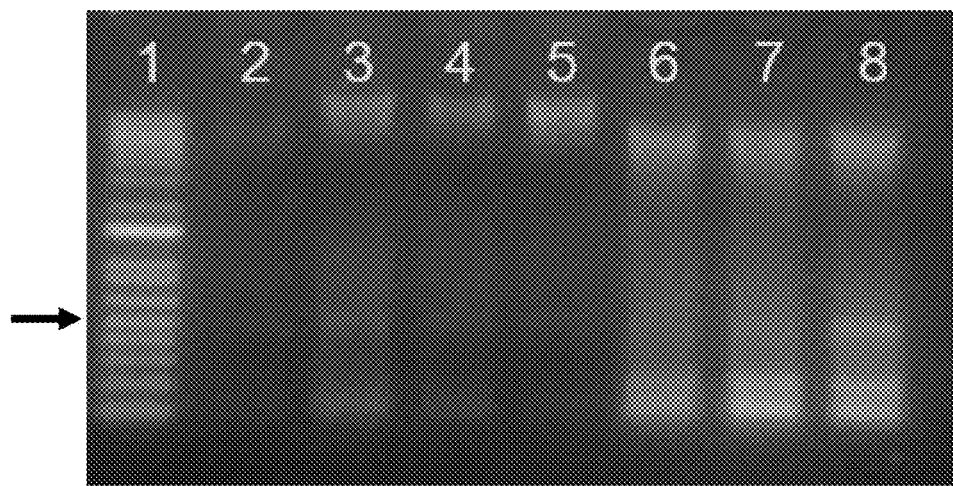
FIG. 20B shows increased dsRNA encapsulation and retention in minicells encapsulating both internally-produced dsRNA internally and exogenously produced dsRNA in the treatment of $CaCl_2$ solution with the presence of DRB4 protein. RNA samples were loaded on a 1% agarose gel in TAE running buffer. Lane 1: 1 kb plus ladder from Invitrogen (Arrow signifies 500 bp mark). Lane 2: the third elution fraction from the same conditions as lanes 3 and 4 of FIG. 20A Lanes 3 and 4: the respective second and third elution fraction from the same conditions as Lane 5 of FIG. 20A. Lane 5: the third elution fraction from the same condition as lanes 6 and 7 of FIG. 20A. Lanes 6 and 7: the respective second and third elution fractions from the same conditions as lane 8 of FIG. 20A. Lane 8: the third elution fraction from the same conditions as lanes 9 and 10 of FIG. 20A.

FIG. 20A and FIG. 20B show increased dsRNA encapsulation and retention in minicells encapsulating both internally-produced dsRNA internally and exogenously produced dsRNA in the treatment of CaCl$_2$ solution with the presence of DRB4 protein.

In FIG. 20A, Lane 2 is RNase T1-digested RNAs that are extracted from sample A (HT115 wild type minicells incubated with externally-produced dsRNA in PBS solution). Lane 3 is RNase T1-digested RNAs that are extracted from sample B (HT115 wild type minicells incubated with externally-produced dsRNA in CaCl$_2$ solution). As was evident in Lane 3, the band was present at the 500 bp mark according to the ladder demonstrating successful encapsulation with in CaCl$_2$ solution. Lane 4 is the second elution of Lane 3.

Lane 5 is RNase T1-digested RNAs that are extracted from sample C (HT115 minicells encapsulating both internally-produced dsRNA and externally-produced dsRNA in PBS solution). Lane 6 is RNase T1-digested RNAs that are extracted from sample D (HT115 minicells encapsulating both internally-produced dsRNA and externally-produced dsRNA in CaCl$_2$ solution). As was evident in Lane 6, the CaCl$_2$ solution resulted in a much stronger band present at 500 bp demonstrating that production of the dsRNA and loading with dsRNA results in more encapsulated dsRNA. Lane 7 is the second elution of Lane 6.

Lane 8 is RNase T1-digested RNAs that are extracted from sample E (HT115 minicells expressing DRB4 protein and encapsulating externally-produced dsRNA in PBS solution). This DRB4 protein was expressed overnight prior to loading of externally-produced dsRNA. The presence of this protein and resulting band present at the 500 bp mark demonstrated that the electrostatic attraction of the dsRNA to the Ca$^{2+}$ cations can be replaced in some capacity with the presence of the DRB4 protein in order to encapsulate the dsRNA within the minicell. Lane 9 is RNase T1-digested RNAs that are extracted from sample F (HT115 minicells expressing DRB4 protein and encapsulating externally-produced dsRNA in CaCl$_2$ solution). Minicells having DRB4 protein were incubated with externally-produced dsRNA in a CaCl$_2$ solution, which resulted in a much stronger band present at the 500 bp mark. Lane 10 is the second elution of Lane 9.

All bands were excised from the gel as described in Figure legend in FIGS. 20A and 20B. The Sample A fractions were not excised due to no bands being present. Other bands were eluted in two fractions of 6 uL each to be sure a complete elution of all captured dsRNA was done. Each elution fraction was quantified using 4 uL via Nanodrop with the following results.

TABLE 18

Eluted RNA Concentration

| Name | Mean (ng/ul) | CV (%) | Name | Mean (ng/ul) | CV (%) |
|---|---|---|---|---|---|
| B1 | 14.478 | 2.367 | B1 Elution 2 | 2.974 | 2.833 |
| B2 | 14.76 | 0.771 | B2 Elution 2 | 3.338 | 2.877 |
| B3 | 3.517 | 11.964 | B3 Elution 2 | 2.055 | 28.246 |
| C1 | 15.779 | 0.902 | C1 Elution 2 | 4.739 | 2.522 |
| C2 | 6.002 | 22.795 | C2 Elution 2 | 1.018 | 97.999 |
| C3 | 6.58 | 30.583 | C3 Elution 2 | 1.384 | 118.154 |
| D1 | 59.831 | 0.92 | D1 Elution 2 | 12.285 | 6.606 |
| D2 | 6.904 | 8.146 | D2 Elution 2 | 1.29 | 0.594 |
| D3 | 1.391 | 16.553 | D3 Elution 2 | 1.932 | 2.704 |
| E1 | 11.127 | 7.989 | E1 Elution 2 | 5.616 | 1.081 |
| E2 | 5.887 | 5.747 | E2 Elution 2 | 2.975 | 8.161 |
| E3 | 6.349 | 0.161 | E3 Elution 2 | 2.254 | 7.945 |
| F1 | 42.593 | 1.688 | F1 Elution 2 | 10.859 | 10.051 |
| F2 | 7.804 | 2.821 | F2 Elution 2 | −2.81 | −442.646 |
| F3 | 11.402 | 4.299 | F3 Elution 2 | 4.839 | 8.161 |

All concentrations under 3 ng/uL were discarded as noise (highlighted) and the remaining elution fractions were multiplied by 6 (6 uL elution volume) and added together if they were from the same band. This created a band total of dsRNA captured. Each of the bands resulting from the T1 digest (1-3) were multiplied by 2.4 to account for the 10 uL running volume limit within the gel. Then all adjusted band totals were added together to arrive at the following result.

TABLE 19

Total dsRNA captured

| | Total RNA Captured (ng) | Cell Line/ Loading Solution |
|---|---|---|
| B | 519.74 | Wild Type/CaCl2 |
| C | 476.64 | CElegans/PBS |
| D | 1137.89 | CElegans/CaCl2 |
| E | 417.30 | DRB4*/PBS |
| F | 1115.96 | DRB4*/CaCl2 |

As can be seen both quantitatively and qualitatively the loading of dsRNA via the CaCl2 treatment resulted in a dramatic improvement of amount encapsulated for all conditions. The inclusion of a dsRNA binding protein (DRB4*) also dramatically improved the amount of encapsulated dsRNA.

Example 12. ACC-Deaminase Expression on Minicell Surface

After construction of expression vector for bacterial surface display fusion protein of ACC-Deamiase using BrkA system was completed, the genetically modified minicell-producing bacterial strain is transformed with a linker protein fused ACC-Deaminase expression plasmid using the same protocols described in Examples 2. Transformation was done using the TransformAid Bacterial Transformation Kit according to their standard protocol into the ribonuclease-deficient cell line, HT115 strain for the Brk surface expression plasmids. The ACC-Deaminase is fused to a linker protein to ensure surface-expression. In order to confirm presence of plasmid, a miniprep was done on a culture from the cell line and the plasmid was submitted for sequencing. All sequencing results came back positive for the surface expression ACC-Deaminase plasmids (GeneJet Plasmid MiniPrep Kit).

The transformed strain was grown overnight in a 5 mL culture with the appropriate antibiotic. The next day, 1:100 inoculation (2.5 mL of overnight culture in 250 mL of 2×YT media) was performed in 2×YT media plus appropriate antibiotic. The 2×YT media provides the surplus of nutrients necessary for efficient protein production. Once the culture reached the exponential growth stage (OD~0.4), it was induced with 1 mM IPTG and is incubated at 30° C. overnight. The culture then was analyzed the next day for ACC-Deaminase production.

Cells were subjected to staining in order to determine the presence of surface-expressed ACC-Deaminase. Slides were developed for permeabilized and non-permeabilized samples for both the ACC-Deaminase-expressing, minicell-producing bacterial strain and the minicell-producing bacterial strain that has not been transformed with a ACC-Deaminase expressing plasmid as a control sample. 250 uL of poly-L-lysine was pipetted on slides for 15 minutes. After washing three times with 500 uL PBS, 500 uL of the correct cell type was pipetted on slides for 15 minutes. After washing three times with 500 uL PBS, 750 uL of 4% paraformaldehyde was pipetted on slides for 15 minutes in order to fix the cell samples to the slides. After washing three times with PBS, 500 uL of 0.1% triton x-100 PBS was added to slides allocated as permeabilized samples for 10 minutes. For non-permeabilized samples, 500 uL of PBS was added to slides during this step to keep samples hydrated on slides. After washing three times with PBS, 100 uL of 2% bovine serum albumin was pipetted on all slides as a blocking agent. After washing three times with PBS, 100 uL of 1 mg/mL THE™ His Tag Antibody [FITC], mAb, Mouse antibody, was pipetted to slides, which binds to the 6×-HIS tag component of the ACC-Deaminase fusion protein. Slides were then incubated with the antibody at room temperature for 1 hour protected from light. After washing 5-10 times with PBS, 3-4 drops of Fluoroshield Mounting Medium with DAPI were applied to coverslips in order to mount coverslips to the slides. Fluorescent microscopy can then be implemented to analyze localization between brightfield cells and fluorescent probes that are indicative of cell presence and surface-expressed protein presence.

The breakdown of 1-aminocyclopropane-1-carboxylate into alpha-ketobutyrate was measured at 540 nm. Minicells surface expressing ACC-Deaminase were incubated in a solution of 1-aminocyclopropane-1-carboxylate with the necessary buffers and then analyzed at 540 nm in the appropriate buffers and compared to the standard curve. Standard curve of alpha-ketobutyrate is made from 0.1 to 1 micromolar.

Figure 24A:
FIG. 24A-D shows His-Tag staining results of ACC-deaminase protein fused with BrK linker protein on the surface of minicells. The minicells were either non-permeabilized (FIGS. 24A and 24C) or permeabilized (FIGS. 24B and 24D). The fusion ACC-deaminase proteins were expressed from the recombinant fusion BrK-ACC deaminase expression vector on the surface of the transformed minicells (FIGS. 24A and 24B), compared to control minicells that did not have the recombinant Brk_ACC deaminase expression vector (FIGS. 24C and 24D).
Figure 24B:
Figure 24C:
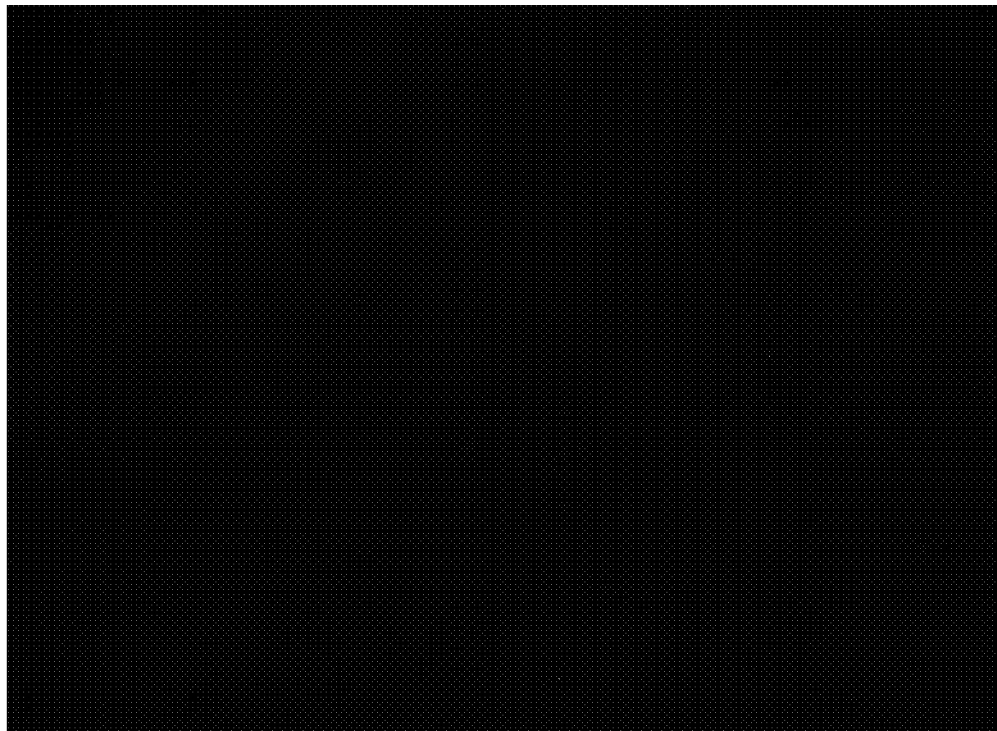
Figure 24D:
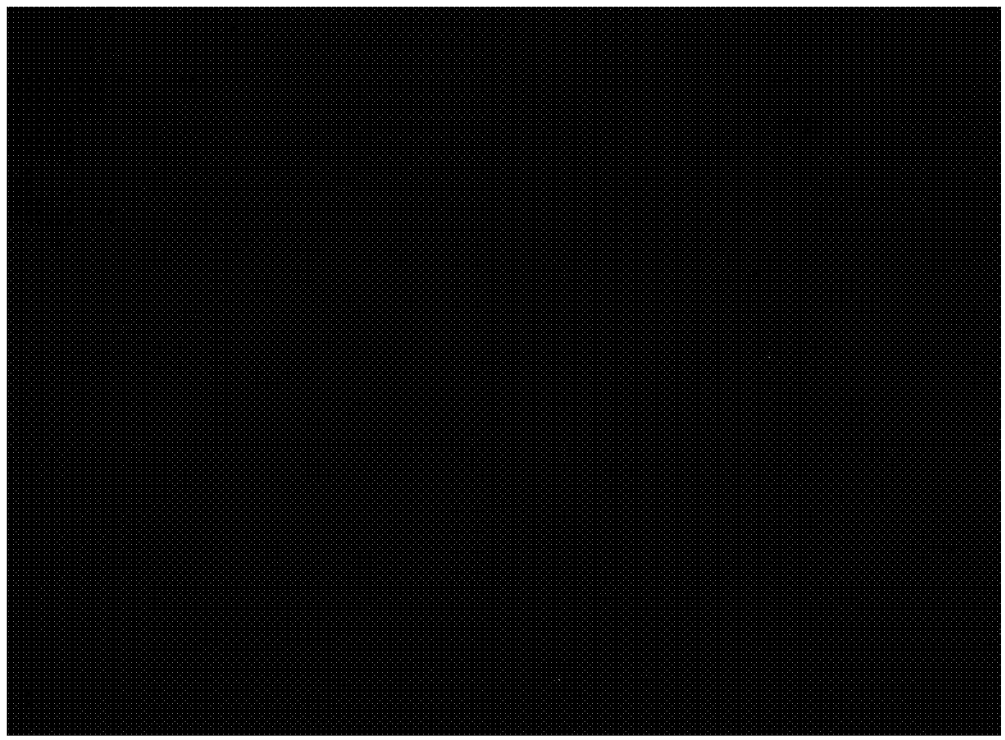
Figure 25A:
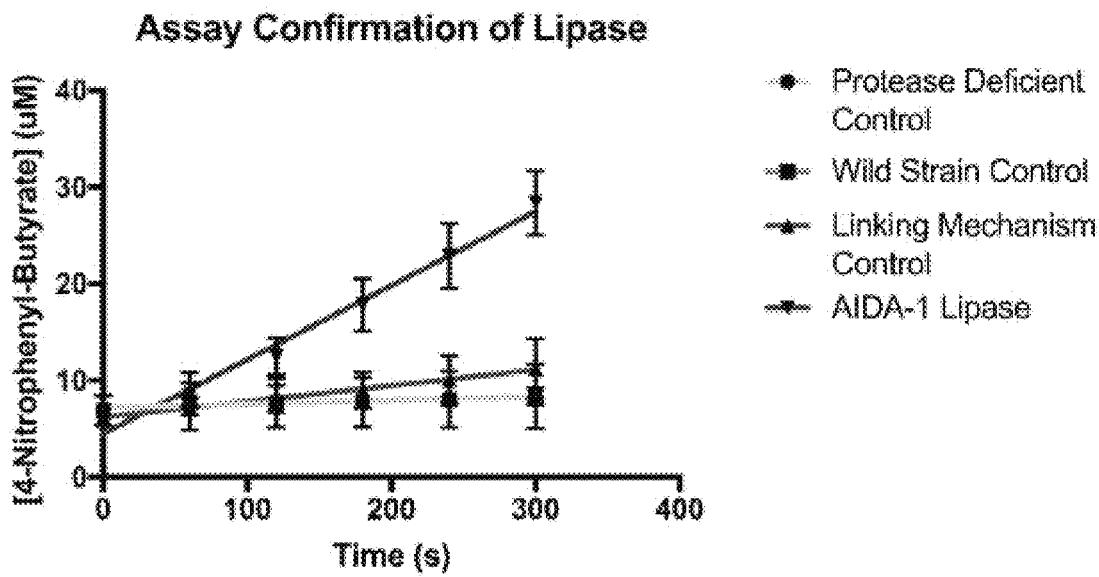
FIG. 25A-C shows lipase activity results of the purified lipase protein fused with three surface expression mechanisms, including AIDA-1, BRK, and InaK, respectively. The lipase was purified from the minicells and tested for its activity using lipase probe 4-nitrophenyl-butyrate.
Figure 25B:
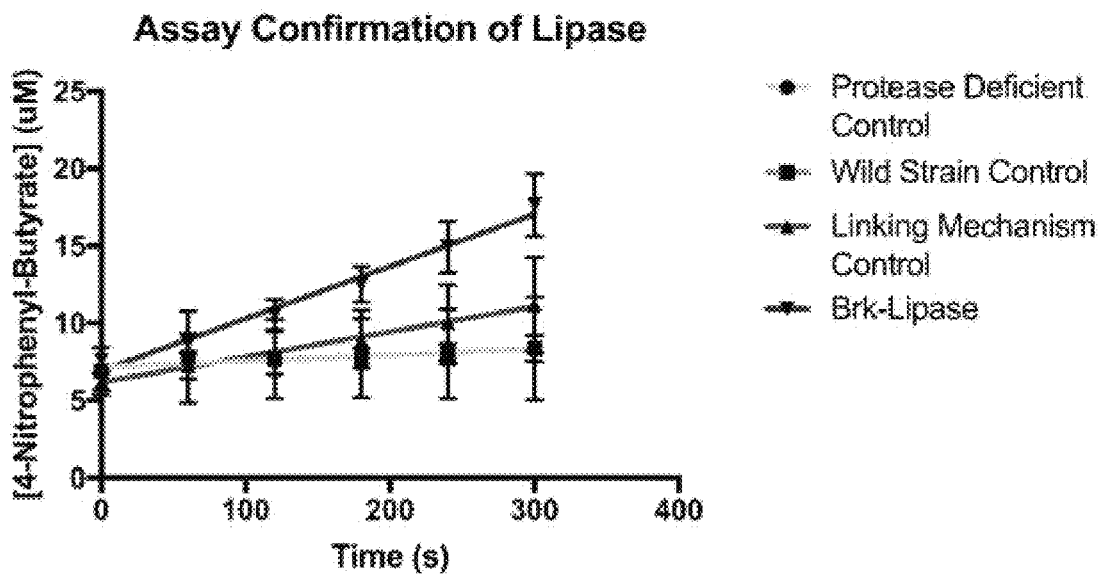
Figure 25C:
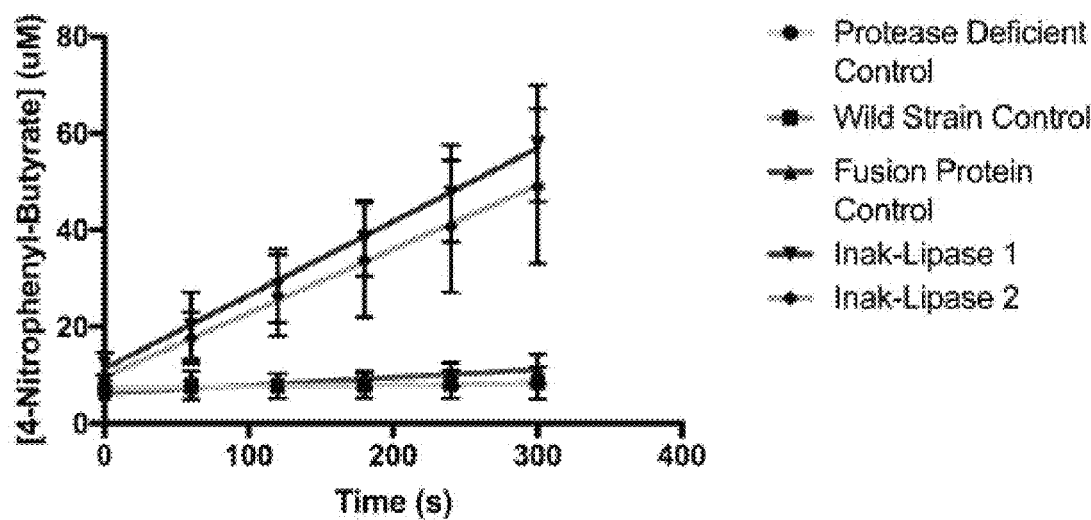

All cells were stained with THE His Tag Antibody [FITC] (Genscript). The experimental minicells were the HT115 B10 minicells which contained the plasmid pGEX-6P-1_BrkACCDeaminase designed to produce a His-tagged ACC deaminase protein which was transported to the surface utilizing the Brk Autotransporter fusion protein. In both permeabilized and nonpermeabilized experimental minicells, the staining with His-tag antibody showed a strong signal in a majority of the population of the cells that expressing Brk-ADD deaminase proteins (FIGS. 24A and 24B). However, the His-tag antibody detected little to no signal from permeabilized and nonpermeabilized experimental minicells (FIGS. 24C and 24D). The control minicells were the HT115 B10 minicells which did not contain a plasmid thus could not be able to produce a His-tagged protein so that the fusion protein cannot be detectable. Therefore, the His tag staining results indicate the expression of the fusion ACC deaminase from the minicells transformed with the recombinant CBM expression plasmid, but not the control cells. Non-permeabilized minicells (FIG. 24A) show the surface expressed ACC deaminase proteins, indicating that ACC deaminase is localized via the BrK linker protein on the surface of the minicells. However, the recombinant ACC deaminase proteins are not all surface expressed from the comparison of non-permeabilized cells with permeabilized cells (FIG. 24B), indicating that recombinant fusion ACC deaminase can be also expressed within the minicells. As was evident, the control cells (FIGS. 24C and 24D) did not produce a signal resulting from the bound his tag antibody while the experimental minicells did produce signals demonstrating expression of the his tagged ACC deaminase. As can also been seen, the nonpermeabilized experimental cells produced a signal from the bound anti-his tag antibody which demonstrated that the Brk Autotransporter successfully localized the ACC Deaminase onto the surface of the minicells.

Example 13. Pheromone Encapsulation within Minicells

In order to test pheromone encapsulation, colonies of minicells are picked in 500 mls of LB media and the culture and let them grow overnight in order to generate seed cultures.

Minicells will be purified from parent cells using a two-step centrifugation purification process. The first centrifugation step at 2000 gs removes most of the parent cells in the pellet. The supernatant from this first step is then spun down again at 10000 gs. This second pellet of purified minicells is then resuspended in PBS (pH 7.4) to reach an OD600 of ~2.0.

3-5 mls of the cell solution is aliquoted out into 50 ml tubes. Equal volume of the pheromone solution is introduced to the cell solution for the experimental sample. The pheromone solution is an aqueous solution that contains 25% Ethanol and 25% PEG600 (v/v %). After mixing the cell solution and the pheromone solution, the effective concentration of cells in solution becomes $8\times10^8$ cells/ml (OD600: ~1) and the effective concentration of PEG600 and Ethanol both become 12.5% (v/v %). For the control sample, the cell solution is mixed with equal volume of PBS with 25% PEG600 and 25% Ethanol (v/v %) to reach the same effective concentration for the solvents as the experimental samples.

The cell and pheromone solution is then allowed to incubate for 2 hours (rpm 180, 37 degrees Celsius). Then, 1 ml samples of the solution are removed from incubation and spun down (15000 g, 10 minutes) to prepare them for analysis. If cells are to be treated with a fixative (e.g. glutaraldehyde), 1 ml samples of the solution are removed from incubation and treated with glutaraldehyde at an effective concentration of 1%. Glutaraldehyde treatment is allowed to proceed overnight at room temperature; then the cell and pheromone solution is spun down to prepare them for analysis.

Cells are analyzed by removing the pheromone solution supernatant and resuspending the pellets in PBS to wash away any residual free pheromone that was not encapsulated. Then, cells are spun down again (15000 g, 10 minutes) and the pellet is resuspended in 850 uls of lysis solution from the GeneJET plasmid miniprep kit.

The lysed solution is then spun down (15000 g, 10 minutes) and the supernatant is analyzed for absorbance at a wavelength that is specific to the pheromone compound using a spectrophotometer. The signal from the control sample (cells incubated with no pheromone but washed and lysed) is subtracted as background from the signal of the experimental sample. This ensures that the analysis accurately represents the concentration of pheromone in solution. Gas chromatography is another method used to analyze pheromone encapsulation.

The pheromone encapsulated minicell will have a significant mass to mass of the pheromone, meaning the mass of the encapsulated pheromone divided by the mass of the encapsulated pheromone and mass of minicell will be at least 1%. High loading (+10%) of the pheromone is expected once the formulation and encapsulation processes are optimized. This encapsulated pheromone product will have tuneable release kinetics from days to many months. Slow release kinetics will be useful for row crops since pheromones are expensive. Faster release kinetics will work for specialty crops.

Example 14. Invasive Delivery of Minicell to Plants

In order to test invasive delivery of minicells encapsulating biologically active compound to a plant, colonies of minicells are picked in Pick a colony of minicell producing bacterial strain in 500 mls of LB media and let grow overnight in order to generate seed cultures.

Minicells are purified from parent cells using a 2 step centrifugation purification process. The first centrifugation step at 2000 gs removes most of the parent cells in the pellet; the supernatant from this first step is then spun down again at 10000 gs. This second pellet of purified minicells is then resuspended in PBS (pH 7.4) to reach an OD600 of ~2.0.

3-5 mls of the cell solution is aliquoted out into 50 ml tubes. Equal volume of the active (for example: fluorescein) solution is introduced to the cell solution for the experimental sample.

The cell and fluorescein solution is then allowed to incubate for 2 hours (rpm 180, 37 degrees Celsius). Then, 1 ml samples of the solution are removed from incubation and spun down (15000 g, 10 minutes) to prepare them for analysis. If cells are to be treated with a fixative (e.g. glutaraldehyde), 1 ml samples of the solution are removed from incubation and treated with glutaraldehyde at an effective concentration of 1%. Glutaraldehyde treatment is allowed to proceed overnight at room temperature; then the cell and fluorescein solution is spun down to prepare them for analysis.

Cells are analyzed by removing the fluorescein solution supernatant and resuspending the pellets in PBS to wash away any residual fluorescein that was not encapsulated. Then, cells are spun down again (15000 g, 10 minutes) and the pellet is resuspended in 850 uls of lysis solution from the GeneJET plasmid miniprep kit.

The lysed solution is then spun down (15000 g, 10 minutes) and the supernatant is analyzed for absorbance at a wavelength that is specific to the fluorescein compound using a spectrophotometer. The signal from the control sample (cells incubated with no pheromone but washed and lysed) is subtracted as background from the signal of the experimental sample. This ensures that the analysis accurately represents the concentration of fluorescein in solution.

Once the amount of fluorescein encapsulated has been analyzed, the greenhouse trial can begin. These variables will be tested:
a. CBM expressing minicells in MSO with encapsulated fluorescein
b. Non-CBM expressing Minicells in MSO with encapsulated fluorescein
c. CBM expressing minicells with encapsulated fluorescein
d. Non-CBM expressing minicells with encapsulated fluorescein
e. Free-standing fluorescein
f. Free-standing fluorescein in MSO One liter of each variable is applied to one soybean plant. The solution is allowed to dry prior to analysis. Leaves are collected from each soybean plant.

Collected leaves are washed to eliminate any errors from any surface residues. Then, leaves are crushed and placed in solvent to extract the penetrated material. The solvent is then analyzed via spectrophotometer or mass spectrometer depending on the accuracy required. The sample from within the leaf can also be imaged to see fluorescein.

Example 15. Application of Minicell Platform Encapsulating Biologically Active Compounds As described in Examples described above, minicells can encapsulate biologically active compounds. The minicells encapsulating biologically active compounds can be formulated as a liquid, dry composition, powder, granule, seed coating, drench, in-furrow composition, or foliar spray. The formulated minicells encapsulating active compounds can be applied to a target cell found in a plant, a pest, an insect, a worm, a bug, a pathogen, a parasite, bacteria, fungi, or viruses, but not a mammalian cell. Experiments will be conducted that directly and/or indirectly applies the formulated minicells encapsulating biologically active compounds unto a target cell of interest.

First, minicells encapsulating at least one biologically active compound described herein can be applied to a crop, including, but are not limited to sorghum, canola, tomato, strawberry, barley, soybean, cotton, rice, maize, and wheat. Second, one of insecticides (e.g. spirotetramat). Also, the minicells can bel applied to an aquatic plant, such as algae, floating plants, submerged plants and emergent plants. Also, the minicells can bel applied to a pest, an insect, a worm, a bug, a pathogen, a parasite, bacteria, fungi, viruses or an aquatic animal, such as a fish, a shellfish, and a crustacean.

Example 16. Treatment of Adjuvants for Invasive Delivery of Minicell Platform Encapsulating Biologically Active Compounds The minicells encapsulating active compounds described in the present disclosure can be applied to a target cell with an agent such as a surfactant, an emulsifier, a crop oil concentrate, a penetrant, a salt or combination thereof. The target cell is found in a plant, a pest, an insect, a worm, a bug, a pathogen, a parasite, bacteria, fungi, or viruses, but not a mammalian cell. The minicells will be applied with the agent such as methylated seed oil, N,N-dimethyldecanamide, and/or N-decyl-N-methyl formamide directly and/or indirectly unto a target cell of interest.

Example 17. Protein Purification and Activity

Minicells are ready to undergo protein purification for functional studies. BL21 and BL21-AI strains were used for protease-deficient minicells and analyzed genetically. Also, the HT115 strain can be used for ribonuclease-deficient minicells and analyzed genetically. The cells were incubated with Lysis Buffer for at least six hours at 37° C. They were then frozen at −20° C. They underwent at least one more freeze-thaw cycle prior to purification. Once the lysis process was complete, the cell samples are centrifuged at 10,000 rcf for 10 minutes to pellet the cell debris. The supernatant was then filtered through a Puradisc 25 mm, sterile Whatman 0.45 uM filter prior to the protein purification process.

The supernatant was incubated in a 20 mL Econopac Gravity Flow column with about 2 mL of HisPur™ Cobalt Superflow Agarose that had been equilibrated with 4 mL of Equilibration Buffer for 30 minutes in an end over end rotary mixer. The supernatant was flowed through the column. Then, the resin was washed three times with 4 mL of wash buffer before elution with 4 fractions of 2 mL each of elution buffer. Equal volumes of glycerol was added to elution fractions 1 and 2 and were dialyzed overnight in 50% glycerol (v/v) and 50 mM Sodium Phosphate buffer solution pH 7.2. After dialysis, the elution fractions were checked for presence of the fusion protein using the lipase assay. Presence of the lipase in each elution fraction was elucidated from the lipase assay described below using 50 mM 4-nitrophenyl-butyrate against a variety of control purifications. At first, the protease-deficient B8 and P678-54 cell lines were used for control, as they contained no recombinant lipase expression plasmids. Thus they do not have recombinant proteins, resulting in no lipase activity in the lipase assay. While P678-54 strain is the wild type minicell-producing strain that is commercially available, the B8 minicell strain was produced from the BL21 (DE3) strain, but the T7 RNA Polymerase activity was additionally silenced along with minC/minD/minCD knock-out effect. This B8 strain is the protease-deficient producing minicell strain without the T7 RNA Polymerase, which make it suitable for lipase assay as a negative control. The protease-deficient B8 strain without fusion lipase is used as Protease Deficient Control. Furthermore, the Brk-CBM and Inak-CBM (CBM: cellulose-binding domain) fusion protein was also used as another Linking Mechanism Control displaying the purified active CBM fusion enzyme that cannot act on the substrate given for the lipase assay. As shown in FIG. 25A-25C, AIDA-1 lipase, Brk-lipase and the Inak-lipase produced measurable lipase activity compared to protease-deficient control, wild strain control and linking mechanism control, respectively, thus demonstrating production of recombinant lipases in the BL21(DE3)-derived minicells.

Example 18. Functional Lipase Activity Analysis

In order to further confirm presence of the functional lipase-fusion protein in both the elution fraction from the protein purification and the surface of the cell as described in Example 17, a lipase activity assay was designed using the lipase substrate, 4-nitrophenyl-butyrate. This assay was designed using the Sigma-Aldrich quality control assay for lipoprotein lipases (EC 3.1.1.34), which can also serve as a substrate for the same type of lipase fused to the surface expression carrier proteins, a triacylglycerol lipase, (EC 3.1.1.3) using Type II Lipase from Porcine Pancreas as well described in Enzymatic Assay of Lipoprotein Lipase protocol found in sigma aldrich online webpage. Kinetic analysis of the enzymatic reaction of lipase was conducted using a method of continuous spectrophotometric rate determination at 400 nm using Beer's law ($A=\varepsilon lC$) and the extinction coefficient 0.0148 ($uM^{-1}*cm^{-1}$). The pathlength, 0.625 cm, was calculated from the known volume of the well (200 uL) and the well's surface area (0.32 cm 2).

Figure 26A:
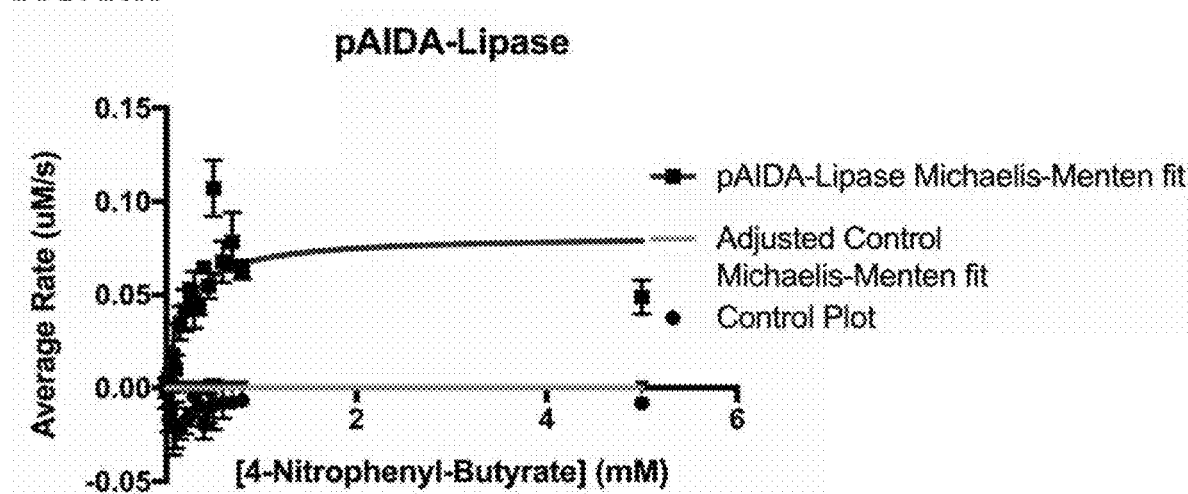
FIG. 26A-C shows lipase activity results of the fusion lipase proteins on the surface of minicells. Kinetic analysis of the reaction was analyzed by continuous spectrophotometric rate determination at 400 nm.
Figure 26B:
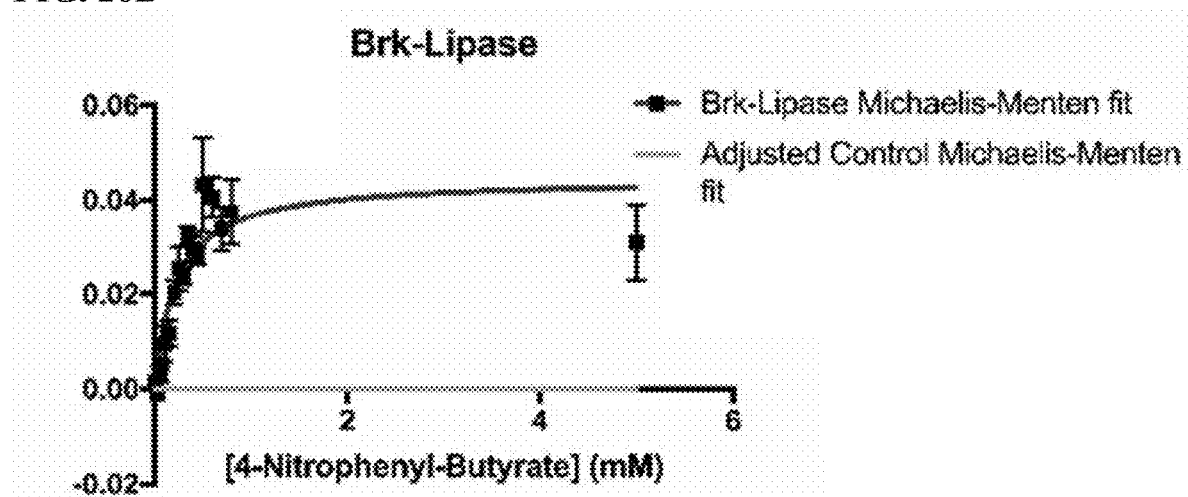
Figure 26C:
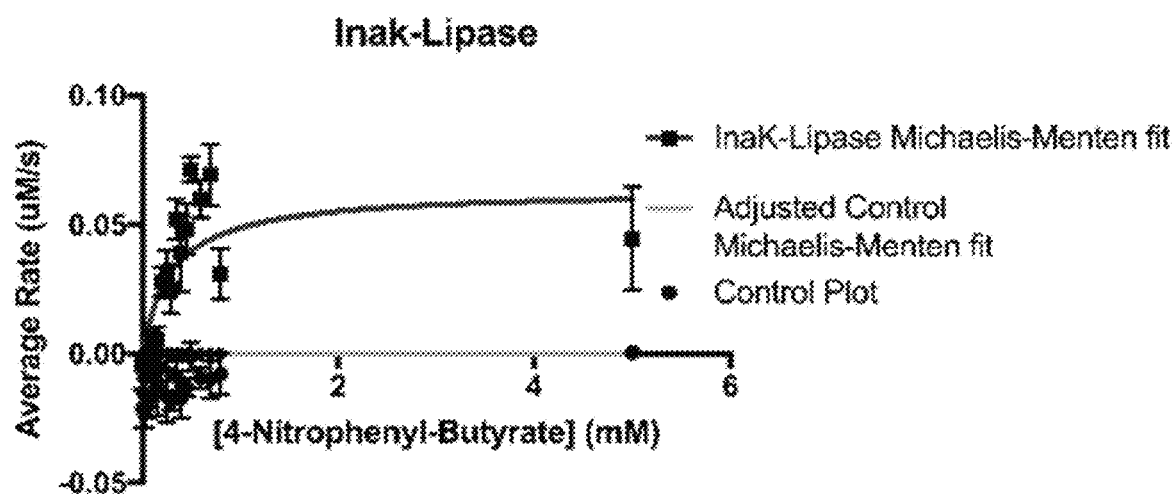

For the enzymatic assay, required are the reaction buffer (100 mM Sodium Phosphate Buffer solution pH 7.2, 0.5% (v/v) Triton-X 100, 150 mM Sodium Chloride), the enzyme/cell solution in 1×PBS, and the substrate solution which is varying concentrations of 4-nitrophenyl-butyrate in acetonitrile. 148 uL of the reaction buffer, 50 uL of the enzyme/cell solution, and 2 uL of the substrate solution were loaded into each well immediate prior to the start of the continuous spectrophotometric rate determination at 37° C. for 5 minutes. Then, rates were calculated by calculating the slope of the line of the concentration increase (Beer's law) versus the time the reaction proceeded in seconds. Activity was determined from a Michaelis-Menten fit of the calculated rates resulting from varying the substrate concentration according to the Table 10. Vmax and Km were calculated using GraphPad Prism Michaelis-Menten fitting parameters. FIG. 26A-C shows that the enzymatic reaction of AIDA-lipase (FIG. 26A and Table 21), Brk-lipase (FIG. 26B and Table 22), and InaK-lipase (FIG. 26C and Table 23) to 4-nitrophenyl-butyrate substrate, respectively.

TABLE 20

Substrate Concentrations for calculating enzymatic reaction rate

| Stock Concentrations (mM) | Concentrations in Well (mM) |
|---|---|
| 0 | 0 |
| 2.5 | 0.025 |
| 5 | 0.05 |
| 7.5 | 0.075 |
| 10 | 0.1 |
| 15 | 0.15 |
| 20 | 0.2 |
| 25 | 0.25 |
| 30 | 0.3 |
| 35 | 0.35 |
| 40 | 0.4 |
| 45 | 0.45 |
| 50 | 0.5 |
| 60 | 0.6 |
| 70 | 0.7 |
| 80 | 0.8 |
| 500 | 5 |

TABLE 21

Enzymatic reaction rate of pAIDA-lipase

| pAIDA-Lipase | Experimental Average Rate (uM/s) |
|---|---|
| Michaelis-Menten Best-fit values | Cells/Well: 99,946,667 |
| Vmax | 0.08174 |
| Km | 0.1803 |
| Std. Error | |
| Vmax | 0.008508 |
| Km | 0.05912 |
| 95% CI (profile likelihood) | |
| Vmax | 0.06857 to 0.09734 |
| Km | 0.104 to 0.2922 |
| Goodness of Fit | |
| Degrees of Freedom | 49 |
| R square | 0.6414 |
| Absolute Sum of Squares | 0.01626 |
| Sy.x | 0.01822 |
| Constraints | |
| Km | Km > 0 |

TABLE 22

Enzymatic reaction rate of Brk-lipase

| Brk-Lipase | Brk-Lipase Average Rate (uM/s) |
|---|---|
| Michaelis-Menten Best-fit values | Cells/Well: 17,706,667 |
| Vmax | 0.04453 |
| Km | 0.2207 |
| Std. Error | |
| Vmax | 0.003487 |
| Km | 0.05025 |
| 95% CI (profile likelihood) | |
| Vmax | 0.03894 to 0.05088 |
| Km | 0.1503 to 0.3134 |
| Goodness of Fit | |
| Degrees of Freedom | 49 |
| R square | 0.7838 |
| Absolute Sum of Squares | 0.002289 |
| Sy.x | 0.006834 |
| Constraints | |
| Km | Km > 0 |

TABLE 23

Enzymatic reaction rate of Inak-lipase

| Inak-Lipase | Experimental Average Rate (uM/s) |
|---|---|
| Michaelis-Menten Best-fit values | Cells/Well: 107,840,000 |
| Vmax | 0.06354 |
| Km | 0.3015 |

TABLE 23-continued

Enzymatic reaction rate of Inak-lipase

| Inak-Lipase | Experimental Average Rate (uM/s) |
|---|---|
| Std. Error | |
| Vmax | 0.009548 |
| Km | 0.1109 |
| 95% CI | |
| (profile likelihood) | |
| Vmax | 0.04894 to 0.08074 |
| Km | 0.1649 to 0.5114 |
| Goodness of Fit | |
| Degrees of Freedom | 49 |
| R square | 0.6375 |
| Absolute Sum of Squares | 0.009709 |
| Sy.x | 0.01539 |
| Constraints | |
| Km | Km > 0 |

Although the foregoing disclosure has been described in some detail by way of illustration and examples, which are for purposes of clarity of understanding, it will be apparent to those skilled in the art that certain changes and modifications may be practiced without departing from the spirit and scope of the disclosure, which is delineated in the appended claims. Therefore, the description should not be construed as limiting the scope of the disclosure.

TABLE 24

Listing of Sequences in Sequence File

| SEQ ID NO | Type | Description |
|---|---|---|
| 1 | DNA | minC 5' recombination site (5' Homologous Arm of minC) |
| 2 | DNA | minC 3' recombination site (3' Homologous Arm of minC) |
| 3 | DNA | minD 5' recombination site (5' Homologous Arm of minD) |
| 4 | DNA | minD 5' recombination site (3' Homologous Arm of minD) |
| 5 | DNA | AIDA-1 surface expression cassette |
| 6 | DNA | BrkAutoTransporter surface expression cassette |
| 7 | DNA | BrkAutoTransporter surface expression cassette fused with CBM-encoding nucleic acid |
| 8 | DNA | CBM (Carbohydrate Binding Module)-encoding nucleic acid |
| 9 | DNA | GFP-Nanobody sequence with CBM-encoding nucleic acid |
| 10 | DNA | InaK surface expression cassette |
| 11 | DNA | InaK surface expression cassette with CBM-encoding nucleic acid |
| 12 | DNA | pAIDA-1 vector |
| 13 | DNA | pAIDA-1 vecotr with CBM-encoding nucleic acid |
| 14 | DNA | pET-9a vector |
| 15 | DNA | pGEX-6P-1 vector without ATG for GST tag |
| 16 | DNA | pGEX-6P-1 vector without ATG for GST tag, containing BrkAutoTransporter surface expression cassette fused with CBM-encoding nucleic acid |
| 17 | DNA | pGEX-6P-1 vector without ATG for GST tag, containing InaK surface expression cassette fused with CBM-encoding nucleic acid |
| 18 | DNA | F2 minCKO primer |
| 19 | DNA | R2 minCKO primer |
| 20 | DNA | F9 minCKO primer |
| 21 | DNA | R9 minCKO primer |
| 22 | DNA | F7 minDKO primer |
| 23 | DNA | R7 minDKO primer |
| 24 | DNA | F10 minDKO primer |
| 25 | DNA | R10 minDKO primer |
| 26 | DNA | F6 minCDKO primer |
| 27 | DNA | R6 minCDKO primer |
| 28 | DNA | F9 minCDKO primer |
| 29 | DNA | R9 minCDKO primer |
| 30 | DNA | 3' minCKO_1 primer |
| 31 | DNA | 3' minCKO_2 primer |
| 32 | DNA | 5' minCKO_1 primer |
| 33 | DNA | 5' minCKO_2 primer |
| 34 | DNA | minC_check_4_1 primer |
| 35 | DNA | minC_check_4_2 primer |
| 36 | DNA | minD_check_2_1 primer |
| 37 | DNA | 3' minCKO_1 primer |
| 38 | DNA | Amplication_dsRNACassette_1 |
| 39 | DNA | Amplication_dsRNACassette_2 |
| 40 | DNA | C. elegans UBC9 target |
| 41 | DNA | Colorado Potato Beetle B-Actin target |
| 42 | DNA | L4440_CElegans vector |
| 43 | DNA | L4440_CPB_B-Actin vector |
| 44 | DNA | BrkAutoTransporter surface expression cassette fused with ACC deaminase-encoding nucleic acid |
| 45 | DNA | pGEX-6P-1 vector without ATG for GST tag, containing BrkAutoTransporter surface expression cassette fused with ACC deaminase-encoding nucleic acid |

Numbered Embodiments of the Disclosure

Notwithstanding the appended claims, the disclosure sets forth the following numbered embodiments:

Agricultural Formulation

1. An agricultural formulation comprising:
   a. an intact minicell comprising at least one biologically active compound within said minicell, wherein said biologically active compound is selected from the group consisting of
      i. a nucleic acid, wherein the nucleic acid targets a transcript encoding a polypeptide within a cell of a target,
      ii. a biocontrol compound, wherein the biocontrol compound is active against a pest, and
      iii. a biostimulant compound, wherein the biostimulant compound stimulates growth or health of a plant, wherein said target is a plant or a pest.
2. The agricultural formulation as in any one of the preceding clauses, wherein said minicell is applied with at least one agricultural suitable additive or adjuvant.
3. The agricultural formulation as in any one of the preceding clauses, wherein said minicell is derived from a prokaryotic cell, a gram-negative bacterial cell, a gram-positive bacterial cell, or an eukaryotic cell.
4. The agricultural formulation as in any one of the preceding clauses, wherein said minicell is derived from endophytes or plant pathogenic bacteria.
5. The agricultural formulation as in any one of the preceding clauses, wherein said minicell is protease deficient or ribonuclease deficient.
6. The agricultural formulation as in any one of the preceding clauses, wherein said minicell is protease deficient.
7. The agricultural formulation as in any one of the preceding clauses, wherein said minicell is ribonuclease deficient.

8. The agricultural formulation as in any one of the preceding clauses, wherein said minicell is protease deficient and ribonuclease deficient.
9. The agricultural formulation as in any one of the preceding clauses, wherein said minicell is protease-deficient, and wherein said biologically active compound is a protein.
10. The agricultural formulation as in any one of the preceding clauses, wherein said minicell is ribonuclease-deficient, and wherein said biologically active compound is a nucleic acid.
11. The agricultural formulation as in any one of the preceding clauses, wherein said biologically active compound is said nucleic acid selected from the group consisting of an antisense nucleic acid, a double-stranded RNA (dsRNA), a short-hairpin RNA (shRNA), a small-interfering RNA (siRNA), a microRNA (miRNA), a ribozyme, an aptamer, and combination thereof.
12. The agricultural formulation as in any one of the preceding clauses, wherein said biologically active compound is inert to a cell other than a cell of said target.
13. The agricultural formulation as in any one of the preceding clauses, wherein said biocontrol compound is a peptide, polypeptide, a fermentation product, a metabolite, an antibody, a semiochemical, or a micronutrient.
14. The agricultural formulation as in any one of the preceding clauses, wherein said biostimulant compound is a peptide, a polypeptide, a fermentation product, a metabolite, an antibody, a semiochemical, or a micronutrient.
15. The agricultural formulation as in any one of the preceding clauses, wherein said target comprises a plant, an insect, a worm, a bacterium, a fungus, a virus and an aquatic animal, wherein said aquatic animal comprises a fish, a shellfish, and a crustacean.
16. The agricultural formulation as in any one of the preceding clauses, further comprising a polypeptide within said minicell, wherein said polypeptide is expressed within said minicell, wherein said polypeptide binds to said nucleic acid.
17. The agricultural formulation as in any one of the preceding clauses, wherein said polypeptide is a dsRNA binding protein, and wherein said dsRNA binding protein increases loading and enhances the stability of dsRNA.
18. The agricultural formulation as in any one of the preceding clauses, wherein said minicell further comprises at least one fusion protein, and wherein said fusion protein is expressed on a surface of said minicell.
19. The agricultural formulation as in any one of the preceding clauses, wherein said fusion protein comprises at least one surface expressing moiety and at least one target cell adhesion moiety, and wherein said target cell adhesion moiety comprises a carbohydrate binding module consisting of cellulose binding domain, xylan binding domain, chitin binding domain, and a lignin binding domain
20. The agricultural formulation as in any one of the preceding clauses, wherein said minicell is treated with a solvent, an agent, a fixative, a preservative, or a cross-linking agent for better solubility, increased stability, or enhanced integrity.
21. The agricultural formulation as in any one of the preceding clauses, wherein said minicell exhibits a controlled release rate of said biologically active compound, wherein the release can be a steady release or an initial burst followed by steady release.
22. A method of delivering at least one biologically active compound, comprising: applying said minicell of any one of the preceding clauses to a target cell.
23. The method of clause 22, wherein said minicell is applied to a target and delivered into a cell of said target by endocytosis.
24. The method of any one of clauses 22-23, further comprising: applying said minicell to said target cell with an agent, wherein said agent is an adjuvant for improving penetration of said minicell into said target cell.
25. The method as in any one of clauses 22-24, wherein said agent is a surfactant, an emulsifier, a crop oil concentrate, a penetrant, a salt or combination thereof.

Method of Delivery

1. A method of delivering at least one biologically active compound, comprising: applying an agriculturally suitable anucleated cell-based platform to a target cell, wherein said agriculturally suitable anucleated cell-based platform comprises:
   a. an intact anucleated cell derived from a bacterial parental cell, comprising said biologically active compound within said cell, wherein said biologically active compound is selected from the group consisting of
      i. a nucleic acid, wherein the nucleic acid targets a transcript encoding a polypeptide within said target cell,
      ii. a biocontrol compound, and
      iii. a biostimulant compound.
2. The method as in any one of the preceding clauses, wherein said biologically active compound is said nucleic acid selected from the group consisting of an antisense nucleic acid, a double-stranded RNA (dsRNA), a short-hairpin RNA (shRNA), a small-interfering RNA (siRNA), a microRNA (miRNA), a ribozyme, an aptamer, and combination thereof.
3. The method as in any one of the preceding clauses, wherein said biocontrol compound is a peptide, a polypeptide, a fermentation product, a metabolite, an antibody, a semiochemical, or a micronutrient.
4. The method as in any one of the preceding clauses, wherein said biostimulant compound is a peptide, a polypeptide, a fermentation product, a metabolite, an antibody, a semiochemical, or a micronutrient.
5. The method as in any one of the preceding clauses, wherein said target cell comprises a plant cell, an insect cell, a worm cell, a bacterial cell, a fungal cell, a virus and a cell of an aquatic animal, wherein said aquatic animal comprises a fish, a shellfish, and a crustacean.
6. The method as in any one of the preceding clauses, wherein said minicell further comprises at least one fusion protein, and wherein said fusion protein is expressed on a surface of said minicell.
7. The method as in any one of the preceding clauses, wherein said fusion protein comprises at least one surface expressing moiety and at least one target cell adhesion moiety, and wherein said target cell adhesion moiety comprises a carbohydrate binding module consisting of a cellulose binding domain, a xylan binding domain, a chitin binding domain, and a lignin binding domain Ribonuclease Deficient Cell Based Platform 1. An industrially suitable anucleated cell-based platform for encapsulation and delivery of at least one biologically active compound, comprising:
   a. an intact anucleated cell derived from a ribonuclease deficient parental cell, comprising at least one biologically active compound within said cell, wherein said biologically active compound is a nucleic acid, wherein the nucleic acid targets a transcript encoding a polypeptide within a target cell, and wherein the target cell is not a mammalian cell.
2. The anucleated cell-based platform as in any one of the preceding clauses, further comprising:
   b. at least one biologically acceptable carrier.
3. The anucleated cell-based platform as in any one of the preceding clauses, wherein said at least one biologically active compound is selected from the group consisting of an antisense nucleic acid, a double-stranded RNA (dsRNA), a short-hairpin RNA (shRNA), a small-interfering RNA (siRNA), a microRNA (miRNA), a ribozyme, an aptamer, and combination thereof.
4. The anucleated cell-based platform as in any one of the preceding clauses, wherein said at least one biologically active compound specifically binds to said transcript and inhibits translation of said transcript.
5. The anucleated cell-based platform as in any one of the preceding clauses, wherein said at least one biologically active compound is inert to a cell other than said target cell.
6. The anucleated cell-based platform as in any one of the preceding clauses, wherein the nucleic acid is an antisense nucleic acid.
7. The anucleated cell-based platform as in any one of the preceding clauses, wherein the nucleic acid is a dsRNA.
8. The anucleated cell-based platform as in any one of the preceding clauses, wherein the nucleic acid is a shRNA.
9. The anucleated cell-based platform as in any one of the preceding clauses, wherein the nucleic acid is a siRNA.
10. The anucleated cell-based platform as in any one of the preceding clauses, wherein the nucleic acid is a miRNA.
11. The anucleated cell-based platform as in any one of the preceding clauses, wherein the nucleic acid is a ribozyme.
12. The anucleated cell-based platform as in any one of the preceding clauses, wherein the nucleic acid is an aptamer.
13. The anucleated cell-based platform as in any one of the preceding clauses, wherein said intact anucleated cell is derived from a prokaryotic cell.
14. The anucleated cell-based platform as in any one of the preceding clauses, wherein said intact anucleated cell is a bacterially derived minicell.
15. The anucleated cell-based platform as in any one of the preceding clauses, wherein said intact anucleated cell is produced from a gram negative bacterial genus.
16. The anucleated cell-based platform as in any one of the preceding clauses, wherein said intact anucleated cell is produced from a bacterial genus selected from the group consisting of: *Escherichia, Salmonella, Shigella, Pseudomonas*, and *Agrobacterium*.
17. The anucleated cell-based platform as in any one of the preceding clauses, wherein said intact anucleated cell is produced from a bacterial species selected from the group consisting of: *Escherichia coli, Salmonella typhimurium, Shigella flexneri*, and *Pseudomonas aeruginosa*.
18. The anucleated cell-based platform as in any one of the preceding clauses, wherein said intact anucleated cell is a bacterially derived minicell that is produced from a parental bacterial cell deficient in ribonuclease.
19. The anucleated cell-based platform as in any one of the preceding clauses, wherein said intact anucleated cell is a bacterially derived minicell that is produced from a ribonuclease deficient *E. coli* parental bacterial cell.
20. The anucleated cell-based platform as in any one of the preceding clauses, wherein said intact anucleated cell is a bacterially derived minicell that is produced from a ribonuclease deficient HT115 *E. coli* parental bacterial cell.
21. The anucleated cell-based platform as in any one of the preceding clauses, wherein said intact anucleated cell is produced from a gram-positive bacterial genus.
22. The anucleated cell-based platform as in any one of the preceding clauses, wherein said intact anucleated cell is produced from a bacterial genus selected from the group consisting of: *Bacillus, Corynebacterium*, and *Lactobacillus*.
23. The anucleated cell-based platform as in any one of the preceding clauses, wherein said intact anucleated cell is produced from a bacterial species selected from the group consisting of: *Bacillus subtilis, Corynebacterium glutamicum*, and *Lactobacillus acidophilus*.
24. The anucleated cell-based platform as in any one of the preceding clauses, wherein said intact anucleated cell is derived from a eukaryotic cell.
25. The anucleated cell-based platform as in any one of the preceding clauses, wherein said target cell comprises a plant cell, an insect cell, a worm cell, a bacterial cell, a fungal cell, a virus and a cell of an aquatic animal, wherein said aquatic animal comprises a fish, a shellfish, and a crustacean.
26. The anucleated cell-based platform as in any one of the preceding clauses, wherein the plant cell is present in a crop, wherein the crop is maize, wheat, soybean or cotton.
27. The anucleated cell-based platform as in any one of the preceding clauses, wherein the plant cell is present in an aquatic plant selected from the group consisting of algae, floating plants, submerged plants, emergent plants, and seaweed.
28. The anucleated cell-based platform as in any one of the preceding clauses, further comprising a polypeptide within said cell, wherein said polypeptide is expressed within said cell, and wherein said polypeptide binds to said at least one biologically active compound within the cell.
29. The anucleated cell-based platform as in any one of the preceding clauses, wherein said at least one biologically active compound is a dsRNA and wherein said polypeptide is a dsRNA binding protein.
30. The anucleated cell-based platform as in any one of the preceding clauses, wherein said dsRNA binding protein increases stability of said dsRNA and protects said dsRNA from degradation.
31. The anucleated cell-based platform as in any one of the preceding clauses, further comprising at least one fusion protein, wherein said fusion protein is expressed on a surface of said intact anucleated cell.

32. The anucleated cell-based platform as in any one of the preceding clauses, wherein said at least one fusion protein comprises at least one surface expressing moiety and at least one target cell adhesion moiety.

33. The anucleated cell-based platform as in any one of the preceding clauses, wherein said at least one fusion protein comprises at least one surface expressing moiety and at least one target cell adhesion moiety, wherein said surface expressing moiety comprises a transmembrane domain and is selected from the group consisting of: an ice nucleation protein (INP), BrkA (*Bordetella* serum-resistance killing protein), and AIDA (Adhesin Involved in Diffuse Adherence).

34. The anucleated cell-based platform as in any one of the preceding clauses, wherein said at least one fusion protein comprises at least one surface expressing moiety and at least one target cell adhesion moiety, wherein said surface expressing moiety comprises an exported bacterial protein and is selected from the group consisting of: LamB (lambda receptor), OprF (*P. aeruginosa* outer membrane protein F), OmpA (outer membrane protein A), Lpp (Lipoprotein), MalE (Maltose binding protein), PhoA (Alkaline phosphatase), Bla (TEM-1 B-lactamase), F1 or M13 major coat (derived from Gene VIII), and F1 or M13 minor coat (Gene III).

35. The anucleated cell-based platform as in any one of the preceding clauses, wherein said at least one fusion protein comprises at least one surface expressing moiety and at least one target cell adhesion moiety, wherein said target cell adhesion moiety comprises a carbohydrate binding module.

36. The anucleated cell-based platform as in any one of the preceding clauses, wherein said at least one fusion protein comprises at least one surface expressing moiety and at least one target cell adhesion moiety, wherein said target cell adhesion moiety comprises a carbohydrate binding module selected from the group consisting of: a cellulose binding domain, a xylan binding domain, a chitin binding domain, and a lignin binding domain.

37. The anucleated cell-based platform as in any one of the preceding clauses, wherein said intact anucleated cell expresses a polypeptide on its surface that increases adhesion to a surface of the target cell.

38. The anucleated cell-based platform as in any one of the preceding clauses, wherein said intact anucleated cell expresses a target adhesion polypeptide on its surface.

39. The anucleated cell-based platform as in any one of the preceding clauses, wherein said intact anucleated cell expresses a carbohydrate binding module that is displayed on its surface.

40. The anucleated cell-based platform as in any one of the preceding clauses, wherein said intact anucleated cell expresses a heterologous carbohydrate binding module that is displayed on its surface.

41. The anucleated cell-based platform of as in any one of the preceding clauses, wherein said intact anucleated cell expresses a cellulose binding domain that is displayed on its surface.

42. The anucleated cell-based platform as in any one of the preceding clauses, wherein said intact anucleated cell expresses a heterologous cellulose binding domain that is displayed on its surface.

43. The anucleated cell-based platform as in any one of the preceding clauses, wherein said intact anucleated cell expresses a chitin binding domain that is displayed on its surface.

44. The anucleated cell-based platform as in any one of the preceding clauses, wherein said intact anucleated cell expresses a heterologous chitin binding domain that is displayed on its surface.

45. The anucleated cell-based platform as in any one of the preceding clauses, wherein the anucleated cell is treated with a solvent.

46. The anucleated cell-based platform as in any one of the preceding clauses, wherein said solvent is $CaCl_2$ solution, ethanol, DMSO, polyethylene glycol, or glycerol.

47. The anucleated cell-based platform as in any one of the preceding clauses, wherein the anucleated cell is treated with an agent, in addition to said solvent.

48. The anucleated cell-based platform as in any one of the preceding clauses, wherein said agent is a fixative, a preservative or a cross-linking agent.

49. The anucleated cell-based platform as in any one of the preceding clauses, wherein said cross-linking agent is glutaraldehyde, formaldehyde, genipin, or epigallocatechin gallat.

50. The anucleated cell-based platform as in any one of the preceding clauses, wherein said solvent increases solubility of said at least one biologically active compound into the anucleated cell.

51. The anucleated cell-based platform as in any one of the preceding clauses, wherein said solvent increases solubility of said at least one biologically active compound into the anucleated cell, and wherein said solvent increases diffusion of said at least one biologically active compound into the anucleated cell.

52. The anucleated cell-based platform as in any one of the preceding clauses, wherein said agent captures said at least one biologically active compound within a membrane of the anucleated cell.

53. The anucleated cell-based platform as in any one of the preceding clauses, wherein said agent captures said at least one biologically active compound within a membrane of the anucleated cell, and wherein said agent cross-links said at least one biologically active compound to the anucleated cell, which improves integrity and stability of the anucleated cell.

54. The anucleated cell-based platform as in any one of the preceding clauses, wherein said agent enhances loading capacity of said at least one biologically active compound into the anucleated cell.

55. The anucleated cell-based platform as in any one of the preceding clauses, wherein said agent enhances loading capacity of said at least one biologically active compound into the anucleated cell, and wherein said agent controls a release rate of said at least one biologically active compound from the anucleated cell.

56. The anucleated cell-based platform as in any one of the preceding clauses, wherein the anucleated cell exhibits a controlled release rate of said at least one biologically active compound.

57. The anucleated cell-based platform as in any one of the preceding clauses, wherein the anucleated cell exhibits a controlled release rate of said at least one biologically active compound, and wherein said at least one biologically active compound is released at a steady rate.

58. The anucleated cell-based platform as in any one of the preceding clauses, wherein the anucleated cell exhibits an initial burst release of said at least one biologically active compound.
59. The anucleated cell-based platform as in any one of the preceding clauses, wherein the anucleated cell exhibits an initial burst release of said at least one biologically active compound, said burst release comprising a release of at least about 40% of said at least one biologically active compound.
60. The anucleated cell-based platform as in any one of the preceding clauses, wherein the anucleated cell exhibits a controlled release rate of said at least one biologically active compound, and wherein the controlled release rate is less than 40%, less than 30%, less than 20%, less than 15%, less than 10%, or less than 5% of said at least one biologically active compound being released from the anucleated cell per day.
61. The anucleated cell-based platform as in any one of the preceding clauses, wherein the controlled release rate is less than 15% of said at least one biologically active compound released from the anucleated cell per day.
62. The anucleated cell-based platform as in any one of the preceding clauses, wherein the controlled release rate is less than 10% of said at least one biologically active compound released from the anucleated cell per day.
63. The anucleated cell-based platform as in any one of the preceding clauses, wherein the controlled release rate is about 5% of said at least one biologically active compound released from the anucleated cell per day.
64. A method of delivering at least one biologically active compound, comprising: applying the anucleated cell of any one of the preceding clauses to a target cell, and wherein the target cell is not a mammalian cell.
65. The method of clause 64, wherein the anucleated cell-based platform applied to said target cell is delivered into said target cell by endocytosis.
66. The method of any one of clauses 64 and 65, further comprising: applying said anucleated cell to said target cell with an agent.
67. The method of any one of clauses 64-66, wherein said agent is an adjuvant for improving penetration of said anucleated cell into the target cell.
68. The method of any one of clauses 64-67, wherein said agent is a surfactant, an emulsifier, a crop oil concentrate, a penetrant, a salt or combination thereof.
69. The method of any one of clauses 64-68, wherein said agent is methylated seed oil.
70. The method of any one of clauses 64-68, wherein said agent is N,N-dimethyldecanamide
71. The method of any one of clauses 64-68, wherein said agent is N-decyl-N-methyl formamide.

Ribonuclease Deficient and/or Protease-Deficient Cell Based Platform

1. An industrially suitable anucleated cell-based platform for encapsulation and delivery of at least one biologically active compound to a target cell, comprising:
   a. an intact anucleated cell derived from a ribonuclease-deficient and/or protease-deficient parental cell, comprising said biologically active compound within said cell, wherein said biologically active compound is a biocontrol or a biostimulant, and wherein the target cell is not a mammalian cell.
2. The anucleated cell-based platform as in any one of the preceding clauses, further comprising:
   b. at least one biologically acceptable carrier.
3. The anucleated cell-based platform as in any one of the preceding clauses, wherein said biocontrol is selected from the group consisting of a nucleic acid, a polypeptide, a semiochemical, a metabolite and a micronutrient.
4. The anucleated cell-based platform as in any one of the preceding clauses, wherein said biostimulant is selected from the group consisting of a nucleic acid, a polypeptide, a semiochemical, a metabolite and a micronutrient.

Platform Derived from Bacterial Cell

1. An industrially suitable anucleated cell-based platform for encapsulation and delivery of at least one biologically active compound to a target cell, comprising:
   a. an intact anucleated bacterial minicell derived from a bacterial parent cell, comprising said biologically active compound within said minicell, wherein said biologically active compound is a biocontrol, and wherein the target cell is not a mammalian cell.
2. The anucleated cell-based platform as in any one of the preceding clauses, further comprising:
   b. at least one biologically acceptable carrier.
3. The anucleated cell-based platform as in any one of the preceding clauses, wherein said biocontrol is a pheromone.
4. The anucleated cell-based platform as in any one of the preceding clauses, wherein said biocontrol is a metabolite.
5. An industrially suitable anucleated cell-based platform for encapsulation and delivery of at least one biologically active compound to a target cell, comprising:
   a. an intact anucleated bacterial minicell derived from a bacterial parent cell, comprising said biologically active compound within said minicell, wherein said biologically active compound is a biostimulant, and wherein the target cell is not a mammalian cell.
6. The anucleated cell-based platform as in any one of the preceding clauses, further comprising:
   b. at least one biologically acceptable carrier.
7. The anucleated cell-based platform as in any one of the preceding clauses, wherein said biostimulant is a pheromone.
8. The anucleated cell-based platform as in any one of the preceding clauses, wherein said biostimulant is a metabolite.

Method of Delivering Biological Active Compounds Using Minicells Derived from Bacterial Cells 1. A method of delivering at least one biologically active compound, comprising: applying an industrially suitable anucleated cell-based platform to a target cell, wherein said industrially suitable anucleated cell-based platform comprises:
   a. an intact anucleated cell derived from a bacterial parental cell, comprising said biologically active compound within said cell, wherein said biologically active compound is a biocontrol or a biostimulant, and wherein the target cell is not a mammalian cell.
2. The method as in any one of the preceding clauses, wherein said anucleated cell further comprises:
   b. at least one biologically acceptable carrier.
3. The method as in any one of the preceding clauses, wherein said biocontrol is selected from the group consisting of a semiochemical, a metabolite and a micronutrient.

4. The method as in any one of the preceding clauses, wherein said biostimulant is selected from the group consisting of a semiochemical, a metabolite and a micronutrient.
5. The method as in any one of the preceding clauses, wherein said metabolite is a fermentation product.
6. The method as in any one of the preceding clauses, wherein said metabolite is a hormone selected from the group consisting of auxin, abscisic acid, cytokinin, ethylene, and gibberellin.
7. The method as in any one of the preceding clauses, wherein said semiochemical comprises a pheromone, an allomone, a kairomone, and a synomone.
8. The method as in any one of the preceding clauses, wherein the pheromone is 2,3-butanediol.
9. The method as in any one of the preceding clauses, wherein the pheromone is (z)-9-hexadecenal, (z)-II-hexadecenal, (z)-13-octadecenal, or combination thereof.
10. The method as in any one of the preceding clauses, wherein said micronutrient is a vitamin
11. The method as in any one of the preceding clauses, wherein said micronutrient is selected from boron (B), chlorine (Cl), copper (Cu), iron (Fe), manganese (Mn), molybdenum (Mo), and Zinc (Zn).
12. The method as in any one of the preceding clauses, wherein said target cell comprises a plant cell, an insect cell, a worm cell, a bacterial cell, a fungal cell, a virus and a cell of an aquatic animal, wherein said aquatic animal comprises a fish, a shellfish, and a crustacean.
13. The method as in any one of the preceding clauses, wherein the plant cell is present in a crop, wherein the crop is maize, wheat, soybean or cotton.
14. The method as in any one of the preceding clauses, wherein the plant cell is present in an aquatic plant selected from the group consisting of algae, floating plants, submerged plants, emergent plants and seaweed.
15. The method as in any one of the preceding clauses, wherein said anucleated cell further comprises at least one fusion protein, wherein said fusion protein is expressed on a surface of said intact anucleated cell.
16. The method as in any one of the preceding clauses, wherein said at least one fusion protein comprises at least one surface expressing moiety and at least one target cell adhesion moiety.
17. The method as in any one of the preceding clauses, wherein said at least one fusion protein comprises at least one surface expressing moiety and at least one target cell adhesion moiety,
wherein said surface expressing moiety comprises a transmembrane domain and is selected from the group consisting of: an ice nucleation protein (INP), BrkA (*Bordetella* serum-resistance killing protein), and AIDA (Adhesin Involved in Diffuse Adherence).
18. The method as in any one of the preceding clauses, wherein said at least one fusion protein comprises at least one surface expressing moiety and at least one target cell adhesion moiety,
wherein said surface expressing moiety comprises an exported bacterial protein and is selected from the group consisting of: LamB (lambda receptor), OprF (*P. aeruginosa* outer membrane protein F), OmpA (outer membrane protein A), Lpp (Lipoprotein), MalE (Maltose binding protein), PhoA (Alkaline phosphatase), Bla (TEM-1 B-lactamase), F1 or M13 major coat (derived from Gene VIII), and F1 or M13 minor coat (Gene III).
19. The method as in any one of the preceding clauses, wherein said at least one fusion protein comprises at least one surface expressing moiety and at least one target cell adhesion moiety,
wherein said target cell adhesion moiety comprises a carbohydrate binding module.
20. The method as in any one of the preceding clauses, wherein said at least one fusion protein comprises at least one surface expressing moiety and at least one target cell adhesion moiety,
wherein said target cell adhesion moiety comprises a carbohydrate binding module selected from the group consisting of: a cellulose binding domain, a xylan binding domain, a chitin binding domain, and a lignin binding domain.
21. The method as in any one of the preceding clauses, wherein said intact anucleated cell expresses a polypeptide on its surface that increases adhesion to a surface of the target cell.
22. The method as in any one of the preceding clauses, wherein said intact anucleated cell expresses a target adhesion polypeptide on its surface.
23. The method as in any one of the preceding clauses, wherein said intact anucleated cell expresses a carbohydrate binding module that is displayed on its surface.
24. The method as in any one of the preceding clauses, wherein said intact anucleated cell expresses a heterologous carbohydrate binding module that is displayed on its surface.
25. The method as in any one of the preceding clauses, wherein said intact anucleated cell expresses a cellulose binding domain that is displayed on its surface.
26. The method as in any one of the preceding clauses, wherein said intact anucleated cell expresses a heterologous cellulose binding domain that is displayed on its surface.
27. The method as in any one of the preceding clauses, wherein said intact anucleated cell expresses a chitin binding domain that is displayed on its surface.
28. The method as in any one of the preceding clauses, wherein said intact anucleated cell expresses a heterologous chitin binding domain that is displayed on its surface.
29. The method as in any one of the preceding clauses, wherein the anucleated cell is treated with a solvent.
30. The method as in any one of the preceding clauses, wherein said solvent is ethanol, DMSO, polyethylene glycol, or glycerol.
31. The method as in any one of the preceding clauses, wherein the anucleated cell is treated with an agent, in addition to said solvent.
32. The method as in any one of the preceding clauses, wherein said agent is a fixative, a preservative or a cross-linking agent.
33. The method as in any one of the preceding clauses, wherein said cross-linking agent is glutaraldehyde, formaldehyde, genipin, or epigallocatechin gallat.
34. The method as in any one of the preceding clauses, wherein said solvent increases solubility of said at least one biologically active compound into the anucleated cell.
35. The method as in any one of the preceding clauses, wherein said solvent increases solubility of said at least one biologically active compound into the anucleated cell, and wherein said solvent increases diffusion of said at least one biologically active compound into the anucleated cell.
36. The method as in any one of the preceding clauses, wherein said agent captures said at least one biologically active compound within a membrane of the anucleated cell.
37. The method as in any one of the preceding clauses, wherein said agent captures said at least one biologically active compound within a membrane of the anucleated cell, and wherein said agent cross-links said at least one biologically active compound to the anucleated cell, which improves integrity and stability of the anucleated cell.
38. The method as in any one of the preceding clauses, wherein said agent enhances loading capacity of said at least one biologically active compound into the anucleated cell.
39. The method as in any one of the preceding clauses, wherein said agent enhances loading capacity of said at least one biologically active compound into the anucleated cell, and wherein said agent controls a release rate of said at least one biologically active compound from the anucleated cell.
40. The method as in any one of the preceding clauses, wherein the anucleated cell exhibits a controlled release rate of said at least one biologically active compound.
41. The method as in any one of the preceding clauses, wherein the anucleated cell exhibits a controlled release rate of said at least one biologically active compound, and wherein said at least one biologically active compound is released at a steady rate.
42. The method as in any one of the preceding clauses, wherein the anucleated cell exhibits an initial burst release of said at least one biologically active compound.
43. The method as in any one of the preceding clauses, wherein the anucleated cell exhibits an initial burst release of said at least one biologically active compound, said burst release comprising a release of at least about 40% of said at least one biologically active compound.
44. The method as in any one of the preceding clauses, wherein the anucleated cell exhibits a controlled release rate of said at least one biologically active compound, and wherein the controlled release rate is less than 40%, less than 30%, less than 20%, less than
15%, less than 10%, or less than 5% of said at least one biologically active compound being released from the anucleated cell per day.
45. The method as in any one of the preceding clauses, wherein the controlled release rate is less than 15% of said at least one biologically active compound released from the anucleated cell per day.
46. The method as in any one of the preceding clauses, wherein the controlled release rate is less than 10% of said at least one biologically active compound released from the anucleated cell per day.
47. The method as in any one of the preceding clauses, wherein the controlled release rate is about 5% of said at least one biologically active compound released from the anucleated cell per day.
48. The method as in any one of the preceding clauses, wherein said at least one fusion protein comprises at least one surface expressing moiety and at least one target cell degradation moiety.
49. The method as in any one of the preceding clauses, wherein said intact anucleated cell expresses a fusion protein, which comprises at least one surface expressing moiety and at least one target cell degradation moiety,
wherein said target cell degradation moiety comprises an cutinase and cellulase.
50. The method as in any one of the preceding clauses, wherein said intact anucleated cell expresses a cutinase on its surface that facilitate said anucleated cell to penetrate through a plant cuticle into the target cell.
51. The method as in any one of the preceding clauses, wherein said intact anucleated cell expresses a heterologous cutinase that is displayed on its surface.
52. The method as in any one of the preceding clauses, wherein said intact anucleated cell expresses a cellulase on its surface that breaks down a target cell wall and facilitate said anucleated cell to penetrate into the target cell.
53. The method as in any one of the preceding clauses, wherein said intact anucleated cell expresses a heterologous cellulase that is displayed on its surface.
54. The method as in any one of the preceding clauses, further comprising: applying with an agent said anucleated cell to said target cell.
55. The method as in any one of the preceding clauses, wherein said agent is an adjuvant for improving penetration of said anucleated cell into the target cell.
56. The method as in any one of the preceding clauses, wherein said agent is a surfactant, an emulsifier, a crop oil concentrate, a penetrant, a salt or combination thereof.
57. The method as in any one of the preceding clauses, wherein said agent is methylated seed oil.
58. The method as in any one of the preceding clauses, wherein said agent is N,N-dimethyldecanamide
59. The method as in any one of the preceding clauses, wherein said agent is N-decyl-N-methylformamide.

Method of Delivering Biological Active Compounds Using Protease Deficient Minicells
1. A method of delivering at least one biologically active compound, comprising: applying an industrially suitable anucleated cell-based platform to a target cell, wherein said industrially suitable anucleated cell-based platform comprises:
   a. an intact anucleated cell derived from a protease deficient parental cell, comprising said biologically active compound within said cell, wherein said biologically active compound is a polypeptide, and wherein the target cell is not a mammalian cell.
2. The method as in any one of the preceding clauses, wherein said anucleated cell further comprises:
   b. at least one biologically acceptable carrier.
3. The method as in any one of the preceding clauses, wherein the polypeptide is an enzyme that is selected from the group consisting of ACC-deaminase, chitinase, cellulase, phytase, chitinase, protease, phosphatase, nucleases, lipases, glucanases, xylanases, amylases, peptidases, peroxidases, ligninases, pectinases, hemicellulases, and keratinases.
4. The method as in any one of the preceding clauses, wherein the ACC-deaminase regulates ethylene levels for plant growth.
5. The method as in any one of the preceding clauses, wherein the polypeptide is a fusion protein.
6. The method as in any one of the preceding clauses, wherein the polypeptide is a protein toxin.

7. The method as in any one of the preceding clauses, wherein the polypeptide is an antibody or antibody derivatives that are exogenous to the parental cell.
8. The method as in any one of the preceding clauses, wherein said target cell comprises a plant cell, an insect cell, a worm cell, a bacterial cell, a fungal cell, a virus and a cell of an aquatic animal, wherein said aquatic animal comprises a fish, a shellfish, and a crustacean.
9. The method as in any one of the preceding clauses, wherein the plant cell is present in a crop.
10. The method as in any one of the preceding clauses, wherein the plant cell is present in an aquatic plant selected from the group consisting of algae, floating plants, submerged plants, emergent plants, and seaweed.
11. The method as in any one of the preceding clauses, wherein said at least one fusion protein comprises at least one surface expressing moiety and at least one target cell stimulation moiety.
12. The method as in any one of the preceding clauses, wherein said at least one fusion protein comprises at least one surface expressing moiety and at least one target cell stimulation moiety,
    wherein said surface expressing moiety comprises a transmembrane domain and is selected from the group consisting of: an ice nucleation protein (INP), BrkA (*Bordetella* serum-resistance killing protein), and AIDA (Adhesin Involved in Diffuse Adherence).
13. The method as in any one of the preceding clauses, wherein said at least one fusion protein comprises at least one surface expressing moiety and at least one target cell stimulation moiety,
    wherein said surface expressing moiety comprises an exported bacterial protein and is selected from the group consisting of: LamB (lambda receptor), OprF (*P. aeruginosa* outer membrane protein F), OmpA (outer membrane protein A), Lpp (Lipoprotein), MalE (Maltose binding protein), PhoA (Alkaline phosphatase), Bla (TEM-1 B-lactamase), F1 or M13 major coat (derived from Gene VIII), and F1 or M13 minor coat (Gene III).
14. The method as in any one of the preceding clauses, wherein said at least one fusion protein comprises at least one surface expressing moiety and at least one target cell stimulation moiety,
    wherein said target cell stimulation moiety comprises a ACC-deaminase.
15. The method as in any one of the preceding clauses, wherein said intact anucleated cell expresses a ACC-deaminase on its surface that modulate plant ethylene levels to promote plant growth and increase resistance of a target plant to biotic and abiotic stresses.
16. The method as in any one of the preceding clauses, wherein said intact anucleated cell expresses a heterologous ACC-deaminase that is displayed on its surface.
17. The method as in any one of the preceding clauses, wherein said anucleated cell further comprises at least one fusion protein, wherein said fusion protein is expressed on a surface of said intact anucleated cell.
18. The method as in any one of the preceding clauses, wherein said at least one fusion protein comprises at least one surface expressing moiety and at least one target cell adhesion moiety.
19. The method as in any one of the preceding clauses, wherein said at least one fusion protein comprises at least one surface expressing moiety and at least one target cell adhesion moiety,
    wherein said surface expressing moiety comprises a transmembrane domain and is selected from the group consisting of: an ice nucleation protein (INP), BrkA (*Bordetella* serum-resistance killing protein), and AIDA (Adhesin Involved in Diffuse Adherence).
20. The method as in any one of the preceding clauses, wherein said at least one fusion protein comprises at least one surface expressing moiety and at least one target cell adhesion moiety,
    wherein said surface expressing moiety comprises an exported bacterial protein and is selected from the group consisting of: LamB (lambda receptor), OprF (*P. aeruginosa* outer membrane protein F), OmpA (outer membrane protein A), Lpp (Lipoprotein), MalE (Maltose binding protein), PhoA (Alkaline phosphatase), Bla (TEM-1 B-lactamase), F1 or M13 major coat (derived from Gene VIII), and F1 or M13 minor coat (Gene III).
21. The method as in any one of the preceding clauses, wherein said at least one fusion protein comprises at least one surface expressing moiety and at least one target cell adhesion moiety,
    wherein said target cell adhesion moiety comprises a carbohydrate binding module.
22. The method as in any one of the preceding clauses, wherein said at least one fusion protein comprises at least one surface expressing moiety and at least one target cell adhesion moiety,
    wherein said target cell adhesion moiety comprises a carbohydrate binding module selected from the group consisting of: a cellulose binding domain, a xylan binding domain, a chitin binding domain, and a lignin binding domain.
23. The method as in any one of the preceding clauses, wherein said intact anucleated cell expresses a polypeptide on its surface that increases adhesion to a surface of the target cell.
24. The method as in any one of the preceding clauses, wherein said intact anucleated cell expresses a target adhesion polypeptide on its surface.
25. The method as in any one of the preceding clauses, wherein said intact anucleated cell expresses a carbohydrate binding module that is displayed on its surface.
26. The method as in any one of the preceding clauses, wherein said intact anucleated cell expresses a heterologous carbohydrate binding module that is displayed on its surface.
27. The method as in any one of the preceding clauses, wherein said intact anucleated cell expresses a cellulose binding domain that is displayed on its surface.
28. The method as in any one of the preceding clauses, wherein said intact anucleated cell expresses a heterologous cellulose binding domain that is displayed on its surface.
29. The method as in any one of the preceding clauses, wherein said at least one fusion protein comprises at least one surface expressing moiety and at least one target cell degradation moiety.
30. The method as in any one of the preceding clauses, wherein said intact anucleated cell expresses a fusion protein, which comprises at least one surface expressing moiety and at least one target cell degradation moiety,
    wherein said target cell degradation moiety comprises an cutinase and cellulase.

31. The method as in any one of the preceding clauses, wherein said intact anucleated cell expresses a cutinase on its surface that facilitate said anucleated cell to penetrate through a plant cuticle into the target cell.
32. The method as in any one of the preceding clauses, wherein said intact anucleated cell expresses a heterologous cutinase that is displayed on its surface.
33. The method as in any one of the preceding clauses, wherein said intact anucleated cell expresses a cellulase on its surface that breaks down a target cell wall and facilitate said anucleated cell to penetrate into the target cell.
34. The method as in any one of the preceding clauses, wherein said intact anucleated cell expresses a heterologous cellulase that is displayed on its surface.
35. The method as in any one of the preceding clauses, wherein said intact anucleated cell expresses a chitin binding domain that is displayed on its surface.
36. The method as in any one of the preceding clauses, wherein said intact anucleated cell expresses a heterologous chitin binding domain that is displayed on its surface.
37. The method as in any one of the preceding clauses, further comprising; applying with a solvent said industrially suitable anucleated cell to said target cell.
38. The method as in any one of the preceding clauses, wherein said solvent is ethanol, DMSO, polyethylene glycol, or glycerol.
39. The method as in any one of the preceding clauses, wherein the anucleated cell is treated with an agent, in addition to said solvent.
40. The method as in any one of the preceding clauses, wherein said agent is a fixative, a preservative or a cross-linking agent.
41. The method as in any one of the preceding clauses, wherein said cross-linking agent is glutaraldehyde, formaldehyde, genipin, or epigallocatechin gallat.
42. The method as in any one of the preceding clauses, wherein said solvent increases solubility of said at least one biologically active compound into the anucleated cell.
43. The method as in any one of the preceding clauses, wherein said solvent increases solubility of said at least one biologically active compound into the anucleated cell, and wherein said solvent increases diffusion of said at least one biologically active compound into the anucleated cell.
44. The method as in any one of the preceding clauses, wherein said agent captures said at least one biologically active compound within a membrane of the anucleated cell.
45. The method as in any one of the preceding clauses, wherein said agent captures said at least one biologically active compound within a membrane of the anucleated cell, and wherein said agent cross-links said at least one biologically active compound to the anucleated cell, which improves stability of the anucleated cell.
46. The method as in any one of the preceding clauses, wherein said agent enhances loading capacity of said at least one biologically active compound into the anucleated cell.
47. The method as in any one of the preceding clauses, wherein said agent enhances loading capacity of said at least one biologically active compound into the anucleated cell, and wherein said agent controls a release rate of said at least one biologically active compound from the anucleated cell.
48. The method as in any one of the preceding clauses, wherein the anucleated cell exhibits a controlled release rate of said at least one biologically active compound.
49. The method as in any one of the preceding clauses, wherein the anucleated cell exhibits a controlled release rate of said at least one biologically active compound, and wherein said at least one biologically active compound is released at a steady rate.
50. The method as in any one of the preceding clauses, wherein the anucleated cell exhibits an initial burst release of said at least one biologically active compound.
51. The method as in any one of the preceding clauses, wherein the anucleated cell exhibits an initial burst release of said at least one biologically active compound, said burst release comprising a release of at least about 40% of said at least one biologically active compound.
52. The method as in any one of the preceding clauses, wherein the anucleated cell exhibits a controlled release rate of said at least one biologically active compound, and wherein the controlled release rate is less than 40%, less than 30%, less than 20%, less than 15%, less than 10%, or less than 5% of said at least one biologically active compound being released from the anucleated cell per day.
53. The method as in any one of the preceding clauses, wherein the controlled release rate is less than 15% of said at least one biologically active compound released from the anucleated cell per day.
54. The method as in any one of the preceding clauses, wherein the controlled release rate is less than 10% of said at least one biologically active compound released from the anucleated cell per day.
55. The method as in any one of the preceding clauses, wherein the controlled release rate is about 5% of said at least one biologically active compound released from the anucleated cell per day.
56. The method as in any one of the preceding clauses, further comprising: applying with an agent said anucleated cell to said target cell.
57. The method as in any one of the preceding clauses, wherein said agent is an adjuvant for improving penetration of said anucleated cell into the target cell.
58. The method as in any one of the preceding clauses, wherein said agent is a surfactant, an emulsifier, a crop oil concentrate, a penetrant, a salt or combination thereof.
59. The method as in any one of the preceding clauses, wherein said agent is methylated seed oil.
60. The method as in any one of the preceding clauses, wherein said agent is N,N-dimethyldecanamide
61. The method as in any one of the preceding clauses, wherein said agent is N-decyl-N-methylformamide.

Platform Derived from Pathogenic Bacterial Cell

1. An industrially suitable anucleated cell-based platform for encapsulation and delivery of at least one biologically active compound to a target cell, comprising:
   a. an intact anucleated bacterial minicell derived a pathogenic bacterial parent cell, comprising said biologically active compound within said minicell, wherein said biologically active compound is a biocontrol or a biostimulant, and wherein the target cell is not a mammalian cell.

2. The anucleated cell-based platform as in any one of the preceding clauses, further comprising:
   b. at least one biologically acceptable carrier.
3. The anucleated cell-based platform as in any one of the preceding clauses, wherein said intact anucleated cell is produced from a pathogenic bacterial genus.
4. The anucleated cell-based platform as in any one of the preceding clauses, wherein said intact anucleated cell is produced from a pathogenic bacterial genus selected from the group consisting of: Pseudomonas, Ralstonia, Agrobacterium, Xanthomonas, Erwinia, Xylella, Dickeya, Pectobacterium, Clavibacter, and Candidatus.
5. The anucleated cell-based platform as in any one of the preceding clauses, wherein said intact anucleated cell is produced from a pathogenic bacterial species selected from the group consisting of: Pseudomonas syringae pathovars, Ralstonia solanacearum, Agrobacterium tumefaciens, Xanthomonas oryzae pv. Oryzae, Xanthomonas campestris, Xanthomonas axonopodis pathovars, Erwinia amylovora, Xylella fastidiosa, Dickeya dadantii, Dickeya solani, Pectobacterium carotovorum, Pectobacterium atrosepticum, Clavibacter michiganensis, Pseudomonas savastanoi, and Candidatus liberibacter asiaticus.

Platform Derived from Endophytes

1. An industrially suitable anucleated cell-based platform for encapsulation and delivery of at least one biologically active compound to a target cell, comprising:
   a. an intact anucleated bacterial minicell derived an endophyte, comprising said biologically active compound within said minicell, wherein said biologically active compound is a biocontrol or a biostimulant, and wherein the target cell is not a mammalian cell.
2. The anucleated cell-based platform as in any one of the preceding clauses, further comprising:
   b. at least one biologically acceptable carrier.
3. The anucleated cell-based platform as in any one of the preceding clauses, wherein said intact anucleated cell is produced from an endophyte genus.
4. The anucleated cell-based platform as in any one of the preceding clauses, wherein said intact anucleated cell is produced from an endophyte genus selected from the group consisting of: Acidovorax, Bradyrhizobium, Rhizobium, Rhodococcus, Colletotrichum, Curvularia, Epichloe, Fusarium, Mycosphaerella, Neotyphodium, Piriformospora, and Serendipita.

Ribonuclease Deficient and Protease Deficient Cell Based Platform

1. A minicell derived from a bacterial parent cell, wherein said bacterial parent cell is protease deficient and ribonuclease deficient.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as an acknowledgment or any form of suggestion that they constitute valid prior art or form part of the common general knowledge in any country in the world.

REFERENCES

AgroSpheres, Inc. Compositions and methods for enzyme immobilization, PCT/US2018/030328

AgroSpheres, Inc. Compositions and methods for the encapsulation and scalable delivery of agrochemicals, PCT/US2018/030329

POURTAHERI P., ZOMORODI S., DAVIS Z. G., SHAKEEL A. M., Frank J., MOSHASHA S. R., KHOKHLACHEV A., Kester M., Compositions and methods for pesticide degradation, WO2017/180650 A1

Sabbadini R., Berkley N., Surber M., Klepper R., Minicell based delivery of biologically active compounds U.S. Pat. No. 9,017,986 B2

Giacalone M. J., Maloy S., Tsuji S., Regulated genetic suicide mechanism compositions and methods, U.S. Pat. No. 9,045,761 B2

Giacalone M. J, Newman M. J., Therapeutic compositions and methods for antibody and fc-containing targeting molecule-based targeted delivery of bioactive molecules by bacterial minicells, US2/012/0207754 A1

Enzyme Immobilization—Advances in Industry, Agriculture, |Alka Dwevedi|Springer. (n.d.). Retrieved from www.springer.com/us/book/9783319414164

Gai, S. A., & Wittrup, K. D. (2007). Yeast surface display for protein engineering and characterization. Current Opinion in Structural Biology, 17(4), 467-473. https://doi.org/10.1016/j.sbi.2007.08.012

Karlsson, S., Holmbom, B., Spetz, P., Mustranta, A., & Buchert, J. (2001). Reactivity of Trametes laccases with fatty and resin acids. Applied Microbiology and Biotechnology, 55(3), 317-320.

Mitra, S. D., Afonina, I., & Kline, K. A. (2016). Right Place, Right Time: Focalization of Membrane Proteins in Gram-Positive Bacteria. Trends in Microbiology, 24(8), 611-621.

Lee, S. H., Lee, S. Y., & Park, B. C. (2005). Cell Surface Display of Lipase in Pseudomonas putida KT2442 Using OprF as an Anchoring Motif and Its Biocatalytic Applications. Applied and Environmental Microbiology, 71(12), 8581-8586.

Routledge, S. J., Mikaliunaite, L., Patel, A., Clare, M., Cartwright, S. P., Bawa, Z., . . . Bill, R. M. (2016). The synthesis of recombinant membrane proteins in yeast for structural studies. Methods, 95, 26-37.

Vinh, D. Khue, N. Study on Minicell Generation of Lactobacillus acidophilus VTCC-B-871 for Drug Delivery. Journal of Applied Pharmaceutical Science. Vol. 3 (05), 33-36.

Wieczorek, A. S., Biot-Pelletier, D., & Martin, V. J. J. (2013). Recombinant Cellulase and Cellulosome Systems.

Patent US20130337545 Minicell Based Delivery of Biologically Active Compounds

Fersht A. Structure and mechanism in protein science: a guide to enzyme catalysis and protein folding. New York: W. H. Freeman & Company; 1998. p. 615.

Powers R. Comparison of protein active site structures for functional annotation of Proteins and drug design. Proteins Struct Funct Bioinf. 2006; 65:124-35.

Nelson J M, Hitchcock D I. The activity of adsorbed invertase. J Am Chem Soc. 1921; 43:1956-61.

Mclaren A D. Concerning the pH dependence of enzyme reactions on cells, particulates and in solution. Science. 1957; 125:697.

Mosbach K, Mosbach R. Entrapment of enzymes and microorganisms in synthetic cross-linked polymers and their application in column techniques. Acta Chem Scand. 1966; 20:2807-10.

Chen L F, Richardson R. Enzyme derivatives containing reactive groups Immobilization of alpha-amylase on human erythrocytes. Pharmacol Res Commun. 1974; 6:273-80.

Kennedy J F, Zamir A. The use of cellulose xanthate for the immobilisation of biological molecules. Carbohydr Res. 1975; 41:227-33.

Cordonnier M, Lawny F, Chapot D, Thomas D. Magnetic enzyme membranes as active elements of electrochemical sensors. Lactose, saccharose, maltose bienzyme electrodes. FEBS Lett. 1975; 59:263-7.

Sin M L, Mach K E, Wong P K, Liao J C. Advances and challenges in biosensor-based diagnosis of infectious diseases. Expert Rev Mol Diagn. 2014; 14:225-44.

Horton H R, Swaisgood H E. Immobilization as a means of investigating the acquisition of tertiary structure in chymotrypsinogen. Methods Enzymol. 1976; 44:516-26.

Das N, Kayastha A M, Malhotra O P Immobilization of urease from pigeonpea (*Cajanus cajan* L.) on polyacrylamide gels and calcium alginate beads. Biotechnol Appl Biochem. 1998; 27:25-9.

Nakarani M, Kayastha A M. Kinetics and diffusion studies in urease-alginate biocatalyst beads. Orient Pharm Exp Med. 2007; 7:79-84.

Alloue W A, Destain J, El Medjoub T, Ghalfi H, Kabran P, Thonart P. Comparison of *Yarrowia lipolytica* lipase immobilization yield of entrapment, adsorption, and covalent bond techniques. Appl Biochem Biotechnol. 2008; 150:51-63.

Hage D S, Walters R R, Hethcote H W. Split-peak affinity chromatographic studies of the immobilization-dependent adsorption kinetics of protein A. Anal Chem. 1986; 58:274-9.

Marquez L D S, Cabral B V, Freitas F F, Cardoso V L, Ribeiro E J. Optimization of invertase immobilization by adsorption in ionic exchange resin for sucrose hydrolysis. J Mol Catal B: Enzym. 2008; 51:86-92.

Das N, Prabhakar P, Kayastha A M, Srivastava R C. Enzyme entrapped inside the reverse micelle in the fabrication of a new urea sensor. Biotechnol Bioeng. 1997; 54:329-32.

Iso M, Shirahase T, Hanamura S, Urushiyama S, Omi S Immobilization of enzyme by microencapsulation and application of the encapsulated enzyme in the catalysis. J Microencapsul. 1989; 6:165-76.

Iso M, Kando T, Omi S. A fundamental study of the microencapsulation procedure utilizing coacervation in a polystyrene-cyclohexane solution. J Microencapsul. 1985; 2:275-87.

Mauguet M C, Legrand J, Brujes L, Carnelle G, Lane C, Popineau Y. Gliadin matrices for microencapsulation processes by simple coacervation method. J Microencapsul. 2002; 19:377-84.

Kayastha A M, Srivastava P K, Miksa B, Slomkowski S. Unique activity of ureases immobilized on poly (styrene-co-acrolein) microspheres. J Bioact Compat Polym. 2003; 18:113-24.

Reddy K R C, Kayastha A M. Improved stability of urease upon coupling to alkylamine and arylamine glass and its analytical use. J Mol Catal B: Enzym. 2006; 38:104-12.

Trevan M D. Enzyme immobilization by covalent bonding. Methods Mol Biol. 1988; 3:495-510.

Williams R A, Blanch H W. Covalent immobilization of protein monolayers for biosensor applications. Biosens Bioelectron. 1994; 9:159-67.

Pierre S J, Thies J C, Dureault A, Cameron N R, van Hest J C M, Carette N, Michon T, Weberskirch R. Covalent enzyme immobilization onto photopolymerized highly porous monoliths. Adv Mater. 2006; 18:1822-6.

Dwevedi A, Kayastha A M. Optimal immobilization of beta-galactosidase from Pea (PsBGAL) onto Sephadex and chitosan beads using response surface methodology and its applications. Bioresour Technol. 2009; 100:2667-75.

Dwevedi A, Kayastha A M. Stabilization of beta-galactosidase (from peas) by immobilization onto amberlite MB-150 beads and its application in lactose hydrolysis. J Agric Food Chem. 2009; 57:682-8.

Mulagalapalli S, Kumar S, Kalathur R C, Kayastha A M Immobilization of urease from pigeonpea (*Cajanus cajan*) on agar tablets and its application in urea assay. Appl Biochem Biotechnol. 2007; 142:291-7.

Das N, Kayastha A M, Malhotra O P Immobilization of urease from pigeonpea (*Cajanus cajan* L.) in polyacrylamide gels and calcium alginate beads. Biotechnol Appl Biochem. 1998; 27:25-9.

Das N, Kayastha A M. Immobilization of urease from pigeonpea (*Cajanus cajan* L.) on flannel cloth using polyethylenimine World J Microbiol Biotechnol. 1998; 14:927-9.

Kayastha A M, Srivastava P K. Pigeonpea (*Cajanus cajan* L.) urease immobilized on glutaraldehyde activated chitosan beads and its analytical applications. Appl Biochem Biotechnol. 2001; 96:41-53.

Tripathi P, Kumari A, Rath P, Kayastha A M Immobilization of α-amylase from mung beans (*Vigna radiata*) on Amberlite MB 150 and chitosan beads: A comparative study. J Mol Catal B: Enzym. 2007; 49:69-74.

Kumar S, Dwevedi A, Kayastha A M Immobilization of soybean (*Glycine max*) urease on alginate and chitosan beads showing improved stability: Analytical applications. J Mol Catal B: Enzym. 2009; 58:138-45.

Neto S A, Forti J C, Zucolotto V, Ciancaglini P, De Andrade A R. The kinetic behavior of dehydrogenase enzymes in solution and immobilized onto nanostructured carbon platforms. Process Biochem. 2011; 46:2347-52.

DeLouise L A, Miller B L. Enzyme Immobilization in porous silicon: Quantitative analysis of the kinetic parameters for glutathione-S-transferases. Anal Chem. 2005; 77:1950-6.

Reddy K R C, Turcu F, Schulte A, Kayastha A M, Schuhmann W. Fabrication of a potentiometric/amperometric bifunctional enzyme microbiosensor. Anal Chem. 2005; 77:5063-7.

Lin E-W, Boehnke N, Maynard H D. Protein—polymer conjugation via ligand affinity and photoactivation of glutathione S-transferase. Bioconjugate Chem. 2014; 25:1902-9.

Alconcel S N S, Baas A S, Maynard H D. FDA approved poly (ethylene glycol)-protein conjugate drugs. Polym Chem. 2011; 2:1442-8.

Canalle L A, Lowik D, van Hest J C M. Polypeptide-polymer bioconjugates. Chem Soc Rev. 2010; 39:329-53.

Self-assembly—Latest research and news|Nature. (n.d.). Retrieved from www.nature.com/subjects/self-assembly Silhavy, T. J., Benson, S. A., & Emr, S. D. (1983). Mechanisms of protein localization. *Microbiological Reviews*, 47(3), 313-344.

Mitra, S. D., Afonina, I., & Kline, K. A. (2016). Right Place, Right Time: Focalization of Membrane Proteins in Gram-Positive Bacteria. *Trends in Microbiology*, 24(8), 611-621.

Routledge, S. J., Mikaliunaite, L., Patel, A., Clare, M., Cartwright, S. P., Bawa, Z., . . . Bill, R. M. (2016). The synthesis of recombinant membrane proteins in yeast for structural studies. *Methods,* 95, 26-37.

H. I. Adler, W. D. Fisher, A. Cohen and Alice A. Hardigree, Miniature *Escherichia coli* Cells Deficient in DNA Proceedings of the National Academy of Sciences of the United States of America Vol. 57, No. 2 (Feb. 15, 1967), pp. 321-326

PIET A. J. DE BOER, ROBIN E. CROSSLEY, AND LAWRENCE I. ROTHFIELD, (1990) Central role for the *Escherichia coli* minC gene product in two different cell division-inhibition systems, Proc. Natl. Acad. Sci. USA Vol. 87, pp. 1129-1133, Xuan-Chuan Yu and William Margolin Deletion of the min Operon Results in Increased Thermosensitivity of an ftsZ84 Mutant and Abnormal FtsZ Ring Assembly, Placement, and Disassembly, J Bacteriol. 2000 November; 182(21): 6203-6213.

Murphy K C. Targeted chromosomal gene knockout using PCR fragments. Methods Mol Biol. 2011; 765:27-42.

Maral Rahimzadeh, Majid Sadeghizadeh, Farhood Najafi, Seyed Arab, and Hamid Mobasheri Impact of heat shock step on bacterial transformation efficiency, Mol Biol Res Commun. 2016 December; 5(4): 257-261.

https://www.sigmaaldrich.com/content/dam/sigma-aldrich/docs/Sigma/General_Information/lipoprotein_lipase.pdf Mitra, S. D., Afonina, I. and Kline, K. A. (2016) Right Place, Right Time: Focalization of Membrane Proteins in Gram-Positive Bacteria. Trends in Microbiology 24(8): 611-621.

Inselburg J, Segregation into and Replication of Plasmid Deoxyribonucleic Acid in Chromosomeless Segregants of *Escherichia coli* 1970 J. Bacteriol. 102(3):642-647

Frazer A C, Curtiss R $3^{rd}$, Production, properties and utility of bacterial minicells 1975, *Curr. Topics Microbiol. Immunol.* 69:1-84

Reeve, J. N., and N. H. Mendelson. 1973. Pronase digestion of amino acid binding components on the surface of *Bacillus subtilis* cells and minicells. Biochem. Biophys. Res. Commun. 53:1325-1330

Tankersley W G, Woodward J M, Brown A. Induction and isolation of a minicell-producing strain of *Salmonella typhimurium*. Proc Soc Exp Biol Med. 1974 March; 145(3):802-805

Reeve J N, Mendelson N H, Coyne S I, Hallock L L, Cole R M, Minicells of *Bacillus subtilis,* 1973, *J. Bacteriol.* 114(2):860-873

Mendelson N H, Reeve J N, Cole R M, Physiological Studies of *Bacillus subtilis* Minicells 1974 *J. Bacteriol.* 117(3):1312-1319.

Yang X, Sun S, Wang H F, Hang H Y 2013, Comparison of Autotransporter and Ice Nucleation Protein as Carrier Proteins for Antibody Display on The Cell Surface of *Escherichia coli* Progress in Biochemistry and Biophysics 40(12):1209-1219

Cid, M., Pedersen, H. L., Kaneko, S., Coutinho, P. M., Henrissat, B., Willats, W. G. T., & Boraston, A. B. (2010). Recognition of the Helical Structure of β-1,4-Galactan by a New Family of Carbohydrate-binding Modules. Journal of Biological Chemistry, 285(46), 35999-36009.

Datta, S., Christena, L. R., & Rajaram, Y. R. S. (2013). Enzyme immobilization: an overview on techniques and support materials. 3 *Biotech,* 3(1), 1-9.

Dimov, N., Kastner, E., Hussain, M., Perrie, Y., & Szita, N. (2017). Formation and purification of tailored liposomes for drug delivery using a module-based micro continuous-flow system. *Scientific Reports,* 7(1), 12045.

*Enzyme Immobilization—Advances in Industry, Agriculture,* |Alka Dwevedi|Springer. (2016). Retrieved from www.springer.com/us/book/9783319414164

Farley, M. M., Hu, B., Margolin, W., & Liu, J. (2016). Minicells, Back in Fashion. *Journal of Bacteriology,* 198(8), 1186-1195.

Gill, H. K., & Garg, H. (2014). Pesticides: Environmental Impacts and Management Strategies.

Jose, J., Maas, R. M., & Teese, M. G. (2012). Autodisplay of enzymes—molecular basis and perspectives. *Journal of Biotechnology,* 161(2), 92-103.

Linder, M., & Teeri, T. T. (1997). The roles and function of cellulose-binding domains. *Journal of Biotechnology,* 57(1), 15-28.

MacDiarmid, J. A., Mugridge, N. B., Weiss, J. C., Phillips, L., Burn, A. L., Paulin, R. P., Brahmbhatt, H. (2007). Bacterially derived 400 nm particles for encapsulation and cancer cell targeting of chemotherapeutics. *Cancer Cell,* 11(5), 431-445.

Mahmood, T., & Yang, P.-C. (2012). Western Blot: Technique, Theory, and Trouble Shooting. *North American Journal of Medical Sciences,* 4(9), 429-434.

Nuruzzaman, M., Rahman, M. M., Liu, Y., & Naidu, R. (2016). Nanoencapsulation, Nano-guard for Pesticides: A New Window for Safe Application. *Journal of Biologically active and Food Chemistry,* 64(7), 1447-1483.

Pimentel, D. (2005). 'Environmental and Economic Costs of the Application of Pesticides Primarily in the United States.' *Environment, Development and Sustainability,* 7(2), 229-252.

Shoseyov, O., Shani, Z., & Levy, I. (2006). Carbohydrate Binding Modules: Biochemical Properties and Novel Applications. *Microbiology and Molecular Biology Reviews,* 70(2), 283-295.

Singh, R., Kumar, M., Mittal, A., & Mehta, P. K. (2016). Microbial enzymes: industrial progress in 21st century. 3 *Biotech,* 6(2).

Sührer, I., Langemann, T., Lubitz, W., Weuster-Botz, D., & Castiglione, K. (2015). A novel one-step expression and immobilization method for the production of biocatalytic preparations. *Microbial Cell Factories,* 14, 180.

Sun, F., Pang, X., Xie, T., Zhai, Y., Wang, G., & Sun, F. (2015). BrkAutoDisplay: functional display of multiple exogenous proteins on the surface of *Escherichia coli* by using BrkA autotransporter. *Microbial Cell Factories,* 14.

Swords, W. E. (2003). Chemical transformation of *E. coli*. Methods in Molecular Biology (Clifton, N.J.), 235, 49-53.

Wendel, S., Fischer, E. C., Martínez, V., Seppälä, S., & Nørholm, M. H. H. (2016). A nanobody:GFP bacterial platform that enables functional enzyme display and easy quantification of display capacity. *Microbial Cell Factories,* 15.

Zhang, S., & Cahalan, M. D. (2007). Purifying Plasmid DNA from Bacterial Colonies Using the Qiagen Miniprep Kit. *Journal of Visualized Experiments: JoVE,* (6).

Zhang, Y., Chen, S., Xu, M., Cavoco-Paulo, A., Wu, J., & Chen, J. (2010). Characterization of *Thermobifida fusca* Cutinase-Carbohydrate-Binding Module Fusion Proteins and Their Potential Application in Bioscouring. *Applied and Environmental Microbiology,* 76(20), 6870-6876.

Raymond J. St. Leger Chengshu, Wang Weiguo Fang (2011) New perspectives on insect pathogens, Fungal Biology Reviews Volume 25, Issue 2: 84-88

R. Jog, G. Nareshkumar and S. Rajkumar (2012) Plant growth promoting potential and soil enzyme production of the most abundant *Streptomyces* spp. from wheat rhizosphere Journal of Applied Microbiology 113: 1154-1164

Arumugam Sathya, Rajendran Vijayabharathi, and Subramaniam Gopalakrishnan (2017), Plant growth-promoting actinobacteria: a new strategy for enhancing sustainable production and protection of grain legumes 3 Biotech 7(2): 102.

Beys da Silva W O, Santi L, Schrank A, Vainstein M H. (2010) *Metarhizium anisopliae* lipolytic activity plays a pivotal role in *Rhipicephalus (Boophilus) microplus* infection. Fungal Biol. 2010 January; 114(1):10-5.

Kanchiswamy C N, Malnoy M, Maffei M E (2015) Bioprospecting bacterial and fungal volatiles for sustainable agriculture, Trends Plant Sci. 20(4):206-211

Choong-Min Ryu, Mohamed A. Farag, Chia-Hui Hu, Munagala S. Reddy, Joseph W. Kloepper, and Paul W. Pare 7. (2004) Bacterial Volatiles Induce Systemic Resistance in *Arabidopsis*' Plant Physiol. 2004 March; 134(3): 1017-1026.

Choong-Min Ryu, Mohamed A. Farag, Chia-Hui Hu, Munagala S. Reddy, Han-Xun Wei, Paul W. Paré, and Joseph W. Kloepper (2003) Bacterial volatiles promote growth in *Arabidopsis*, PNAS 100(8):4927-4932

Witzgall P, Kirsch P, Cork A. (2010) Sex pheromones and their impact on pest management, J Chem Ecol. 36(1): 80-100.

A. Cork, K. De Souza, K. Krishnaiah, D. V. S. S. R. Kumar (1996) Control of yellow stem borer, *Scirpophaga incertulas* (*lepidoptera: pyralidae*) by mating disruption on rice in India: effect of unnatural pheromone blends and application time on efficacy, 86 (5):515-524

RathPichyangkura SupachitraChadchawan (2015) Biostimulant activity of chitosan in horticulture, Scientia Horticulturae 196(3):49-65

Giuseppe Colla, Lori Hoagland, Maurizio Ruzzi, Mariateresa Cardarelli, Paolo Bonini, Renaud Canaguier, and Youssef Rouphael, (2017) Biostimulant Action of Protein Hydrolysates: Unraveling Their Effects on Plant Physiology and Microbiome, Front Plant Sci. 8:2202.

T. Alshaal* and H. El-Ramady, (2017) Foliar Application: from Plant Nutrition to Biofortification Env. Biodiv. Soil Security 1:71-83

C. J. Wang Z. Q. Liu (2007) Foliar uptake of pesticides—Present status and future challenge Pesticide Biochemistry and Physiology 87(1):1-8

Schwab F, Zhai G, Kern M, Turner A, Schnoor J L, Wiesner M R (2016) Barriers, pathways and processes for uptake, translocation and accumulation of nanomaterials in plants—Critical review, Nanotoxicology. 2016; 10(3): 257-78.

Weiqing Zeng, Maeli Melotto, and Sheng Yang He (2010) Plant stomata: a checkpoint of host immunity and pathogen virulence, Curr Opin Biotechnol. 2010 October; 21(5): 599-603.

Gao F K, Dai C C, Liu X Z. Mechanism of fungal endophytes in plant protection against pathogen. Afr J Microbiol Res. 2010; 4(13): 1346-1351.

What is claimed is:

1. An agricultural composition, comprising:
   a) an insecticide and
   b) a minicell encapsulating a nucleic acid that is capable of inducing RNA interference in an agricultural target pest.

2. The agricultural composition of claim 1, wherein the nucleic acid is RNA.

3. The agricultural composition of claim 1, wherein the nucleic acid is at least one selected from the group consisting of: a double-stranded RNA (dsRNA), a short-hairpin RNA (shRNA), a small-interfering RNA (siRNA), and a microRNA (miRNA).

4. The agricultural composition of claim 1, wherein the nucleic acid is dsRNA.

5. The agricultural composition of claim 1, wherein the nucleic acid is shRNA.

6. The agricultural composition of claim 1, wherein the nucleic acid is siRNA.

7. The agricultural composition of claim 1, wherein the nucleic acid is miRNA.

8. The agricultural composition of claim 1, wherein the nucleic acid is capable of inducing RNA interference in at least one agricultural target pest selected from the group consisting of: fungus, insect, nematode, mite, and tick.

9. The agricultural composition of claim 1, wherein the nucleic acid is capable of inducing RNA interference in an insect.

10. The agricultural composition of claim 1, wherein the nucleic acid is capable of inducing RNA interference in at least one member from an order selected from the group consisting of: *coleoptera, diptera, hymenoptera, lepidoptera, homoptera, hemiptera, orthoptera, thysanoptera, dermaptera, siphonaptera*, and *trichoptera*.

11. The agricultural composition of claim 1, wherein the nucleic acid is capable of inducing RNA interference in a member of the order *lepidoptera*.

12. The agricultural composition of claim 1, wherein the nucleic acid is capable of inducing RNA interference in a member of the genus *Plutella*.

13. The agricultural composition of claim 1, wherein the nucleic acid is capable of inducing RNA interference in a member of the genus *Spodoptera*.

14. The agricultural composition of claim 1, wherein the minicell is ribonuclease deficient.

15. The agricultural composition of claim 1, wherein the minicell comprises at least one fusion protein.

16. The agricultural composition of claim 1, wherein the minicell comprises at least one fusion protein expressed on a surface of the minicell.

17. The agricultural composition of claim 1, wherein the minicell comprises at least one fusion protein expressed on a surface of the minicell, said fusion protein comprising at least one target cell adhesion moiety.

18. The agricultural composition of claim 1, wherein the minicell comprises at least one fusion protein expressed on a surface of the minicell, said fusion protein comprising a carbohydrate binding molecule.

19. The agricultural composition of claim 1, wherein the insecticide is cyantraniliprole.

20. The agricultural composition of claim 1, wherein the insecticide is chlorantraniliprole.

21. The agricultural composition of claim 1,
wherein the insecticide is cyantraniliprole and/or chlorantraniliprole, and wherein the nucleic acid is capable of inducing RNA interference in a member of the genus *Plutella* and/or *Spodoptera*.

22. An agricultural composition, comprising:
a minicell encapsulating a nucleic acid that is capable of inducing RNA interference in a member of the order *lepidoptera*.

23. The agricultural composition of claim 22, wherein the nucleic acid is capable of inducing RNA interference in a member of the genus *Plutella*.

24. The agricultural composition of claim 22,
wherein the nucleic acid is capable of inducing RNA interference in a member of the genus *Spodoptera*.

* * * * *